(12) United States Patent
Hadida-Ruah et al.

(10) Patent No.: US 9,051,270 B2
(45) Date of Patent: Jun. 9, 2015

(54) PYRIDONE AMIDES AS MODULATORS OF SODIUM CHANNELS

(71) Applicant: Vertex Pharmaceuticals Incorporated, Boston, MA (US)

(72) Inventors: Sara Sabina Hadida-Ruah, La Jolla, CA (US); Corey Anderson, San Diego, CA (US); Vijayalaksmi Arumugam, San Marco, CA (US); Iuliana Luci Asgian, San Diego, CA (US); Brian Richard Bear, Carlsbad, CA (US); Andreas P. Termin, Encinitas, CA (US); James Philip Johnson, San Diego, CA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 14/167,759

(22) Filed: Jan. 29, 2014

(65) Prior Publication Data

US 2014/0213616 A1    Jul. 31, 2014

Related U.S. Application Data

(60) Provisional application No. 61/759,059, filed on Jan. 31, 2013.

(51) Int. Cl.
| | |
|---|---|
| A61K 31/04 | (2006.01) |
| C07D 213/75 | (2006.01) |
| C07D 405/12 | (2006.01) |
| C07D 401/12 | (2006.01) |

(52) U.S. Cl.
CPC ............ C07D 213/75 (2013.01); C07D 405/12 (2013.01); C07D 401/12 (2013.01)

(58) Field of Classification Search
CPC ..... A61K 31/04; C07D 213/75; C07D 405/12
USPC .......................................... 546/261; 514/335
See application file for complete search history.

(56) References Cited

U.S. PATENT DOCUMENTS

| | | | |
|---|---|---|---|
| 8,389,734 B2* | 3/2013 | Chen et al. ..................... | 546/304 |
| 8,486,950 B2* | 7/2013 | Goodacre et al. .............. | 514/256 |
| 8,519,137 B2* | 8/2013 | Joshi et al. .................... | 546/214 |
| 2007/0238733 A1 | 10/2007 | Joshi | |
| 2009/0099233 A1 | 4/2009 | Joshi | |
| 2009/0118333 A1 | 5/2009 | Chen | |
| 2009/0118338 A1 | 5/2009 | Chen | |
| 2013/0231370 A1 | 9/2013 | Chen | |

FOREIGN PATENT DOCUMENTS

| | | |
|---|---|---|
| JP | 2003/034671 A | 2/2003 |
| WO | WO2009/049181 A1 | 4/2009 |
| WO | WO2009/049183 A1 | 4/2009 |

OTHER PUBLICATIONS

Akopian, A.N., L. Sivilotti, and J.N. Wood, "A tetrodotoxin-resistant voltage-gated sodium channel expressed by sensory neurons." *Nature*, 1996. 379(6562): p. 257-62).
Black, J.A., et al., "Multiple sodium channel isoforms and mitogen-activated protein kinases are present in painful human neuromas." *Ann Neurol*, 2008. 64(6): p. 644-53.
Blair, N.T. and B.P. Bean, "Roles of tetrodotoxin (TTX)-sensitive Na+ current, TTX-resistant Na+ current, and Ca2+ current in the action potentials of nociceptive sensory neurons." *J Neurosci.*, 2002. 22(23): p. 10277-90).
Catterall, W. A., Goldin, A. L., and Waxman, S. G., International Union of Pharmacology. XLVII. "Nomenclature and structure-function relationships of voltage-gated sodium channels." *Pharmacol Rev* 57 (4), p. 397 (2005).
Chahine, M., Chatelier, A., Babich, O., and Krupp, J. J., "Voltage-gated sodium channels in neurological disorders." *CNS Neurol Disord Drug Targets* 7 (2), p. 144-58 (2008).
Choi, J.S. and S.G. Waxman, "Physiological interactions between NaV1.7 and NaV1.8 sodium channels: a computer simulation study." *J Neurophysiol.* 106(6): p. 3173-84.
Coward, K., et al., "Immunolocalization of SNS/PN3 and NaN/SNS2 sodium channels in human pain states." *Pain*, 2000. 85(1-2): p. 41-50.
Dieleman, J.P., et al., "Incidence rates and treatment of neuropathic pain conditions in the general population." *Pain*, 2008. 137(3): p. 681-8.

(Continued)

*Primary Examiner* — D Margaret M Seaman
(74) *Attorney, Agent, or Firm* — Brinks Gilson & Lione

(57) ABSTRACT

The invention relates to pyridone amide compounds of formula I and I' or pharmaceutically acceptable salts thereof, useful as inhibitors of sodium channels:

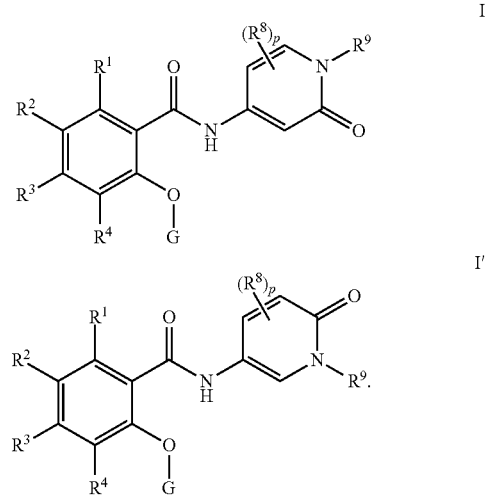

The invention also provides pharmaceutically acceptable compositions comprising the compounds of the invention and methods of using the compositions in the treatment of various disorders, including pain.

29 Claims, No Drawings

(56) References Cited

OTHER PUBLICATIONS

Dong, X.W., et al., "Small interfering RNA-mediated selective knockdown of Na(V)1.8 tetrodotoxin-resistant sodium channel reverses mechanical allodynia in neuropathic rats." *Neuroscience*, 2007. 146(2): p. 812-21.

England, S., "Voltage-gated sodium channels: the search for subtype-selective analgesics." *Expert Opin Investig Drugs* 17 (12), p. 1849-64 (2008).

Huang, H.L., et al., "Proteomic profiling of neuromas reveals alterations in protein composition and local protein synthesis in hyperexcitable nerves." *Mol Pain*, 2008. 4: p. 33.

Jarvis, M.F., et al., "A-803467, a potent and selective NaV1.8 sodium channel blocker, attenuates neuropathic and inflammatory pain in the rat." *Proc Natl Acad Sci. U S A*, 2007. 104(20): p. 8520-5.

Joshi, S.K., et al., "Involvement of the TTX-resistant sodium channel Nav1.8 in inflammatory and neuropathic,but not post-operative, pain states." Pain, 2006. 123(1-2): pp. 75-82.

Krafte, D. S. and Bannon, A. W.,"Sodium channels and nociception: recent concepts and therapeutic opportunities." *Curr Opin Pharmacol* 8 (1), p. 50-56 (2008).

Lai, J., et al., "Inhibition of neuropathic pain by decreased expression of the tetrodotoxin-resistant sodium channel, NaV1.8." *Pain*, 2002. 95(1-2): p. 143-52.

Qiu, F., et al.,"Increased expression of tetrodotoxin-resistant sodium channels NaV1.8 and NaV1.9 within dorsal root ganglia in a rat model of bone cancer pain." *Neurosci. Lett.* 512(2): p. 61-6).

Renganathan, M., T.R. Cummins, and S.G. Waxman, "Contribution of Na(V)1.8 sodium channels to action potential electrogenesis in DRG neurons." *J Neurophysiol.*, 2001. 86(2): p. 629-40.

Roza, C., et al., "The tetrodotoxin-resistant Na+ channel NaV1.8 is essential for the expression of spontaneous activity in damaged sensory axons of mice." *J Physiol.*, 2003. 550(Pt 3): p. 921-6).

Ruangsri, S., et al., "Relationship of axonal voltage-gated sodium channel 1.8 (NaV1.8) mRNA accumulation to sciatic nerve injury-induced painful neuropathy in rats." *J Biol Chem.* 286(46): p. 39836-47).

Rush, A.M. and T.R. Cummins, "Painful Research: Identification of a Small-Molecule Inhibitor that Selectively Targets NaV1.8 Sodium Channels." *Mol Interv*, 2007. 7(4): p. 192-5).

Rush, A.M., et al., "A single sodium channel mutation produces hyper- or hypoexcitability in different types of neurons." *Proc Natl Acad Sci USA*, 2006. 103(21): p. 8245-50).

Soderpalm, B., "Anticonvulsants: aspects of their mechanisms of action." *Eur J Pain* 6 Suppl A, p. 3-9 (2002).

Strickland, I.T., et al., "Changes in the expression of NaV1.7, NaV1.8 and NaV1.9 in a distinct population of dorsal root ganglia innervating the rat knee joint in a model of chronic inflammatory joint pain." *Eur J Pain*, 2008. 12(5): p. 564-72.

Sun, W., et al., "Reduced conduction failure of the main axon of polymodal nociceptive C-fibres contributes to painful diabetic neuropathy in rats." Brain. 135(Pt 2): p. 359-75.

Wang, G. K., Mitchell, J., and Wang, S. Y., "Block of persistent late Na+ currents by antidepressant sertraline and paroxetine." *J Membr Biol* 222 (2), p. 79-90 (2008).

Yiangou, Y., et al., "SNS/PN3 and SNS2/NaN sodium channel-like immunoreactivity in human adult and neonate injured sensory nerves." *FEBS Lett*, 2000. 467(2-3): p. 249-52.

International Search Report and Written Opinion of the International Searching Authority, International Patent Application No. PCT/US2014/013652 (Apr. 2, 2014).

* cited by examiner

PYRIDONE AMIDES AS MODULATORS OF SODIUM CHANNELS

CROSS-REFERENCE TO RELATED APPLICATIONS

This application claims the benefit of U.S. Provisional Patent Application No. 61/759,059, filed Jan. 31, 2013, the entire contents of which are incorporated herein by reference.

TECHNICAL FIELD OF THE INVENTION

The invention relates to compounds useful as inhibitors of sodium channels. The invention also provides pharmaceutically acceptable compositions comprising the compounds of the invention and methods of using the compositions in the treatment of various disorders including pain.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post herpetic neuropathy, diabetic neuropathy, and drug-induced neuropathy. Discrete nerve injuries indications include post amputation pain, post-surgical nerve injury pain, and nerve entrapment injuries like neuropathic back pain.

Voltage-gated sodium channels ($Na_V$'s) play a critical role in pain signaling. $Na_V$'s are key biological mediators of electrical signaling as they are the primary mediators of the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$'s in pain sensation (Rush, A. M. and T. R. Cummins, *Painful Research: Identification of a Small-Molecule Inhibitor that Selectively Targets $Na_V$1.8 Sodium Channels*. Mol Interv, 2007. 7(4): p. 192-5); England, S., Voltage-gated sodium channels: the search for subtype-selective analgesics. *Expert Opin Investig Drugs* 17 (12), p. 1849-64 (2008); Krafte, D. S. and Bannon, A. W., Sodium channels and nociception: recent concepts and therapeutic opportunities. *Curr Opin Pharmacol* 8 (1), p. 50-56 (2008)). $Na_V$'s are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role $Na_V$'s play in the initiation and propagation of neuronal signals, antagonists that reduce $Na_V$ currents can prevent or reduce neural signaling and $Na_V$ channels have long been considered likely targets to reduce pain in conditions where hyper-excitability is observed (Chahine, M., Chatelier, A., Babich, O., and Krupp, J. J., Voltage-gated sodium channels in neurological disorders. *CNS Neurol Disord Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur J Pain* 6 Suppl A, p. 3-9 (2002); Wang, G. K., Mitchell, J., and Wang, S. Y., Block of persistent late $Na^+$ currents by antidepressant sertraline and paroxetine. *J Membr Biol* 222 (2), p. 79-90 (2008)).

The $Na_V$'s form a subfamily of the voltage-gated ion channel super-family and comprises 9 isoforms, designated $Na_V1.1$-$Na_V1.9$. The tissue localizations of the nine isoforms vary greatly. $Na_V1.4$ is the primary sodium channel of skeletal muscle, and $Na_V1.5$ is primary sodium channel of cardiac myocytes. $Na_V$'s 1.7, 1.8 and 1.9 are primarily localized to the peripheral nervous system, while $Na_V$'s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005)).

Immediately upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379(6562): p. 257-62). Since then, $Na_V1.8$ has been shown to be the most significant carrier of the sodium current that maintains action potential firing in small DRG neurons (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J Neurosci.*, 2002. 22(23): p. 10277-90). $Na_V1.8$ is essential for spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc Natl Acad. Sci. USA*, 2007. 104(20): p. 8520-5; Joshi, S. K., et al., Involvement of the TTX-resistant sodium channel Nav1.8 in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na_{(V)}$ 1.8 tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol Pain*, 2008. 4: p. 33; Black, J. A., et al., Multiple sodium channel isoforms and mitogen-activated protein kinases are present in painful human neuromas. Ann Neurol, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J Biol. Chem.* 286(46): p. 39836-47). The small DRG neurons where $Na_V1.8$ is expressed include the nociceptors critical for pain signaling. $Na_V1.8$ is the primary channel that mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J Neurosci.*, 2002. 22(23): p. 10277-90). $Na_V1.8$ is necessary for rapid repetitive action potentials in nociceptors, and for spontaneous activity of damaged neurons. (Choi, J. S. and S. G. Waxman, Physiological interactions between $Na_V1.7$ and $Na_V1.8$ sodium channels: a computer simulation study. *J Neurophysiol.* 106(6): p. 3173-84; Renganathan, M., T. R. Cummins, and S. G. Waxman, Contribution of $Na_{(V)}1.8$ sodium channels to action potential electrogenesis in DRG neurons. *J Neurophysiol.*, 2001. 86(2): p. 629-40; Roza, C., et al., The tetrodotoxin-resistant $Na^+$ channel $Na_V1.8$ is essential for the expression of spontaneous activity in damaged sensory axons of mice. *J Physiol.*, 2003. 550(Pt 3): p. 921-6). In depolarized or damaged DRG neurons, $Na_V1.8$ appears to be the primary driver of hyper-excitablility (Rush, A. M., et al., A single sodium channel mutation produces hyper- or hypoexcitability in different types of neurons. *Proc Natl Acad Sci USA*, 2006. 103 (21): p. 8245-50). In some animal pain models, $Na_V1.8$ mRNA expression levels have been shown to increase in the DRG (Sun, W., et al., Reduced conduction failure of the main axon of polymodal nociceptive C-fibres contributes to painful diabetic neuropathy in rats. *Brain.* 135(Pt 2): p. 359-75; Strickland, I. T., et al., Changes in the expression of NaV1.7, $Na_V1.8$ and $Na_V1.9$ in a distinct population of dorsal root ganglia innervating the rat knee joint in a model of chronic inflammatory joint pain. *Eur J Pain*, 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.* 512(2): p. 61-6).

The primary drawback to the known $Na_V$ inhibitors is their poor therapeutic window, and this is likely a consequence of their lack of isoform selectivity. Since $Na_V1.8$ is primarily restricted to the neurons that sense pain, selective $Na_V1.8$ blockers are unlikely to induce the adverse events common to non-selective $Na_V$ blockers. Accordingly, there remains a need to develop additional $Na_V$ channel antagonists preferably those that are more Nav1.8 selective and more potent with increased metabolic stability and with fewer side effects.

SUMMARY OF THE INVENTION

It has now been found that compounds of this invention, and pharmaceutically acceptable compositions thereof, are useful as inhibitors of voltage-gated sodium channels. These compounds have the general formula I or I':

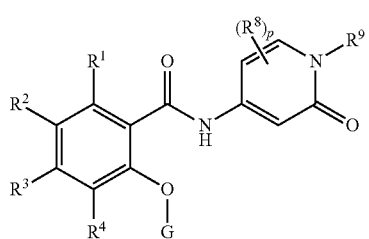

I

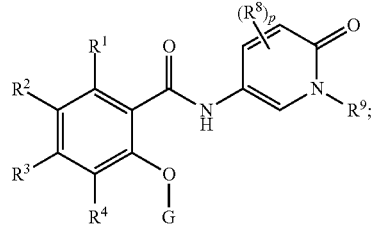

I' or a pharmaceutically acceptable salt thereof.

These compounds and pharmaceutically acceptable compositions are useful for treating or lessening the severity of a variety of diseases, disorders, or conditions, including, but not limited to, chronic pain, gut pain, neuropathic pain, musculoskeletal pain, acute pain, inflammatory pain, cancer pain, idiopathic pain, multiple sclerosis, Charcot-Marie-Tooth syndrome, incontinence or cardiac arrhythmia.

DETAILED DESCRIPTION OF THE INVENTION

In one aspect, the invention provides compounds of formula I or I'

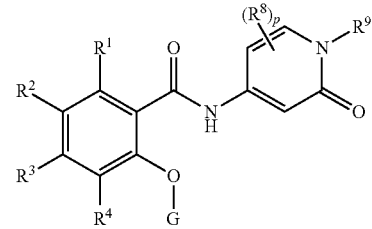

I

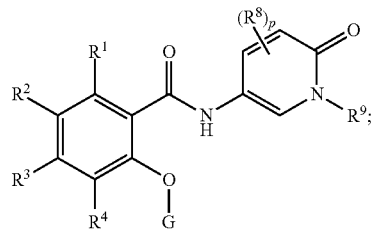

I' or a pharmaceutically acceptable salt thereof,
wherein, independently for each occurrence:
G is

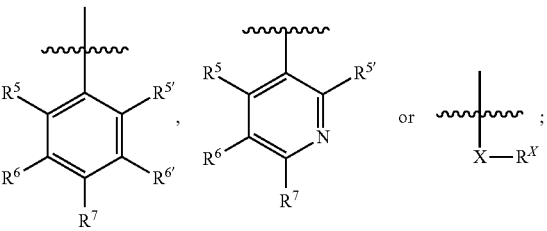

X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^1$ is H, halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^2$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^3$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^4$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
$R^8$ is halogen, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th, Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. As described herein, the variables $R^1$-$R^9$ in formula I or I' encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The phrase "optionally substituted" may be used interchangeably with the phrase "substituted or unsubstituted." In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to," as used herein, refers to zero or any integer number that is equal or less than the number following the phrase. For example, "up to 4" means any one of 0, 1, 2, 3, and 4.

The term "aliphatic," "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups.

The terms "cycloaliphatic" or "cycloalkyl" mean a monocyclic hydrocarbon ring, or a polycyclic hydrocarbon ring system that is completely saturated or that contains one or more units of unsaturation, but which is not aromatic and has a single point of attachment to the rest of the molecule. The term "polycyclic ring system," as used herein, includes bicyclic and tricyclic 4- to 12-membered structures that form at least two rings, wherein the two rings have at least one atom in common (e.g., 2 atoms in common) including fused, bridged, or spirocyclic ring systems.

The term "halogen" or "halo" as used herein, means F, Cl, Br or I. Unless otherwise specified, the term "heterocycle," "heterocyclyl," "heterocycloaliphatic," "heterocycloalkyl," or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle," "heterocyclyl," "heterocycloaliphatic," "heterocycloalkyl," or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation but is not aromatic.

The term "alkoxy," or "thioalkyl," as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl," "aralkoxy," or "aryloxyalkyl," refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring."

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic."

"D" and "d" both refer to deuterium.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I and I'. The structures also include zwitterioinc forms of the compounds or salts of formula I and formula I' where appropriate.

Additionally, unless otherwise stated, structures depicted herein are also meant to include compounds that differ only in the presence of one or more isotopically enriched or isotopically-labeled atoms. The isotopically-labeled compounds may have one or more atoms replaced by an atom having an atomic mass or mass number usually found in nature. Examples of isotopes present in compounds of formula I and formula I' include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{35}$S and $^{18}$F. Certain isotopically-labeled compounds of formula I or formula I', in addition to being useful as as therapeutic agents, are also useful in drug and/or substrate tissue distribution assays, as analytical tools or as probes in other biological assays. In one aspect of the present invention, tritiated (e.g., $^3$H) and carbon-14 (e.g., $^{14}$C) isotopes are useful given their ease of detectability. In another aspect of the present invention, replacement of one or more hydrogen atoms with heavier isotopes such as deuterium, (e.g., $^2$H) can afford certain therapeutic advantages.

In the formulas and drawings, a line transversing a ring and bonded to an R group such as in

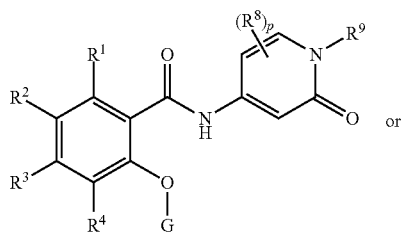

or

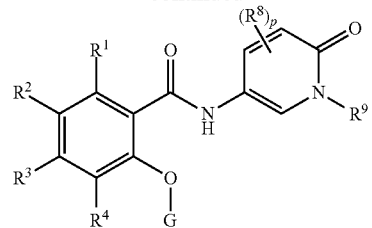

means that the R group, i.e. the $R^8$ group can be bonded to any carbon of that ring as valency allows.

Within a definition of a term as, for example, X, $R^X$, $R^1$, $R^2$, $R^3$, $R^4$, $R^8$, or $R^9$ when a $CH_2$ unit or, interchangeably, methylene unit may be replaced by —O—, it is meant to include any $CH_2$ unit, including a $CH_2$ within a terminal methyl group. For example, $CH_2CH_2CH_2OH$ is within the definition of $C_1$-$C_6$ alkyl wherein up to two non-adjacent $CH_2$ units may be replaced by —O— because the $CH_2$ unit of the terminal methyl group has been replaced by —O—.

In another embodiment, the invention features a compound of formula I or I' and the attendant definitions, wherein $R^1$ is H. In another embodiment, $R^1$ is halogen. In another embodiment, $R^1$ is CN. In another embodiment, $R^1$ is $C_1$-$C_6$ alkyl wherein said $C_1$-$C_6$ alkyl is substituted with 0-6 halogen. In another embodiment, $R^1$ is $CF_3$.

In another embodiment, the invention features a compound of formula I or I' and the attendant definitions, wherein $R^2$ is H. In another embodiment, $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I or I' and the attendant definitions, wherein $R^3$ is H. In another embodiment, $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I or I' and the attendant definitions, wherein $R^4$ is H. In another embodiment, $R^4$ is halogen. In another embodiment, $R^4$ is CN. In another embodiment, $R^4$ is $C_1$-$C_6$ alkyl wherein said $C_1$-$C_6$ alkyl is substituted with 0-6 halogen. In another embodiment, $R^4$ is $CF_3$.

In another embodiment, the invention features a compound of formula I or I' and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I or I' and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one CH$_2$ unit of said C$_1$-C$_6$ alkyl is replaced with —O—. In another embodiment, R$^9$ is CH$_2$CH$_2$OH.

In another embodiment, the invention features a compound of formula I or I' and the attendant definitions, wherein G is

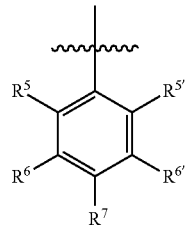

wherein:
R$^5$ is H, halogen, CN, or —X—R$^X$;
R$^{5'}$ is H, halogen, CN, or —X—R$^X$;
R$^6$ is H, halogen, CN, or —X—R$^X$;
R$^{6'}$ is H, halogen, CN, or —X—R$^X$;
R$^7$ is H, halogen, CN, or —X—R$^X$;
X is a bond or C$_1$-C$_6$ alkyl wherein said C$_1$-C$_6$ alkyl is substituted with 0-6 halogen and wherein up to two non-adjacent CH$_2$ units of said C$_1$-C$_6$ alkyl may be replaced with —O—; and
R$^X$ is absent, H, or C$_3$-C$_8$ cycloaliphatic, wherein up to two non-adjacent CH$_2$ units of said C$_3$-C$_8$ cycloaliphatic may be replaced with —O— and said C$_3$-C$_8$ cycloaliphatic is substituted with 0-3 substituents selected from halogen and C$_1$-C$_4$ alkyl.

In another embodiment, the invention features a compound of formula I or I' and the attendant definitions, wherein G is

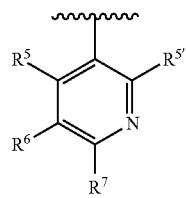

wherein:
R$^5$ is H or —X—R$^X$;
R$^{5'}$ is H or —X—R$^X$;
R$^6$ is H, halogen, CN, or —X—R$^X$;
R$^7$ is H or —X—R$^X$;
X is a bond or C$_1$-C$_6$ alkyl wherein said C$_1$-C$_6$ alkyl is substituted with 0-6 halogen, wherein up to two non-adjacent CH$_2$ units of said C$_1$-C$_6$ alkyl may be replaced with —O—; and
R$^X$ is absent, H, or C$_3$-C$_8$ cycloaliphatic, wherein up to two non-adjacent CH$_2$ units of said C$_3$-C$_8$ cycloaliphatic may be replaced with —O— and said C$_3$-C$_8$ cycloaliphatic is substituted with 0-3 substituents selected from halogen and C$_1$-C$_4$ alkyl.

In another embodiment, the invention features a compound of formula I or I' and the attendant definitions, wherein G is

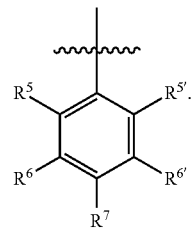

In one embodiment R$^5$ is H. In another embodiment, R$^5$ is halogen. In another embodiment, R$^5$ is Cl. In another embodiment, R$^5$ is F. In another embodiment, R$^5$ is CN. In another embodiment, R$^5$ is —X—R$^X$. In another embodiment, R$^5$ is —X—R$^X$ wherein R$^X$ is absent. In another embodiment, R$^5$ is —X—R$_X$ wherein R$^X$ is absent and X is C$_1$-C$_6$ alkyl wherein said C$_1$-C$_6$ alkyl is substituted with 0-6 halogen. In another embodiment, R$^5$ is CH$_3$. In another embodiment, R$^5$ is —X—R$^X$ wherein R$^X$ is absent and X is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, R$^5$ is OCH$_3$, OCH$_2$CH$_3$, OCH$_2$CH$_2$CH$_3$, or OCH(CH$_3$)$_2$. In another embodiment, R$^5$ is OCH$_3$. In another embodiment, R$^5$ is CH$_2$OH. In another embodiment, R$^5$ is OCF$_3$. In another embodiment, R$^5$ is OCHF$_2$.

In another embodiment, the invention features a compound of formula I or I' and the attendant definitions, wherein G is

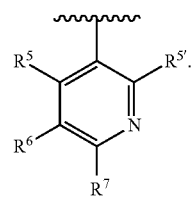

In one embodiment, R$^5$ is H. In another embodiment, R$^5$ is —X—R$^X$. In another embodiment, R$^5$ is —X—R$^X$ wherein R$^X$ is absent. In another embodiment, R$^5$ is —X—R$^X$ wherein R$^X$ is absent and X is C$_1$-C$_6$ alkyl wherein said C$_1$-C$_6$ alkyl is substituted with 0-6 halogen. In another embodiment, R$^5$ is CH$_3$. In another embodiment, R$^5$ is —X—R$^X$ wherein R$^X$ is absent and X is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, R$^5$ is OCH$_3$, OCH$_2$CH$_3$, OCH$_2$CH$_2$CH$_3$, or OCH(CH$_3$)$_2$. In another embodiment, R$^5$ is OCH$_3$. In another embodiment, R$^5$ is CH$_2$OH. In another embodiment, R$^5$ is OCF$_3$. In another embodiment, R$^5$ is OCHF$_2$.

In another embodiment, the invention features a compound of formula I or I' and the attendant definitions, wherein G is

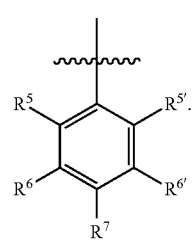

In one embodiment $R^{5'}$ is H. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I or I' and the attendant definitions, wherein G is

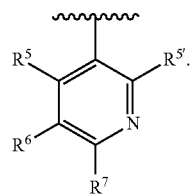

In one embodiment, $R^5$ is H. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I or I' and the attendant definitions, wherein G is

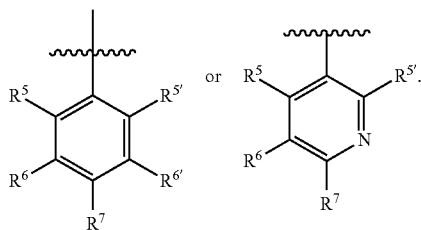

In one embodiment $R^6$ is H. In another embodiment, $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I or I' and the attendant definitions, wherein G is

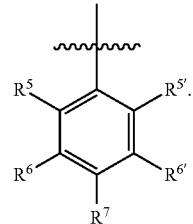

In one embodiment, $R^{6'}$ is H. In another embodiment, $R^{6'}$ is halogen. In another embodiment, $R^{6'}$ is Cl. In another embodiment, $R^{6'}$ is F. In another embodiment, $R^{6'}$ is CN. In another embodiment, $R^{6'}$ is —X—$R^X$. In another embodiment, $R^{6'}$ is —X—$R^X$ wherein $R^X$ is absent. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{6'}$ is $CH_3$. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{6'}$ is $OCH_3$.

In another embodiment, the invention features a compound of formula I or I' and the attendant definitions, wherein G is

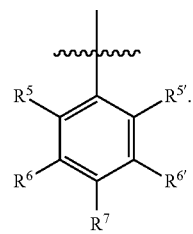

In one embodiment, $R^7$ is H. In another embodiment, $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$ $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I or I' and the attendant definitions, wherein G is

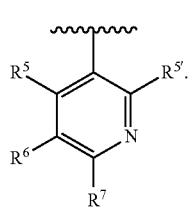

In one embodiment, $R^7$ is H In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I or I' and the attendant definitions, wherein G is

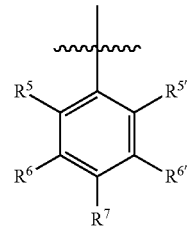

In one embodiment, $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I or I' and the attendant definitions, wherein G is In one embodiment, $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with up 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I or I' and the attendant definitions, wherein G is:

and G is selected from:

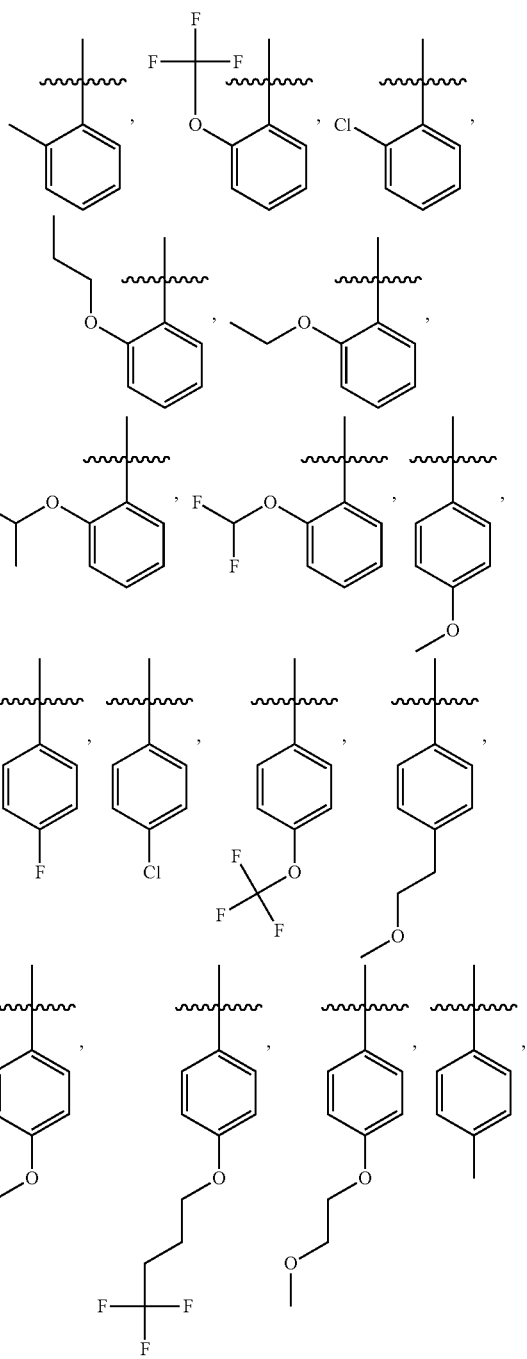

-continued
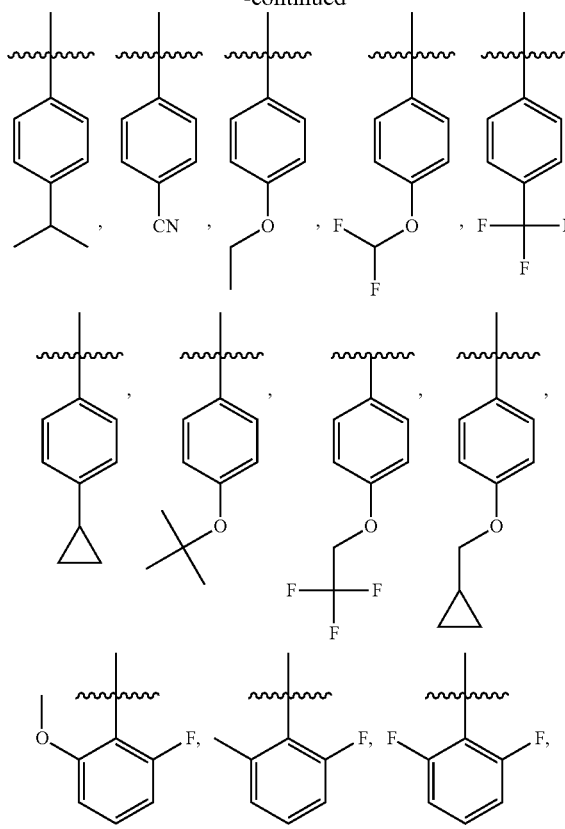
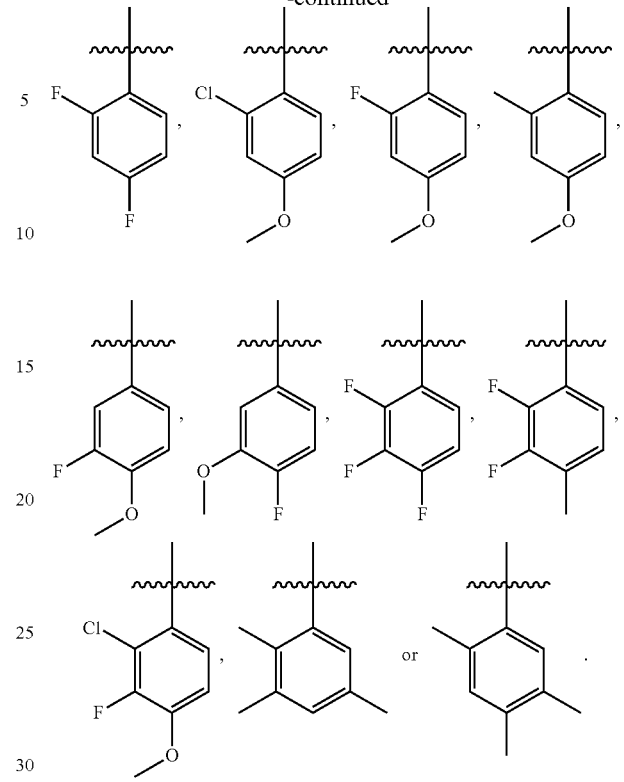
In another embodiment, the invention features a compound of formula I or I' and the attendant definitions, wherein G is:
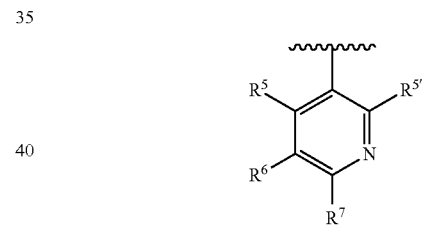
and G is selected from
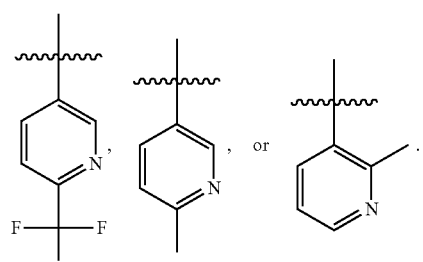
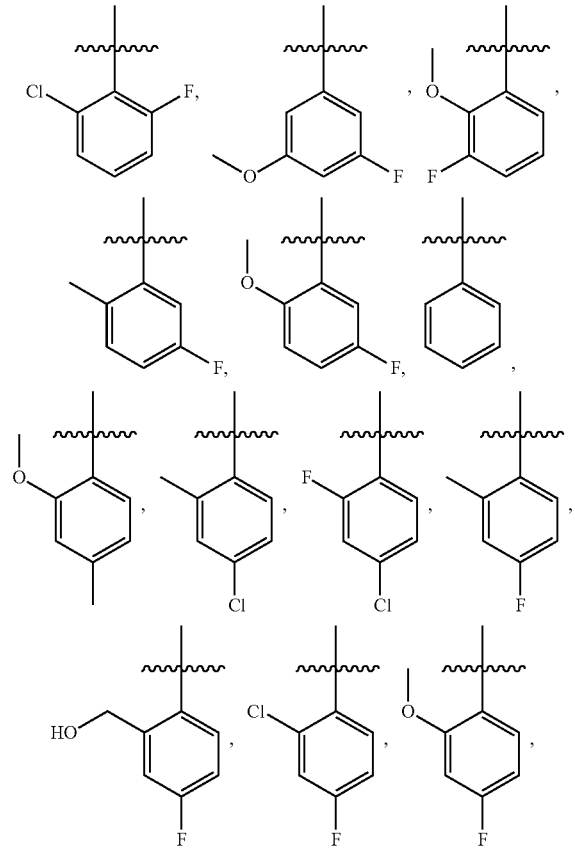
In another embodiment, the invention features a compound of formula I or I' and the attendant definitions, wherein G is
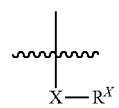

wherein:

X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and $R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with up 0-3 substituents selected from halogen and $C_1$-$C_4$ alkyl.

In another embodiment, the invention features a compound of formula I or I' and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is absent. In another embodiment, X is $CH_2CH_2CH(CH_3)_3$ or $CH_2CH(CH_3)_2$ and $R^X$ is absent. In another embodiment, X is $CH_2CH_2CH_2CF_3$ or $CH_2CH_2CF_3$ and $R^X$ is absent.

In another embodiment, the invention features a compound of formula I or I' and the attendant definitions, wherein G is —X—$R^X$ wherein X is a bond and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is a bond and $R^X$ is cyclobutane, cyclohexane, bicyclo[2.2.1]heptane, or bicyclo[3.1.0]hexane.

In another embodiment, the invention features a compound of formula I or I' and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is $C_3$-$C_8$ cycloaliphatic wherein up to two non-adjacent $CH_2$ units of said $C_3$-$C_8$ cycloaliphatic may be replaced with —O—; and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic. In another embodiment, X is $CH_2$ and $R^X$ is cyclopropyl or cyclopentyl. In another embodiment, X is $CH_2$ and $R^X$ is $C_3$-$C_8$ cycloaliphatic with up to 3 substituents selected from halogen and $C_1$-$C_4$ alkyl. In another embodiment, X is $CH_2$ and $R^X$ is 1-methylcylopropyl, 2,2-dimethylcyclopropyl or 2,2-difluorocyclopropyl.

In another embodiment, the invention features a compound of formula I or I' and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl are replaced with —O— and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic wherein one $CH_2$ unit of said $C_3$-$C_8$ cycloaliphatic is replaced with —O—. In another embodiment, X is $CH_2$ and $R^X$ is 3-tetrahydrofuran.

In another embodiment, the invention features a compound of formula I or I' and the attendant definitions, wherein G is —X—$R^X$ and —X—$R^X$ is selected from:

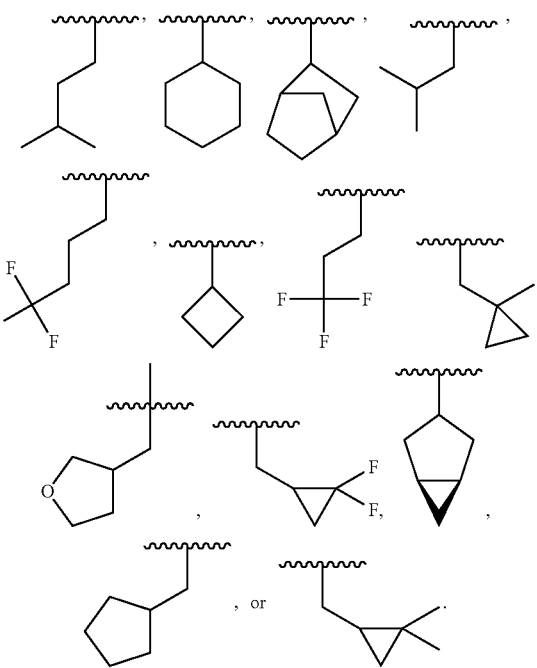

In another aspect, the invention provides a compound of formula I-A or I'-A:

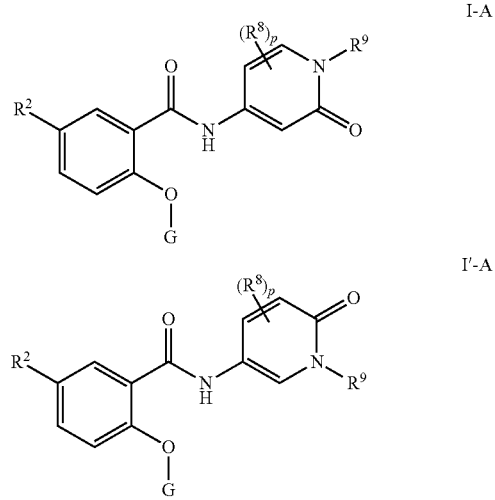

or a pharmaceutically acceptable salt thereof,
wherein, independently for each occurrence:

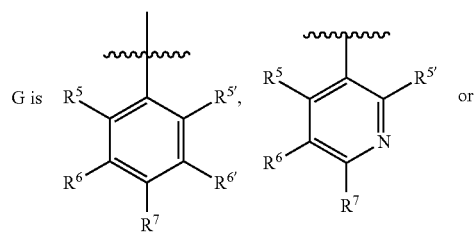

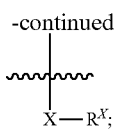

X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is H, halogen, CN, or —X—$R^X$;

$R^{5'}$ is H, halogen, CN, or —X—$R^X$;

$R^6$ is H, halogen, CN, or —X—$R^X$;

$R^{6'}$ is H, halogen, CN, or —X—$R^X$;

$R^7$ is H, halogen, CN, or —X—$R^X$;

$R^8$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-A or I'-A and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-A or I'-A and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-A or I'-A and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-A or I'-A and the attendant definitions, wherein G is

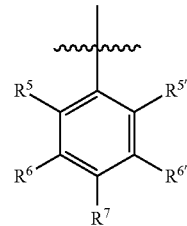

wherein:
$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-A or I'-A and the attendant definitions, wherein G is

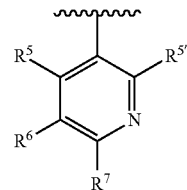

wherein:
$R^5$ is H, or —X—$R^X$;
$R^{5'}$ is H, or —X—$R^X$;
$R^6$ is H, halogen, CN, or —X—$R^X$;
$R^7$ is H, or —X—$R^X$;
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-A or I'-A and the attendant definitions, wherein G is

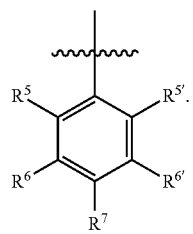

In one embodiment, $R^5$ is H. In another embodiment, $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-A or I'-A and the attendant definitions, wherein G is

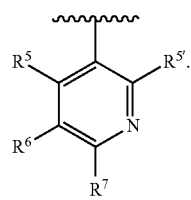

In one embodiment, $R^5$ is H. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-A or I'-A and the attendant definitions, G is

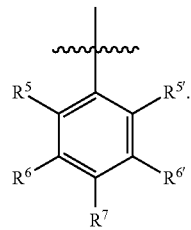

In one embodiment $R^{5'}$ is H. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-A or I'-A and the attendant definitions, G is

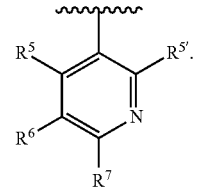

In one embodiment $R^{5'}$ is H. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-A or I'-A and the attendant definitions, wherein G is

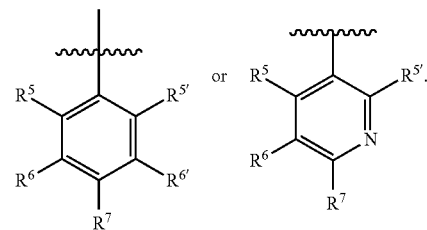

In one embodiment, $R^6$ is H. In another embodiment, $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-A or I'-A and the attendant definitions, wherein G is

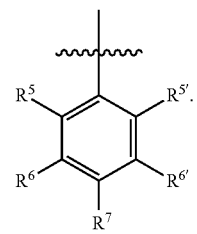

In one embodiment, $R^{6'}$ is H. In another embodiment, $R^{6'}$ is halogen. In another embodiment, $R^{6'}$ is Cl. In another embodiment, $R^{6'}$ is F. In another embodiment, $R^{6'}$ is CN. In another embodiment, $R^{6'}$ is —X—$R^X$. In another embodiment, $R^{6'}$ is —X—$R^X$ wherein $R^X$ is absent. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{6'}$ is $CH_3$. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{6'}$ is $OCH_3$.

In another embodiment, the invention features a compound of formula I-A or I'-A and the attendant definitions, wherein G is

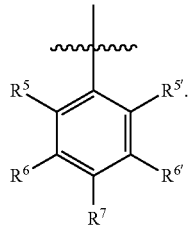

In one embodiment, $R^7$ is H. In another embodiment, $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-A or I'-A and the attendant definitions, wherein G is

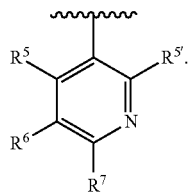

In one embodiment, $R^7$ is H. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-A or I'-A and the attendant definitions, wherein G is

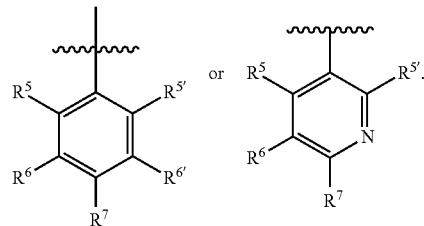

In one embodiment, $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-A or I'-A and the attendant definitions, wherein G is

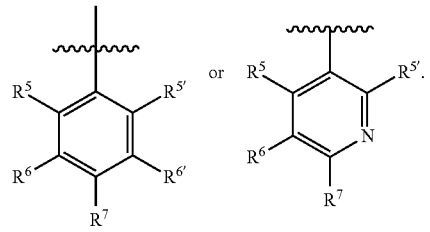

In one embodiment, $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-A or I'-A and the attendant definitions, wherein G is:

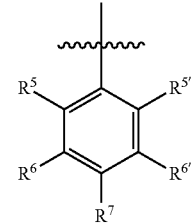

and G is selected from:

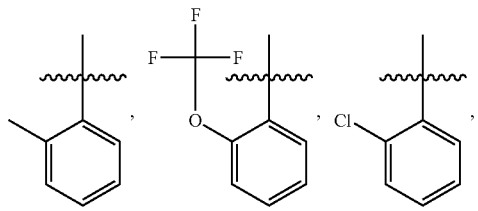

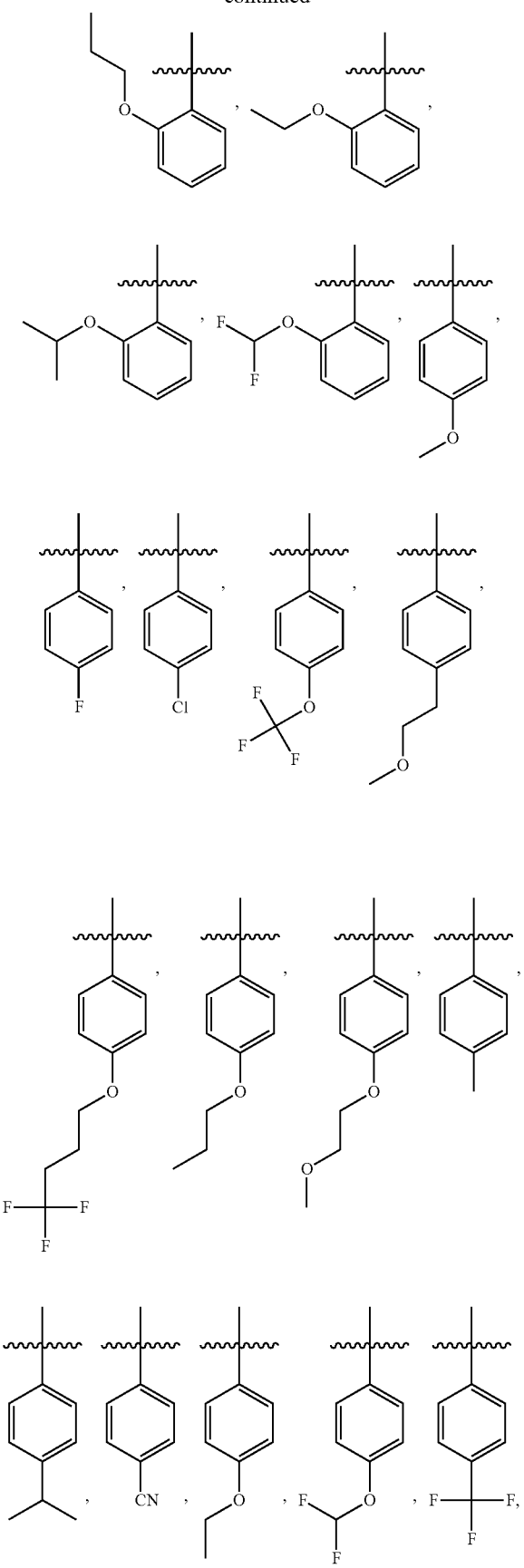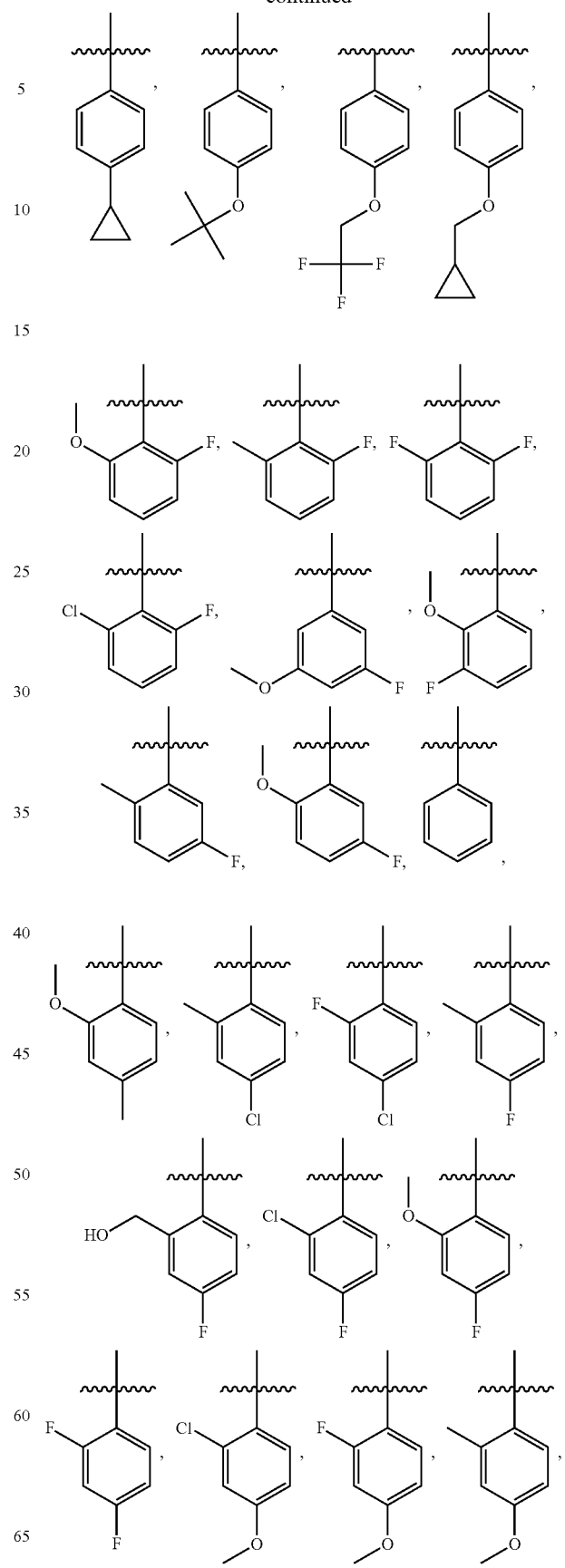

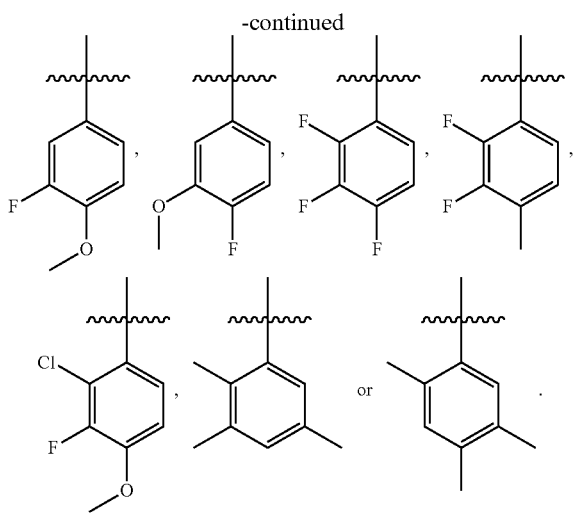

In another embodiment, the invention features a compound of formula I-A or I'-A and the attendant definitions, wherein G is:

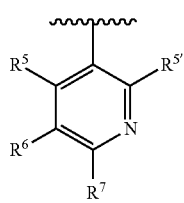

and G is selected from

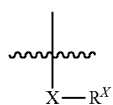

In another embodiment, the invention features a compound of formula I-A or I'-A and the attendant definitions, wherein G is

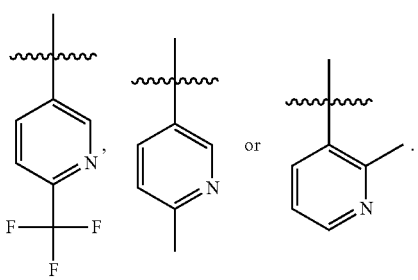

wherein:
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-A or I'-A and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is absent. In another embodiment, X is $CH_2CH_2CH(CH_3)_3$ or $CH_2CH(CH_3)_2$ and $R^X$ is absent. In another embodiment, X is $CH_2CH_2CH_2CF_3$ or $CH_2CH_2CF_3$ and $R^X$ is absent.

In another embodiment, the invention features a compound of formula I-A or I'-A and the attendant definitions, wherein G is —X—$R^X$ wherein X is a bond and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is a bond and $R^X$ is cyclobutane, cyclohexane, bicyclo[2.2.1]heptane, or bicyclo[3.1.0]hexane.

In another embodiment, the invention features a compound of formula I-A or I'-A and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is $C_3$-$C_8$ cycloaliphatic wherein up to two non-adjacent $CH_2$ units of said $C_3$-$C_8$ cycloaliphatic may be replaced with —O—; and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic. In another embodiment, X is $CH_2$ and $R^X$ is cyclopropyl or cyclopentyl. In another embodiment, X is $CH_2$ and $R^X$ is $C_3$-$C_8$ cycloaliphatic with up to 3 substituents selected from halogen and $C_1$-$C_4$ alkyl. In another embodiment, X is $CH_2$ and $R^X$ is 1-methylcylopropyl, 2,2-dimethylcyclopropyl or 2,2-difluorocyclopropyl.

In another embodiment, the invention features a compound of formula I-A or I'-A and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl are replaced with —O— and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic wherein one $CH_2$ unit of said $C_3$-$C_8$ cycloaliphatic is replaced with —O—. In another embodiment, X is $CH_2$ and $R^X$ is 3-tetrahydrofuran.

In another embodiment, the invention features a compound of formula I-A or I'-A and the attendant definitions, wherein G is —X—$R^X$ and —X—$R^X$ is selected from:

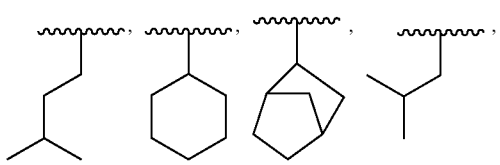

-continued

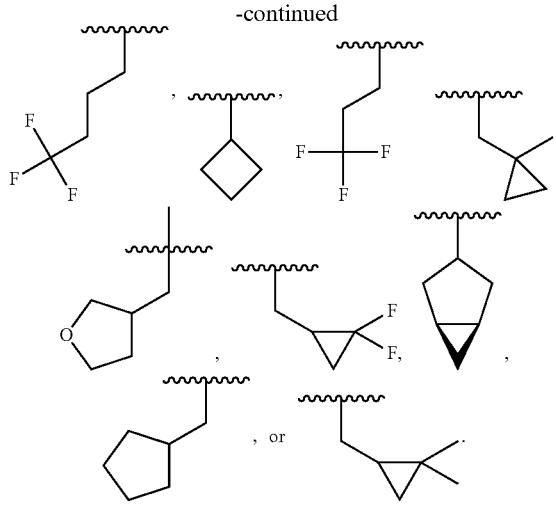

In another aspect, the invention provides a compound of formula I-B or I'-B:

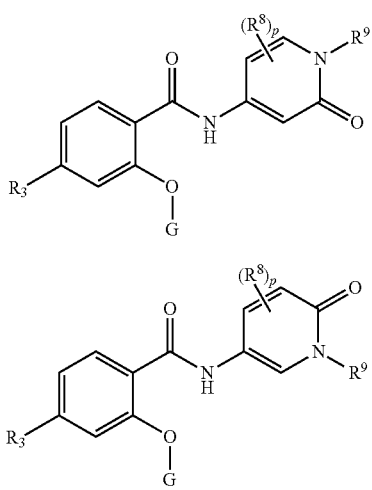

or a pharmaceutically acceptable salt thereof,
wherein, independently for each occurrence:

G is

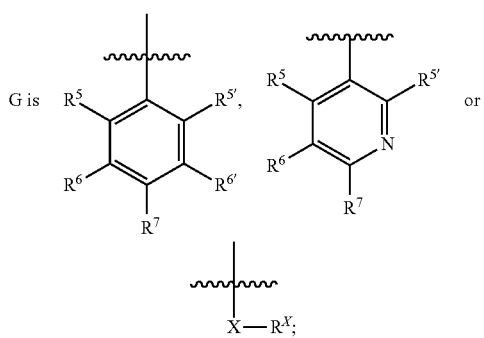

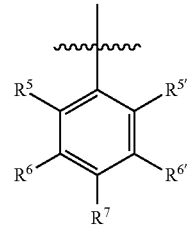

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
$R^8$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and
$R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-B or I'-B and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-B or I'-B and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$. In another embodiment, p is an integer from 1 to 3 and $R^8$ is D.

In another embodiment, the invention features a compound of formula I-B or I'-B and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-B or I'-B and the attendant definitions, wherein G is wherein:
$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and $R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-B or I'-B and the attendant definitions, wherein G is

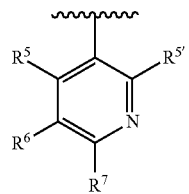

wherein:
$R^5$ is H, or —X—$R^X$;
$R^{5'}$ is H, or —X—$R^X$;
$R^6$ is H, halogen, CN, or —X—$R^X$;
$R^7$ is H, or —X—$R^X$;
X is a bond or $C_1$-$C_6$ alkyl wherein said $C_1$-$C_6$ alkyl is substituted with 0-6 halogen and wherein up to two nonoadjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-B or I'-B and the attendant definitions, wherein G is

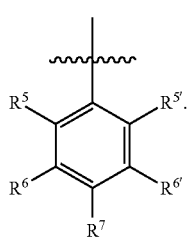

In one embodiment, $R^5$ is H. In another embodiment, $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is $CD_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$ or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-B or I'-B and the attendant definitions, wherein G is

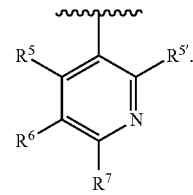

In one embodiment, $R^5$ is H. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is $CD_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$ or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-B or I'-B and the attendant definitions, wherein G is

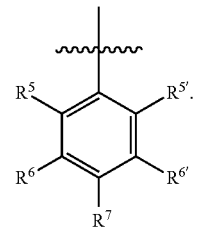

In one embodiment, $R^{5'}$ is H. In another embodiment, $R^{5'}$ is D. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$ or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-B or I'-B and the attendant definitions, wherein G is

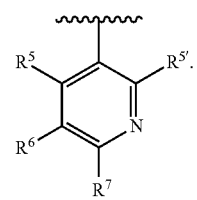

In one embodiment, $R^{5'}$ is H. In another embodiment, $R^{5'}$ is D. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$ or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-B or I'-B and the attendant definitions, wherein G is

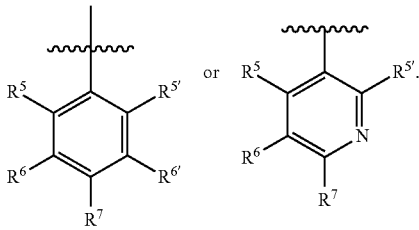

In one embodiment, $R^6$ is H. In another embodiment, $R^6$ is D. In another embodiment, $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-B or I'-B and the attendant definitions, wherein G is

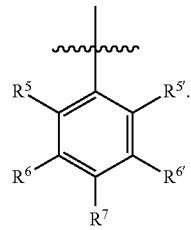

In one embodiment, $R^{6'}$ is H. In another embodiment, $R^{6'}$ is halogen. In another embodiment, $R^{6'}$ is D. In another embodiment, $R^{6'}$ is Cl. In another embodiment, $R^{6'}$ is F. In another embodiment, $R^{6'}$ is CN. In another embodiment, $R^{6'}$ is —X—$R^X$. In another embodiment, $R^{6'}$ is —X—$R^X$ wherein $R^X$ is absent. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{6'}$ is $CH_3$. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{6'}$ is $OCH_3$.

In another embodiment, the invention features a compound of formula I-B or I'-B and the attendant definitions, wherein G is

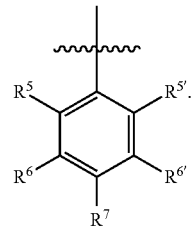

In one embodiment, $R^7$ is H. In another embodiment, $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CF_3$, or $OCHF_2$.

In another embodiment, the invention features a compound of formula I-B or I'-B and the attendant definitions, wherein G is

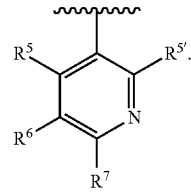

In one embodiment, $R^7$ is H. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-B or I'-B and the attendant definitions, wherein G is

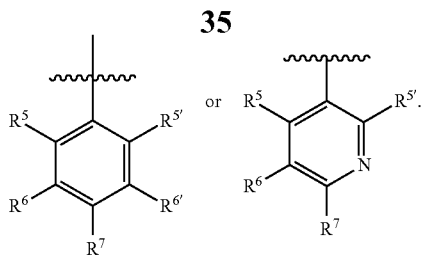

In one embodiment, $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-B or I'-B and the attendant definitions, wherein G is

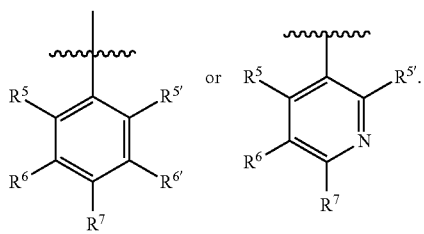

In one embodiment, $R^7$ is —X—$R^X$ wherein X is $C_1$-$C_6$ alkyl wherein said $C_1$-$C_6$ alkyl is substituted with 0-6 halogen and wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-B or I'-B and the attendant definitions, wherein G is selected from:

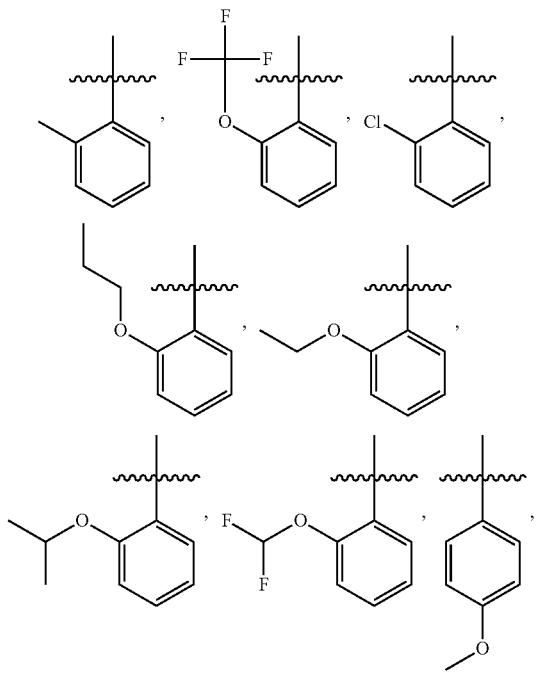

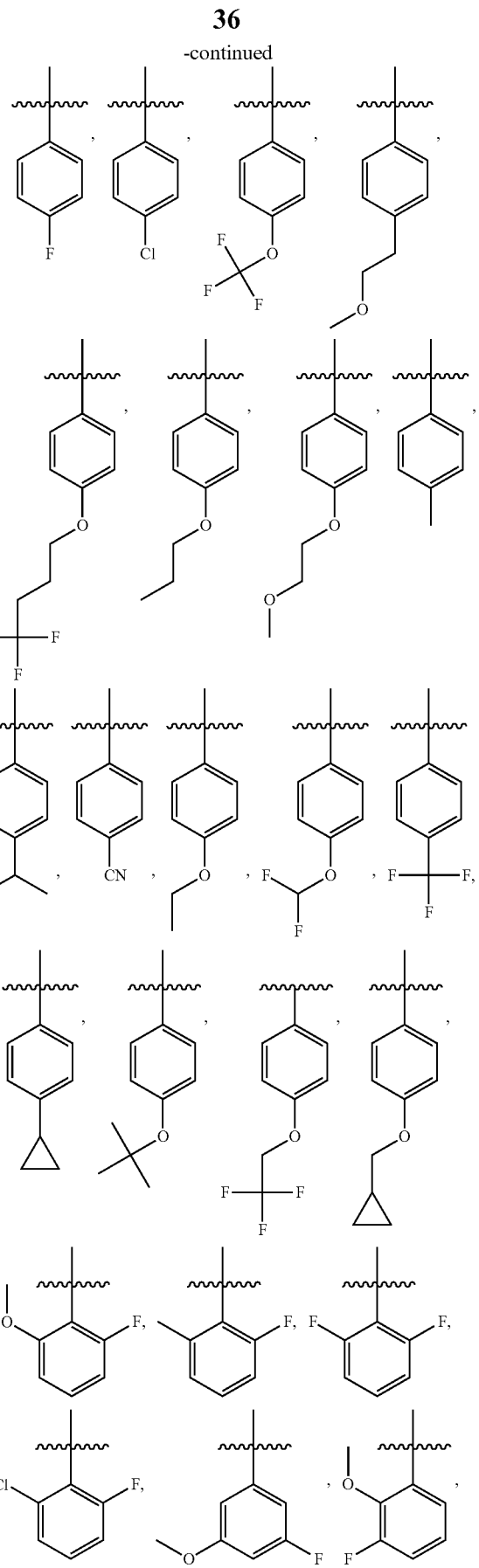

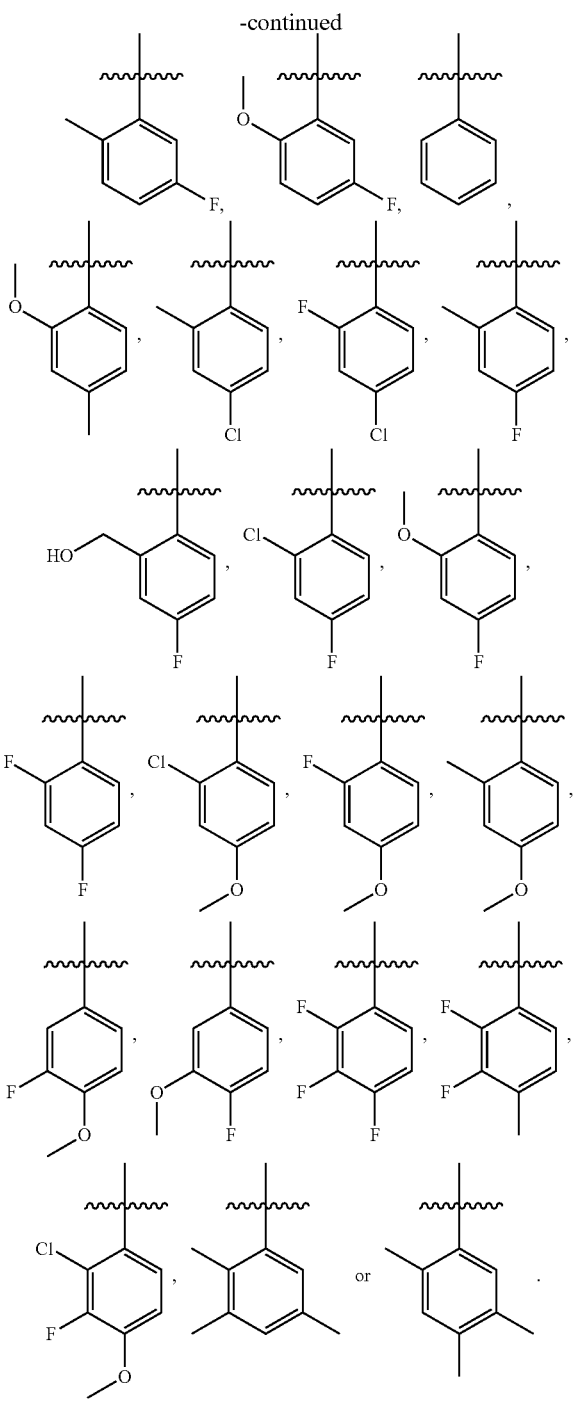

In another embodiment, the invention features a compound of formula I-B or I'-B and the attendant definitions, wherein G is:

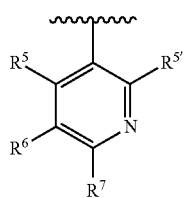

and G is selected from

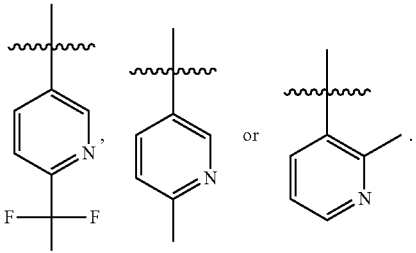

In another embodiment, the invention features a compound of formula I-B or I'-B and the attendant definitions, wherein G is

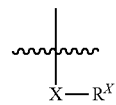

wherein:
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-B or I'-B and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is absent. In another embodiment, X is $CH_2CH_2C(CH_3)_3$ or $CH_2CH(CH_3)_2$ and $R^X$ is absent. In another embodiment, X is $CH_2CH_2CH_2CF_3$ or $CH_2CH_2CF_3$ and $R^X$ is absent.

In another embodiment, the invention features a compound of formula I-B or I'-B and the attendant definitions, wherein G is —X—$R^X$ wherein X is a bond and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is a bond and $R^X$ is cyclobutane, cyclohexane, bicyclo[2.2.1]heptane, or bicyclo[3.1.0]hexane.

In another embodiment, the invention features a compound of formula I-B or I'-B and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is $C_3$-$C_8$ cycloaliphatic wherein up to two non-adjacent $CH_2$ units of said $C_3$-$C_8$ cycloaliphatic may be replaced with —O—; and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic. In another embodiment, X is $CH_2$ and $R^X$ is cyclopropyl or cyclopentyl. In another embodiment, X is $CH_2$ and $R^X$ is $C_3$-$C_8$ cycloaliphatic with up to 3 substituents selected from halogen and $C_1$-$C_4$ alkyl. In another embodiment, X is $CH_2$ and $R^X$ is 1-methylcylopropyl, 2,2-dimethylcyclopropyl or 2,2-difluorocyclopropyl.

In another embodiment, the invention features a compound of formula I-B or I'-B and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl are replaced with —O— and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic wherein one $CH_2$ unit of said $C_3$-$C_8$ cycloaliphatic is replaced with —O—. In another embodiment, X is $CH_2$ and $R^X$ is 3-tetrahydrofuran.

In another embodiment, the invention features a compound of formula I-B or I'-B and the attendant definitions, wherein G is selected from:

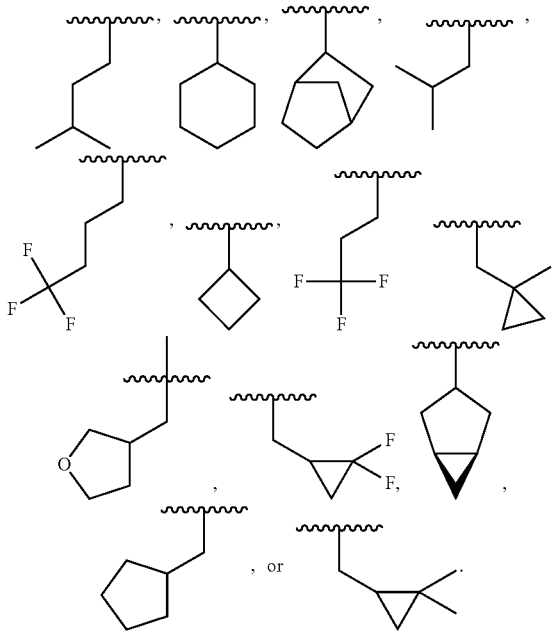

In another aspect, the invention provides a compound of formula I-C or I'-C:

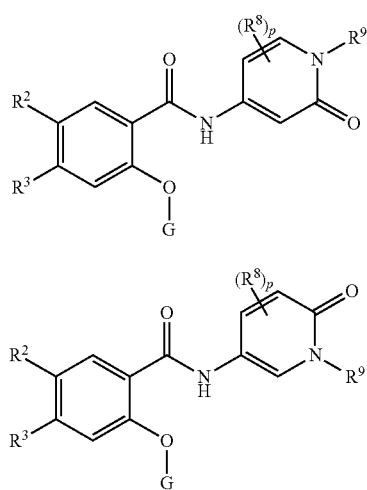

or a pharmaceutically acceptable salt thereof, wherein, independently for each occurrence:

G is

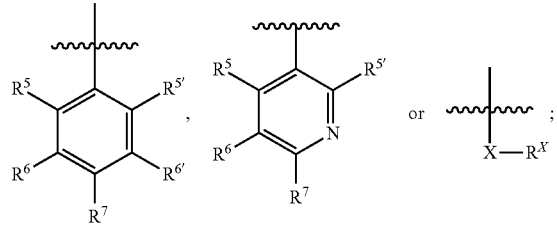

X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-C or I'-C and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-C or I'-C and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-C or I'-C and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-C or I'-C and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-C or I'-C and the attendant definitions, wherein G is

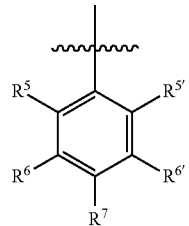

wherein:
$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-C or I'-C and the attendant definitions, wherein G is

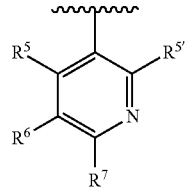

wherein:
$R^5$ is H, or —X—$R^X$;
$R^{5'}$ is H, or —X—$R^X$;
$R^6$ is H, halogen, CN, or —X—$R^X$;
$R^7$ is H, or —X—$R^X$;
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-C or I'-C and the attendant definitions, wherein G is

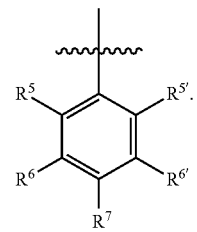

In one embodiment, $R^5$ is H. In another embodiment, $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-C or I'-C and the attendant definitions, wherein G is

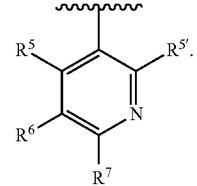

In one embodiment $R^5$ is H. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-C or I'-C and the attendant definitions, wherein G is

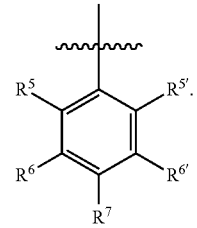

In one embodiment $R^{5'}$ is H. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-C or I'-C and the attendant definitions, wherein G is

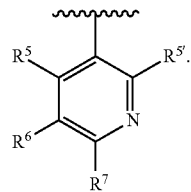

In one embodiment $R^{5'}$ is H. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-C or I'-C and the attendant definitions, wherein G is

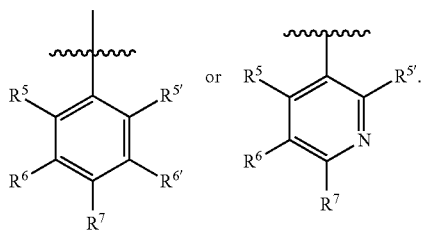

In one embodiment, $R^6$ is H. In another embodiment, $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-C or I'-C and the attendant definitions, wherein G is

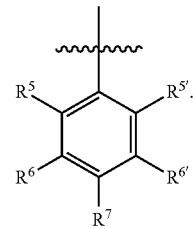

In another embodiment, $R^{6'}$ is H. In another embodiment, $R^{6'}$ is halogen. In another embodiment, $R^{6'}$ is Cl. In another embodiment, $R^{6'}$ is F. In another embodiment, $R^{6'}$ is CN. In another embodiment, $R^{6'}$ is —X—$R^X$. In another embodiment, $R^{6'}$ is —X—$R^X$ wherein $R^X$ is absent. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{6'}$ is $CH_3$. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{6'}$ is $OCH_3$.

In another embodiment, the invention features a compound of formula I-C or I'-C and the attendant definitions, wherein G is

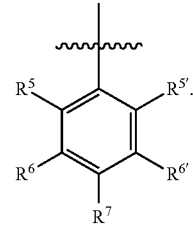

In one embodiment, $R^7$ is H. In another embodiment, $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-C or I'-C and the attendant definitions, wherein G is

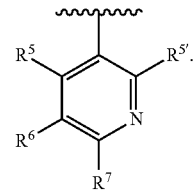

In one embodiment, $R^7$ is H. In another embodiment, $R^7$ is $-X-R^X$. In another embodiment, $R^7$ is $-X-R^X$ wherein $R^X$ is absent. In another embodiment, $R^7$ is $-X-R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is $-X-R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with $-O-$. In another embodiment, $R^7$ is $OCH_2CH_2OCH_3$. In another embodiment, $R^7$ is $-X-R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with $-O-$. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-C or I'-C and the attendant definitions, wherein G is

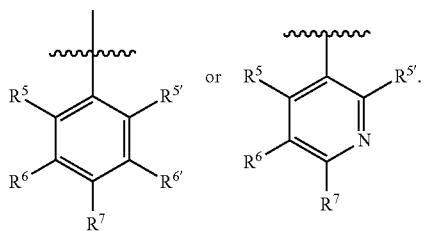

In one embodiment, $R^7$ is $-X-R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is $-X-R^X$ wherein X is a bond and $R^X$ is cyclopropyl.

In another embodiment, the invention features a compound of formula I-C or I'-C and the attendant definitions, wherein G is

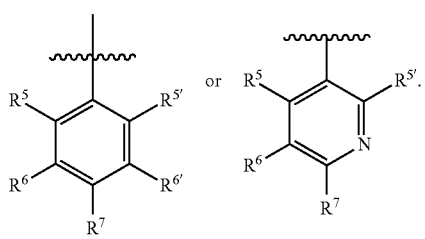

In one embodiment, $R^7$ is $-X-R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with $-O-$ and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is $-X-R^X$ wherein X is $OCH_2$ and $R^X$ is cyclopropyl.

In another embodiment, the invention features a compound of formula I-C or I'-C and the attendant definitions, wherein G is:

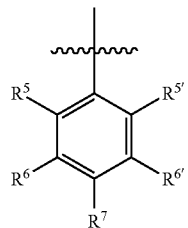

and G is selected from:

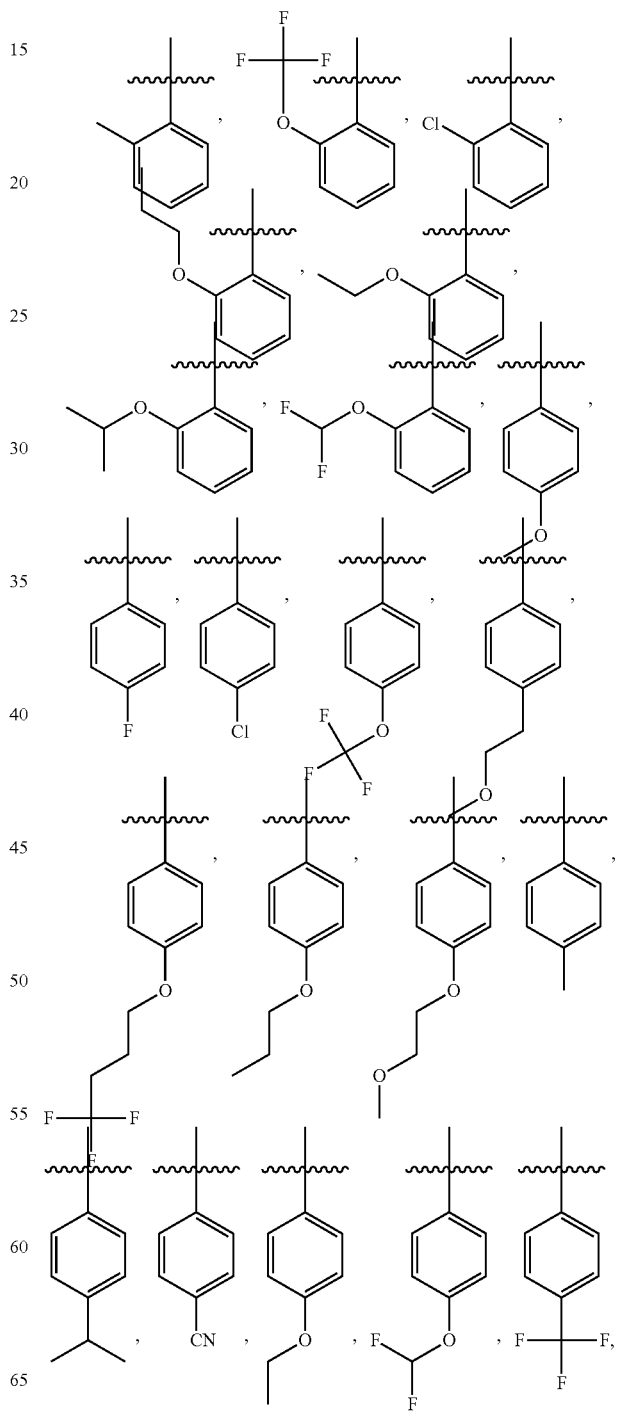

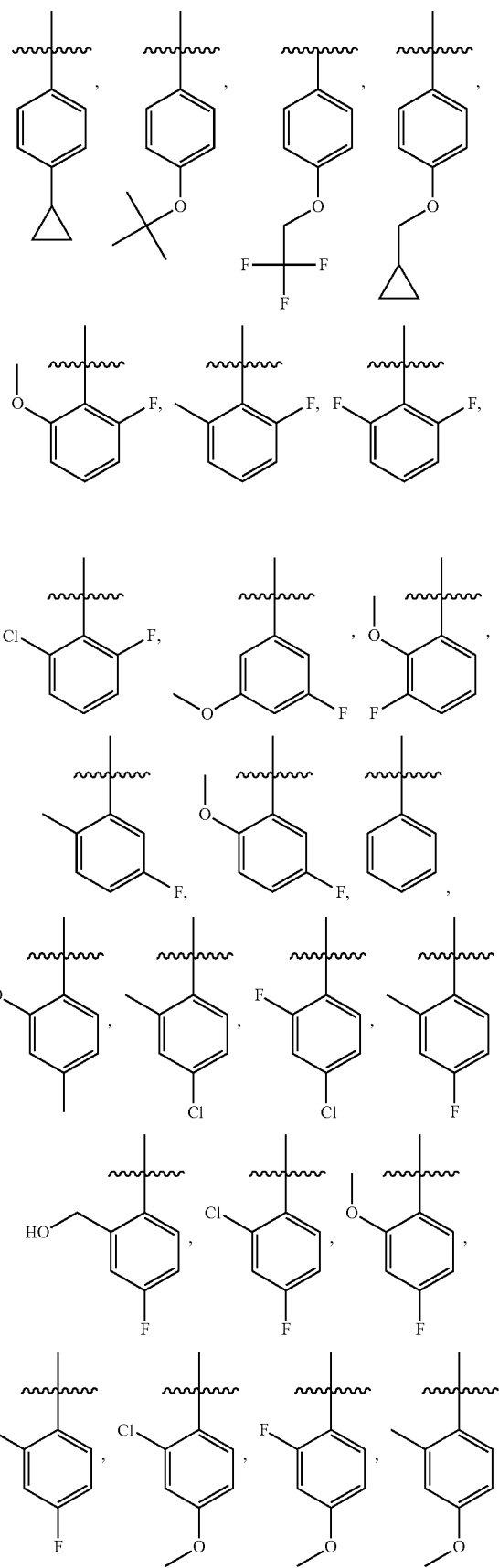

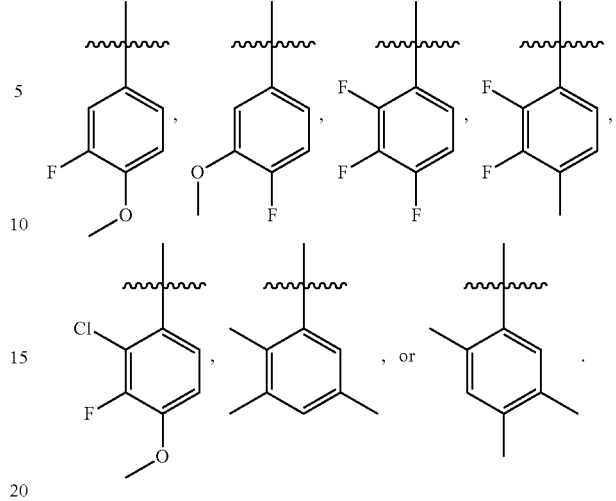

In another embodiment, the invention features a compound of formula I-C or I'-C and the attendant definitions, wherein G is:

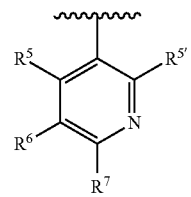

and G is selected from

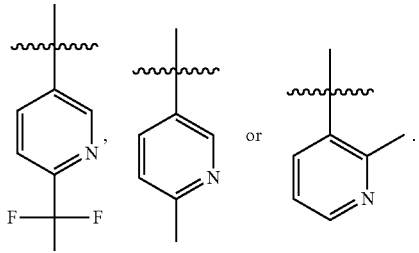

In another embodiment, the invention features a compound of formula I-C or I'-C and the attendant definitions, wherein G is

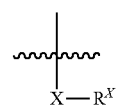

wherein:
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-C or I'-C and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is absent. In another embodiment, X is $CH_2CH_2C(CH_3)_3$ or $CH_2CH(CH_3)_2$ and $R^X$ is absent. In another embodiment, X is $CH_2CH_2CH_2CF_3$ or $CH_2CH_2CF_3$ and $R^X$ is absent.

In another embodiment, the invention features a compound of formula I-C or I'-C and the attendant definitions, wherein G is —X—$R^X$ wherein X is a bond and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is a bond and $R^X$ is cyclobutane, cyclohexane, bicyclo[2.2.1]heptane, or bicyclo[3.1.0]hexane.

In another embodiment, the invention features a compound of formula I-C or I'-C and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is $C_3$-$C_8$ cycloaliphatic wherein up to two non-adjacent $CH_2$ units of said $C_3$-$C_8$ cycloaliphatic may be replaced with —O—; and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic. In another embodiment, X is $CH_2$ and $R^X$ is cyclopropyl or cyclopentyl. In another embodiment, X is $CH_2$ and $R^X$ is $C_3$-$C_8$ cycloaliphatic with up to 3 substituents selected from halogen and $C_1$-$C_4$ alkyl. In another embodiment, X is $CH_2$ and $R^X$ is 1-methylcylopropyl, 2,2-dimethylcyclopropyl or 2,2-difluorocyclopropyl.

In another embodiment, the invention features a compound of formula I-C or I'-C and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl are replaced with —O— and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic wherein one $CH_2$ unit of said $C_3$-$C_8$ cycloaliphatic is replaced with —O—. In another embodiment, X is $CH_2$ and $R^X$ is 3-tetrahydrofuran.

In another embodiment, the invention features a compound of formula I-C or I'-C and the attendant definitions, wherein G is selected from:

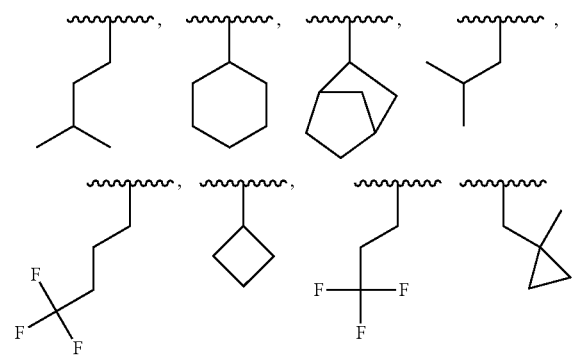

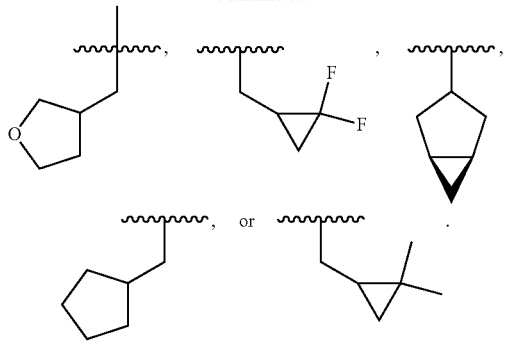

In another aspect, the invention provides a compound of formula I-D or I'-D:

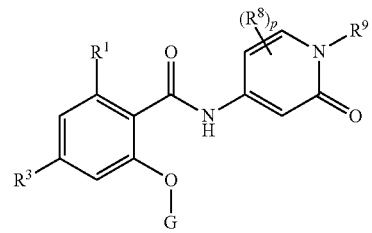

I-D

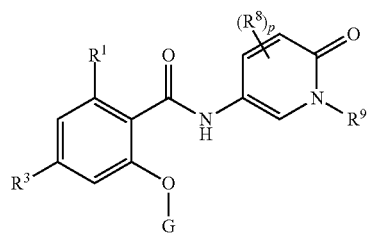

I'-D or a pharmaceutically acceptable salt thereof,
wherein, independently for each occurrence:
G is

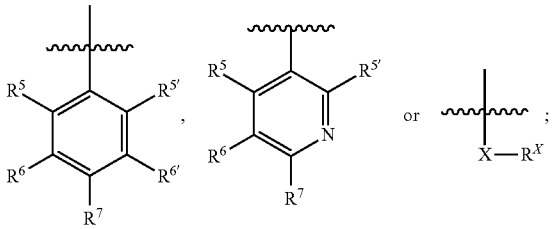

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^1$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

R³ is halogen, CN, or C₁-C₆ alkyl wherein said C₁-C₆ alkyl is substituted with 0-6 halogen and wherein up to two non-adjacent CH₂ units of said C₁-C₆ alkyl may be replaced with —O—;
R⁵ is H, halogen, CN, or —X—Rˣ;
R⁵' is H, halogen, CN, or —X—Rˣ;
R⁶ is H, halogen, CN, or —X—Rˣ;
R⁶' is H, halogen, CN, or —X—Rˣ;
R⁷ is H, halogen, CN, or —X—Rˣ;
R⁸ is halogen, or C₁-C₆ alkyl wherein said C₁-C₆ alkyl is substituted with 0-6 halogen and wherein up to two non-adjacent CH₂ units of said C₁-C₆ alkyl may be replaced with —O—;
p is an integer from 0 to 3 inclusive; and
R⁹ is H, or C₁-C₆ alkyl wherein up to two non-adjacent CH₂ units of said C₁-C₆ alkyl may be replaced with —O—.

In another embodiment, the invention features a compound of formula I-D or I'-D and the attendant definitions, wherein R¹ is halogen. In another embodiment, R¹ is CN. In another embodiment, R¹ is C₁-C₆ alkyl wherein said C₁-C₆ alkyl is substituted with 0-6 halogen. In another embodiment, R¹ is CF₃.

In another embodiment, the invention features a compound of formula I-D or I'-D and the attendant definitions, wherein R³ is halogen. In another embodiment, R³ is Cl. In another embodiment, R³ is F. In another embodiment, R³ is CN. In another embodiment, R³ is C₁-C₆ alkyl wherein said C₁-C₆ alkyl is substituted with 0-6 halogen. In another embodiment, R³ is t-butyl. In another embodiment, R³ is CF₃. In another embodiment, R³ is CF₂CF₃.

In another embodiment, the invention features a compound of formula I-D or I'-D and the attendant definitions, wherein p is zero. In another embodiment, p is an integer from 1 to 3 and R⁸ is halogen. In another embodiment, p is an integer from 1 to 3 and R⁸ is Cl. In another embodiment, p is an integer from 1 to 3 and R⁸ is C₁-C₆ alkyl wherein said C₁-C₆ alkyl wherein said C₁-C₆ alkyl is substituted with 0-6 halogen wherein one CH₂ unit of said C₁-C₆ alkyl is replaced with —O—. In another embodiment, p is an integer from 1 to 3 and R⁸ is CH₃.

In another embodiment, the invention features a compound of formula I-D or I'-D and the attendant definitions, wherein R⁹ is H. In another embodiment, R⁹ is C₁-C₆ alkyl. In another embodiment, R⁹ is CH₃. In another embodiment, R⁹ is C₁-C₆ alkyl wherein said C₁-C₆ alkyl is substituted with 0-6 halogen wherein one CH₂ unit of said C₁-C₆ alkyl is replaced with —O—. In another embodiment, R⁹ is CH₂CH₂OH.

In another embodiment, the invention features a compound of formula I-D or I'-D and the attendant definitions, wherein G is

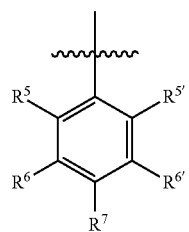

wherein:
R⁵ is H, halogen, CN, or —X—Rˣ;
R⁵' is H, halogen, CN, or —X—Rˣ;
R⁶ is H, halogen, CN, or —X—Rˣ;
R⁶' is H, halogen, CN, or —X—Rˣ;
R⁷ is H, halogen, CN, or —X—Rˣ;

X is a bond or C₁-C₆ alkyl wherein said C₁-C₆ alkyl is substituted with 0-6 halogen and wherein up to two non-adjacent CH₂ units of said C₁-C₆ alkyl may be replaced with —O—; and
Rˣ is absent, H, or C₃-C₈ cycloaliphatic, wherein up to two non-adjacent CH₂ units of said C₃-C₈ cycloaliphatic may be replaced with —O— and said C₃-C₈ cycloaliphatic is substituted with 0-3 substituents selected from halogen and C₁-C₄ alkyl.

In another embodiment, the invention features a compound of formula I-D or I'-D and the attendant definitions, wherein G is

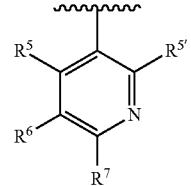

wherein:
R⁵ is H, or —X—Rˣ;
R⁵' is H, or —X—Rˣ;
R⁶ is H, halogen, CN, or —X—Rˣ;
R⁷ is H, or —X—Rˣ;
X is a bond or C₁-C₆ alkyl wherein said C₁-C₆ alkyl is substituted with 0-6 halogen and wherein up to two non-adjacent CH₂ units of said C₁-C₆ alkyl may be replaced with —O—; and
Rˣ is absent, H, or C₃-C₈ cycloaliphatic, wherein up to two non-adjacent CH₂ units of said C₃-C₈ cycloaliphatic may be replaced with —O— and said C₃-C₈ cycloaliphatic is substituted with 0-3 substituents selected from halogen and C₁-C₄ alkyl.

In another embodiment, the invention features a compound of formula I-D or I'-D and the attendant definitions, wherein G is

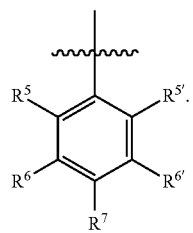

In one embodiment, R⁵ is H. In another embodiment, R⁵ is halogen. In another embodiment, R⁵ is Cl. In another embodiment, R⁵ is F. In another embodiment, R⁵ is CN. In another embodiment, R⁵ is —X—Rˣ. In another embodiment, R⁵ is —X—Rˣ wherein Rˣ is absent. In another embodiment, R⁵ is —X—Rˣ wherein Rˣ is absent and X is C₁-C₆ alkyl wherein said C₁-C₆ alkyl is substituted with 0-6 halogen. In another embodiment, R⁵ is CH₃. In another embodiment, R⁵ is —X—Rˣ wherein Rˣ is absent and X is C₁-C₆ alkyl wherein said C₁-C₆ alkyl is substituted with 0-6 halogen wherein one CH₂ unit of said C₁-C₆ alkyl is replaced with —O—. In another embodiment, R⁵ is OCH₃, OCH₂CH₃, OCH₂CH₂CH₃, or OCH(CH₃)₂. In another embodiment, R⁵ is OCH₃. In another embodiment, R⁵ is CH₂OH. In another embodiment, R⁵ is OCF₃. In another embodiment, R⁵ is OCHF₂.

In another embodiment, the invention features a compound of formula I-D or I'-D and the attendant definitions, wherein G is

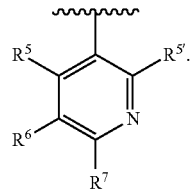

In one embodiment, $R^5$ is H. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-D or I'-D and the attendant definitions, wherein G is

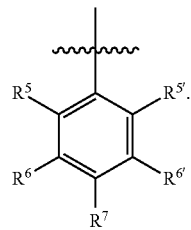

In one embodiment $R^{5'}$ is H. In another embodiment, $R^{5'}$ is halogen. In another embodiment, $R^{5'}$ is Cl. In another embodiment, $R^{5'}$ is F. In another embodiment, $R^{5'}$ is CN. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-D or I'-D and the attendant definitions, wherein G is

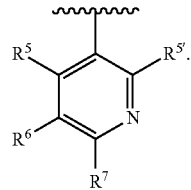

In one embodiment $R^{5'}$ is H. In another embodiment, $R^{5'}$ is —X—$R^X$. In another embodiment, $R^{5'}$ is —X—$R^X$ wherein $R^X$ is absent. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{5'}$ is $CH_3$. In another embodiment, $R^{5'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{5'}$ is $OCH_3$, $OCH_2CH_3$, $OCH_2CH_2CH_3$, or $OCH(CH_3)_2$. In another embodiment, $R^{5'}$ is $OCH_3$. In another embodiment, $R^{5'}$ is $CH_2OH$. In another embodiment, $R^{5'}$ is $OCF_3$. In another embodiment, $R^{5'}$ is $OCHF_2$.

In another embodiment, the invention features a compound of formula I-D or I'-D and the attendant definitions, wherein G is

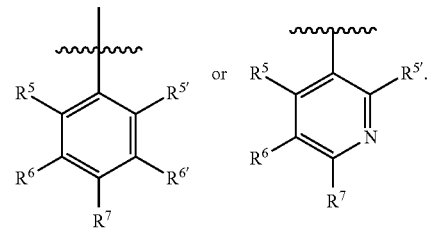

In one embodiment, $R^6$ is H. In another embodiment, $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-D or I'-D and the attendant definitions, wherein G is

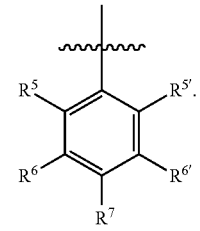

In one embodiment, $R^{6'}$ is H. In another embodiment, $R^{6'}$ is halogen. In another embodiment, $R^{6'}$ is Cl. In another embodiment, $R^{6'}$ is F. In another embodiment, $R^{6'}$ is CN. In another embodiment, $R^{6'}$ is —X—$R^X$. In another embodiment, $R^{6'}$ is —X—$R^X$ wherein $R^X$ is absent. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen. In another embodiment, $R^{6'}$ is $CH_3$. In another embodiment, $R^{6'}$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^{6'}$ is $OCH_3$.

In another embodiment, the invention features a compound of formula I-D or I'-D and the attendant definitions, wherein G is

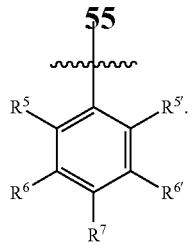

In one embodiment, $R^7$ is H. In another embodiment, $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-D or I'-D and the attendant definitions, wherein G is

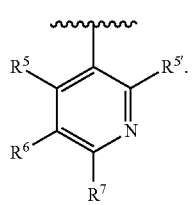

In one embodiment, $R^7$ is H. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-D or I'-D and the attendant definitions, wherein G is

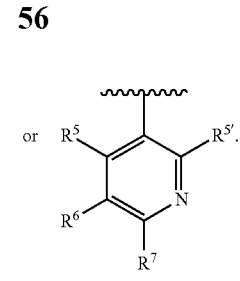

In one embodiment, $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-D or I'-D and the attendant definitions, wherein G is

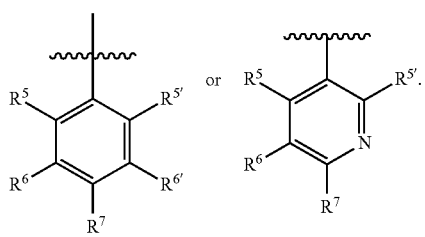

In one embodiment, $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-D or I'-D and the attendant definitions, wherein G is:

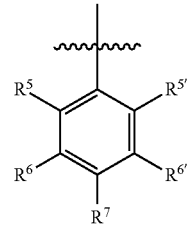

and G is selected from:

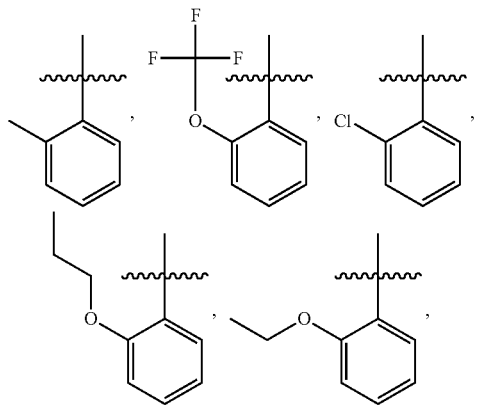

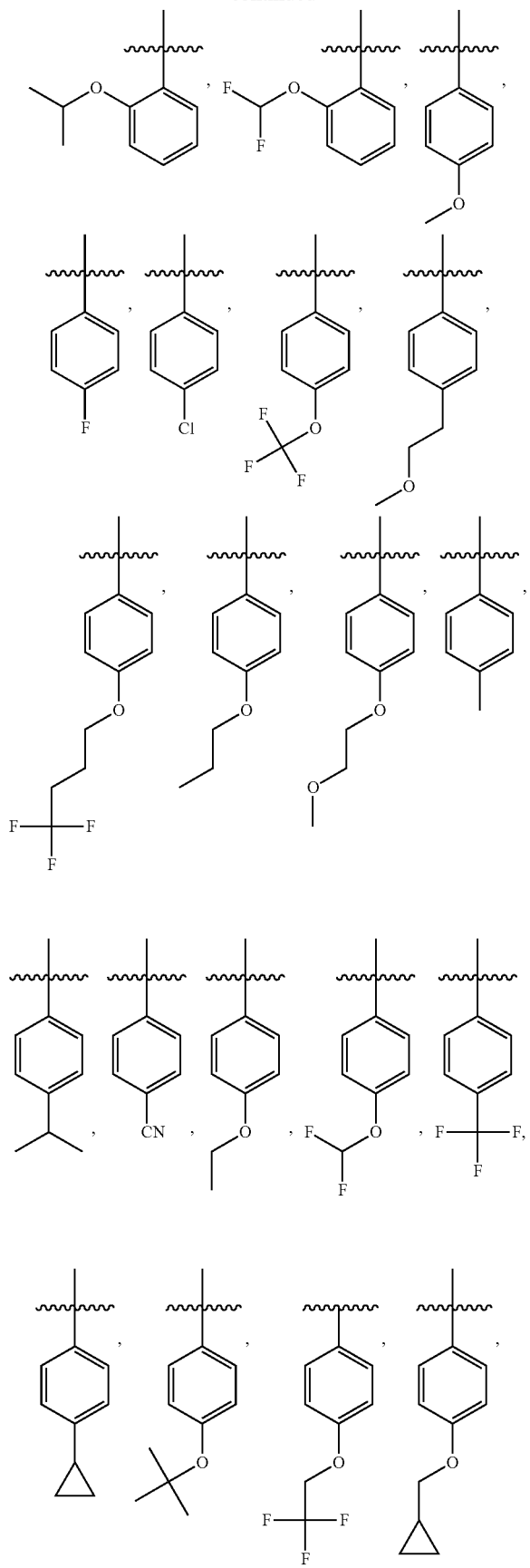
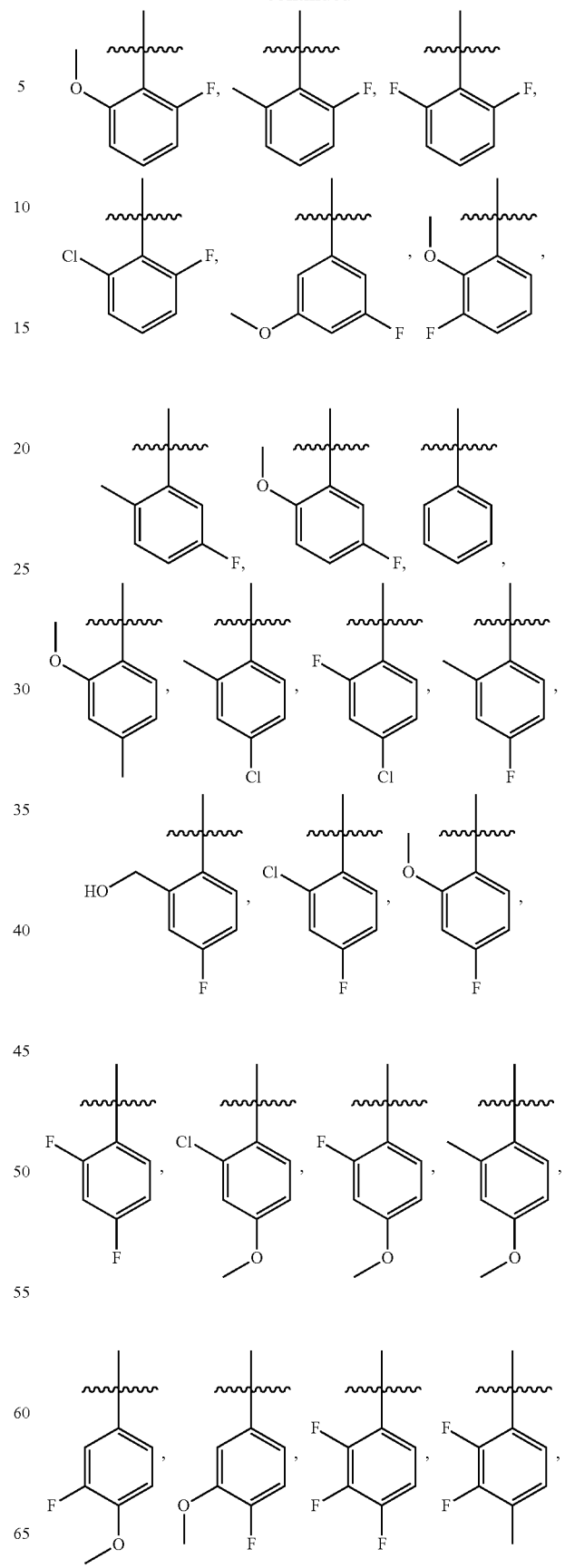

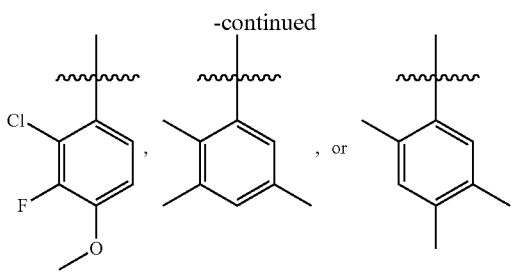

In another embodiment, the invention features a compound of formula I-D or I'-D and the attendant definitions, wherein G is:

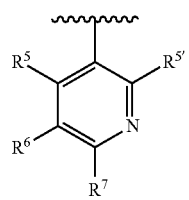

and G is selected from

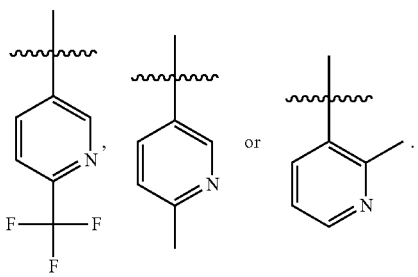

In another embodiment, the invention features a compound of formula I-D or I'-D and the attendant definitions, wherein G is

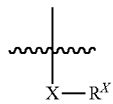

wherein:
X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—; and
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

In another embodiment, the invention features a compound of formula I-D or I'-D and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is absent. In another embodiment, X is $CH_2CH_2C(CH_3)_3$ or $CH_2CH(CH_3)_2$ and $R^X$ is absent. In another embodiment, X is $CH_2CH_2CH_2CF_3$ or $CH_2CH_2CF_3$ and $R^X$ is absent.

In another embodiment, the invention features a compound of formula I-D or I'-D and the attendant definitions, wherein G is —X—$R^X$ wherein X is a bond and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is a bond and $R^X$ is cyclobutane, cyclohexane, bicyclo[2.2.1]heptane, or bicyclo[3.1.0]hexane.

In another embodiment, the invention features a compound of formula I-D or I'-D and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl may be replaced with —O— and $R^X$ is $C_3$-$C_8$ cycloaliphatic wherein up to two non-adjacent $CH_2$ units of said $C_3$-$C_8$ cycloaliphatic may be replaced with —O—; and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic. In another embodiment, X is $CH_2$ and $R^X$ is cyclopropyl or cyclopentyl. In another embodiment, X is $CH_2$ and $R^X$ is $C_3$-$C_8$ cycloaliphatic with up to 3 substituents selected from halogen and $C_1$-$C_4$ alkyl. In another embodiment, X is $CH_2$ and $R^X$ is 1-methylcylopropyl, 2,2-dimethylcyclopropyl or 2,2-difluorocyclopropyl.

In another embodiment, the invention features a compound of formula I-D or I'-D and the attendant definitions, wherein G is —X—$R^X$ wherein X is $C_1$-$C_6$ alkyl wherein said $C_1$-$C_6$ alkyl is substituted with 0-6 halogen wherein up to two non-adjacent $CH_2$ units of said $C_1$-$C_6$ alkyl are replaced with —O— and $R^X$ is $C_3$-$C_8$ cycloaliphatic wherein up to two non-adjacent $CH_2$ of said $C_3$-$C_8$ cycloaliphatic may be replaced with —O— and said $C_3$-$C_8$ cycloaliphatic is substituted with 0-3 substituents selected from halogen and $C_1$-$C_4$ alkyl. In another embodiment, X is $CH_2$ and $R^X$ is $C_3$-$C_8$ cycloaliphatic wherein one $CH_2$ unit of said $C_3$-$C_8$ cycloaliphatic is replaced with —O—. In another embodiment, X is $CH_2$ and $R^X$ is 3-tetrahydrofuran.

In another embodiment, the invention features a compound of formula I-D or I'-D and the attendant definitions, wherein G is selected from:

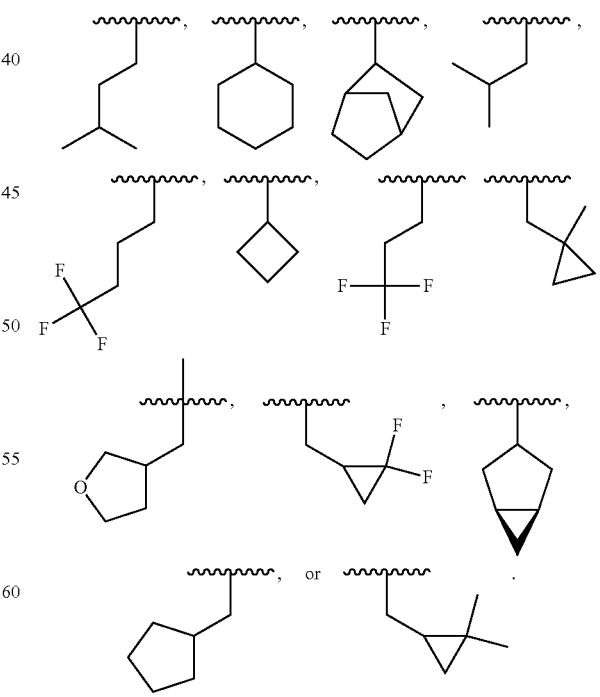

In another aspect, the invention provides a compound of formula I-E or I'-E

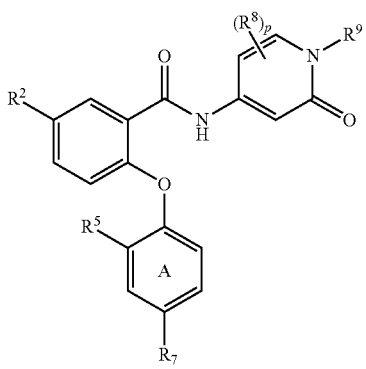

I-E

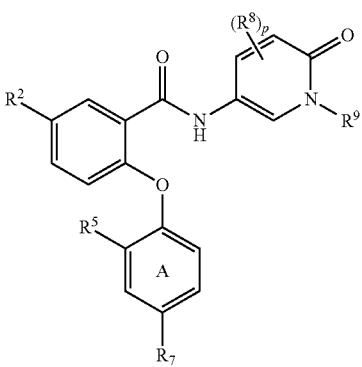

I'-E or a pharmaceutically acceptable salt thereof,
wherein, independently for each occurrence:
$R^2$ is halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;
$R^5$ is halogen, CN, or —X—$R^X$;
$R^7$ is halogen, CN, or —X—$R^X$;
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;
$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
p is an integer from 0 to 3 inclusive; and
$R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-E or I'-E and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-E or I'-E and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-E or I'-E and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-E or I'-E and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-E or I'-E and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-E or I'-E and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-E or I'-E and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-E or I'-E and the attendant definitions, wherein ring A is selected from:

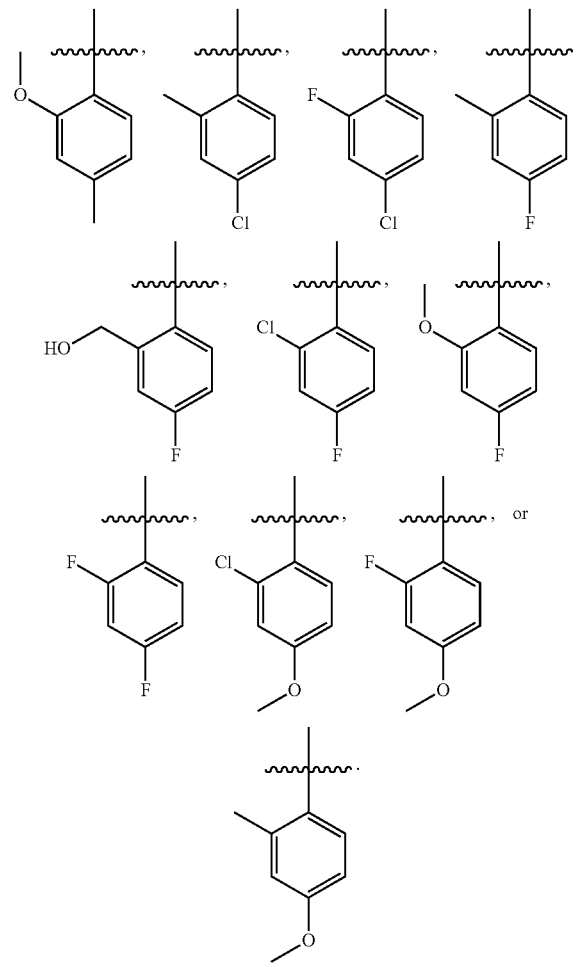

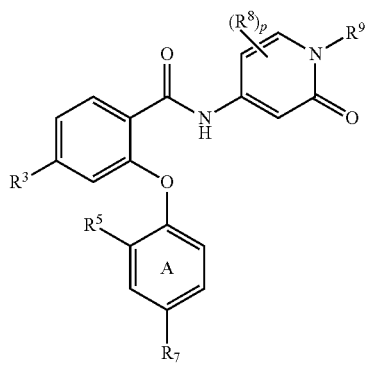

In another aspect, the invention provides a compound of formula I-F or I'-F:

I-F

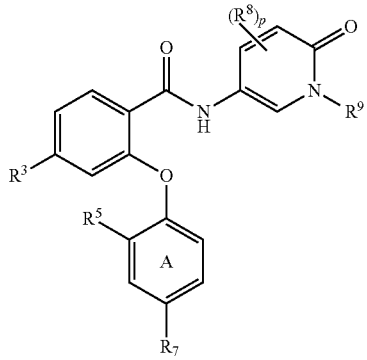

I'-F or a pharmaceutically acceptable salt thereof,
wherein, independently for each occurrence:
$R^3$ is halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;
$R^5$ is halogen, CN, or —X—$R^X$;
$R^7$ is halogen, CN, or —X—$R^X$;
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;
$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
p is an integer from 0 to 3 inclusive; and
$R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-F or I'-F and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-F or I'-F and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is $CD_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-F or I'-F and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-F or I'-F and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-F or I'-F and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-F or I'-F and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$. In another embodiment, p is an integer from 1 to 3 and $R^8$ is D.

In another embodiment, the invention features a compound of formula I-F or I'-F and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-F or I'-F and the attendant definitions, wherein ring A is selected from:

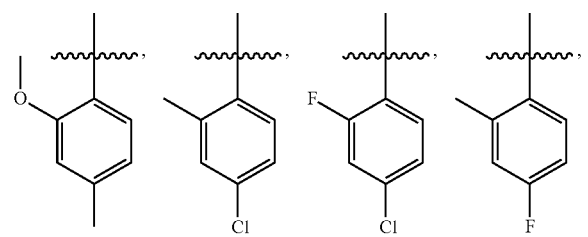

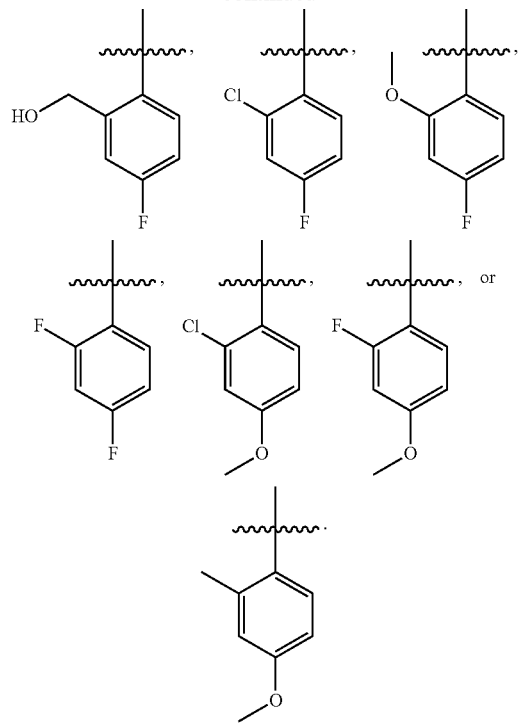

In another aspect, the invention provides a compound of formula I-G or I'-G:

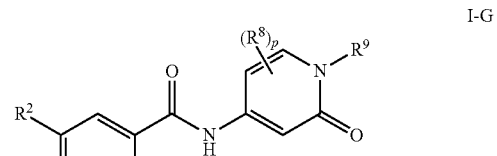

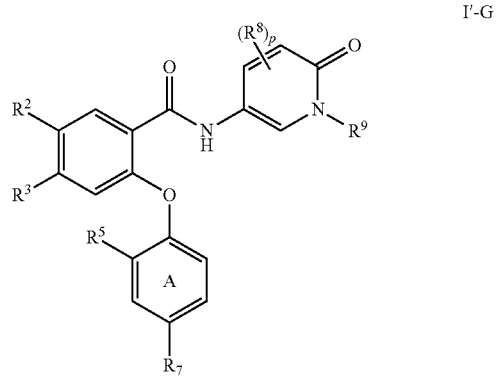

or a pharmaceutically acceptable salt thereof, wherein, independently for each occurrence:

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-G or I'-G and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-G or I'-G and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-G or I'-G and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-G or I'-G and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-G or I'-G and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-G or I'-G and the attendant definitions, wherein $R^7$ is —X—$R^X$ wherein X is $C_1$-$C_6$ alkyl wherein said $C_1$-$C_6$ alkyl is substituted with 0-6 halogen and wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-G or I'-G and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-G or I'-G and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-G or I'-G and the attendant definitions, wherein ring A is selected from:

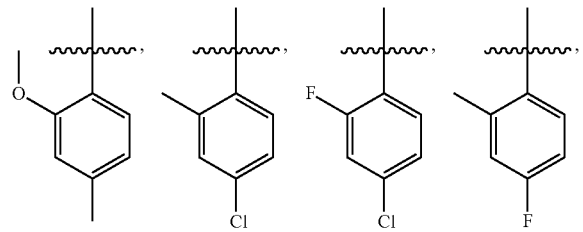

-continued

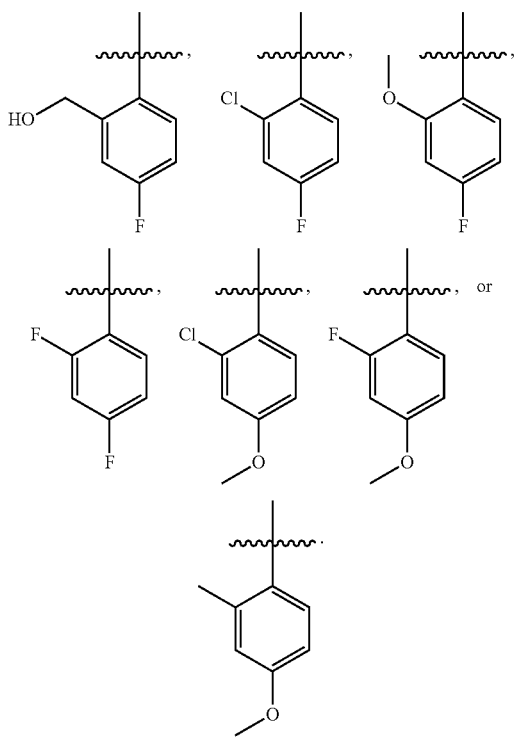

In another aspect, the invention provides a compound of formula I-H or I'-H:

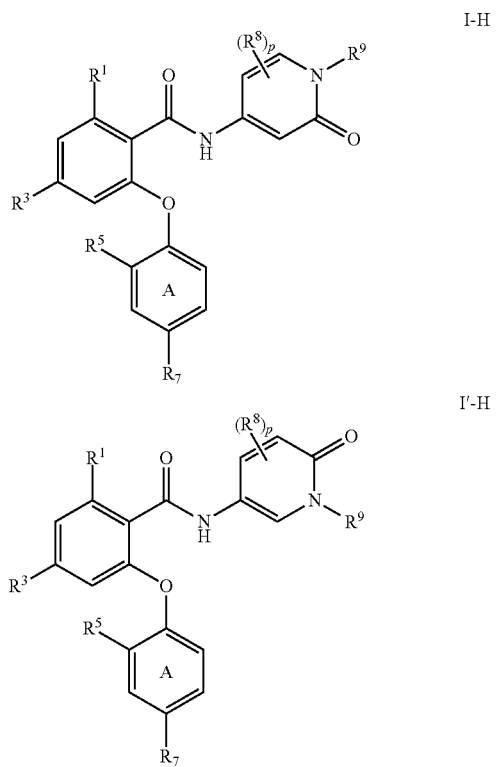

or a pharmaceutically acceptable salt thereof,
wherein, independently for each occurrence:

$R^1$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-H or I'-H and the attendant definitions, wherein $R^1$ is halogen. In another embodiment, $R^1$ is CN. In another embodiment, $R^1$ is $C_1$-$C_6$ alkyl wherein said $C_1$-$C_6$ alkyl is substituted with 0-6 halogen. In another embodiment, $R^1$ is $CF_3$.

In another embodiment, the invention features a compound of formula I-H or I'-H and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-H or I'-H and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-H or I'-H and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$.

In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-H or I'-H and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-H or I'-H and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-H or I'-H and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-H or I'-H and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-H or I'-H and the attendant definitions, wherein ring A is selected from:

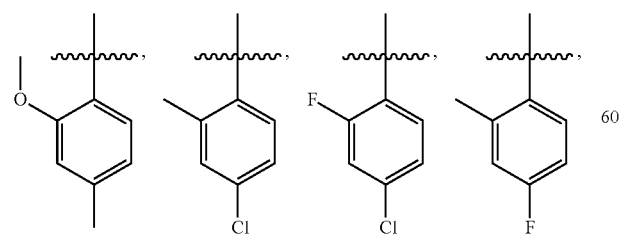

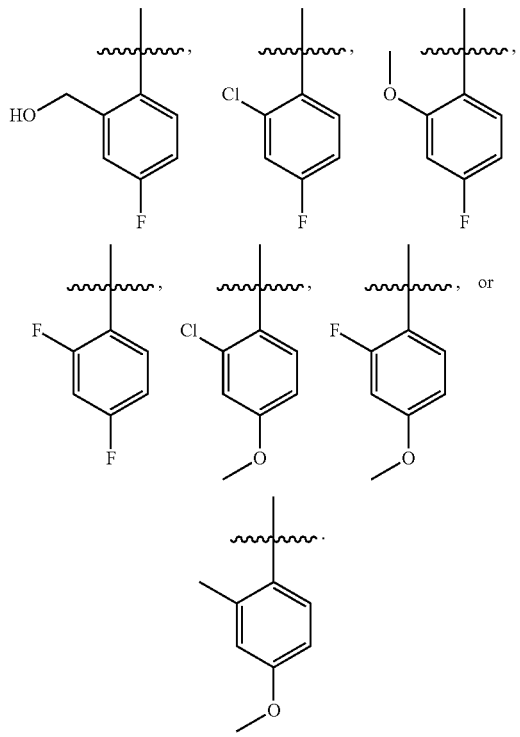

In another aspect, the invention provides a compound of formula I-J or I'-J:

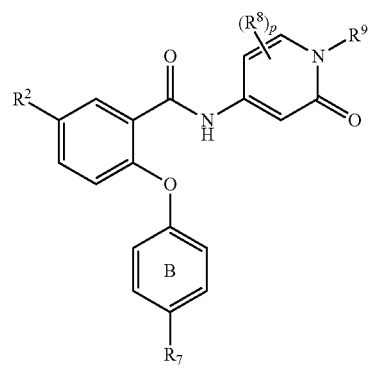

I-J

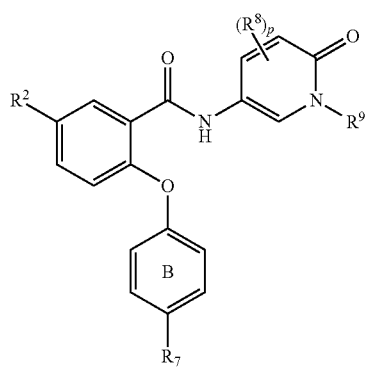

I'-J or a pharmaceutically acceptable salt thereof,
wherein, independently for each occurrence:

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is H, halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-J or I'-J and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-J or I'-J and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-J or I'-J and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-J or I'-J and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-J or I'-J and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-J or I'-J and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-J or I'-J and the attendant definitions, wherein ring B is selected from:

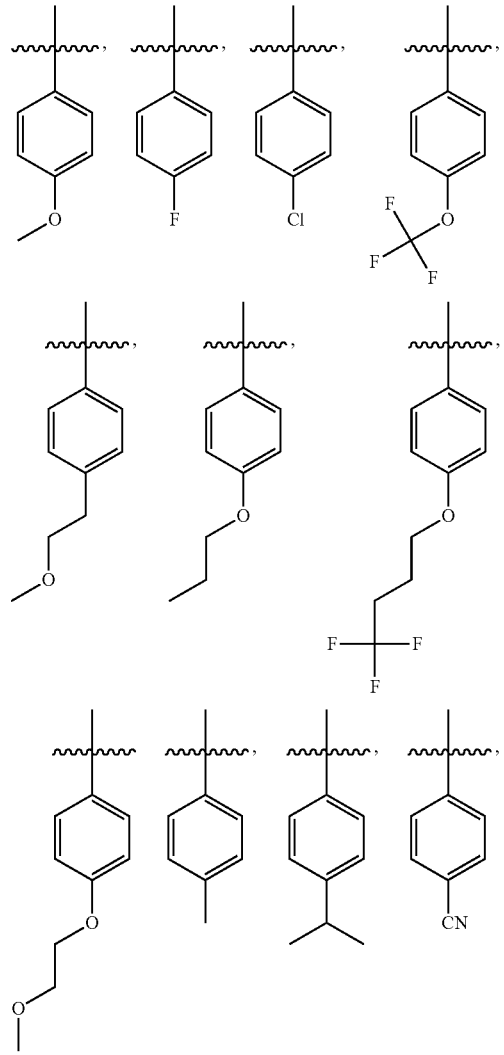

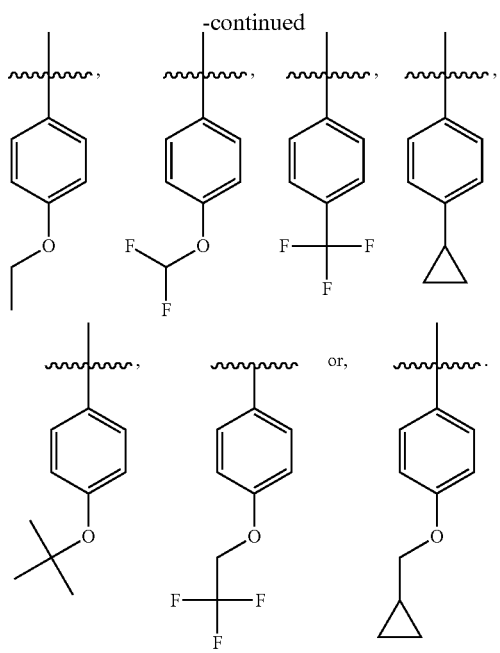

In another aspect, the invention provides a compound of formula I-K or I'-K:

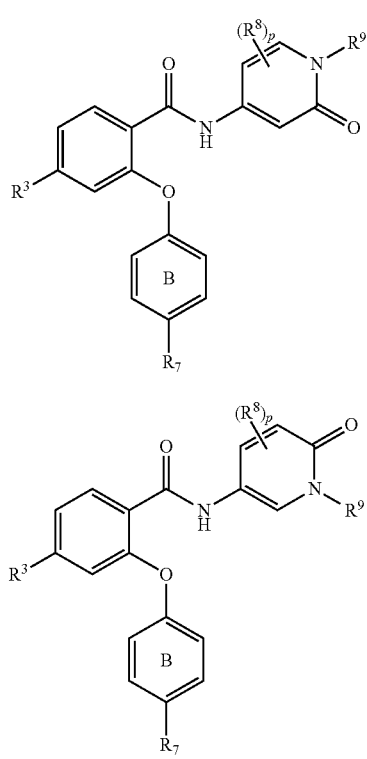

or a pharmaceutically acceptable salt thereof,
wherein, independently for each occurrence:
$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;
$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
p is an integer from 0 to 3 inclusive; and
$R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-K or I'-K and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-K or I'-K and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-K or I'-K and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-K or I'-K and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-K or I'-K and the attendant definitions, wherein p is zero. In another embodiment, p is an integer from 1 to 3 and $R^8$ is halogen. In another embodiment, wherein p is an integer from 1 to 3 and $R^8$ is Cl. In another embodiment, wherein p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^8$ is $CH_3$.

In another embodiment, the invention features a compound of formula I-K or I'-K and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-K or I'-K and the attendant definitions, wherein ring B is selected from:

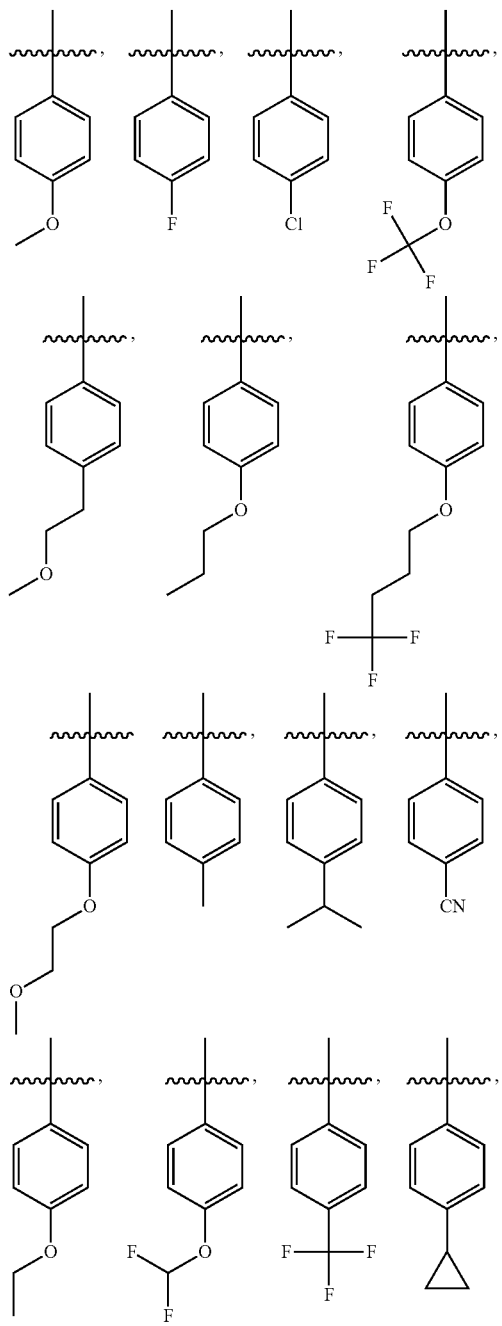

-continued

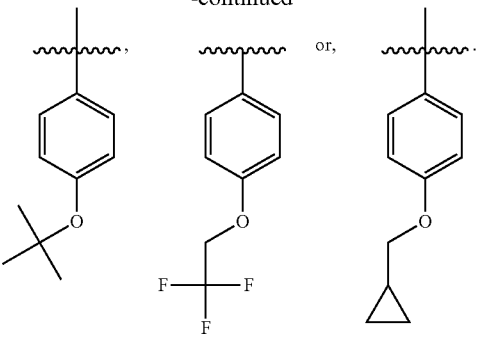

In another aspect, the invention provides a compound of formula I-L or I'-L:

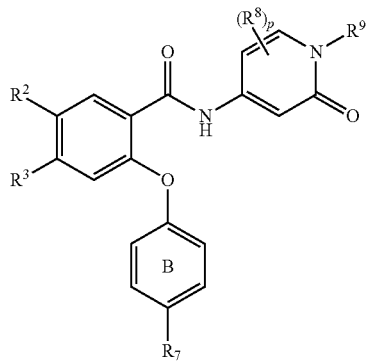
I-L

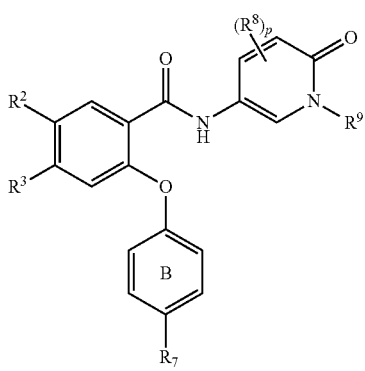
I'-L or a pharmaceutically acceptable salt thereof,
wherein, independently for each occurrence:
$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^7$ is halogen, CN, or —X—$R^X$;
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-L or I'-L and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-L or I'-L and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-L or I'-L and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-L or I'-L and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-L or I'-L and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-L or I'-L and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-L or I'-L and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-L or I'-L and the attendant definitions, wherein ring B is selected from:

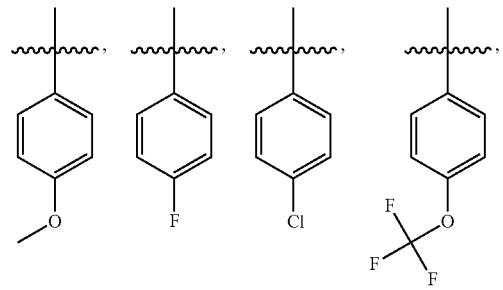

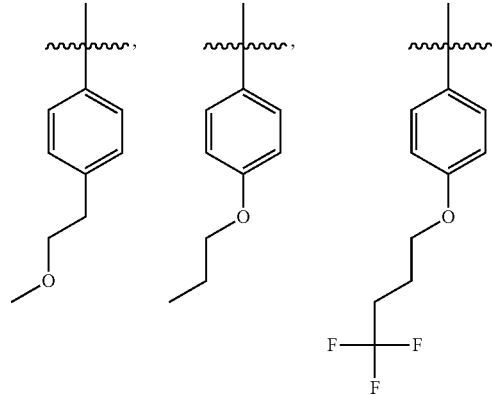

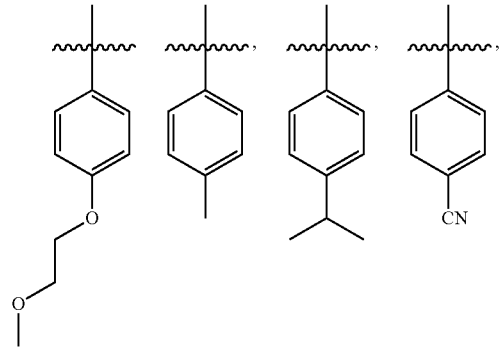

-continued

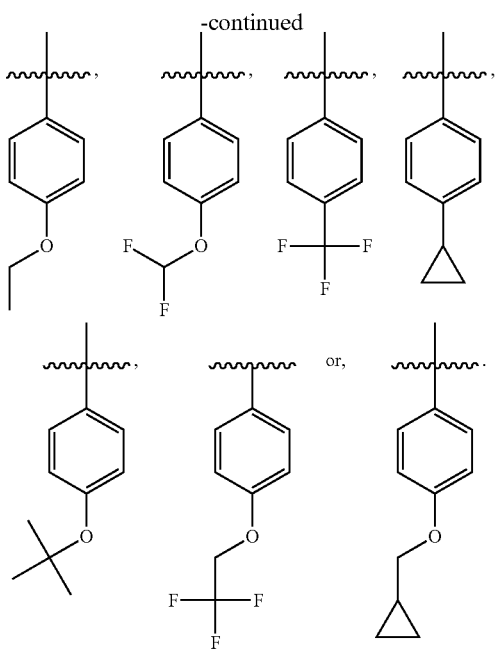

In another aspect, the invention provides a compound of formula I-M or I'-M:

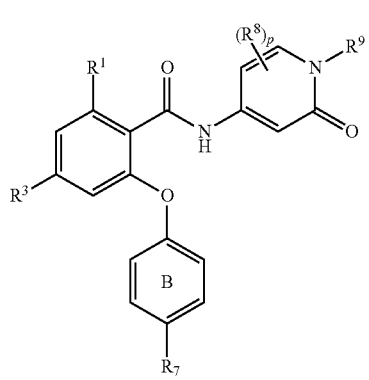

I-M

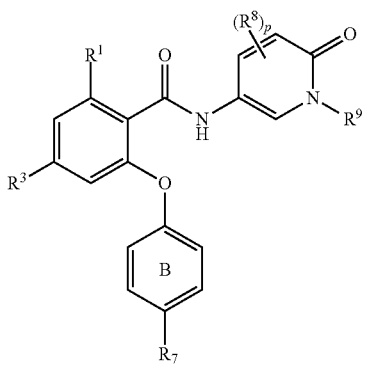

I'-M or a pharmaceutically acceptable salt thereof,
wherein, independently for each occurrence:
$R^1$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is H, halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-M or I'-M and the attendant definitions, wherein $R^1$ is halogen. In another embodiment, $R^1$ is CN. In another embodiment, $R^1$ is $C_1$-$C_6$ alkyl wherein said $C_1$-$C_6$ alkyl is substituted with 0-6 halogen. In another embodiment, $R^1$ is $CF_3$.

In another embodiment, the invention features a compound of formula I-M or I'-M and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-M or I'-M and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-M or I'-M and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-M or I'-M and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-M or I'-M and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-M or I'-M and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-M or I'-M and the attendant definitions, wherein ring B is selected from:

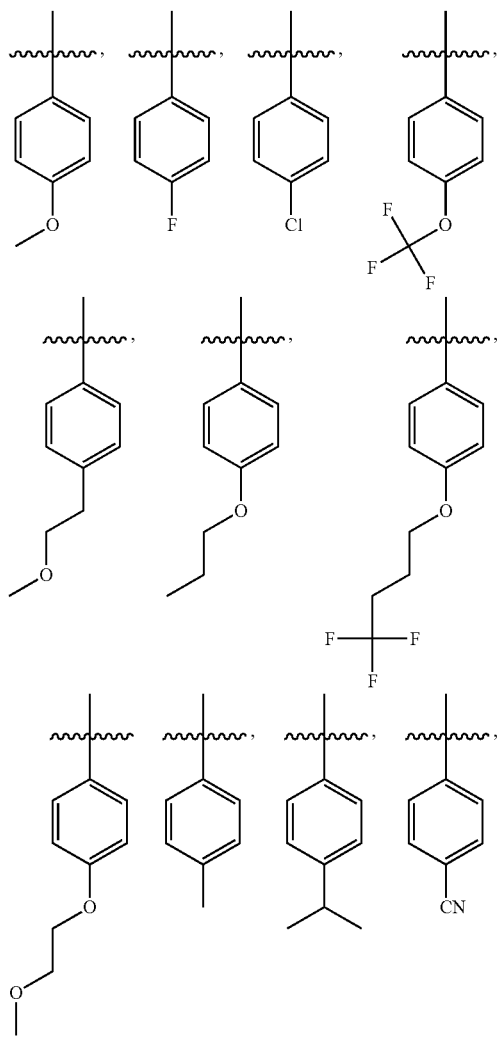

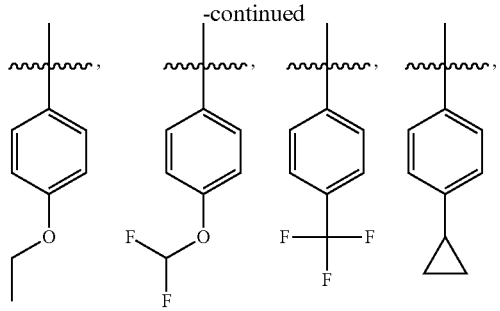

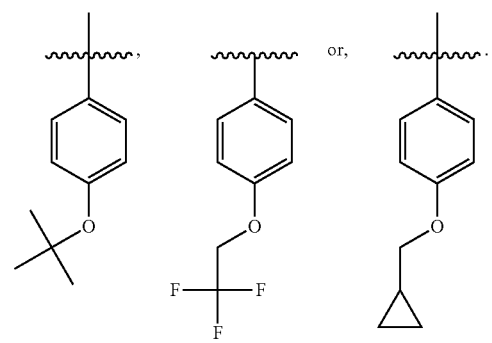

In another aspect, the invention provides a compound of formula I-N or I'-N:

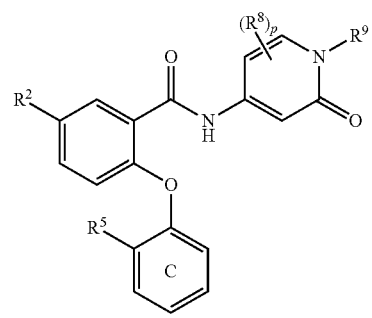

I-N

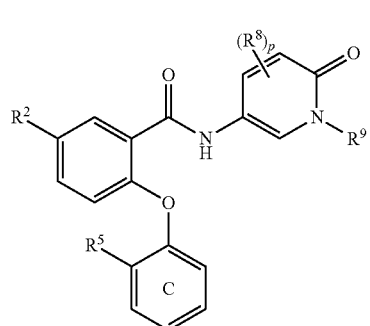

I'-N or a pharmaceutically acceptable salt thereof,
wherein, independently for each occurrence:
$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-N or I'-N and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-N or I'-N and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-N or I'-N and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-N or I'-N and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-N or I'-N and the attendant definitions, wherein ring C is selected from:

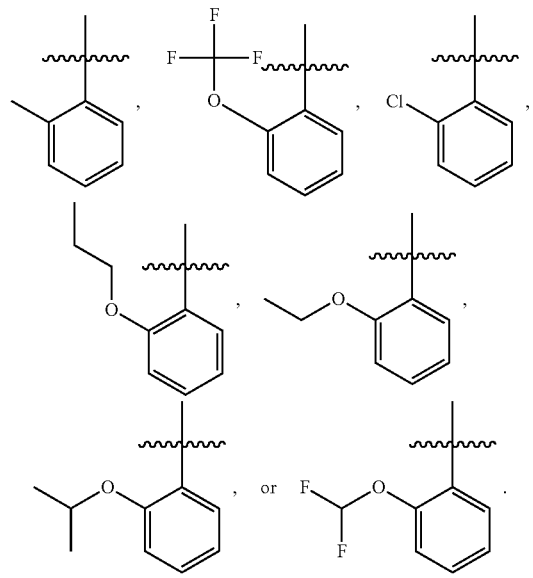

In another aspect, the invention provides a compound of formula I-O or I'-O:

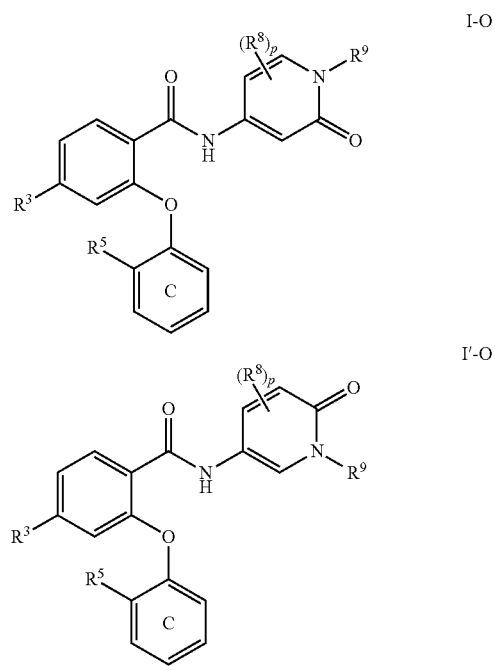

or a pharmaceutically acceptable salt thereof, wherein, independently for each occurrence:

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-O or I'-O and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-O or I'-O and the attendant definitions, wherein $R^5$ is halogen. In another embodiment, $R^5$ is Cl. In another embodiment, $R^5$ is F. In another embodiment, $R^5$ is CN. In another embodiment, $R^5$ is —X—$R^X$. In another embodiment, $R^5$ is —X—$R^X$ wherein $R^X$ is absent. In another embodiment, $R^5$ is —X—$R^X$ wherein $R^X$ is absent and X is $C_1$-$C_6$ alkyl wherein said $C_1$-$C_6$ alkyl is substituted with 0-6 halogen. In another embodiment, $R^5$ is $CH_3$. In another embodiment, $R^5$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$, $OCH_2CH_3$, $OCH_2CH_2CH_3$, or $OCH(CH_3)_2$. In another embodiment, $R^5$ is $OCH_3$. In another embodiment, $R^5$ is $CH_2OH$. In another embodiment, $R^5$ is $OCF_3$. In another embodiment, $R^5$ is $OCHF_2$.

In another embodiment, the invention features a compound of formula I-O or I'-O and the attendant definitions, wherein p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-O or I'-O and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-O or I'-O and the attendant definitions, wherein ring C is selected from:

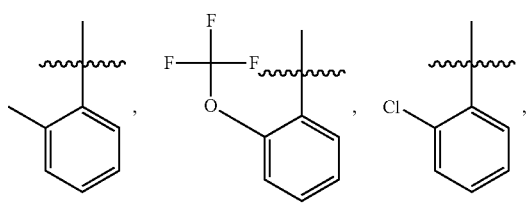

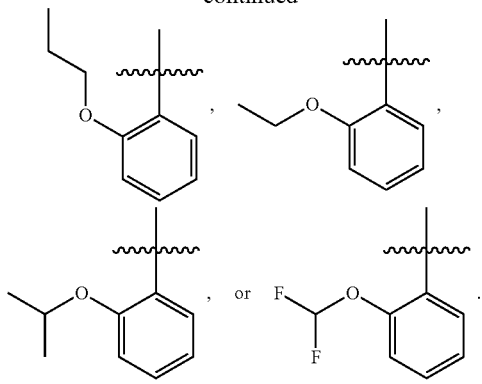

In another aspect, the invention provides a compound of formula I-P or I'-P:

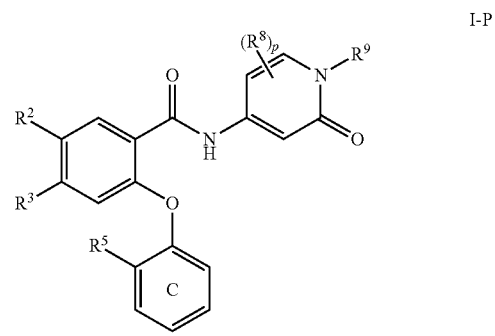

I-P

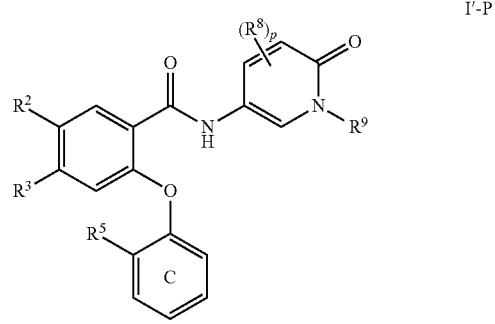

I'-P or a pharmaceutically acceptable salt thereof,
wherein, independently for each occurrence:

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

R$^8$ is H, halogen, or C$_1$-C$_6$ alkyl wherein said C$_1$-C$_6$ alkyl is substituted with 0-6 halogen, wherein up to two non-adjacent CH$_2$ units of said C$_1$-C$_6$ alkyl may be replaced with —O—;

p is an integer from 0 to 3 inclusive; and

R$^9$ is H, or C$_1$-C$_6$ alkyl wherein up to two non-adjacent CH$_2$ units of said C$_1$-C$_6$ alkyl may be replaced with —O—.

In another embodiment, the invention features a compound of formula I-P or I'—P and the attendant definitions, wherein R$^2$ is halogen. In another embodiment, R$^2$ is Cl. In another embodiment, R$^2$ is F. In another embodiment, R$^2$ is CN. In another embodiment, R$^2$ is C$_1$-C$_6$ alkyl wherein said C$_1$-C$_6$ alkyl is substituted with 0-6 halogen. In another embodiment, R$^2$ is CF$_3$. In another embodiment, R$^2$ is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, R$^2$ is OCF$_3$. In another embodiment, R$^2$ is F, Cl, CN, CF$_3$ or OCF$_3$.

In another embodiment, the invention features a compound of formula I-P or I'—P and the attendant definitions, wherein R$^3$ is halogen. In another embodiment, R$^3$ is Cl. In another embodiment, R$^3$ is F. In another embodiment, R$^3$ is CN. In another embodiment, R$^3$ is C$_1$-C$_6$ alkyl wherein said C$_1$-C$_6$ alkyl is substituted with 0-6 halogen. In another embodiment, R$^3$ is t-butyl. In another embodiment, R$^3$ is CF$_3$. In another embodiment, R$^3$ is CF$_2$CF$_3$.

In another embodiment, the invention features a compound of formula I-P or I'-P and the attendant definitions, wherein R$^5$ is halogen. In another embodiment, R$^5$ is Cl. In another embodiment, R$^5$ is F. In another embodiment, R$^5$ is CN. In another embodiment, R$^5$ is —X—R$^X$. In another embodiment, R$^5$ is —X—R$^X$ wherein R$^X$ is absent. In another embodiment, R$^5$ is —X—R$^X$ wherein R$^X$ is absent and X is C$_1$-C$_6$ alkyl wherein said C$_1$-C$_6$ alkyl is substituted with 0-6 halogen. In another embodiment, R$^5$ is CH$_3$. In another embodiment, R$^5$ is —X—R$^X$ wherein R$^X$ is absent and X is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, R$^5$ is OCH$_3$, OCH$_2$CH$_3$, OCH$_2$CH$_2$CH$_3$, or OCH(CH$_3$)$_2$. In another embodiment, R$^5$ is OCH$_3$. In another embodiment, R$^5$ is CH$_2$OH. In another embodiment, R$^5$ is OCF$_3$. In another embodiment, R$^5$ is OCHF$_2$.

In another embodiment, the invention features a compound of formula I-P or I'-P and the attendant definitions, wherein p is zero. In another embodiment, p is an integer from 1 to 3 and R$^8$ is halogen. In another embodiment, p is an integer from 1 to 3 and R$^8$ is Cl. In another embodiment, p is an integer from 1 to 3 and R$^8$ is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, p is an integer from 1 to 3 and R$^8$ is CH$_3$.

In another embodiment, the invention features a compound of formula I-P or I'-P and the attendant definitions, wherein R$^9$ is H. In another embodiment, R$^9$ is C$_1$-C$_6$ alkyl. In another embodiment, R$^9$ is CH$_3$. In another embodiment, R$^9$ is C$_1$-C$_6$ alkyl wherein said C$_1$-C$_6$ alkyl is substituted with 0-6 halogen wherein one CH$_2$ unit of said C$_1$-C$_6$ alkyl is replaced with —O—. In another embodiment, R$^9$ is CH$_2$CH$_2$OH.

In another embodiment, the invention features a compound of formula I-P or I'-P and the attendant definitions, wherein ring C is selected from:

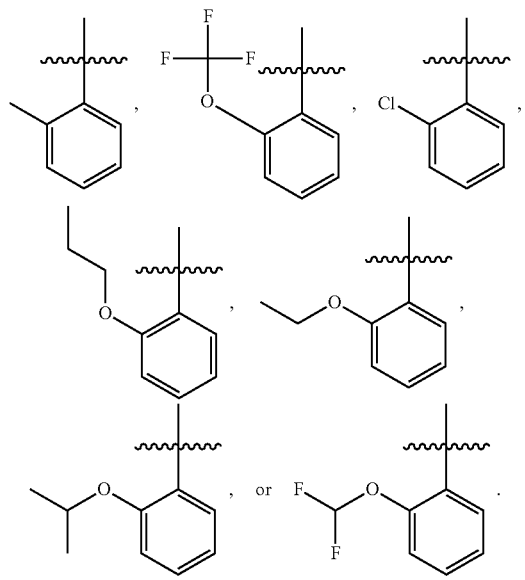

In another aspect, the invention provides a compound of formula I-Q or I'-Q:

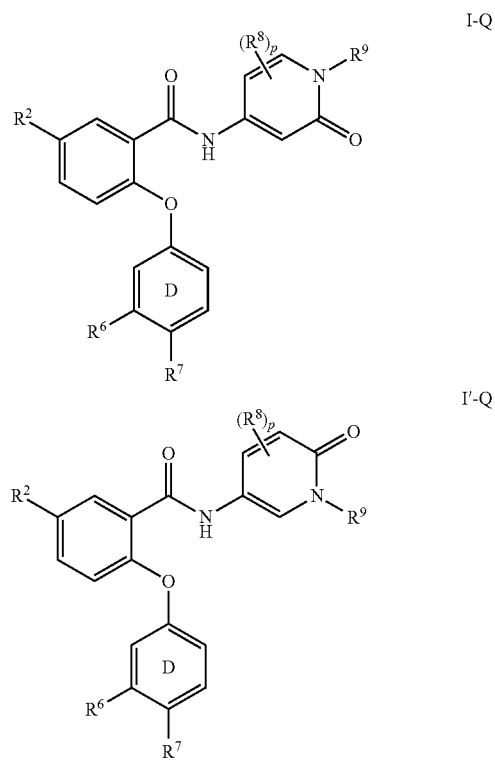

or a pharmaceutically acceptable salt thereof, wherein, independently for each occurrence:

R$^2$ is halogen, CN, or C$_1$-C$_6$ alkyl wherein said C$_1$-C$_6$ alkyl is substituted with 0-6 halogen and wherein up to two non-adjacent CH$_2$ units of said C$_1$-C$_6$ alkyl may be replaced with —O—;

R$^6$ is halogen, CN, or —X—R$^X$;

R$^7$ is halogen, CN, or —X—R$^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is H, halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-Q or I'-Q and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-Q or I'-Q and the attendant definitions, wherein $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-Q or I'-Q and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-Q or I'-Q and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-Q or I'-Q and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-Q or I'-Q and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-Q or I'-Q and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-Q or I'-Q and the attendant definitions, wherein ring D is selected from:

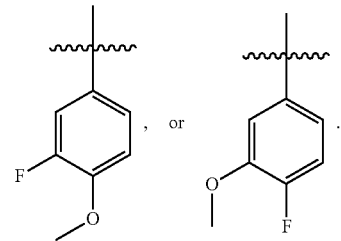

In another aspect, the invention provides a compound of formula I-R or I'-R:

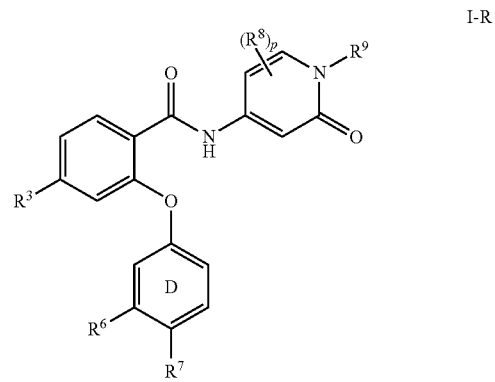

I-R

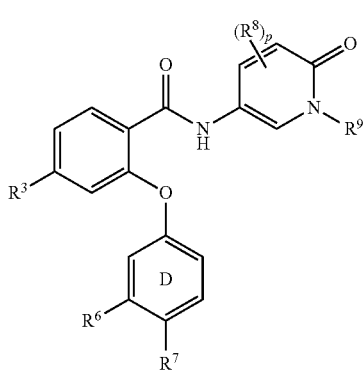

or a pharmaceutically acceptable salt thereof,
wherein, independently for each occurrence:
$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^6$ is halogen, CN, or —X—$R^X$;
$R^7$ is halogen, CN, or —X—$R^X$;
X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;
$R^8$ is H, halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
p is an integer from 0 to 3 inclusive; and
$R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-R or I'-R and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-R or I'-R and the attendant definitions, wherein $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-R or I'-R and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-R or I'-R and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-R or I'-R and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-R or I'-R and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-R or I'-R and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-R or I'-R and the attendant definitions, wherein ring D is selected from:

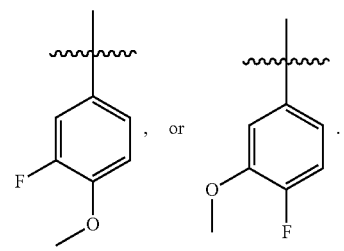

In another aspect, the invention provides a compound of formula I-S or I'-S:

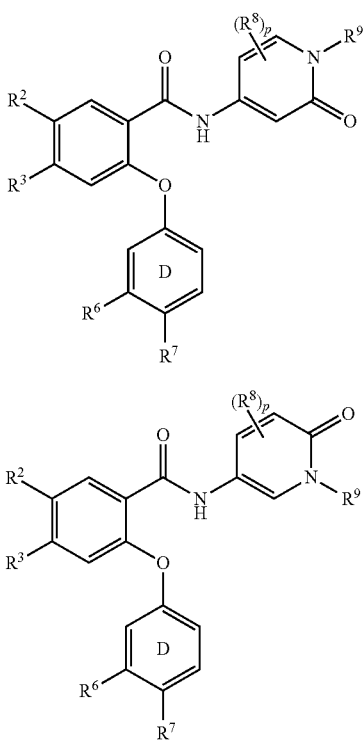

or a pharmaceutically acceptable salt thereof,
wherein, independently for each occurrence:

$R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^6$ is halogen, CN, or —X—$R^X$;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

In another embodiment, the invention features a compound of formula I-S or I'-S and the attendant definitions, wherein $R^2$ is halogen. In another embodiment, $R^2$ is Cl. In another embodiment, $R^2$ is F. In another embodiment, $R^2$ is CN. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^2$ is $OCF_3$. In another embodiment, $R^2$ is F, Cl, CN, $CF_3$ or $OCF_3$.

In another embodiment, the invention features a compound of formula I-S or I'-S and the attendant definitions, wherein $R^3$ is halogen. In another embodiment, $R^3$ is Cl. In another embodiment, $R^3$ is F. In another embodiment, $R^3$ is CN. In another embodiment, $R^3$ is $C_1$-$C_6$ alkyl wherein said $C_1$-$C_6$ alkyl is substituted with 0-6 halogen. In another embodiment, $R^3$ is t-butyl. In another embodiment, $R^3$ is $CF_3$. In another embodiment, $R^3$ is $CF_2CF_3$.

In another embodiment, the invention features a compound of formula I-S or I'-S and the attendant definitions, wherein $R^6$ is halogen. In another embodiment, $R^6$ is Cl. In another embodiment, $R^6$ is F. In another embodiment, $R^6$ is CN. In another embodiment, $R^6$ is —X—$R^X$. In another embodiment, $R^6$ is —X—$R^X$ wherein $R^X$ is absent. In another embodiment, $R^6$ is —X—$R^X$ wherein $R^X$ is absent and X is $C_1$-$C_6$ alkyl wherein said $C_1$-$C_6$ alkyl is substituted with 0-6 halogen. In another embodiment, $R^6$ is $CH_3$. In another embodiment, $R^6$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^6$ is $OCH_3$.

In another embodiment, the invention features a compound of formula I-S or I'-S and the attendant definitions, wherein $R^7$ is halogen. In another embodiment, $R^7$ is Cl. In another embodiment, $R^7$ is F. In another embodiment, $R^7$ is CN. In another embodiment, $R^7$ is —X—$R^X$. In another embodiment, $R^7$ is —X—$R^X$ wherein $R^X$ is absent. In another embodiment, $R^7$ is —X—$R^X$ wherein $R^X$ is absent and X is $C_1$-$C_6$ alkyl wherein said $C_1$-$C_6$ alkyl is substituted with 0-6 halogen. In another embodiment, $R^7$ is $CH_3$, $CH_2CH_3$, $CH_2CH_2CH_3$ or isopropyl. In another embodiment, $R^7$ is $CF_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_2CH_2OCH_3$. In another embodiment, $R^7$ is —X—$R^X$ wherein $R^X$ is absent and X is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^7$ is $OCH_3$, $OCH_2CH_3$, $OCH_2CH_2CH_3$, $OC(CH_3)_3$, $CH_2CH_2OCH_3$. In another embodiment, $R^7$ is $OCF_3$, $OCH_2CF_3$, $OCH_2CH_2CH_2CF_3$, or $OCHF_2$.

In another embodiment, the invention features a compound of formula I-S or I'-S and the attendant definitions, wherein $R^7$ is —X—$R^X$ wherein X is a bond and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is a bond and $R^X$ is cyclopropyl.

In another embodiment, the invention features a compound of formula I-S or I'-S and the attendant definitions, wherein $R^7$ is —X—$R^X$ wherein X is $C_1$-$C_6$ alkyl wherein said $C_1$-$C_6$ alkyl is substituted with 0-6 halogen wherein one $CH_2$ unit of said $C_1$-$C_6$ alkyl is replaced with —O— and $R^X$ is $C_3$-$C_8$ cycloaliphatic and said $C_3$-$C_8$ cycloaliphatic is substituted with 0-3 substituents selected from halogen and $C_1$-$C_4$ alkyl. In another embodiment, $R^7$ is —X—$R^X$ wherein X is $OCH_2$ and $R^X$ is cyclopropyl.

In another embodiment, the invention features a compound of formula I-S or I'-S and the attendant definitions, wherein p is zero. In another embodiment, p is an integer from 1 to 3 and $R^8$ is halogen. In another embodiment, p is an integer from 1 to 3 and $R^8$ is Cl. In another embodiment, p is an integer from 1 to 3 and $R^8$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, p is an integer from 1 to 3 and $R^8$ is $CH_3$.

In another embodiment, the invention features a compound of formula I-S or I'-S and the attendant definitions, wherein $R^9$ is H. In another embodiment, $R^9$ is $C_1$-$C_6$ alkyl. In another embodiment, $R^9$ is $CH_3$. In another embodiment, $R^9$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^9$ is $CH_2CH_2OH$.

In another embodiment, the invention features a compound of formula I-S or I'-S and the attendant definitions, wherein ring D is selected from:

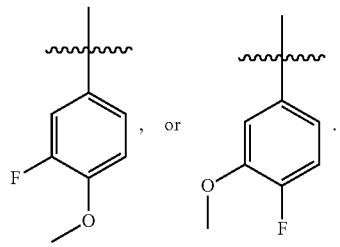

In another embodiment, the invention features a compound of formula I or I', wherein the compound or a pharmaceutically acceptable salt thereof, is selected from Table 1. Compounds names in Table 1 were generated using ChemBioDrawUltra version 12.0 from Cambridge Soft/Chem Office 2010.

TABLE 1

Compound Numbers, Structures and Chemical Names

| 1 | 2-(4-fluorophenoxy)-N-(2-oxo-1,2-dihydropyridin-4-yl)benzamide |
| 2 | 2-(4-fluorophenoxy)-N-(2-oxo-1,2-dihydropyridin-4-yl)-5-(trifluoromethyl)benzamide |
| 3 | 2-(4-fluorophenoxy)-N-(6-oxo-1,6-dihydropyridin-3-yl)benzamide |
| 4 | 2-(4-fluorophenoxy)-N-(6-oxo-1,6-dihydropyridin-3-yl)-5-(trifluoromethyl)benzamide |

TABLE 1-continued

Compound Numbers, Structures and Chemical Names

| # | Structure | Name |
|---|---|---|
| 5 | 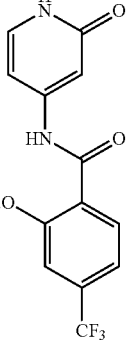 | 2-(4-fluorophenoxy)-N-(2-oxo-1,2-dihydropyridin-4-yl)-4-(trifluoromethyl)benzamide |
| 6 | 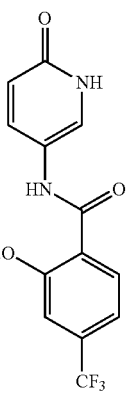 | 2-(4-fluorophenoxy)-N-(6-oxo-1,6-dihydropyridin-3-yl)-4-(trifluoromethyl)benzamide |
| 7 | 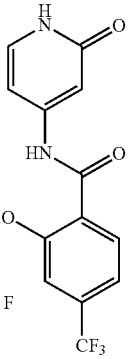 | 2-(2,4-difluorophenoxy)-N-(2-oxo-1,2-dihydropyridin-4-yl)-4-(trifluoromethyl)benzamide |
| 8 | 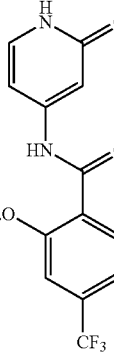 | 2-(4-(2-methoxyethoxy)phenoxy)-N-(2-oxo-1,2-dihydropyridin-4-yl)-4-(trifluoromethyl)benzamide |
| 9 |  | N-(2-oxo-1,2-dihydropyridin-4-yl)-2-phenoxy-4-(trifluoromethyl)benzamide |
| 10 | 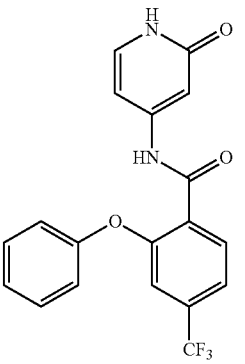 [SMILES: O=C(Nc1cc[nH]c(=O)c1)c1ccc(C(F)(F)F)cc1Oc1ccccc1] | 2-(4-fluoro-2-methylphenoxy)-N-(2-oxo-1,2-dihydropyridin-4-yl)-4-(trifluoromethyl)benzamide |

TABLE 1-continued

Compound Numbers, Structures and Chemical Names

11 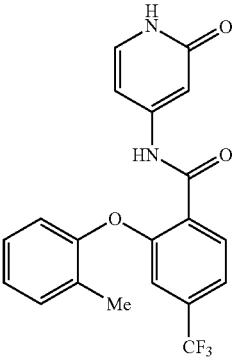 [SMILES: Cc1ccccc1Oc1cc(C(F)(F)F)ccc1C(=O)Nc1cc[nH]c(=O)c1]
N-(2-oxo-1,2-dihydropyridin-4-yl)-2-(o-tolyloxy)-4-(trifluoromethyl)benzamide 12 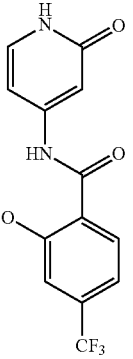
N-(2-oxo-1,2-dihydropyridin-4-yl)-2-(p-tolyloxy)-4-(trifluoromethyl)benzamide 13 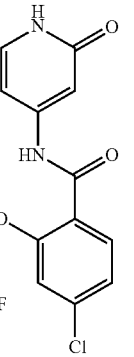
4-chloro-2-(2,4-difluorophenoxy)-N-(2-oxo-1,2-dihydropyridin-4-yl)benzamide 14 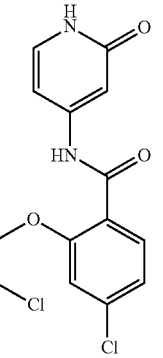
4-chloro-2-(2-chloro-4-fluorophenoxy)-N-(2-oxo-1,2-dihydropyridin-4-yl)benzamide 15 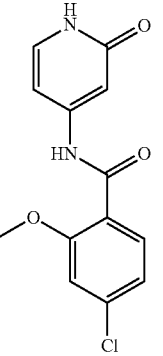
4-chloro-2-(4-fluorophenoxy)-N-(2-oxo-1,2-dihydropyridin-4-yl)benzamide 16 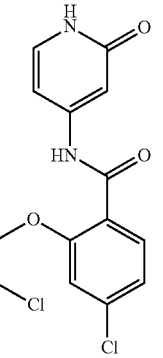
4-chloro-2-(4-fluoro-2-methoxyphenoxy)-N-(2-oxo-1,2-dihydropyridin-4-yl)benzamide TABLE 1-continued Compound Numbers, Structures and Chemical Names

17

4-chloro-2-(2-fluoro-6-methylphenoxy)-N-(2-oxo-1,2-dihydropyridin-4-yl)benzamide

18

4-chloro-2-(2-chloro-6-fluorophenoxy)-N-(2-oxo-1,2-dihydropyridin-4-yl)benzamide

19

4-chloro-2-(2,6-difluorophenoxy)-N-(2-oxo-1,2-dihydropyridin-4-yl)benzamide

20

4-chloro-2-(4-fluoro-2-methylphenoxy)-N-(2-oxo-1,2-dihydropyridin-4-yl)benzamide

21

4-cyano-2-(4-fluorophenoxy)-N-(2-oxo-1,2-dihydropyridin-4-yl)benzamide

22

4-cyano-2-(4-fluoro-2-methoxyphenoxy)-N-(2-oxo-1,2-dihydropyridin-4-yl)benzamide TABLE 1-continued Compound Numbers, Structures and Chemical Names

23

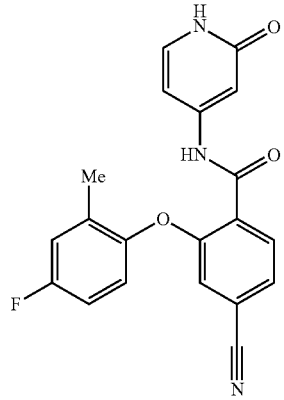 [SMILES: Cc1cc(F)ccc1Oc1cc(C#N)ccc1C(=O)Nc1cc[nH]c(=O)c1]

4-cyano-2-(4-fluoro-2-
methylphenoxy)-N-(2-oxo-1,2-
dihydropyridin-4-yl)benzamide

24

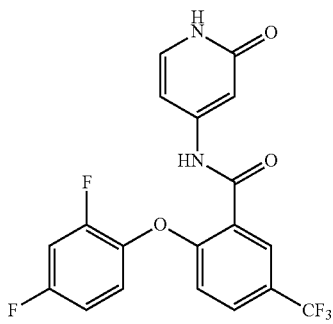 [SMILES: O=C(Nc1cc[nH]c(=O)c1)c1cc(C(F)(F)F)ccc1Oc1ccc(F)cc1F]

2-(2,4-difluorophenoxy)-N-(2-
oxo-1,2-dihydropyridin-4-yl)-5-
(trifluoromethyl)benzamide

25

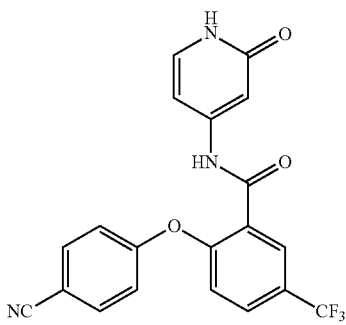 [SMILES: N#Cc1ccc(Oc2ccc(C(F)(F)F)cc2C(=O)Nc2cc[nH]c(=O)c2)cc1]

2-(4-cyanophenoxy)-N-(2-oxo-
1,2-dihydropyridin-4-yl)-5-
(trifluoromethyl)benzamide TABLE 1-continued Compound Numbers, Structures and Chemical Names

26

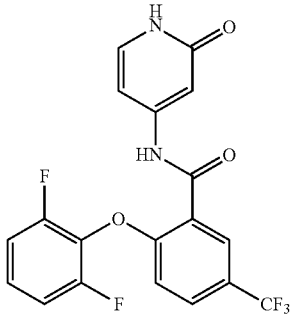 [SMILES: O=C(Nc1cc[nH]c(=O)c1)c1cc(C(F)(F)F)ccc1Oc1c(F)cccc1F]

2-(2,6-difluorophenoxy)-N-(2-
oxo-1,2-dihydropyridin-4-yl)-5-
(trifluoromethyl)benzamide

27

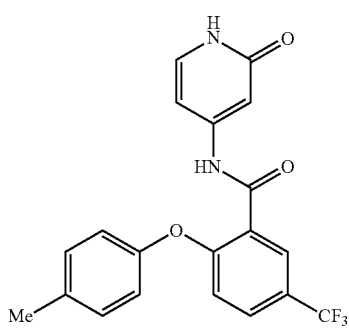

N-(2-oxo-1,2-dihydropyridin-4-
yl)-2-(p-tolyloxy)-5-
(trifluoromethyl)benzamide

28

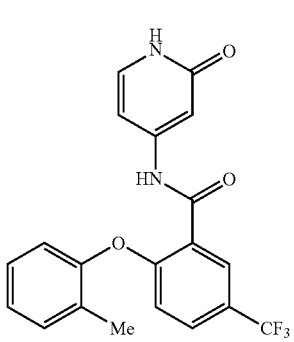 [SMILES: Cc1ccccc1Oc1ccc(C(F)(F)F)cc1C(=O)Nc1cc[nH]c(=O)c1]

N-(2-oxo-1,2-dihydropyridin-4-
yl)-2-(o-tolyloxy)-5-
(trifluoromethyl)benzamide

TABLE 1-continued

Compound Numbers, Structures and Chemical Names

29

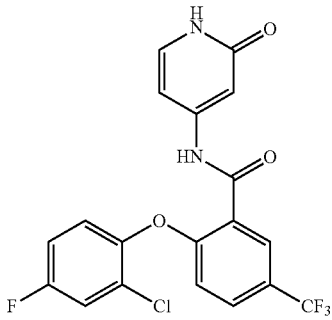 [SMILES: O=C(Nc1cc[nH]c(=O)c1)c1cc(C(F)(F)F)ccc1Oc1ccc(F)cc1Cl]

2-(2-chloro-4-fluorophenoxy)-N-
(2-oxo-1,2-dihydropyridin-4-yl)-5-
(trifluoromethyl)benzamide

30

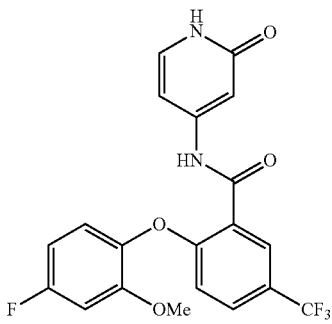 [SMILES: COc1cc(F)ccc1Oc1ccc(C(F)(F)F)cc1C(=O)Nc1cc[nH]c(=O)c1]

2-(4-fluoro-2-methoxyphenoxy)-
N-(2-oxo-1,2-dihydropyridin-4-
yl)-5-(trifluoromethyl)benzamide

31

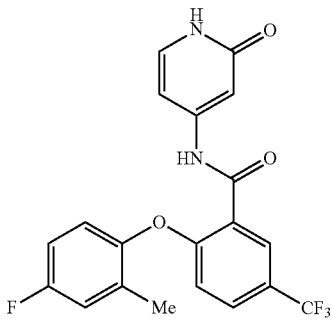 [SMILES: Cc1cc(F)ccc1Oc1ccc(C(F)(F)F)cc1C(=O)Nc1cc[nH]c(=O)c1]

2-(4-fluoro-2-methylphenoxy)-N-
(2-oxo-1,2-dihydropyridin-4-yl)-5-
(trifluoromethyl)benzamide

TABLE 1-continued

Compound Numbers, Structures and Chemical Names

32

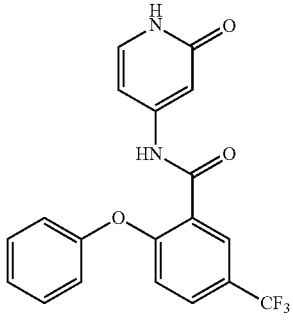 [SMILES: O=C(Nc1cc[nH]c(=O)c1)c1cc(C(F)(F)F)ccc1Oc1ccccc1]

N-(2-oxo-1,2-dihydropyridin-4-
yl)-2-phenoxy-5-
(trifluoromethyl)benzamide

33

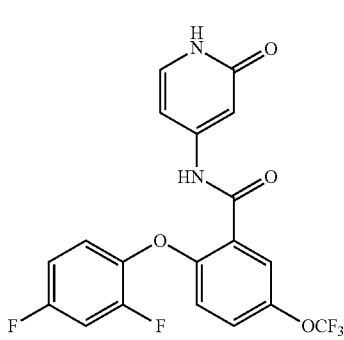 [SMILES: O=C(Nc1cc[nH]c(=O)c1)c1cc(OC(F)(F)F)ccc1Oc1ccc(F)cc1F]

2-(2,4-difluorophenoxy)-N-(2-
oxo-1,2-dihydropyridin-4-yl)-5-
(trifluoromethoxy)benzamide

34

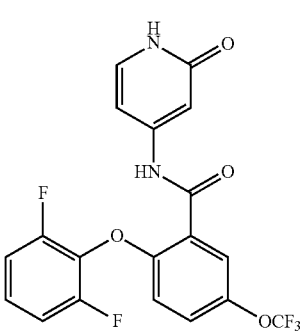 [SMILES: O=C(Nc1cc[nH]c(=O)c1)c1cc(OC(F)(F)F)ccc1Oc1c(F)cccc1F]

2-(2,6-difluorophenoxy)-N-(2-
oxo-1,2-dihydropyridin-4-yl)-5-
(trifluoromethoxy)benzamide TABLE 1-continued Compound Numbers, Structures and Chemical Names

35

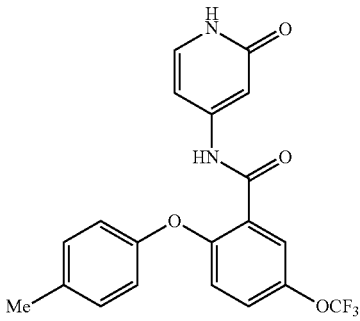 [SMILES: Cc1ccc(Oc2ccc(OC(F)(F)F)cc2C(=O)Nc2cc[nH]c(=O)c2)cc1]

N-(2-oxo-1,2-dihydropyridin-4-
yl)-2-(p-tolyloxy)-5-
(trifluoromethoxy)benzamide

36

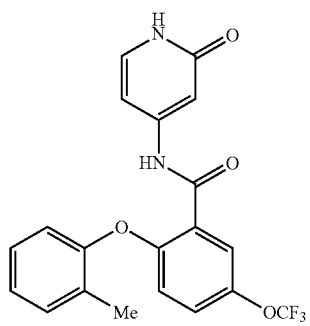 [SMILES: Cc1ccccc1Oc1ccc(OC(F)(F)F)cc1C(=O)Nc1cc[nH]c(=O)c1]

N-(2-oxo-1,2-dihydropyridin-4-
yl)-2-(o-tolyloxy)-5-
(trifluoromethoxy)benzamide

37

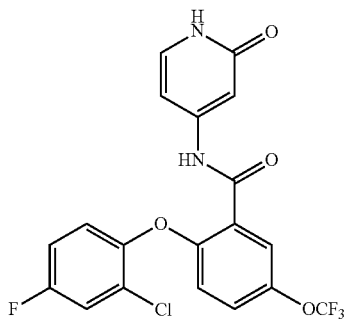

2-(2-chloro-4-fluorophenoxy)-N-
(2-oxo-1,2-dihydropyridin-4-yl)-5-
(trifluoromethoxy)benzamide TABLE 1-continued Compound Numbers, Structures and Chemical Names

38

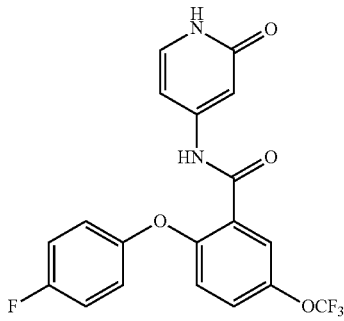

2-(4-fluorophenoxy)-N-(2-oxo-
1,2-dihydropyridin-4-yl)-5-
(trifluoromethoxy)benzamide

39

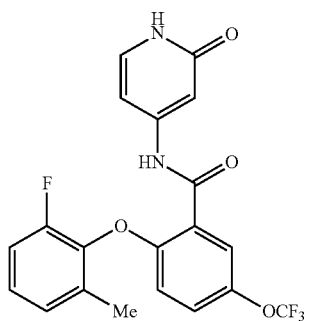

2-(2-fluoro-6-methylphenoxy)-N-
(2-oxo-1,2-dihydropyridin-4-yl)-5-
(trifluoromethoxy)benzamide

40

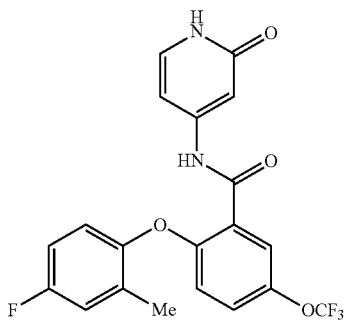 [SMILES: O=C(Nc1cc[nH]c(=O)c1)c1cc(OC(F)(F)F)ccc1Oc1ccc(F)cc1Cl]

2-(4-fluoro-2-methylphenoxy)-N-
(2-oxo-1,2-dihydropyridin-4-yl)-5-
(trifluoromethoxy)benzamide TABLE 1-continued Compound Numbers, Structures and Chemical Names

41

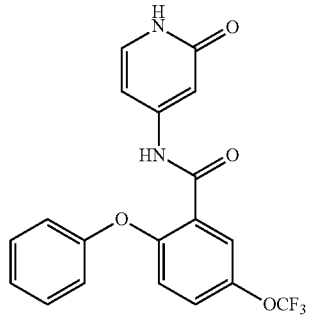

N-(2-oxo-1,2-dihydropyridin-4-
yl)-2-phenoxy-5-
(trifluoromethoxy)benzamide

42

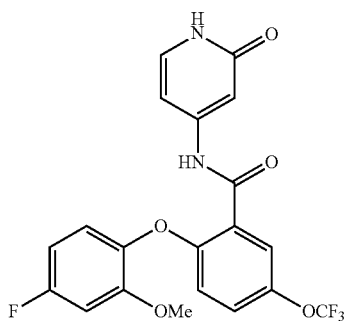

2-(4-fluoro-2-methoxyphenoxy)-
N-(2-oxo-1,2-dihydropyridin-4-
yl)-5-(trifluoromethoxy)benzamide

43

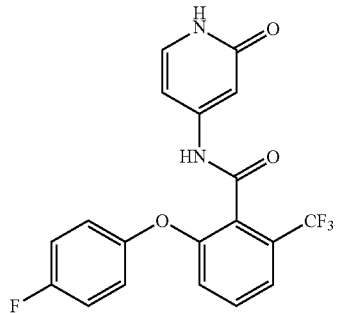 [SMILES: O=C(Nc1cc[nH]c(=O)c1)c1c(Oc2ccc(F)cc2)cccc1C(F)(F)F]

2-(4-fluorophenoxy)-N-(2-oxo-
1,2-dihydropyridin-4-yl)-6-
(trifluoromethyl)benzamide TABLE 1-continued Compound Numbers, Structures and Chemical Names

44

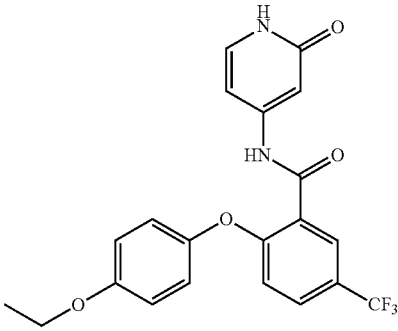 [SMILES: CCOc1ccc(Oc2ccc(C(F)(F)F)cc2C(=O)Nc2cc[nH]c(=O)c2)cc1]

2-(4-ethoxyphenoxy)-N-(2-oxo-
1,2-dihydropyridin-4-yl)-5-
(trifluoromethyl)benzamide

45

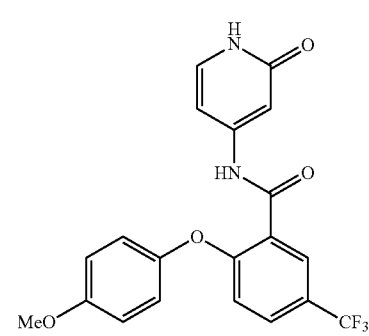 [SMILES: COc1ccc(Oc2ccc(C(F)(F)F)cc2C(=O)Nc2cc[nH]c(=O)c2)cc1]

2-(4-methoxyphenoxy)-N-(2-oxo-
1,2-dihydropyridin-4-yl)-5-
(trifluoromethyl)benzamide

46

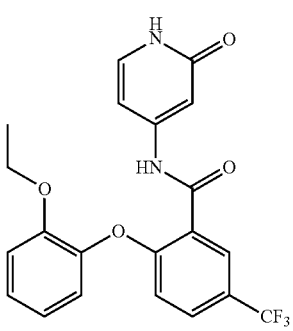

2-(2-ethoxyphenoxy)-N-(2-oxo-
1,2-dihydropyridin-4-yl)-5-
(trifluoromethyl)benzamide

| | |
|---|---|
| 47 | 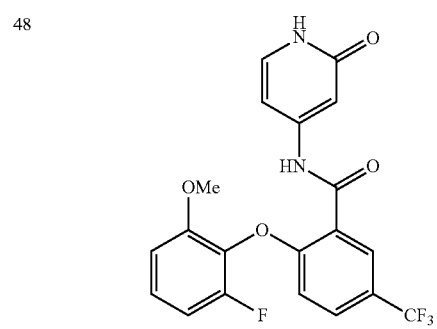<br>2-(2-methoxy-4-methylphenoxy)-N-(2-oxo-1,2-dihydropyridin-4-yl)-5-(trifluoromethyl)benzamide |
| 48 | 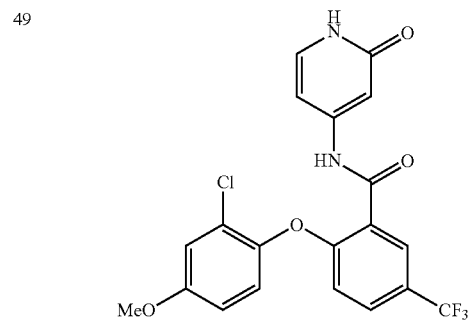<br>2-(2-fluoro-6-methoxyphenoxy)-N-(2-oxo-1,2-dihydropyridin-4-yl)-5-(trifluoromethyl)benzamide |
| 49 | 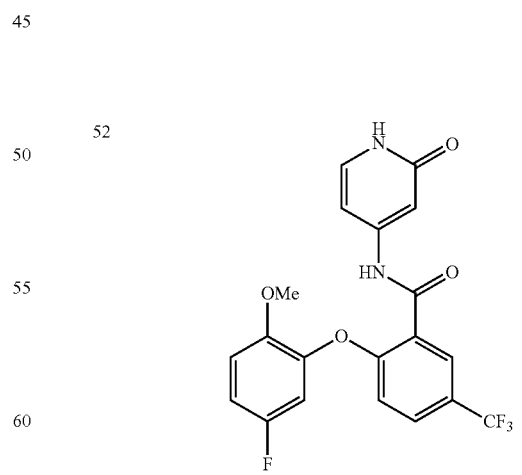<br>2-(2-chloro-4-methoxyphenoxy)-N-(2-oxo-1,2-dihydropyridin-4-yl)-5-(trifluoromethyl)benzamide |
| 50 | 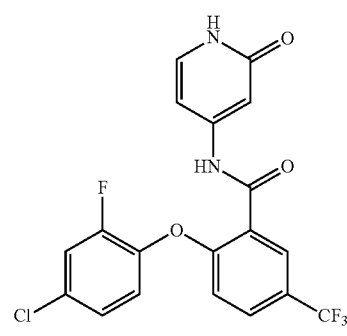 [SMILES: O=C(Nc1cc[nH]c(=O)c1)c1cc(C(F)(F)F)ccc1Oc1ccc(Cl)cc1F]<br>2-(4-chloro-2-methylphenoxy)-N-(2-oxo-1,2-dihydropyridin-4-yl)-5-(trifluoromethyl)benzamide |
| 51 | 2-(4-chloro-2-fluorophenoxy)-N-(2-oxo-1,2-dihydropyridin-4-yl)-5-(trifluoromethyl)benzamide |
| 52 | 2-(5-fluoro-2-methoxyphenoxy)-N-(2-oxo-1,2-dihydropyridin-4-yl)-5-(trifluoromethyl)benzamide |

TABLE 1-continued

Compound Numbers, Structures and Chemical Names

53

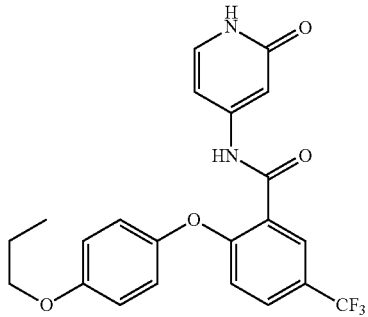 [SMILES: CCCOc1ccc(Oc2ccc(C(F)(F)F)cc2C(=O)Nc2cc[nH]c(=O)c2)cc1]

N-(2-oxo-1,2-dihydropyridin-4-
yl)-2-(4-propoxyphenoxy)-5-
(trifluoromethyl)benzamide

54

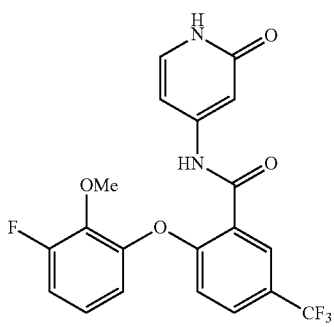 [SMILES: COc1c(F)cccc1Oc1ccc(C(F)(F)F)cc1C(=O)Nc1cc[nH]c(=O)c1]

2-(3-fluoro-2-methoxyphenoxy)-
N-(2-oxo-1,2-dihydropyridin-4-
yl)-5-(trifluoromethyl)benzamide

55

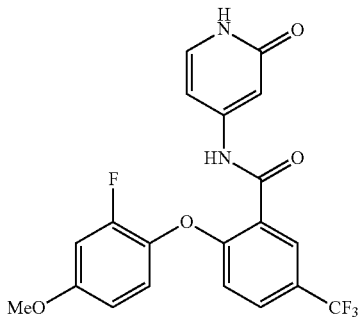 [SMILES: COc1ccc(Oc2ccc(C(F)(F)F)cc2C(=O)Nc2cc[nH]c(=O)c2)c(F)c1]

2-(2-fluoro-4-methoxyphenoxy)-
N-(2-oxo-1,2-dihydropyridin-4-
yl)-5-(trifluoromethyl)benzamide TABLE 1-continued Compound Numbers, Structures and Chemical Names

56

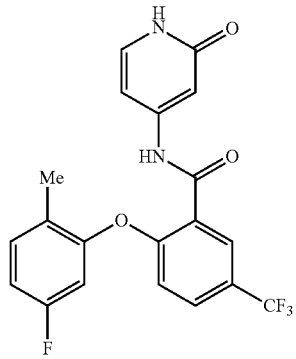 [SMILES: Cc1ccc(F)cc1Oc1ccc(C(F)(F)F)cc1C(=O)Nc1cc[nH]c(=O)c1]

2-(5-fluoro-2-methylphenoxy)-N-
(2-oxo-1,2-dihydropyridin-4-yl)-5-
(trifluoromethyl)benzamide

57

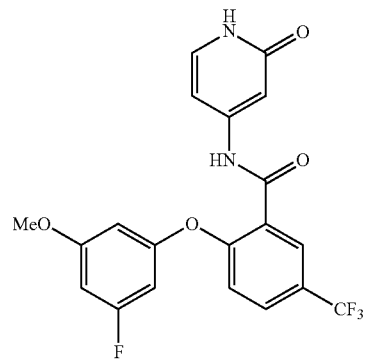 [SMILES: COc1cc(F)cc(Oc2ccc(C(F)(F)F)cc2C(=O)Nc2cc[nH]c(=O)c2)c1]

2-(3-fluoro-5-methoxyphenoxy)-
N-(2-oxo-1,2-dihydropyridin-4-
yl)-5-(trifluoromethyl)benzamide

58

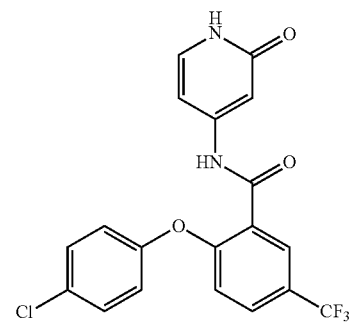 [SMILES: O=C(Nc1cc[nH]c(=O)c1)c1cc(C(F)(F)F)ccc1Oc1ccc(Cl)cc1]

2-(4-chlorophenoxy)-N-(2-oxo-
1,2-dihydropyridin-4-yl)-5-
(trifluoromethyl)benzamide TABLE 1-continued Compound Numbers, Structures and Chemical Names 59
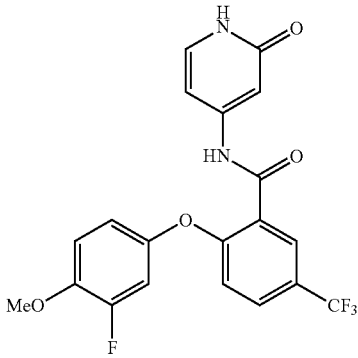 [SMILES: COc1ccc(Oc2ccc(C(F)(F)F)cc2C(=O)Nc2cc[nH]c(=O)c2)cc1F]
2-(3-fluoro-4-methoxyphenoxy)-N-(2-oxo-1,2-dihydropyridin-4-yl)-5-(trifluoromethyl)benzamide 60
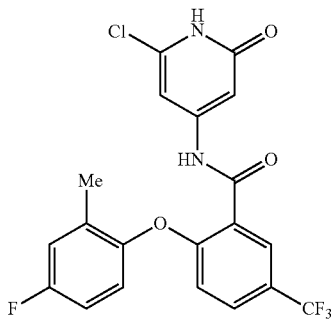 [SMILES: Cc1cc(F)ccc1Oc1ccc(C(F)(F)F)cc1C(=O)Nc1cc(Cl)[nH]c(=O)c1]
N-(6-chloro-2-oxo-1,2-dihydropyridin-4-yl)-2-(4-fluoro-2-methylphenoxy)-5-(trifluoromethyl)benzamide 61
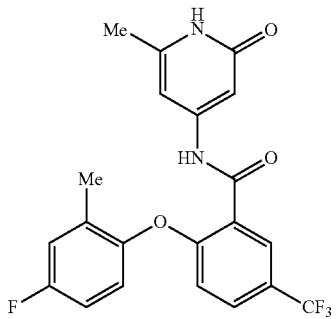
2-(4-fluoro-2-methylphenoxy)-N-(6-methyl-2-oxo-1,2-dihydropyridin-4-yl)-5-(trifluoromethyl)benzamide TABLE 1-continued Compound Numbers, Structures and Chemical Names 62
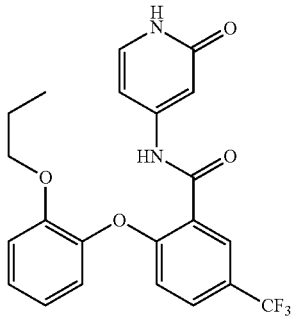 [SMILES: CCCOc1ccccc1Oc1ccc(C(F)(F)F)cc1C(=O)Nc1cc[nH]c(=O)c1]
N-(2-oxo-1,2-dihydropyridin-4-yl)-2-(2-propoxyphenoxy)-5-(trifluoromethyl)benzamide 63
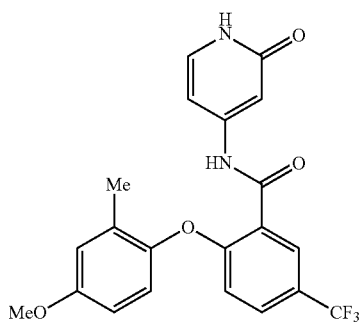 [SMILES: COc1ccc(Oc2ccc(C(F)(F)F)cc2C(=O)Nc2cc[nH]c(=O)c2)c(C)c1]
2-(4-methoxy-2-methylphenoxy)-N-(2-oxo-1,2-dihydropyridin-4-yl)-5-(trifluoromethyl)benzamide 64
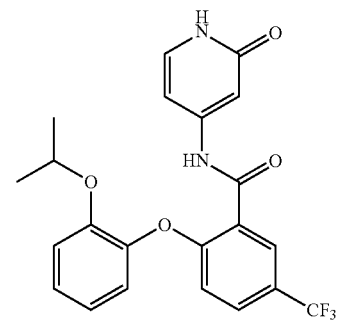 [SMILES: CC(C)Oc1ccccc1Oc1ccc(C(F)(F)F)cc1C(=O)Nc1cc[nH]c(=O)c1]
2-(2-isopropoxyphenoxy)-N-(2-oxo-1,2-dihydropyridin-4-yl)-5-(trifluoromethyl)benzamide TABLE 1-continued Compound Numbers, Structures and Chemical Names

65

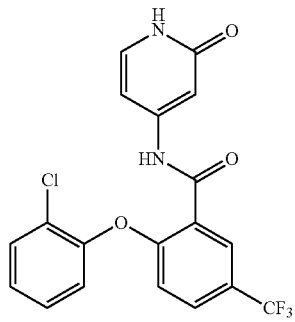

2-(2-chlorophenoxy)-N-(2-oxo-
1,2-dihydropyridin-4-yl)-5-
(trifluoromethyl)benzamide

66

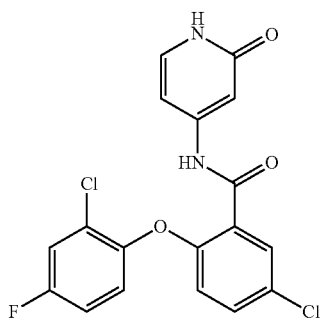 [SMILES: O=C(Nc1cc[nH]c(=O)c1)c1cc(Cl)ccc1Oc1ccc(F)cc1Cl]

5-chloro-2-(2-chloro-4-
fluorophenoxy)-N-(2-oxo-1,2-
dihydropyridin-4-yl)benzamide

67

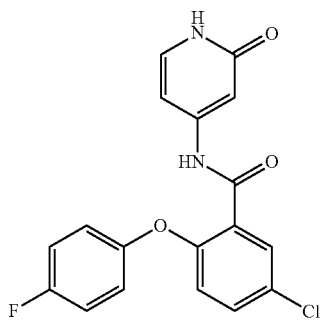 [SMILES: O=C(Nc1cc[nH]c(=O)c1)c1cc(Cl)ccc1Oc1ccc(F)cc1]

5-chloro-2-(4-fluorophenoxy)-N-
(2-oxo-1,2-dihydropyridin-4-
yl)-benzamide

68

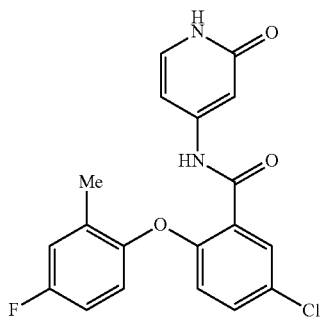 [SMILES: Cc1cc(F)ccc1Oc1ccc(Cl)cc1C(=O)Nc1cc[nH]c(=O)c1]

5-chloro-2-(4-fluoro-2-
methylphenoxy)-N-(2-oxo-1,2-
dihydropyridin-4-yl)benzamide TABLE 1-continued Compound Numbers, Structures and Chemical Names

69

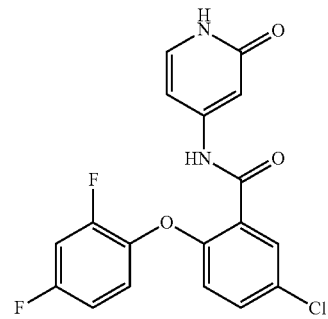

5-chloro-2-(2,4-difluorophenoxy)-
N-(2-oxo-1,2-dihydropyridin-4-
yl)benzamide

70

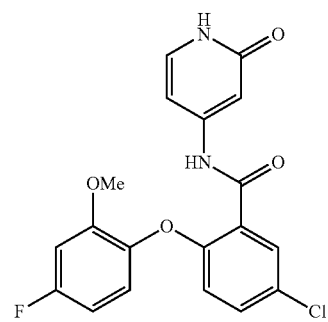 [SMILES: COc1cc(F)ccc1Oc1ccc(Cl)cc1C(=O)Nc1cc[nH]c(=O)c1]

5-chloro-2-(4-fluoro-2-
methoxyphenoxy)-N-(2-oxo-1,2-
dihydropyridin-4-yl)benzamide

71

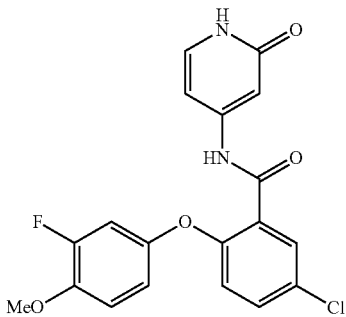 [SMILES: COc1ccc(Oc2ccc(Cl)cc2C(=O)Nc2cc[nH]c(=O)c2)cc1F]

5-chloro-2-(3-fluoro-4-
methoxyphenoxy)-N-(2-oxo-1,2-
dihydropyridin-4-yl)benzamide TABLE 1-continued Compound Numbers, Structures and Chemical Names

72

N-(2-oxo-1,2-dihydropyridin-4-yl)-2-(4-(trifluoromethoxy)phenoxy)-5-(trifluoromethyl)benzamide

73

2-(4-(difluoromethoxy)phenoxy)-N-(2-oxo-1,2-dihydropyridin-4-yl)-5-(trifluoromethyl)benzamide

74

N-(2-oxo-1,2-dihydropyridin-4-yl)-5-(trifluoromethyl)-2-(4-(trifluoromethyl)phenoxy)benzamide

75

N-(2-oxo-1,2-dihydropyridin-4-yl)-2-(2-(trifluoromethoxy)phenoxy)-5-(trifluoromethyl)benzamide

76

2-(2-(difluoromethoxy)phenoxy)-N-(2-oxo-1,2-dihydropyridin-4-yl)-5-(trifluoromethyl)benzamide

77

2-(2-chloro-4-fluorophenoxy)-N-(2-oxo-1,2-dihydropyridin-4-yl)-4-(trifluoromethyl)benzamide TABLE 1-continued Compound Numbers, Structures and Chemical Names

78

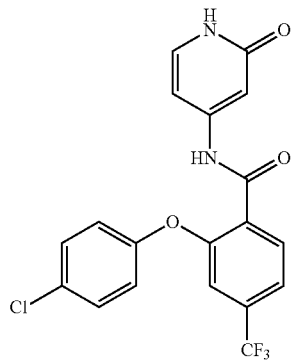 [SMILES: O=C(Nc1cc[nH]c(=O)c1)c1ccc(C(F)(F)F)cc1Oc1ccc(Cl)cc1]

2-(4-chlorophenoxy)-N-(2-oxo-
1,2-dihydropyridin-4-yl)-4-
(trifluoromethyl)benzamide

79

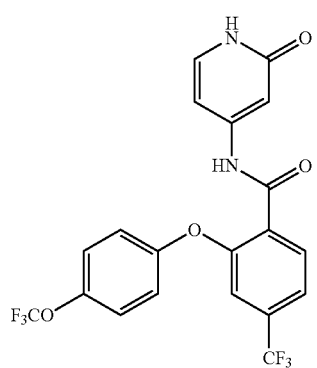 [SMILES: O=C(Nc1cc[nH]c(=O)c1)c1ccc(C(F)(F)F)cc1Oc1ccc(OC(F)(F)F)cc1]

N-(2-oxo-1,2-dihydropyridin-4-
yl)-2-(4-
(trifluoromethoxy)phenoxy)-4-
(trifluoromethyl)benzamide

80

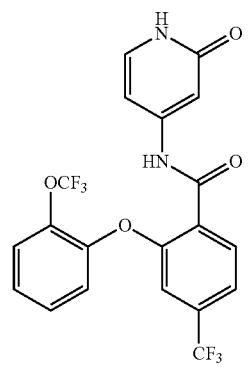 [SMILES: O=C(Nc1cc[nH]c(=O)c1)c1ccc(C(F)(F)F)cc1Oc1ccccc1OC(F)(F)F]

N-(2-oxo-1,2-dihydropyridin-4-
yl)-2-(2-
(trifluoromethoxy)phenoxy)-4-
(trifluoromethyl)benzamide TABLE 1-continued Compound Numbers, Structures and Chemical Names

81

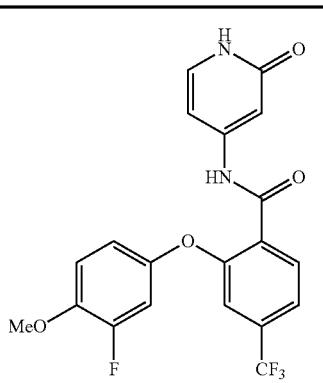

2-(3-fluoro-4-methoxyphenoxy)-
N-(2-oxo-1,2-dihydropyridin-4-
yl)-4-(trifluoromethyl)benzamide

82

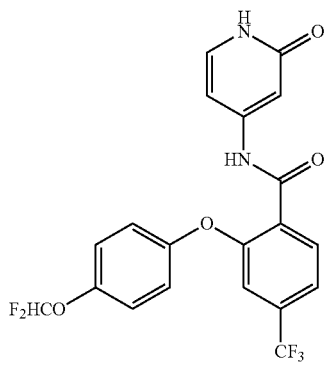 [SMILES: O=C(Nc1cc[nH]c(=O)c1)c1ccc(C(F)(F)F)cc1Oc1ccc(OC(F)F)cc1]

2-(4-(difluoromethoxy)phenoxy)-
N-(2-oxo-1,2-dihydropyridin-4-
yl)-4-(trifluoromethyl)benzamide

83

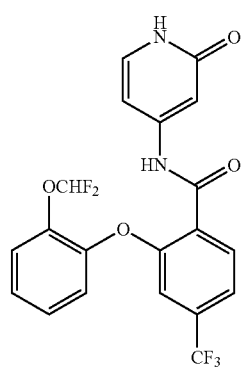 [SMILES: O=C(Nc1cc[nH]c(=O)c1)c1ccc(C(F)(F)F)cc1Oc1ccccc1OC(F)F]

2-(2-(difluoromethoxy)phenoxy)-
N-(2-oxo-1,2-dihydropyridin-4-
yl)-4-(trifluoromethyl)benzamide TABLE 1-continued Compound Numbers, Structures and Chemical Names 84
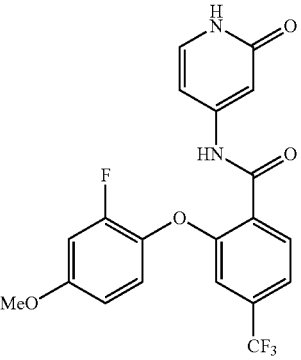
2-(2-fluoro-4-methoxyphenoxy)-
N-(2-oxo-1,2-dihydropyridin-4-
yl)-4-(trifluoromethyl)benzamide 85
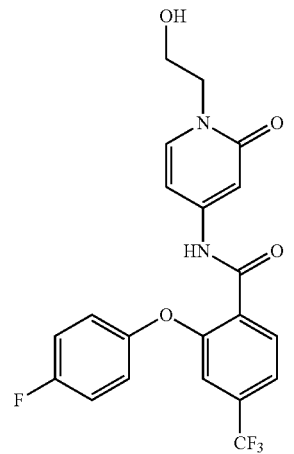 [SMILES: O=C(Nc1ccn(CCO)c(=O)c1)c1ccc(C(F)(F)F)cc1Oc1ccc(F)cc1]
2-(4-fluorophenoxy)-N-(1-(2-
hydroxyethyl)-2-oxo-1,2-
dihydropyridin-4-yl)-4-
(trifluoromethyl)benzamide 86
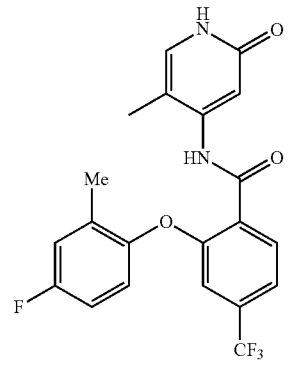 [SMILES: Cc1c[nH]c(=O)cc1NC(=O)c1ccc(C(F)(F)F)cc1Oc1ccc(F)cc1C]
2-(4-fluoro-2-methylphenoxy)-N-
(5-methyl-2-oxo-1,2-
dihydropyridin-4-yl)-4-
(trifluoromethyl)benzamide 87
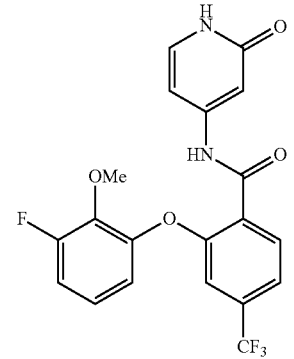
2-(3-fluoro-2-methoxyphenoxy)-
N-(2-oxo-1,2-dihydropyridin-4-
yk)-4-(trifluoromethyl)benzamide 88
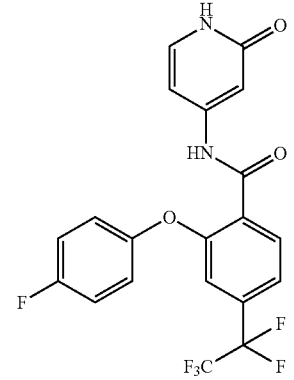
2-(4-fluorophenoxy)-N-(2-oxo-
1,2-dihydropyridin-4-yl)-4-
(perfluoroethyl)benzamide 89
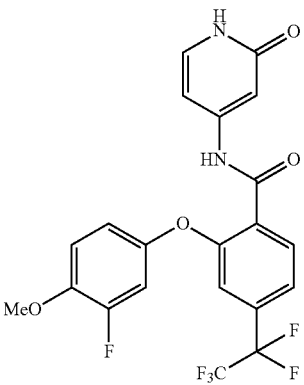
2-(3-fluoro-4-methoxyphenoxy)-
N-(2-oxo-1,2-dihydropyridin-4-
yl)-4-(perfluoroethyl)benzamide TABLE 1-continued Compound Numbers, Structures and Chemical Names 90 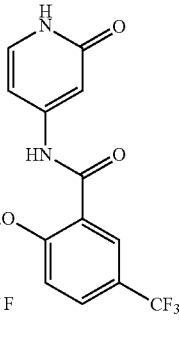
N-(2-oxo-1,2-dihydropyridin-4-yl)-5-(trifluoromethyl)-2-(2,3,4-trifluorophenoxy)benzamide 91 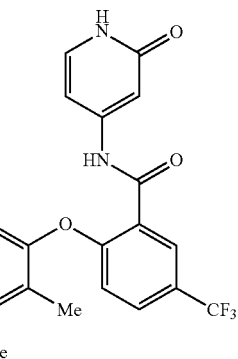
N-(2-oxo-1,2-dihydropyridin-4-yl)-5-(trifluoromethyl)-2-(2,3,5-trimethylphenoxy)benzamide 92 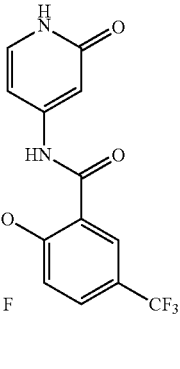
2-(2,3-difluoro-4-methylphenoxy)-N-(2-oxo-1,2-dihydropyridin-4-yl)-5-(trifluoromethyl)benzamide 93 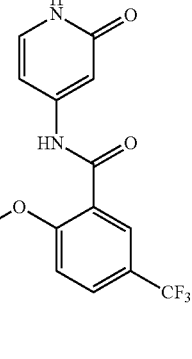
N-(2-oxo-1,2-dihydropyridin-4-yl)-5-(trifluoromethyl)-2-(2,4,5-trimethylphenoxy)benzamide 94 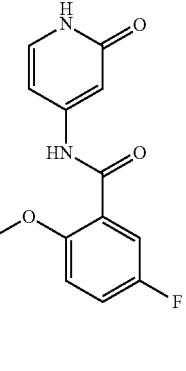
5-fluoro-N-(2-oxo-1,2-dihydropyridin-4-yl)-2-(2,3,5-trimethylphenoxy)benzamide 95 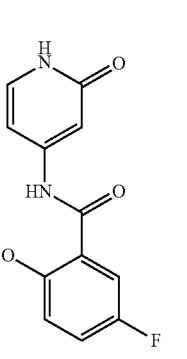
5-fluoro-N-(2-oxo-1,2-dihydropyridin-4-yl)-2-phenoxybenzamide TABLE 1-continued Compound Numbers, Structures and Chemical Names 96 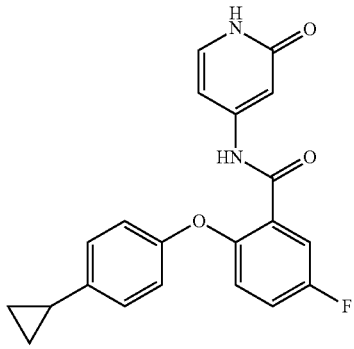 [SMILES: O=C(Nc1cc[nH]c(=O)c1)c1cc(F)ccc1Oc1ccc(C2CC2)cc1]

2-(4-cyclopropylphenoxy)-5-fluoro-N-
(2-oxo-1,2-dihydropyridin-4-yl)benzamide

97 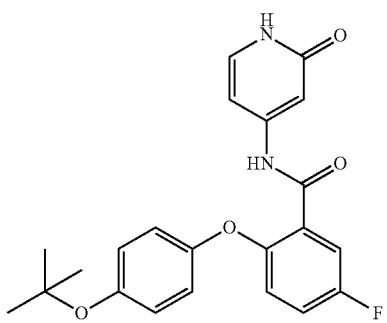 [SMILES: CC(C)(C)Oc1ccc(Oc2ccc(F)cc2C(=O)Nc2cc[nH]c(=O)c2)cc1]

2-(4-(tert-butoxy)phenoxy)-5-fluoro-N-
(2-oxo-1,2-dihydropyridin-4-yl)benzamide

98 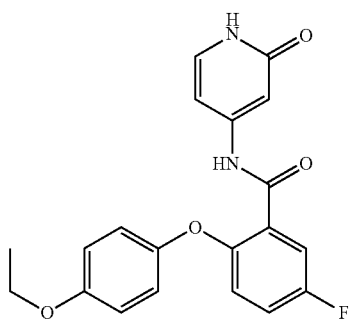 [SMILES: CCOc1ccc(Oc2ccc(F)cc2C(=O)Nc2cc[nH]c(=O)c2)cc1]

2-(4-ethoxyphenoxy)-5-fluoro-N-
(2-oxo-1,2-dihydropyridin-4-
yl)benzamide

99 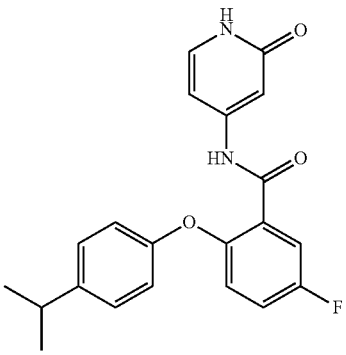 [SMILES: CC(C)c1ccc(Oc2ccc(F)cc2C(=O)Nc2cc[nH]c(=O)c2)cc1]

5-fluoro-2-(4-isopropylphenoxy)-
N-(2-oxo-1,2-dihydropyridin-4-
yl)benzamide

100 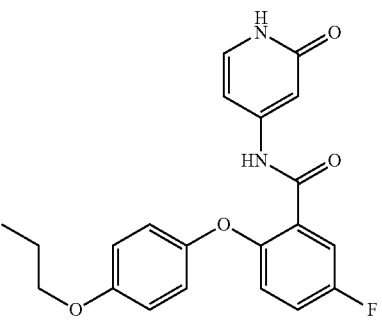 [SMILES: CCCOc1ccc(Oc2ccc(F)cc2C(=O)Nc2cc[nH]c(=O)c2)cc1]

5-fluoro-N-(2-oxo-1,2-dihydropyridin-4-yl)-2-
(4-propoxyphenoxy)benzamide

101 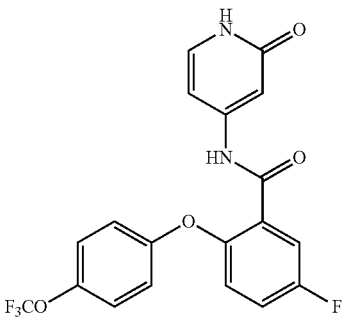 [SMILES: O=C(Nc1cc[nH]c(=O)c1)c1cc(F)ccc1Oc1ccc(OC(F)(F)F)cc1]

5-fluoro-N-(2-oxo-1,2-dihydropyridin-4-yl)-
2-(4-(trifluoromethoxy)phenoxy)benzamide 102 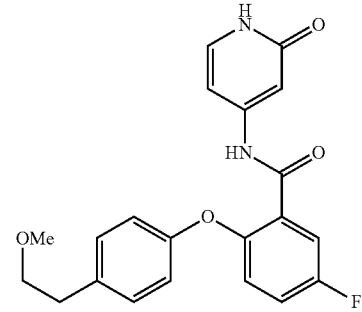 [SMILES: COCCc1ccc(Oc2ccc(F)cc2C(=O)Nc2cc[nH]c(=O)c2)cc1]

5-fluoro-2-(4-(2-methoxyethyl)phenoxy)-N-
(2-oxo-1,2-dihydropyridin-4-yl)benzamide

TABLE 1-continued

Compound Numbers, Structures and Chemical Names

103

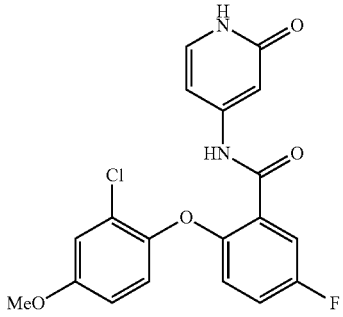 [SMILES: COc1ccc(Oc2ccc(F)cc2C(=O)Nc2cc[nH]c(=O)c2)c(Cl)c1]

2-(2-chloro-4-methoxyphenoxy)-5-fluoro-
N-(2-oxo-1,2-dihydropyridin-4-
yl)benzamide

104

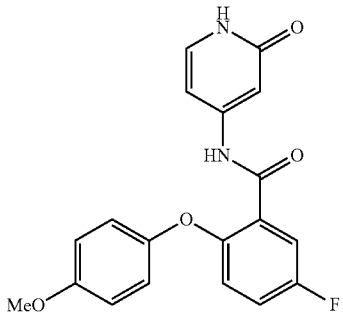 [SMILES: COc1ccc(Oc2ccc(F)cc2C(=O)Nc2cc[nH]c(=O)c2)cc1]

5-fluoro-2-(4-methoxyphenoxy)-
N-(2-oxo-1,2-dihydropyridin-4-
yl)benzamide

105

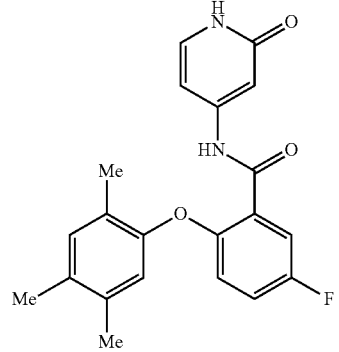 [SMILES: Cc1cc(C)c(Oc2ccc(F)cc2C(=O)Nc2cc[nH]c(=O)c2)cc1C]

5-fluoro-N-(2-oxo-1,2-dihydropyridin-4-
yl)-2-(2,4,5-trimethylphenoxy)benzamide

TABLE 1-continued

Compound Numbers, Structures and Chemical Names

106

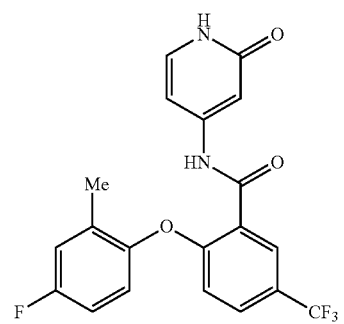 [SMILES: Cc1cc(F)ccc1Oc1ccc(C(F)(F)F)cc1C(=O)Nc1cc[nH]c(=O)c1]

2-(4-fluoro-2-methylphenoxy)-N-
(2-oxo-1,2-dihydropyridin-4-yl)-5-
(trifluoromethyl)benzamide

107

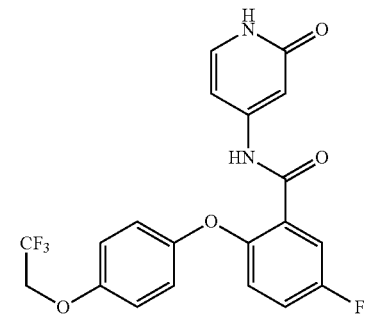 [SMILES: O=C(Nc1cc[nH]c(=O)c1)c1cc(F)ccc1Oc1ccc(OCC(F)(F)F)cc1]

5-fluoro-N-(2-oxo-1,2-dihydropyridin-4-yl)-2-
(4-(2,2,2-trifluoroethoxy)phenoxy)benzamide

108

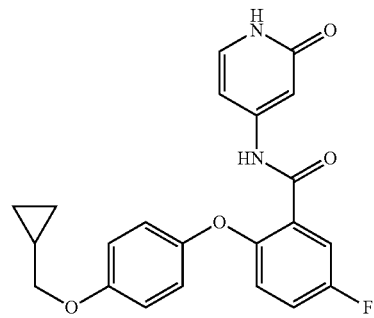 [SMILES: O=C(Nc1cc[nH]c(=O)c1)c1cc(F)ccc1Oc1ccc(OCC2CC2)cc1]

2-(4-(cyclopropylmethoxy)phenoxy)-5-
fluoro-N-(2-oxo-1,2-dihydropyridin-4-
yl)benzamide TABLE 1-continued Compound Numbers, Structures and Chemical Names

109

4-chloro-2-(2-chloro-4-fluorophenoxy)-5-fluoro-N-(2-oxo-1,2-dihydropyridin-4-yl)benzamide

110

2-(2-chloro-3-fluoro-4-methoxyphenoxy)-N-(2-oxo-1,2-dihydropyridin-4-yl)-4-(trifluoromethyl)benzamide

111

2-(4-fluoro-2-methoxyphenoxy)-N-(2-oxo-1,2-dihydropyridin-4-yl)-4-(perfluoroethyl)benzamide

112

2-(4-fluoro-2-methylphenoxy)-N-(2-oxo-1,2-dihydropyridin-4-yl)-4-(perfluoroethyl)benzamide

113

4,5-dichloro-2-(4-fluorophenoxy)-N-(2-oxo-1,2-dihydropyridin-4-yl)benzamide

114

4,5-dichloro-2-(4-fluoro-2-methoxyphenoxy)-N-(2-oxo-1,2-dihydropyridin-4-yl)benzamide TABLE 1-continued Compound Numbers, Structures and Chemical Names

115

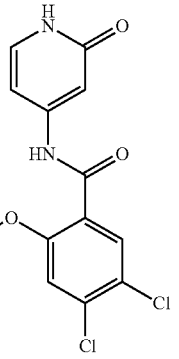

4,5-dichloro-2-(3-fluoro-4-methoxyphenoxy)-N-(2-oxo-1,2-dihydropyridin-4-yl)benzamide

116

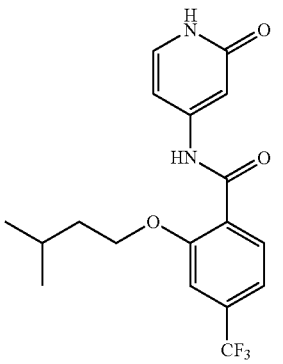 [SMILES: CC(C)CCOc1cc(C(F)(F)F)ccc1C(=O)Nc1cc[nH]c(=O)c1]

2-(isopentyloxy)-N-(2-oxo-1,2-dihydropyridin-4-yl)-4-(trifluoromethyl)benzamide

117

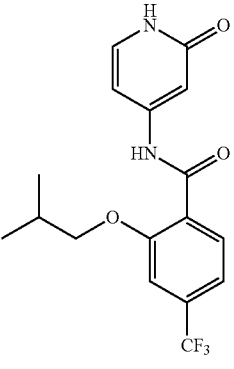 [SMILES: CC(C)COc1cc(C(F)(F)F)ccc1C(=O)Nc1cc[nH]c(=O)c1]

2-isobutoxy-N-(2-oxo-1,2-dihydropyridin-4-yl)-4-(trifluoromethyl)benzamide

118

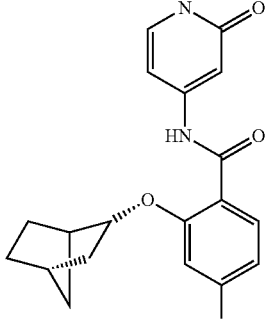

2-((2R)-bicyclo[2.2.1]heptan-2-yloxy)-N-(2-oxo-1,2-dihydropyridin-4-yl)-4-(trifluoromethyl)benzamide

119

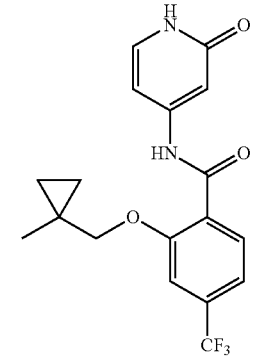 [SMILES: CC1(COc2cc(C(F)(F)F)ccc2C(=O)Nc2cc[nH]c(=O)c2)CC1]

methylcyclopropyl)methoxy)-N-(2-oxo-1,2-dihydropyridin-4-yl)-4-(trifluoromethyl)benzamide

120

2-(cyclopentylmethoxy)-N-(2-oxo-1,2-dihydropyridin-4-yl)-4-(trifluoromethyl)benzamide TABLE 1-continued Compound Numbers, Structures and Chemical Names

121

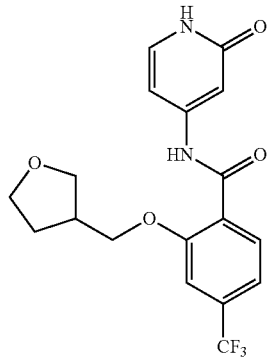 [SMILES: O=C(Nc1cc[nH]c(=O)c1)c1ccc(C(F)(F)F)cc1OCC1CCOC1]

N-(2-oxo-1,2-dihydropyridin-4-
yl)-2-((tetrahydrofuran-3-
yl)methoxy)-4-
(trifluoromethyl)benzamide

122

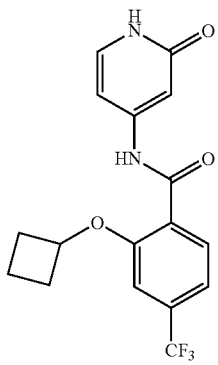 [SMILES: O=C(Nc1cc[nH]c(=O)c1)c1ccc(C(F)(F)F)cc1OC1CCC1]

2-cyclobutoxy-N-(2-oxo-
1,2-dihydropyridin-4-yl)-4-
(trifluoromethyl)benzamide

123

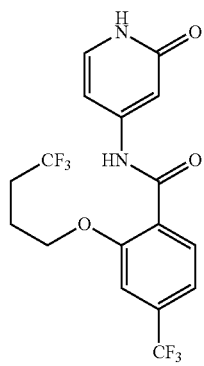 [SMILES: O=C(Nc1cc[nH]c(=O)c1)c1ccc(C(F)(F)F)cc1OCCCC(F)(F)F]

N-(2-oxo-1,2-
dihydropyridin-4-yl)-2-
(4,4,4-trifluorobutoxy)-4-
(trifluoromethyl)benzamide TABLE 1-continued Compound Numbers, Structures and Chemical Names

124

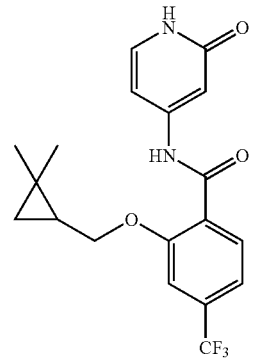 [SMILES: CC1(C)CC1COc1cc(C(F)(F)F)ccc1C(=O)Nc1cc[nH]c(=O)c1]

2-((2,2-
dimethylcyclopropyl)methoxy)-
N-(2-oxo-1,2-dihydropyridin-4-
yl)-4-(trifluoromethyl)benzamide

125

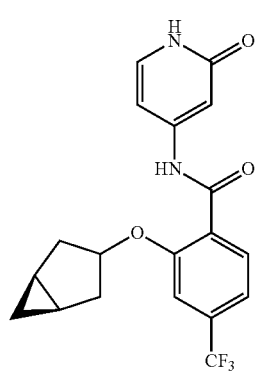 [SMILES: O=C(Nc1cc[nH]c(=O)c1)c1ccc(C(F)(F)F)cc1OC1C[C@@H]2C[C@@H]2C1]

2-(((1R,5S)-bicyclo[3.1.0]hexan-
3-yloxy)-N-(2-oxo-1,2-
dihydropyridin-4-yl)-4-
(trifluoromethyl)benzamide

126

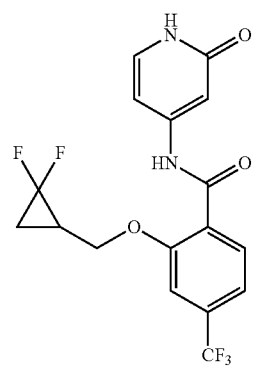

2-((2,2-
difluorocyclopropyl)methoxy)-
N-(2-oxo-1,2-dihydropyridin-4-
yl)-4-(trifluoromethyl)benzamide TABLE 1-continued Compound Numbers, Structures and Chemical Names 127
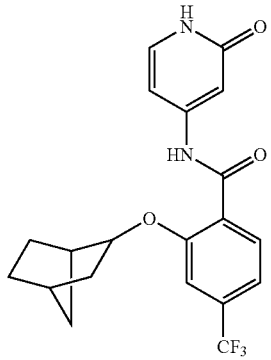 [SMILES: O=C(Nc1cc[nH]c(=O)c1)c1ccc(C(F)(F)F)cc1OC1CC2CCC1C2]
2-(bicyclo[2.2.1]heptan-2-yloxy)-
N-(2-oxo-1,2-dihydropyridin-4-
yl)-4-(trifluoromethyl)benzamide 128
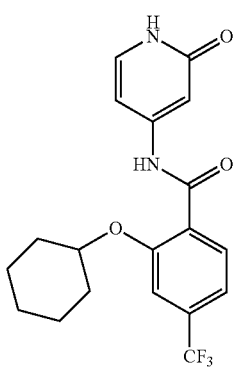 [SMILES: O=C(Nc1cc[nH]c(=O)c1)c1ccc(C(F)(F)F)cc1OC1CCCCC1]
2-(cyclohexyloxy)-N-(2-oxo-
1,2-dihydropyridin-4-yl)-4-
(trifluoromethyl)benzamide 129
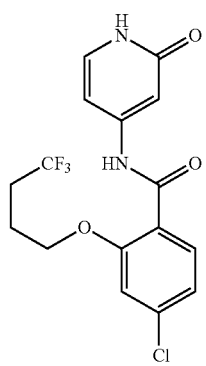 [SMILES: O=C(Nc1cc[nH]c(=O)c1)c1ccc(Cl)cc1OCCCC(F)(F)F]
4-chloro-N-(2-oxo-1,2-
dihydropyridin-4-yl)-2-
(4,4,4-
trifluorobutoxy)benzamide 130
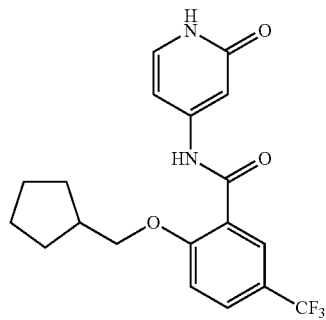 [SMILES: O=C(Nc1cc[nH]c(=O)c1)c1cc(C(F)(F)F)ccc1OCC1CCCC1]
2-(cyclopentylmethoxy)-N-(2-oxo-1,2-
dihydropyridin-4-yl)-5-
(trifluoromethyl)benzamide 131
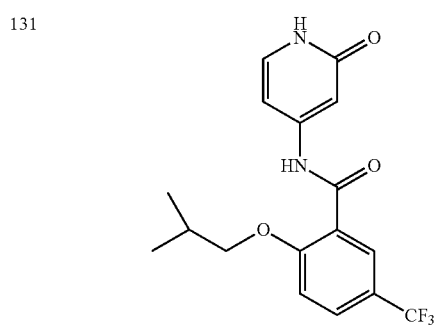
2-isobutoxy-N-(2-oxo-1,2-
dihydropyridin-4-yl)-5-
(trifluoromethyl)benzamide 132
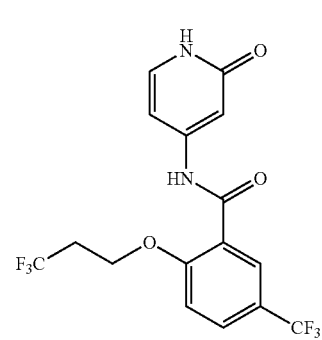 [SMILES: O=C(Nc1cc[nH]c(=O)c1)c1cc(C(F)(F)F)ccc1OCCC(F)(F)F]
N-(2-oxo-1,2-dihydropyridin-4-yl)-5-
(trifluoromethyl)-2-(3,3,3-
trifluoropropoxy)benzamide TABLE 1-continued Compound Numbers, Structures and Chemical Names

133

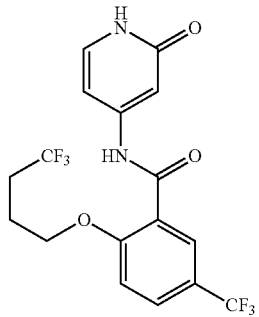 [SMILES: O=C(Nc1cc[nH]c(=O)c1)c1cc(C(F)(F)F)ccc1OCCCC(F)(F)F]

N-(2-oxo-1,2-dihydropyridin-4-yl)-2-(4,4,4-trifluorobutoxy)-5-(trifluoromethyl)benzamide

134

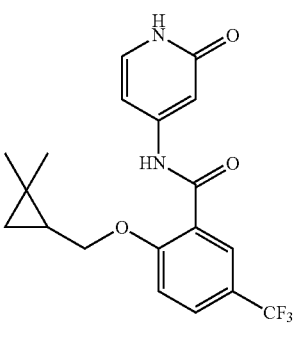 [SMILES: CC1(C)CC1COc1ccc(C(F)(F)F)cc1C(=O)Nc1cc[nH]c(=O)c1]

2-((2,2-dimethylcyclopropyl)methoxy)-N-(2-oxo-1,2-dihydropyridin-4-yl)-5-(trifluoromethyl)benzamide

135

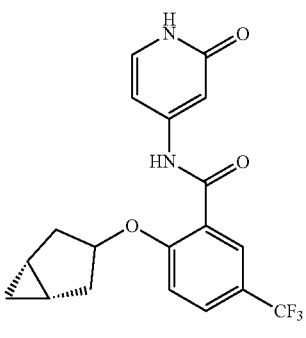

2-((1R,5S)-bicyclo[3.1.0]hexan-3-N-(2-oxo-1,2-dihydropyridin-4-yl)-5-(trifluoromethyl)benzamide TABLE 1-continued Compound Numbers, Structures and Chemical Names

136

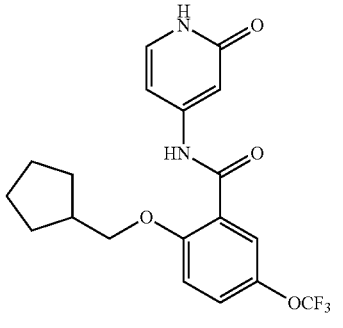 [SMILES: O=C(Nc1cc[nH]c(=O)c1)c1cc(OC(F)(F)F)ccc1OCC1CCCC1]

2-(cyclopentylmethoxy)-N-(2-oxo-1,2-dihydropyridin-4-yl)-5-(trifluoromethoxy)benzamide

137

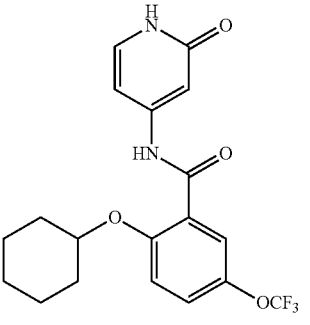 [SMILES: O=C(Nc1cc[nH]c(=O)c1)c1cc(OC(F)(F)F)ccc1OC1CCCCC1]

2-(cyclohexyloxy)-N-(2-oxo-1,2-dihydropyridin-4-yl)-5-(trifluoromethoxy)benzamide

138

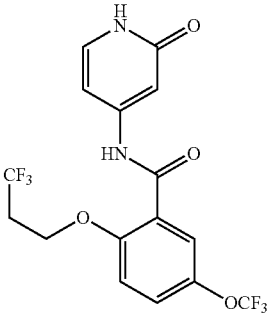

N-(2-oxo-1,2-dihydropyridin-4-yl)-5-(trifluoromethoxy)-2-(3,3,3-trifluoropropoxy)benzamide TABLE 1-continued Compound Numbers, Structures and Chemical Names

139

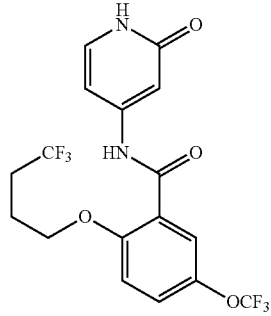 [SMILES: O=C(Nc1cc[nH]c(=O)c1)c1cc(OC(F)(F)F)ccc1OCCCC(F)(F)F]

N-(2-oxo-1,2-dihydropyridin-4-yl)-2-(4,4,4-trifluorobutoxy)-5-(trifluoromethoxy)benzamide

140

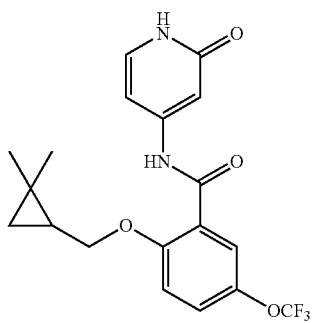 [SMILES: CC1(C)CC1COc1ccc(OC(F)(F)F)cc1C(=O)Nc1cc[nH]c(=O)c1]

2-((2,2-dimethylcyclopropyl)methoxy)-N-(2-oxo-1,2-dihydropyridin-4-yl)-5-(trifluoromethoxy)benzamide

141

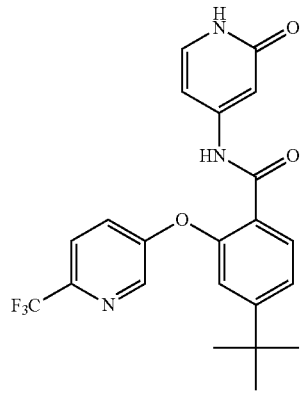 [SMILES: CC(C)(C)c1ccc(C(=O)Nc2cc[nH]c(=O)c2)c(Oc2ccc(C(F)(F)F)nc2)c1]

4-(tert-butyl)-N-(2-oxo-1,2-dihydropyridin-4-yl)-2-((6-(trifluoromethyl)pyridin-3-yl)oxy)benzamide

142

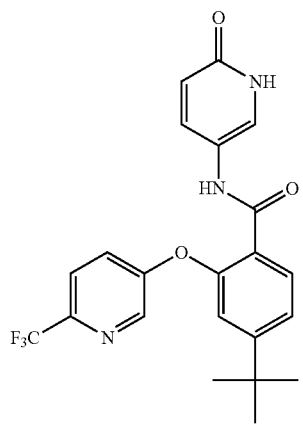 [SMILES: CC(C)(C)c1ccc(C(=O)Nc2ccc(=O)[nH]c2)c(Oc2ccc(C(F)(F)F)nc2)c1]

4-(tert-butyl)-N-(6-oxo-1,6-dihydropyridin-3-yl)-2-((6-(trifluoromethyl)pyridin-3-yl)oxy)benzamide

143

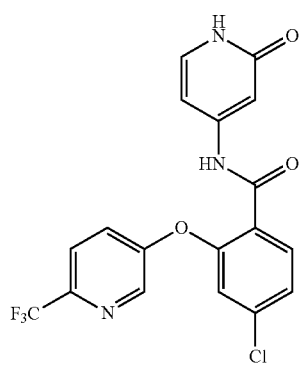 [SMILES: O=C(Nc1cc[nH]c(=O)c1)c1ccc(Cl)cc1Oc1ccc(C(F)(F)F)nc1]

4-chloro-N-(2-oxo-1,2-dihydropyridin-4-yl)-2-((6-(trifluoromethyl)pyridin-3-yl)oxy)benzamide

144

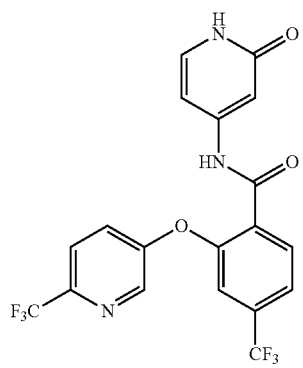 [SMILES: Cc1ccc(Oc2cc(C(F)(F)F)ccc2C(=O)Nc2cc[nH]c(=O)c2)cn1]

N-(2-oxo-1,2-dihydropyridin-4-yl)-4-(trifluoromethyl)-2-((6-(trifluoromethyl)pyridin-3-yl)oxy)benzamide TABLE 1-continued Compound Numbers, Structures and Chemical Names

145

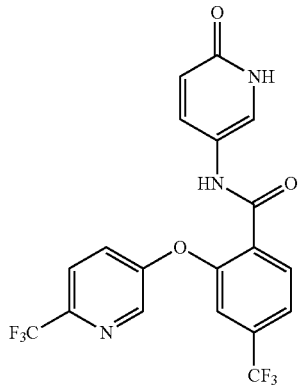

N-(6-oxo-1,6-dihydropyridin-3-yl)-4-
(trifluoromethyl)-2-((6-
(trifluoromethyl)pyridin-3-
yl)oxy)benzamide

146

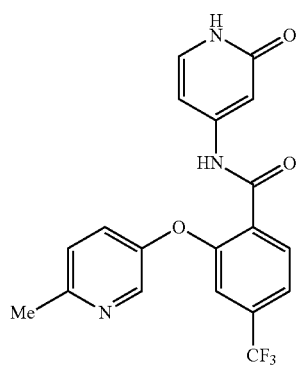

2-((6-methylpyridin-3-yl)oxy)-N-
(2-oxo-1,2-dihydropyridin-4-yl)-4-
(trifluoromethyl)benzamide

147

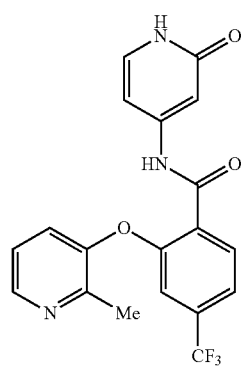

2-((2-methylpyridin-3-yl)oxy)-
N-(2-oxo-1,2-dihydropyridin-
4-yl)-4-
(trifluoromethyl)benzamide TABLE 1-continued Compound Numbers, Structures and Chemical Names

148

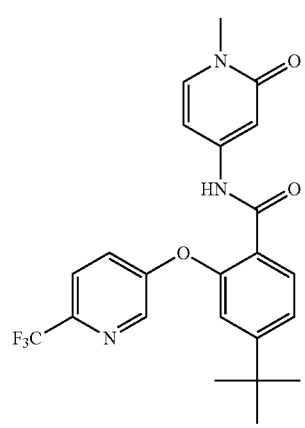 [SMILES: Cn1ccc(NC(=O)c2ccc(C(C)(C)C)cc2Oc2ccc(C(F)(F)F)nc2)cc1=O]

4-(tert-butyl)-N-(1-methyl-2-oxo-
1,2-dihydropyridin-4-yl)-2-((6-
(trifluoromethyl)pyridin-3-
yl)oxy)benzamide

149

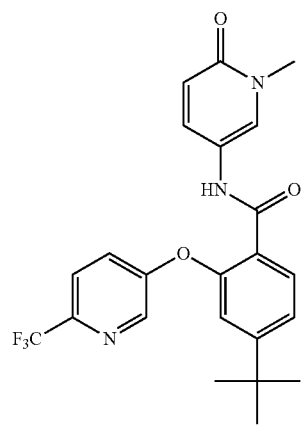 [SMILES: Cn1cc(NC(=O)c2ccc(C(C)(C)C)cc2Oc2ccc(C(F)(F)F)nc2)ccc1=O]

4-(tert-butyl)-N-(1-methyl-6-oxo-
1,6-dihydropyridin-3-yl)-2-((6-
(trifluoromethyl)pyridin-3-
yl)oxy)benzamide

150

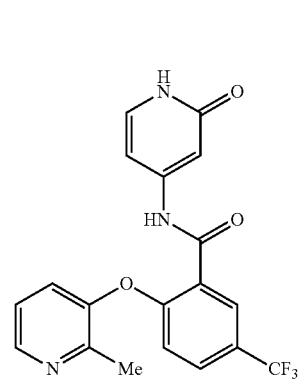

2-((2-methylpyridin-3-yl)oxy)-N-
(2-oxo-1,2-dihydropyridin-4-yl)-5-
(trifluoromethyl)benzamide TABLE 1-continued Compound Numbers, Structures and Chemical Names 151
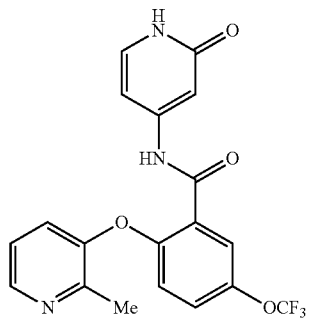 [SMILES: Cc1ncccc1Oc1ccc(OC(F)(F)F)cc1C(=O)Nc1cc[nH]c(=O)c1]
2-((2-methylpyridin-3-yl)oxy)-N-
(2-oxo-1,2-dihydropyridin-4-yl)-5-
(trifluoromethoxy)benzamide 152
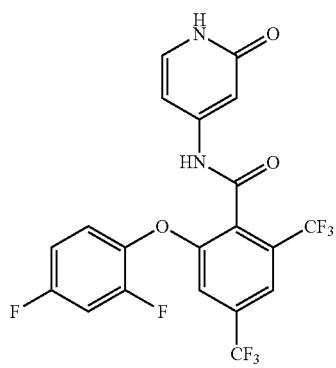 [SMILES: O=C(Nc1cc[nH]c(=O)c1)c1c(Oc2ccc(F)cc2F)cc(C(F)(F)F)cc1C(F)(F)F]
2-(2,4-difluorophenoxy)-N-(2-
oxo-1,2-dihydropyridin-4-yl)-4,6-
bis(trifluoromethyl)benzamide 153
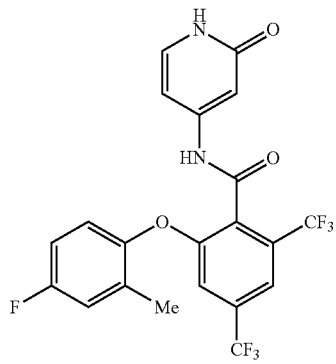
2-(4-fluoro-2-methylphenoxy)-N-
(2-oxo-1,2-dihydropyridin-4-yl)-
4,6-bis(trifluoromethyl)benzamide TABLE 1-continued Compound Numbers, Structures and Chemical Names 154
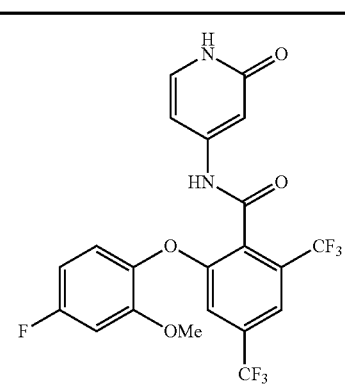
2-(4-fluoro-2-methoxyphenoxy)-N-(2-oxo-
1,2-dihydropyridin-4-yl)-4,6-
bis(trifluoromethyl)benzamide 155
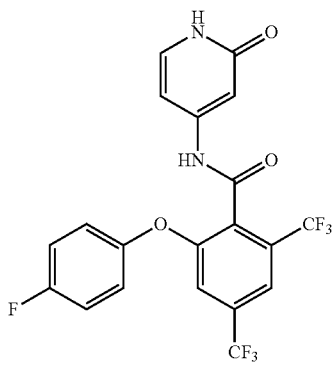 [SMILES: O=C(Nc1cc[nH]c(=O)c1)c1c(Oc2ccc(F)cc2)cc(C(F)(F)F)cc1C(F)(F)F]
2-(4-fluorophenoxy)-N-(2-oxo-1,2-
dihydropyridin-4-yl)-4,6-
bis(trifluoromethyl)benzamide 156
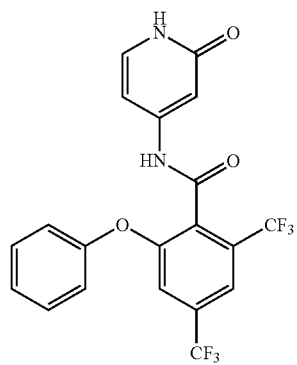 [SMILES: O=C(Nc1cc[nH]c(=O)c1)c1c(Oc2ccccc2)cc(C(F)(F)F)cc1C(F)(F)F]
N-(2-oxo-1,2-dihydropyridin-4-
yl)-2-phenoxy-4,6-
bis(trifluoromethyl)benzamide

TABLE 1-continued

Compound Numbers, Structures and Chemical Names

157

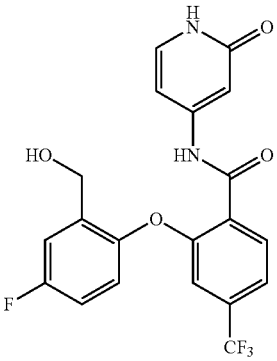 [SMILES: O=C(Nc1cc[nH]c(=O)c1)c1ccc(C(F)(F)F)cc1Oc1ccc(F)cc1CO]

2-(4-fluoro-2-(hydroxymethyl)phenoxy)-N-(2-oxo-1,2-dihydropyridin-4-yl)-4-(trifluoromethyl)benzamide

158

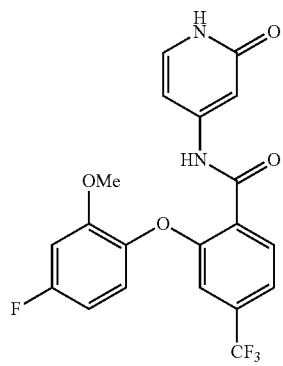 [SMILES: COc1cc(F)ccc1Oc1cc(C(F)(F)F)ccc1C(=O)Nc1cc[nH]c(=O)c1]

2-(4-fluoro-2-methoxyphenoxy)-N-(2-oxo-1,2-dihydropyridin-4-yl)-4-(trifluoromethyl)benzamide

159

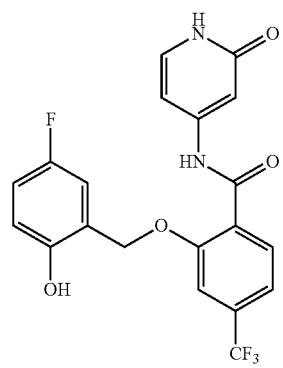 [SMILES: O=C(Nc1cc[nH]c(=O)c1)c1ccc(C(F)(F)F)cc1OCc1cc(F)ccc1O]

2-((5-fluoro-2-hydroxybenzyl)oxy)-N-(2-oxo-1,2-dihydropyridin-4-yl)-4-(trifluoromethyl)benzamide

TABLE 1-continued

Compound Numbers, Structures and Chemical Names

160

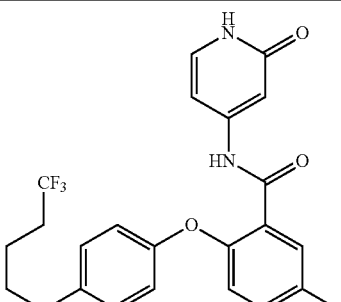

5-fluoro-N-(2-oxo-1,2-dihydropyridin-4-yl)-2-(4-(4,4,4-trifluorobutoxy)phenoxy)benzamide In one embodiment, the compound is 4,5-dichloro-2-(4-fluoro-2-methoxyphenoxy)-N-(2-oxo-1,2-dihydropyridin-4-yl)benzamide or a pharmaceutically acceptable salt thereof.

In another embodiment, the compound is 2-(4-fluoro-2-methoxyphenoxy)-N-(2-oxo-1,2-dihydropyridin-4-yl)-4-(perfluoroethyl)benzamide or a pharmaceutically acceptable salt thereof.

In another embodiment, the compound is 4,5-dichloro-2-(4-fluorophenoxy)-N-(2-oxo-1,2-dihydropyridin-4-yl)benzamide or a pharmaceutically acceptable salt thereof.

In another embodiment, the compound is 4,5-dichloro-2-(3-fluoro-4-methoxyphenoxy)-N-(2-oxo-1,2-dihydropyridin-4-yl)benzamide or a pharmaceutically acceptable salt thereof.

In another embodiment, the compound is 2-(4-fluoro-2-methoxyphenoxy)-N-(2-oxo-1,2-dihydropyridin-4-yl)-5-(trifluoromethyl)benzamide or a pharmaceutically acceptable salt thereof.

In another embodiment, the compound is N-(2-oxo-1,2-dihydropyridin-4-yl)-2-(4-(trifluoromethoxy)phenoxy)-4-(trifluoromethyl)benzamide or a pharmaceutically acceptable salt thereof.

In another embodiment, the compound is 2-(4-fluorophenoxy)-N-(2-oxo-1,2-dihydropyridin-4-yl)-4-(perfluoroethyl)benzamide or a pharmaceutically acceptable salt thereof.

In another embodiment, the compound is 5-chloro-2-(4-fluoro-2-methoxyphenoxy)-N-(2-oxo-1,2-dihydropyridin-4-yl)benzamide or a pharmaceutically acceptable salt thereof.

In another embodiment, the compound is N-(2-oxo-1,2-dihydropyridin-4-yl)-2-(4-(trifluoromethoxy)phenoxy)-5-(trifluoromethyl)benzamide or a pharmaceutically acceptable salt thereof.

In another embodiment, the compound is 2-(4-fluoro-2-methylphenoxy)-N-(2-oxo-1,2-dihydropyridin-4-yl)-4-(trifluoromethyl)benzamide or a pharmaceutically acceptable salt thereof.

In another embodiment, the compound is 2-(4-fluoro-2-methylphenoxy)-N-(2-oxo-1,2-dihydropyridin-4-yl)-5-(trifluoromethyl)benzamide or a pharmaceutically acceptable salt thereof.

In another embodiment, the compound is 2-(2-chloro-4-fluorophenoxy)-N-(2-oxo-1,2-dihydropyridin-4-yl)-5-(trifluoromethyl)benzamide or a pharmaceutically acceptable salt thereof.

In another embodiment, the compound is 5-chloro-2-(4-fluoro-2-methylphenoxy)-N-(2-oxo-1,2-dihydropyridin-4-yl)benzamide or a pharmaceutically acceptable salt thereof.

In another embodiment, the compound is 4-chloro-2-(4-fluoro-2-methylphenoxy)-N-(2-oxo-1,2-dihydropyridin-4-yl)benzamide or a pharmaceeutically acceptable salt thereof.

In another embodiment, the compound is 5-chloro-2-(2-chloro-4-fluorophenoxy)-N-(2-oxo-1,2-dihydropyridin-4-yl)benzamide or a pharmaceutically acceptable salt thereof.

In another embodiment, the compound is 2-((5-fluoro-2-hydroxybenzyl)oxy)-N-(2-oxo-1,2-dihydropyridin-4-yl)-4-(trifluoromethyl)benzamide or a pharmaceutically acceptable salt thereof.

In another embodiment, the compound is N-(2-oxo-1,2-dihydropyridin-4-yl)-2-(o-tolyloxy)-5-(trifluoromethyl)benzamide or a pharmaceutically acceptable salt thereof.

In another embodiment, the compound is 2-(2,4-difluorophenoxy)-N-(2-oxo-1,2-dihydropyridin-4-yl)-4-(trifluoromethyl)benzamide or a pharmaceutically acceptable salt thereof.

In another embodiment, the compound is N-(2-oxo-1,2-dihydropyridin-4-yl)-2-(2-(trifluoromethoxy)phenoxy)-5-(trifluoromethyl)benzamide or a pharmaceutically acceptable salt thereof.

In another embodiment, the compound is 2-(4-fluorophenoxy)-N-(2-oxo-1,2-dihydropyridin-4-yl)-5-(trifluoromethyl)benzamide or a pharmaceutically acceptable salt thereof.

Salts, Compositions, Uses, Formulation, Administration and Additional Agents
Pharmaceutically Acceptable Salts and Compositions As discussed herein, the invention provides compounds that are inhibitors of voltage-gated sodium channels, and thus the present compounds are useful for the treatment of diseases, disorders, and conditions including, but not limited to chronic pain, gut pain, neuropathic pain, musculoskeletal pain, acute pain, inflammatory pain, cancer pain, idiopathic pain, multiple sclerosis, Charcot-Marie-Tooth syndrome, incontinence or cardiac arrhythmia. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising the compound of the invention and a pharmaceutically acceptable carrier.

In another aspect, the invention features a pharmaceutical composition comprising a therapeutically effective amount of the compound or a pharmaceutically acceptable salt thereof of the compounds of formula I or formula I' and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of formula I or formula I' or a pharmaceutically acceptable salt thereof or a pharmaceutical composition thereof. In another aspect, the voltage-gated sodium channel is Nav1.8.

In yet another aspect, the invention features a method of treating or lessening the severity in a subject of chronic pain, gut pain, neuropathic pain, musculoskeletal pain, acute pain, inflammatory pain, cancer pain, idiopathic pain, multiple sclerosis, Charcot-Marie-Tooth syndrome, incontinence or cardiac arrhythmia comprising administering an effective amount of a compound, a pharmaceutically acceptable salt thereof or a pharmaceutical composition of the compounds of formula I or formula I'.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound, a pharmaceutically acceptable salt thereof or a pharmaceutical composition of the compounds of formula I or formula I'.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia wherein said method comprises administering an effective amount of a compound, a pharmaceutically acceptable salt thereof or a pharmaceutical composition of the compounds of formula I or formula I'.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound, a pharmaceutically acceptable salt thereof or a pharmaceutical composition of the compounds of formula I or formula I'.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound, a pharmaceutically acceptable salt thereof or a pharmaceutical composition of the compounds of formula I or formula I'.

In yet another aspect, the invention features a method of treating or lessening the severity in a subject of idiopathic pain, wherein idiopathic pain comprises fibromyalgia pain wherein said method comprises administering an effective amount of a compound, a pharmaceutically acceptable salt thereof or a pharmaceutical composition of the compounds of formula I or formula I'.

In yet another aspect, the invention features a method wherein the subject is treated with one or more additional therapeutic agents administered concurrently with, prior to, or subsequent to treatment with an effective amount of a compound, a pharmaceutically acceptable salt thereof or a pharmaceutical composition of the compounds of formula I or formula I'.

In another aspect, the invention features a method of inhibiting a voltage-gated sodium channel in a subject comprising administering to the subject an effective amount of a compound, a pharmaceutically acceptable salt thereof or a pharmaceutical composition of the compounds of formula I or formula I'. In another aspect, the voltage-gated sodium channel is Nav1.8.

In another aspect, the invention features a method of inhibiting a voltage-gated sodium channel in a biological sample comprising contacting the biological sample with an effective amount of a compound, a pharmaceutically acceptable salt thereof or a pharmaceutical composition of the compounds of formula I or formula I'. In another aspect, the voltage-gated sodium channel is Nav1.8.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain, cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound, a pharmaceutically acceptable salt thereof or a pharmaceutical composition of the compounds of formula I or formula I'.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; hyperactivity bladder; painful bladder syndrome; interstitial cystitis (IC); prostatitis; complex regional pain syndrome (CRPS), type I and type II; widespread pain, paroxysmal extreme pain, pruritis, tinnitus, or angina-induced pain, comprising administering an effective amount of a compound, a pharmaceutically acceptable salt thereof or a pharmaceutical composition of the compounds of formula I or formula I'.

In another aspect, the invention features a method of treating or lessening the severity in a subject of neuropathic pain comprising administering an effective amount of a compound, a pharmaceutically acceptable salt thereof or a pharmaceutical composition of the compounds of formula I or formula I'. In one aspect, the neuropathic pain is selected from post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic cephalalgia.

Manufacture of Medicaments

In one aspect, the invention provides the use of a compound or pharmaceutical composition described herein for the manufacture of a medicament for use in inhibiting a voltage-gated sodium channel. In another aspect, the voltage-gated sodium channel is Nav1.8.

In yet another aspect, the invention provides the use of a compound or pharmaceutical composition described herein for the manufacture of a medicament for use in treating or lessening the severity in a subject of chronic pain, gut pain, neuropathic pain, musculoskeletal pain, acute pain, inflammatory pain, cancer pain, idiopathic pain, multiple sclerosis, Charcot-Marie-Tooth syndrome, incontinence or cardiac arrhythmia.

In yet another aspect, the invention provides the use of a compound or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides the use of a compound or pharmaceutical composition described herein for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic neuropathy.

In yet another aspect, the invention provides the use of a compound or pharmaceutical composition described herein for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention the invention provides the use of a compound or pharmaceutical composition described herein for the manufacture of a medicament for use in treating or lessening the severity in a subject of inflammatory pain, wherein inflammatory pain comprises rheumatoid arthritis pain or vulvodynia.

In yet another aspect, the invention provides the use of a compound or pharmaceutical composition described herein for the manufacture of a medicament for use in treating or lessening the severity in a subject of idiopathic pain, wherein idiopathic pain comprises fibromyalgia pain.

In yet another aspect, the invention provides the use of a compound or pharmaceutical composition described herein for the manufacture of a medicament in combination with one or more additional therapeutic agents administered concurrently with, prior to, or subsequent to treatment with the compound or pharmaceutical composition.

In another aspect, the invention provides the use of a compound or pharmaceutical composition described herein for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head pain, neck pain, severe pain, intractable pain, nociceptive pain, breakthrough pain, post-surgical pain, cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound or pharmaceutical composition described herein for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitus, or angina-induced pain.

In another aspect, the invention provides the use of a compound or pharmaceutical composition described herein for the manufacture of a medicament for use in treating or lessening the severity of neuropathic pain. In one aspect, the neuropathic pain is selected from post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic cephalalgia.

Administration of Pharmaceutically Acceptable Salts and Compositions.

In certain embodiments of the invention an "effective amount" of the compound, a pharmaceutically acceptable salt thereof or pharmaceutically acceptable composition is that amount effective for treating or lessening the severity of one or more of chronic pain, gut pain, neuropathic pain, musculoskeletal pain, acute pain, inflammatory pain, cancer pain, idiopathic pain, multiple sclerosis, Charcot-Marie-Tooth syndrome, incontinence or cardiac arrhythmia.

The compounds and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds and compositions of the invention are inhibitors of $Na_V1.8$ and thus, without wishing to be bound by any particular theory, the compounds and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in the Examples herein, or according to methods available to one of ordinary skill in the art.

Additional Therapeutic Agents

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anaesthetic such as mexiletine;

(20) a corticosteroid such as dexamethasone;

(21) a 5-HT receptor agonist or antagonist, particularly a $5\text{-HT}_{1B/1D}$ agonist such as eletriptan, sumatriptan, naratriptan, zolmitriptan or rizatriptan;

(22) a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]

indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethyl-venlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) an $Na_V1.7$ blocker, such as XEN-402 and such as those disclosed in WO2011/140425; WO2012/106499; WO2012/112743; WO2012/125613 or PCT/US2013/21535 the entire contents of each application hereby incorporated by reference.

(39) an $Na_V1.8$ blocker, such as those disclosed in WO2008/135826 and WO2006/011050 the entire contents of each application hereby incorporated by reference.

(40) a combined $Na_V1.7$ and $Na_V1.8$ blocker, such as DSP-2230 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

The amount of additional therapeutic agent present in the compositions of this invention will be no more than the amount that would normally be administered in a composition comprising that therapeutic agent as the only active agent. The amount of additional therapeutic agent in the presently disclosed compositions will range from about 10% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of formula I or formula I' or a composition comprising said compound. The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

Schemes and Examples

The compounds of the invention may be prepared readily using the following methods. Illustrated below in Scheme 1 through Scheme 3 are general methods for preparing the compounds of the present invention.

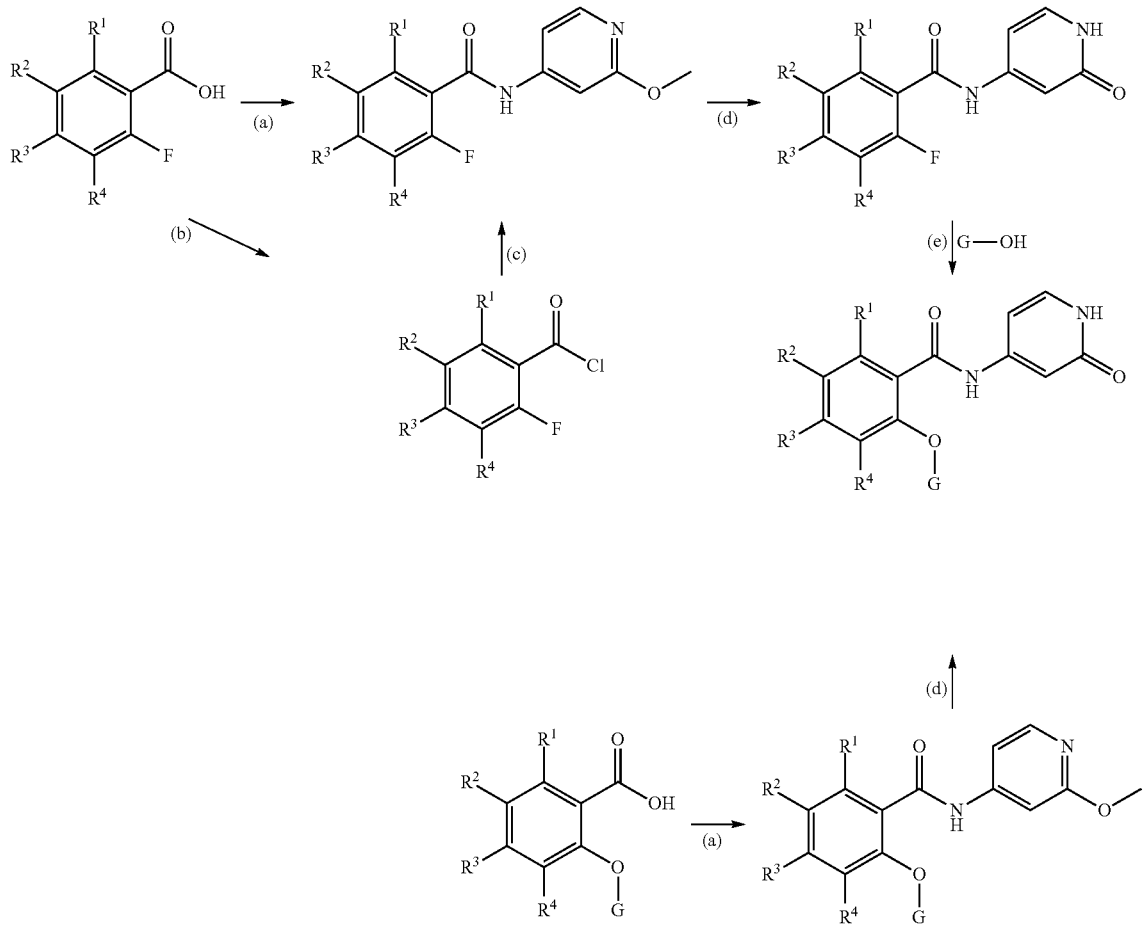

Scheme 1: General Preparation of Compounds of Formula I (a) 2-Methoxypyridin-4-amine, coupling agent (i.e. HATU, EDCI, HOBT), base (i.e. N-methylmorpholine, $Et_3N$), solvent (i.e. DMF, dichloromethane); (b) $SO_2Cl_2$, DMF in a solvent (i.e. dichloromethane); (c) 2-Methoxypyridin-4-amine, base (i.e. pyridine), solvent (i.e. dichloromethane, DMF); (d) TMSI or HBr, solvent (i.e. acetonitrile or acetic acid); (e) base (i.e. $Cs_2CO_3$, $Na_2CO_3$, $K_2CO_3$, $NaHCO_3$), solvent (DMF, NMP, dioxane), heat.

Scheme 2: General Preparation of Compunds of Formula I'

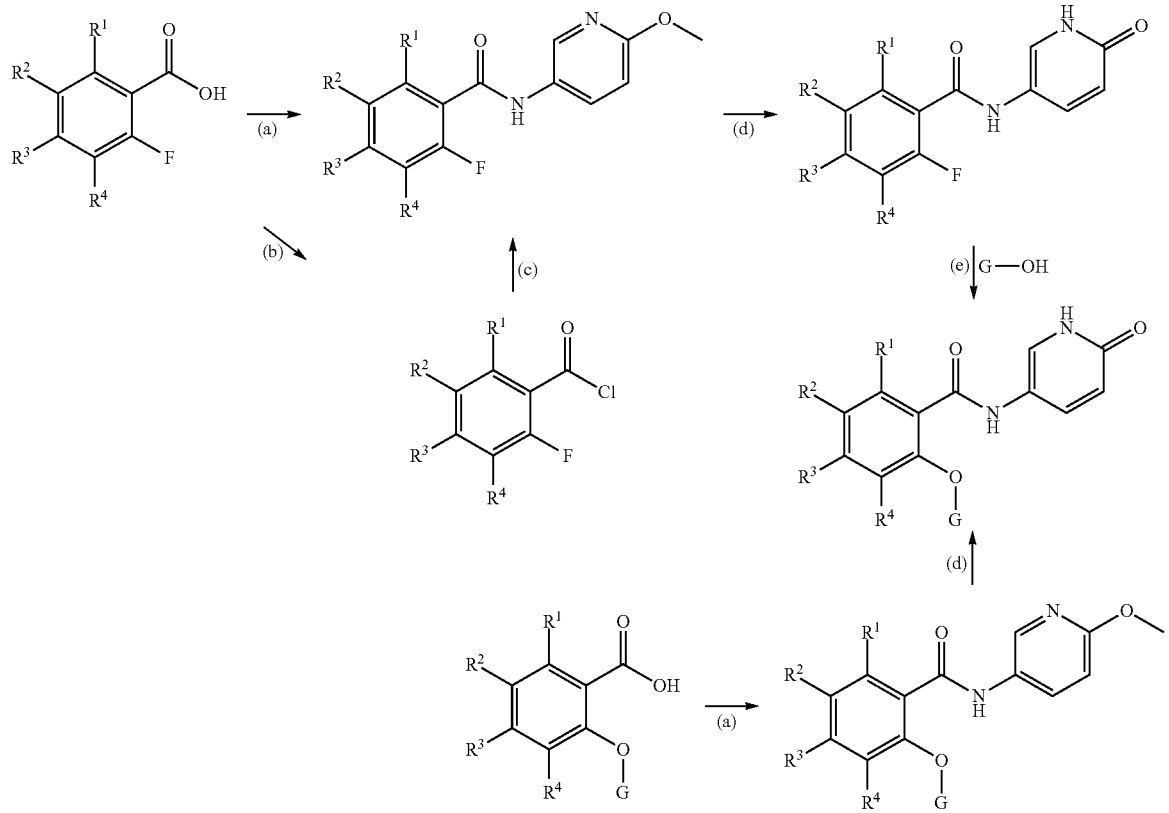

(a) 6-Methoxypyridin-3-amine, coupling agent (i.e. HATU, EDCI, HOBT), base (i.e. N-methylmorpholine, Et₃N), solvent (i.e. DMF, dichloromethane); (b) SO₂Cl₂, DMF in a solvent (i.e. dichloromethane); (c) 6-Methoxypyridin-3-amine, base (i.e. pyridine), solvent (i.e. dichloromethane, DMF); (d) TMSI or HBr, solvent (i.e. acetonitrile or acetic acid); (e) base (i.e. Cs₂CO₃, Na₂CO₃, K₂CO₃, NaHCO₃), solvent (DMF, NMP, dioxane), heat.

Scheme 3: General Preparation of Compounds of Formula I

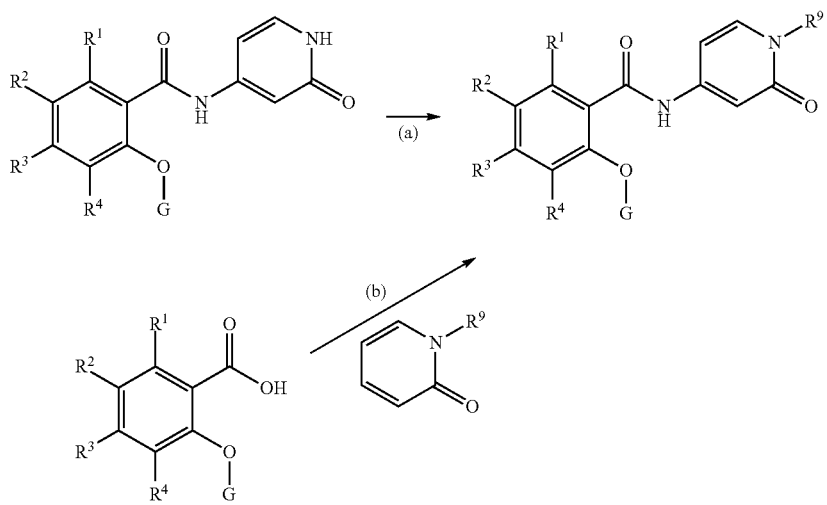

(a) R⁹—X (X=Cl, Br or I), base (i.e. NaH), solvent (i.e., DMF), heat or (b) coupling agent (i.e. HATU), base (i.e. Et₃N), solvent (i.e. dichloromethane).

EXAMPLES

General Methods $^1$H NMR (400 MHz) spectra were obtained as solutions in an appropriate deuterated solvent such as dimethyl sulfoxide-$d_6$ (DMSO). Mass spectra (MS) were obtained using an Applied Biosystems API EX LC/MS system. Compound purity and retention times were determined by reverse phase HPLC using a Kinetix C18 column (50×2.1 mm, 1.7 µm particle) from Phenomenex (pn: 00B-4475-AN)), and a dual gradient run from 1-99% mobile phase B over 3 minutes. Mobile phase A=$H_2O$ (0.05% $CF_3CO_2H$). Mobile phase B=$CH_3CN$ (0.05% $CF_3CO_2H$). Flow rate=2 mL/min, injection volume=3 µL, and column temperature=50° C. Silica gel chromatography was performed using silica gel-60 with a particle size of 230-400 mesh. Pyridine, dichloromethane ($CH_2Cl_2$), tetrahydrofuran (THF), dimethylformamide (DMF), acetonitrile (ACN), methanol (MeOH), and 1,4-dioxane were from Baker or Aldrich and in some cases the reagents were Aldrich Sure-Seal bottles kept under dry nitrogen. All reactions were stirred magnetically unless otherwise noted.

Example 1

Preparation of 2-fluoro-N-(2-oxo-1,2-dihydropyridin-4-yl)-4-(trifluoromethyl)benzamide

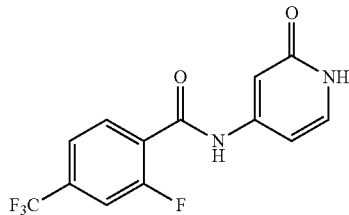 [SMILES: O=C(Nc1cc[nH]c(=O)c1)c1ccc(C(F)(F)F)cc1F]

A solution of 2-fluoro-4-(trifluoromethyl)benzoyl chloride (25.0 g, 110.3 mmol) in dichloromethane (125.0 mL) was added drop-wise to a mixture of 2-methoxypyridin-4-amine (13.7 g, 110.3 mmol), pyridine (26.8 mL, 330.9 mmol) and dichloromethane (500.0 mL) at 0° C. The mixture was allowed to warm to room temperature and was stirred at that temperature overnight. The mixture was poured into 1N HCl (200 mL) and dichloromethane (200 mL). The layers were separated and the organic layer was dried over sodium sulfate, filtered and concentrated under reduced pressure. The product was slurried in hexane, the hexane was decanted and the product was dried under reduced pressure to yield 2-fluoro-N-(2-methoxy-4-pyridyl)-4-(trifluoromethyl)benzamide (25.7 g, 74%) as a cream solid. ESI-MS m/z calc. 314.07. found 315.3 (M+1)$^+$; Retention time: 1.49 minutes (3 minutes run). $^1$H NMR (400 MHz, DMSO-d6) δ 10.96 (s, 1H), 8.15-8.04 (m, 1H), 8.00-7.85 (m, 2H), 7.76 (d, J=8.1 Hz, 1H), 7.26-7.15 (m, 2H), 3.85 (s, 3H) ppm.

To 2-fluoro-N-(2-methoxy-4-pyridyl)-4-(trifluoromethyl)benzamide (1.00 g, 3.18 mmol) in acetic acid (6.0 mL) was added HBr (33% in acetic acid) (3.9 mL of 33% w/v, 15.91 mmol) and the mixture stirred at 100° C. for 6 hours. Additional HBr (2 mL, 33% in acetic acid) was added and the mixture was stirred at room temperature overnight. The mixture was then heated at 100° C. for 2 hours before it was cooled to room temperature. The mixture was partitioned between ethyl acetate and water. The layers were separated and the aqueous layer was extracted with ethyl acetate (3×). The combined organics were washed with water and brine (2×), dried over sodium sulfate, filtered and concentrated under reduced pressure. The solid was slurried in methyl-tert-butyl ether and filtered to give 2-fluoro-N-(2-oxo-1H-pyridin-4-yl)-4-(trifluoromethyl)benzamide (731 mg, 76%). ESI-MS m/z calc. 301.05. found 301.3 (M+1)$^+$; Retention time: 1.35 minutes (3 minute run). $^1$H NMR (400 MHz, DMSO-d6) δ 11.33 (s, 1H), 10.70 (s, 1H), 7.96-7.85 (m, 2H), 7.75 (d, J=8.2 Hz, 1H), 7.35 (d, J=7.2 Hz, 1H), 6.81 (d, J=1.9 Hz, 1H), 6.41 (dd, J=7.2, 2.1 Hz, 1H) ppm.

Example 2

Preparation of 2-fluoro-N-(2-oxo-1,2-dihydropyridin-4-yl)-5-(trifluoromethyl)benzamide

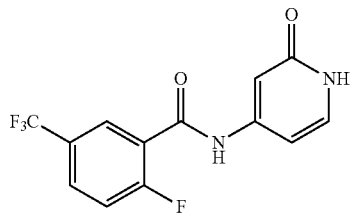 [SMILES: O=C(Nc1cc[nH]c(=O)c1)c1cc(C(F)(F)F)ccc1F]

A solution of 2-fluoro-5-(trifluoromethyl)benzoyl chloride (25 g, 110.3 mmol) in dichloromethane (125.0 mL) was added drop-wise to a mixture of 2-methoxypyridin-4-amine (13.7 g, 110.3 mmol), pyridine (26.8 mL, 330.9 mmol) and dichloromethane (500.0 mL) at 0° C. The mixture was allowed to warm to room temperature and was stirred at that temperature overnight. The mixture was poured into 1N HCl (200 mL) and dichloromethane (200 mL). The layers were separated and the organic layer was dried over sodium sulfate, filtered and concentrated under reduced pressure to give 2-fluoro-N-(2-methoxy-4-pyridyl)-5-(trifluoromethyl)benzamide (33.6 g, 97.00%) as an off-white solid. ESI-MS m/z calc. 314.07. found 315.2 (M+1)+; Retention time: 1.44 minutes (3 minutes run). $^1$H NMR (400 MHz, DMSO-d6) δ 10.94 (s, 1H), 8.12-8.07 (m, 2H), 8.07-7.98 (m, 1H), 7.65 (t, J=9.2 Hz, 1H), 7.24-7.19 (m, 2H), 3.85 (s, 3H) ppm.

To 2-fluoro-N-(2-methoxy-4-pyridyl)-5-(trifluoromethyl)benzamide (3.54 g, 11.27 mmol) in acetonitrile (118.0 mL) was added TMSI (4.0 mL, 28.18 mmol). The reaction was stirred at 50° C. overnight. The acetonitrile was evaporated and the crude re-dissolved in ethyl acetate. The organics were washed with water, dried over sodium sulfate, filtered and concentrated. Purification by silica gel chromatography using a gradient of ethyl acetate in hexanes (0-100%) and then methanol in dichloromethane (0-20%) gave 2-fluoro-N-(2-oxo-1H-pyridin-4-yl)-5-(trifluoromethyl)benzamide (3 g, 89%), as a brown solid. ESI-MS m/z calc. 300.05. found 301.3 (M+1)$^+$; Retention time: 1.34 minutes (3 minutes run). $^1$H NMR (400 MHz, DMSO-d6) δ 10.85 (s, 1H), 8.10 (dd, J=6.0, 2.2 Hz, 1H), 8.03 (m, 1H), 7.65 (t, J=9.2 Hz, 1H), 7.49 (d, J=7.1 Hz, 1H), 6.97 (d, J=2.0 Hz, 1H), 6.57 (dd, J=7.2, 2.1 Hz, 1H), 5.07 (s, 2H) ppm.

Example 3

Preparation of 4-chloro-2-fluoro-N-(2-oxo-1,2-dihydropyridin-4-yl)benzamide

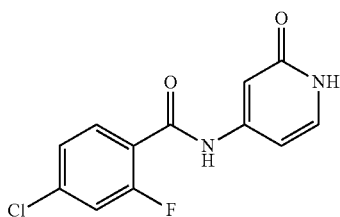 [SMILES: O=C(Nc1cc[nH]c(=O)c1)c1ccc(Cl)cc1F]

A solution of 4-chloro-2-fluoro-benzoic acid (7.0 g, 40.10 mmol), HATU (15.25 g, 40.10 mmol), 2-methoxypyridin-4-amine (4.98 g, 40.10 mmol) and Et$_3$N (22.4 mL, 160.4 mmol) in dichloromethane (63.0 mL) was stirred at room temperature overnight. The crude mixture was purified by column chromatography eluting with a gradient of ethyl acetate in hexanes (0-50%) to yield 4-chloro-2-fluoro-N-(2-methoxy-4-pyridyl)benzamide (4.35 g, 39%), as a white solid. ESI-MS m/z calc. 280.04. found 281.3 (M+1)$^+$; Retention time: 1.31 minutes (3 minutes run). $^1$H NMR (400 MHz, DMSO-d6) δ 10.80 (s, 1H), 8.09 (m, 1H), 7.73 (t, J=8.0 Hz, 1H), 7.66 (dd, J=10.1, 1.9 Hz, 1H), 7.46 (dd, J=8.3, 1.9 Hz, 1H), 7.21 (m, 2H), 3.84 (s, 3H) ppm.

To 4-chloro-2-fluoro-N-(2-methoxy-4-pyridyl)benzamide (4.35 g, 15.50 mmol) in acetonitrile (145.0 mL) was added TMSI (8.8 mL, 62.0 mmol). The reaction was stirred at 50° C. overnight. The acetonitrile was evaporated and the crude solid was triturated with ethyl acetate. The solid was isolated by filtration and washed with ethyl acetate to give 4-chloro-2-fluoro-N-(2-oxo-1H-pyridin-4-yl)benzamide (3.8 g, 92%). ESI-MS m/z calc. 266.02. found 267.1 (M+1)+; Retention time: 1.23 minutes (3 minutes run). $^1$H NMR (400 MHz, DMSO-d6) δ 10.86 (s, 1H), 7.73 (t, J=8.0 Hz, 1H), 7.68 (dd, J=10.1, 1.9 Hz, 1H), 7.60 (d, J=7.1 Hz, 1H), 7.47 (dd, J=8.3, 2.0 Hz, 1H), 7.11 (d, J=2.0 Hz, 1H), 6.71 (dd, J=7.1, 2.1 Hz, 1H) ppm.

Example 4

Preparation of 5-chloro-2-fluoro-N-(2-oxo-1,2-dihydropyridin-4-yl)benzamide

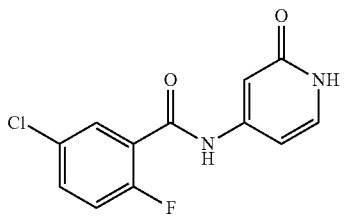 [SMILES: O=C(Nc1cc[nH]c(=O)c1)c1cc(Cl)ccc1F]

A solution of 5-chloro-2-fluoro-benzoic acid (5.0 g, 28.64 mmol), HATU (10.89 g, 28.64 mmol), 2-methoxypyridin-4-amine (3.6 g, 28.64 mmol) and Et$_3$N (15.98 mL, 114.60 mmol) in dichloromethane (45.0 mL) was stirred at room temperature overnight. The crude mixture was purified by column chromatography eluting with a gradient of ethyl acetate in hexanes (0-50%) to yield 5-chloro-2-fluoro-N-(2-methoxy-4-pyridyl)benzamide (3.8 g, 47%) as a white solid. ESI-MS m/z calc. 280.04. found 281.3 (M+1)$^+$; Retention time: 1.31 minutes (3 minutes run).

To 5-chloro-2-fluoro-N-(2-methoxy-4-pyridyl)benzamide (3.8 g, 13.50 mmol) in acetonitrile (126.3 mL) was added TMSI (7.7 mL, 54.00 mmol). The reaction was stirred at 50° C. overnight. The acetonitrile was evaporated and the crude re-dissolved in ethyl acetate. The organics were washed with water, dried over sodium sulfate, filtered and concentrated. Purification by silica gel chromatography using a gradient of ethyl acetate in hexanes (0-100%) and then methanol in dichloromethane (0-20%) yielded 5-chloro-2-fluoro-N-(2-oxo-1H-pyridin-4-yl)benzamide (950 mg, 26%) as a white solid. ESI-MS m/z calc. 266.03. found 267.1 (M+1)$^+$; Retention time: 1.24 minutes (3 minutes run).

Example 5

Preparation of 5-chloro-2-fluoro-N-(2-oxo-1,2-dihydropyridin-4-yl)benzamide

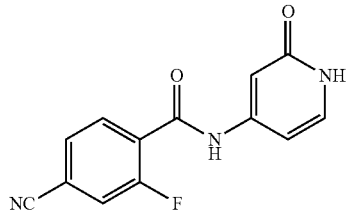 [SMILES: N#Cc1ccc(C(=O)Nc2cc[nH]c(=O)c2)c(F)c1]

A solution of 4-cyano-2-fluoro-benzoic acid (6.7 g, 40.58 mmol), HATU (15.4 g, 40.58 mmol), 2-methoxypyridin-4-amine (5.0 g, 40.58 mmol) and Et$_3$N (22.62 mL, 162.3 mmol) in dichloromethane (60.3 mL) was stirred at room temperature overnight. The crude mixture was purified by column chromatography using a gradient of ethyl acetate in hexanes (0-50%) to yield 4-cyano-2-fluoro-N-(2-methoxy-4-pyridyl)benzamide (7.3 g, 66%) as a white solid. ESI-MS m/z calc. 271.07. found 272.1 (M+1)$^+$; Retention time: 1.17 minutes (3 minutes run).

To 4-cyano-2-fluoro-N-(2-methoxy-4-pyridyl)benzamide (7.3 g, 26.99 mmol) in acetonitrile (244.0 mL) was added TMSI (9.99 mL, 70.17 mmol). The reaction was stirred at 50° C. overnight. The acetonitrile was evaporated and the crude solid was triturated with ethyl acetate. The solid was isolated by filtration and washed with ethyl acetate to give 4-cyano-2-fluoro-N-(2-oxo-1H-pyridin-4-yl)benzamide as a tan solid. ESI-MS m/z calc. 257.06. found 258.1 (M+1)$^+$; Retention time: 1.08 minutes (3 minutes run). $^1$H NMR (400 MHz, DMSO-d6) δ 10.94 (s, 1H), 8.11 (t, J=11.4 Hz, 1H), 7.88 (m, 2H), 7.53 (d, J=7.1 Hz, 1H), 7.01 (d, J=2.0 Hz, 1H), 6.60 (dd, J=7.2, 2.1 Hz, 1H) ppm.

Example 6

Preparation of 2-fluoro-N-(2-oxo-1,2-dihydropyridin-4-yl)-5-(trifluoromethoxy)benzamide

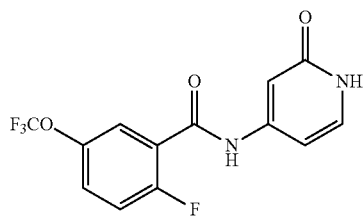 [SMILES: O=C(Nc1cc[nH]c(=O)c1)c1cc(OC(F)(F)F)ccc1F]

A solution of 2-fluoro-5-(trifluoromethoxy)benzoic acid (5.3 g, 23.47 mmol), HATU (8.92 g, 23.47 mmol), 2-methoxypyridin-4-amine (2.9 g, 23.47 mmol) and Et$_3$N (13.09 mL, 93.88 mmol) in dichloromethane (47.4 mL) was stirred at room temperature overnight. The crude mixture was purified by column chromatography eluting with a gradient of ethyl acetate in hexanes (0-50%) to yield 2-fluoro-N-(2-methoxy-4-pyridyl)-5-(trifluoromethoxy)benzamide (5.03 g, 65%) as a white solid. ESI-MS m/z calc. 330.06. found 331.1 (M+1)$^+$; Retention time: 1.48 minutes (3 minutes run). $^1$H NMR (400 MHz, DMSO-d6) δ 10.90 (s, 1H), 8.10 (m, 1H), 7.73 (dd, J=5.1, 3.2 Hz, 1H), 7.66 (m, 1H), 7.55 (t, J=9.2 Hz, 1H), 7.21 (dd, J=3.7, 1.8 Hz, 2H), 3.84 (s, 3H) ppm.

To 2-fluoro-N-(2-methoxy-4-pyridyl)-5-(trifluoromethoxy)benzamide (5.0 g, 15.23 mmol) in acetonitrile (167.6 mL) was added TMSI (5.6 mL, 39.60 mmol). The reaction was stirred at 50° C. overnight. The acetonitrile was evaporated and the crude re-dissolved in ethyl acetate. The organics were washed with water, dried over sodium sulfate, filtered and concentrated. Purification by silica gel chromatography a gradient of ethyl acetate in hexanes (0-100%) followed by methanol in dichloromethane (0-20%) yielded 2-fluoro-N-(2-oxo-1H-pyridin-4-yl)-5-(trifluoromethoxy) benzamide (3 g, 62%), as a grey solid. ESI-MS m/z calc. 316.05. found 317.1 (M+1)$^+$; Retention time: 1.39 minutes (3 minutes run). $^1$H NMR (400 MHz, DMSO-d6) δ 10.80 (s, 1H), 7.73 (m, 1H), 7.67 (dd, J=8.7, 3.7 Hz, 1H), 7.55 (t, J=9.1 Hz, 1H), 7.48 (d, J=7.1 Hz, 1H), 6.96 (d, J=2.0 Hz, 1H), 6.55 (dd, J=7.2, 2.1 Hz, 1H) ppm.

Example 7

Preparation of 2-fluoro-N-(2-oxo-1,2-dihydropyridin-4-yl)-4-(perfluoroethyl)benzamide

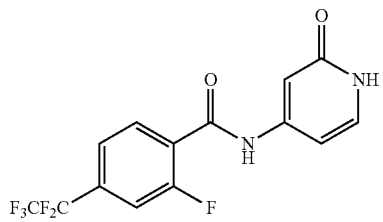

A solution of 4-bromo-2-fluoro-benzoyl chloride (2 g, 8.42 mmol) in dichloromethane (10.0 mL) was added drop-wise to a mixture of 2-methoxypyridin-4-amine (1.0 g, 8.42 mmol), pyridine (2.0 mL, 25.27 mmol) and dichloromethane (40.0 mL) at 0° C. The mixture was allowed to warm to room temperature and was stirred at that temperature overnight. The mixture was poured into 1N HCl (200 mL) and dichloromethane (200 mL). The layers were separated and the organic layer was dried over sodium sulfate, filtered and concentrated under reduced pressure to give 4-bromo-2-fluoro-N-(2-methoxy-4-pyridyl)benzamide (1.2 g, 44%) as an off-white solid. ESI-MS m/z calc. 323.99. found 325.1 (M+1)$^+$; Retention time: 1.37 minutes (3 minutes run). $^1$H NMR (400 MHz, DMSO-d6) δ 10.80 (s, 1H), 8.11-8.06 (m, 1H), 7.79 (dd, J=9.8, 1.7 Hz, 1H), 7.68-7.62 (m, 1H), 7.59 (dd, J=8.3, 1.7 Hz, 1H), 7.23-7.18 (m, 2H), 3.84 (s, 3H) ppm.

To a stirred solution of 4-bromo-2-fluoro-N-(2-methoxy-4-pyridyl)benzamide (800 mg, 2.46 mmol) and copper (1.6 g, 24.61 mmol) in DMSO (15 mL), in a bomb, 1,1,1,2,2-pentafluoro-2-iodo-ethane (4.1 g, 16.47 mmol) was bubbled through. The vessel was sealed and heated at 120° C. for 16 hours. The reaction mixture was diluted with water and filtered through a plug of silica and then extracted with ethyl acetate (4×). The organics combined, washed with brine, dried over Na$_2$SO$_4$, filtered and evaporated to dryness to yield a crude mixture that was purified by column chromatography using a gradient of ethyl acetate in hexanes (0-40%) to give 2-fluoro-N-(2-methoxy-4-pyridyl)-4-(1,1,2,2,2-pentafluoroethyl)benzamide (200 mg, 22%) as an off white solid. ESI-MS m/z calc. 364.06. found 365.3 (M+1)+; Retention time: 1.39 minutes (3 minutes run). $^1$H NMR (400 MHz, DMSO-d6) δ 10.98 (s, 1H), 8.11 (d, J=6.3 Hz, 1H), 7.95 (dd, J=7.4 Hz, 1H), 7.89 (d, J=9.9 Hz, 1H), 7.72 (d, J=9.1 Hz, 1H), 7.23-7.19 (m, 2H), 3.85 (s, 3H) ppm.

2-fluoro-N-(2-methoxy-4-pyridyl)-4-(1,1,2,2,2-pentafluoroethyl)benzamide (200 mg, 0.55 mmol) in HBr in acetic acid (1.3 mL of 33% w/v, 5.49 mmol) was stirred at 100° C. for 2 hours, at this time 1 ml of HBr in acetic acid (33% w/v) was added and the mixture was stirred at 100° C. for 4 hours, then cooled to room temperature. The reaction mixture was diluted with water and a precipitate formed. The precipitate was filtered off, washed with water (2×), cold methyl-tert-butyl ether and dried under vacuum to give 2-fluoro-N-(2-oxo-1H-pyridin-4-yl)-4-(1,1,2,2,2-pentafluoroethyl)benzamide (138 mg, 72%) as a light grey solid. ESI-MS m/z calc. 350.05. found 351.3 (M+1)+; Retention time: 1.3 minutes (3 minutes run).

Example 8

Preparation of 2,5-difluoro-N-(2-oxo-1,2-dihydropyridin-4-yl)benzamide

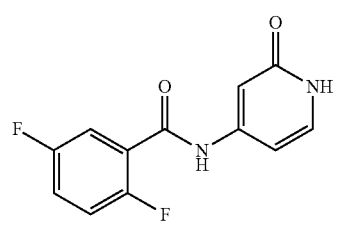 [SMILES: O=C(Nc1cc[nH]c(=O)c1)c1cc(F)ccc1F]

A solution of 2,5-difluorobenzoyl chloride (2.0 mL, 16.14 mmol) and dichloromethane (14.25 mL) was added dropwise to a mixture of 2-methoxypyridin-4-amine (2.0 g, 16.14 mmol), pyridine (3.9 mL, 48.42 mmol) and dichloromethane (57.0 mL) at 0° C. The mixture was allowed to warm to room temperature and was stirred at that temperature overnight. The mixture was poured into 1N HCl and dichloromethane. The layers were separated and the organic layer was dried over sodium sulfate, filtered and concentrated under reduced pressure to give a tan solid. The solid was slurried in hexanes (150 mL) and was filtered to give 2,5-difluoro-N-(2-methoxy-4-pyridyl)benzamide (2.61 g, 61%) as a tan solid. ESI-MS m/z calc. 264.07. found 265.3 (M+1)+; Retention time: 1.22 minutes (3 minutes run). $^1$H NMR (400 MHz, DMSO-d6) δ 10.83 (s, 1H), 8.12-8.05 (m, 1H), 7.58 (ddd, J=8.3, 5.4, 2.9 Hz, 1H), 7.52-7.41 (m, 2H), 7.25-7.19 (m, 2H), 3.84 (s, 3H) ppm.

To 2,5-difluoro-N-(2-methoxy-4-pyridyl)benzamide (2.60 g, 9.84 mmol) in acetic acid (15.60 mL) was added HBr 33% in acetic acid (12.1 mL of 33% w/v, 49.20 mmol) and the mixture was stirred at 90° C. for 5 h. Additional HBr (10 mL, 33% in acetic acid) was added and the mixture was stirred at 90° C. overnight. The mixture was cooled to room temperature and was poured into water (200 mL). The mixture was stirred and the solid was collected by filtration. The solid was washed with water (2×50 mL). The solid was slurried in hexanes (2×50 mL) and filtered to give 2,5-difluoro-N-(2-oxo-1H-pyridin-4-yl)benzamide (2.30 g, 9.19 mmol, 93%). ESI-MS m/z calc. 250.05. found 251.3 (M+1)+; Retention time: 1.16 minutes (3 minutes run). $^1$H NMR (400 MHz, DMSO-d6) δ 11.31 (s, 1H), 10.59 (s, 1H), 7.56 (ddd, J=8.2, 5.4, 3.0 Hz, 1H), 7.46 (pd, J=9.1, 4.4 Hz, 2H), 7.33 (d, J=7.2 Hz, 1H), 6.81 (d, J=2.0 Hz, 1H), 6.42 (dd, J=7.2, 2.1 Hz, 1H) ppm.

Example 9

Preparation of 4,5-dichloro-2-fluoro-N-(2-oxo-1,2-dihydropyridin-4-yl)benzamide

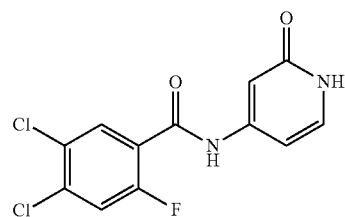 [SMILES: O=C(Nc1cc[nH]c(=O)c1)c1cc(Cl)c(Cl)cc1F]

A solution of 2-methoxypyridin-4-amine (186.2 mg, 1.5 mmol), 4,5-dichloro-2-fluoro-benzoic acid (285.1 mg, 1.36 mmol), HATU (622.4 mg, 1.64 mmol) and n-methylmorpholine (299.9 µL, 2.73 mmol) in DMF (3 mL) was stirred at room temperature for 16 hours. The reaction mixture was poured into water and extracted with ethyl acetate (3×). The organics were combined, washed with water (3×), brine and dried over Na$_2$SO$_4$, filtered through a short plug of silica and evaporated to dryness. The material was taken up in HBr (in acetic acid) (6.689 mL of 33% w/v, 27.28 mmol) and stirred at 95° C. for 16 h. The solution was cooled to room temperature, filtered and solid product washed with water (2×) and then ether (2×) and dried under vacuum to give 4,5-dichloro-2-fluoro-N-(2-oxo-1H-pyridin-4-yl)benzamide (250 mg, 61%) as an off white solid. ESI-MS m/z calc. 299.99. found 301.3 (M+1)+; Retention time: 1.16 minutes (3 minutes run).

Example 10

Preparation of 4-chloro-2,5-difluoro-N-(2-oxo-1,2-dihydropyridin-4-yl)benzamide

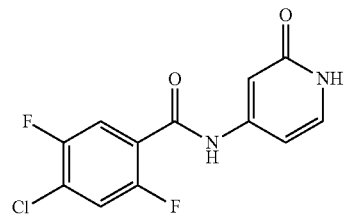 [SMILES: O=C(Nc1cc[nH]c(=O)c1)c1cc(F)c(Cl)cc1F]

A solution of 4-chloro-2,5-difluoro-benzoyl chloride (5 g, 23.70 mmol) in dichloromethane (25 mL) was added dropwise to a mixture of 2-methoxypyridin-4-amine (2.94 g, 23.70 mmol), pyridine (5.75 mL, 71.10 mmol) and dichloromethane (100.0 mL) at 0° C. The mixture was allowed to warm to room temperature and was stirred at that temperature for 43 hours. The mixture was poured into 1N HCl (50 mL). The mixture was filtered using dichloromethane and the solid was isolated. The solid was dried under vacuum to yield 4-chloro-2,5-difluoro-N-(2-methoxy-4-pyridyl)benzamide (6.2 g, 88%) as a pink solid. $^1$H NMR (400 MHz, DMSO-d6) δ 10.89 (s, 1H), 8.16-8.05 (m, 1H), 7.97-7.75 (m, 2H), 7.29-7.15 (m, 2H), 3.85 (s, 3H) ppm. ESI-MS m/z calc. 298.03. found 299.3 (M+1)+; Retention time: 1.43 minutes (3 minutes run).

To 4-chloro-2,5-difluoro-N-(2-methoxy-4-pyridyl)benzamide (3 g, 10.04 mmol) in HOAc (15.9 mL) was added HBr 33% in HOAc (12.31 mL of 33% w/v, 50.20 mmol) and the mixture was stirred at 90° C. for 5 h. Additional HBr (10 mL, 33% in HOAc) was added and the mixture was stirred at 90° C. overnight. The mixture was cooled to room temperature and was poured into water (100 mL). The mixture was stirred and the solid was collected by filtration. The solid was washed with water (2×50 mL). The solid was slurried in hexanes (2×50 mL) and filtered to give 4-chloro-2,5-difluoro-N-(2-oxo-1H-pyridin-4-yl)benzamide (969.7 mg, 34%) as a cream colored solid. ESI-MS m/z calc. 284.02. found 285.3 (M+1)+; Retention time: 1.36 minutes (3 min run).

Example 11

Preparation of 2-fluoro-N-(2-oxo-1,2-dihydropyridin-4-yl)-4,6-bis(trifluoromethyl)benzamide

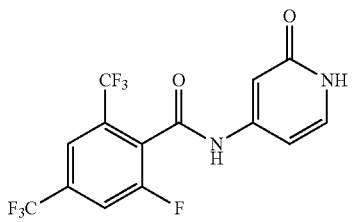 [SMILES: O=C(Nc1cc[nH]c(=O)c1)c1c(F)cc(C(F)(F)F)cc1C(F)(F)F]

2-Methoxypyridin-4-amine (632.1 mg, 5.09 mmol) and DIEA (1.8 mL, 10.18 mmol) were dissolved in DMF (15 mL)

and treated dropwise with a solution of 2-fluoro-4,6-bis(trifluoromethyl)benzoyl chloride (1500 mg, 5.09 mmol) in DMF (2 mL). After 2 hours, the reaction was diluted with ethyl acetate, washed with 50% saturated sodium bicarbonate solution (2×20 mL), water, and brine. The solution was dried over anhydrous $Na_2SO_4$, filtered, and dried down to a purple residue. Silica gel chromatography using a gradient of ethyl acetate/hexane (10-99%) provided 2-fluoro-N-(2-methoxypyridin-4-yl)-4,6-bis(trifluoromethyl)benzamide (1.2 g, 67%) as a beige solid. $^1$H NMR (400 MHz, DMSO-d6) δ 11.29 (s, 1H), 8.42 (d, J=8.6 Hz, 1H), 8.17 (s, 1H), 8.13 (dd, J=5.4, 0.9 Hz, 1H), 7.14-7.10 (m, 2H), 3.85 (s, 3H) ppm. ESI-MS m/z calc. 382.05. found 383.1 (M+1)+; Retention time: 1.48 minutes (3 minutes run).

To a mixture of sodium iodide (2.54 g, 16.95 mmol) in acetonitrile (75 mL) under nitrogen was added TMSCl (2.15 mL, 16.95 mmol) and the mixture was stirred at 25° C. for 30 min. Thereafter, anhydrous acetonitrile (130.0 ml) was added to this solution followed by 2-fluoro-N-(2-methoxy-4-pyridyl)-4,6-bis(trifluoromethyl)benzamide (1.2 g, 3.14 mmol). The resulting reaction mixture was heated with stirring at 80° C. for 5 h and at 60° C. for 12 hours. The reaction was cooled, diluted with water, and extracted with ethyl acetate. The organic layer was dried over $Na_2SO_4$, filtered and concentrated to a dark yellow-orange solid. The solid was triturated with ethyl acetate/hexanes several times to remove dark red color, then with dichloromethane to remove yellow color, then finally with hexanes. The resulting solid was dried under vacuum to provide 2-fluoro-N-(2-oxo-1H-pyridin-4-yl)-4,6-bis(trifluoromethyl)benzamide (960 mg, 83%) as an off-white solid. $^1$H NMR (400 MHz, DMSO-d6) δ 11.41 (s, 1H), 11.03 (s, 1H), 8.41 (d, J=8.4 Hz, 1H), 8.16 (d, J=1.7 Hz, 1H), 7.37 (d, J=7.1 Hz, 1H), 6.71 (d, J=2.0 Hz, 1H), 6.31 (dd, J=7.2, 2.1 Hz, 1H) ppm. ESI-MS m/z calc. 368.04. found 369.1 (M+1)+; Retention time: 1.28 minutes (3 minutes run).

Example 12

Preparation of N-(2-oxo-1,2-dihydropyridin-4-yl)-2-(4-(trifluoromethoxy)phenoxy)-4-(trifluoromethyl)benzamide (79)

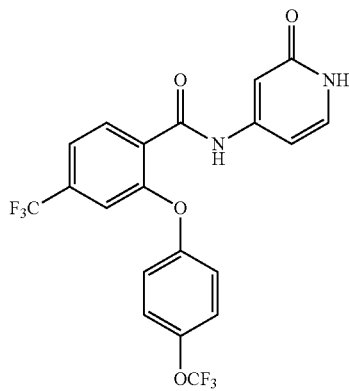 [SMILES: O=C(Nc1cc[nH]c(=O)c1)c1ccc(C(F)(F)F)cc1Oc1ccc(OC(F)(F)F)cc1]

$Cs_2CO_3$ (651.6 mg, 2 mmol) was added to a solution of 2-fluoro-N-(2-oxo-1,2-dihydropyridin-4-yl)-4-(trifluoromethyl)benzamide (60.0 mg, 0.2 mmol) and 4-(trifluoromethoxy)phenol (259.1 μL, 2 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield N-(2-oxo-1,2-dihydropyridin-4-yl)-2-(4-(trifluoromethoxy)phenoxy)-4-(trifluoromethyl)benzamide (79) (25.7 mg, 28%). ESI-MS m/z calc. 458.07. found 459.5 (M+1)+; Retention time: 1.80 minutes (3 minutes run)

Example 13

Preparation of 2-((5-fluoro-2-hydroxybenzyl)oxy)-N-(2-oxo-1,2-dihydropyridin-4-yl)-4-(trifluoromethyl)benzamide (159)

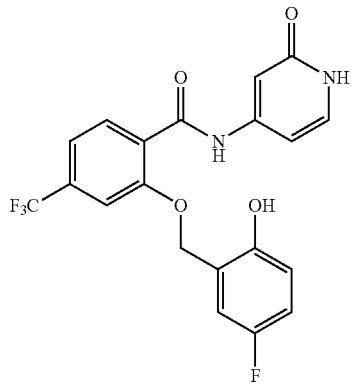 [SMILES: O=C(Nc1cc[nH]c(=O)c1)c1ccc(C(F)(F)F)cc1OCc1cc(F)ccc1O]

To a solution of 2-fluoro-N-(2-oxo-1H-pyridin-4-yl)-4-(trifluoromethyl)benzamide (211.2 mg, 0.70 mmol) and 4-fluoro-2-(hydroxymethyl)phenol (100 mg, 0.70 mmol) in N-methylpyrrolidinone (3 mL) was added cesium carbonate (687.8 mg, 2.1 mmol) and the mixture was heated at 100° C. for 2 hours. The reaction was cooled to 25° C., filtered and purified by reverse phase HPLC using a gradient of acetonitrile/water (10 to 99%) and HCl as a modifier to yield 2-[(5-fluoro-2-hydroxy-phenyl)methoxy]-N-(2-oxo-1H-pyridin-4-yl)-4-(trifluoromethyl)benzamide (159) (10.5 mg, 3%) as a yellow solid. $^1$H NMR (400 MHz, DMSO-d6) δ 11.52 (s, 1H), 10.49 (s, 1H), 10.04 (s, 1H), 7.84 (d, J=8.2 Hz, 1H), 7.78 (d, J=7.4 Hz, 1H), 7.33-7.23 (m, 2H), 7.05-6.91 (m, 2H), 6.91-6.79 (m, 2H), 6.61 (dd, J=7.4, 2.4 Hz, 1H), 4.96 (s, 2H) ppm. ESI-MS m/z calc. 422.09. found 423.3 (M+1)+; Retention time: 1.83 minutes (3 minutes).

Example 14

Preparation of 2-(4-fluoro-2-methylphenoxy)-N-(2-oxo-1,2-dihydropyridin-4-yl)-4-(trifluoromethyl)benzamide (10)

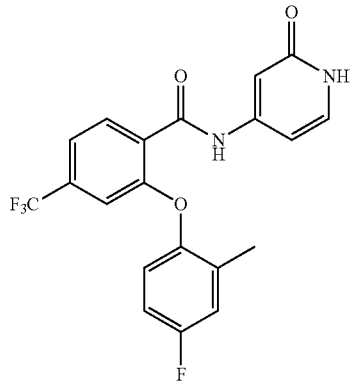 [SMILES: Cc1cc(F)ccc1Oc1cc(C(F)(F)F)ccc1C(=O)Nc1cc[nH]c(=O)c1]

A mixture of 2-fluoro-N-(2-oxo-1H-pyridin-4-yl)-4-(trifluoromethyl)-benzamide (13.6 g, 45.30 mmol), 4-fluoro-2-methyl-phenol (17.1 g, 135.9 mmol), $Cs_2CO_3$ (44.28 g, 135.9 mmol) and DMF (340.0 mL) was heated at 100° C. for 1.5 hours. The mixture was cooled to room temperature and was poured into water (500 mL). The mixture was stirred vigorously for 30 min before it was filtered. The solid was washed with water (250 mL) and was slurried with methyl tert-butyl ether (200 mL). The mixture was filtered and the solid was slurried with hexanes (2×400 mL) and the filtrate was dried under vacuum to give 2-(4-fluoro-2-methyl-phenoxy)-N-(2-oxo-1H-pyridin-4-yl)-4-(trifluoromethyl)benzamide (10) (13.1 g, 70%) as a solid. ESI-MS m/z calc. 406.09. found 407.5 (M+1)+; Retention time: 1.73 minutes (3 minutes run). $^1$H NMR (400 MHz, DMSO-d6) δ 11.28 (s, 1H), 10.63 (s, 1H), 7.84 (d, J=7.8 Hz, 1H), 7.60 (d, J=7.1 Hz, 1H), 7.31 (d, J=7.2 Hz, 1H), 7.26-7.20 (m, 1H), 7.14-7.06 (m, 2H), 7.00-6.95 (m, 1H), 6.75 (d, J=1.8 Hz, 1H), 6.38 (dd, J=7.2, 2.1 Hz, 1H), 2.16 (s, 3H) ppm.

Example 15

Preparation of 2-(4-fluoro-2-(hydroxymethyl)phenoxy)-N-(2-oxo-1,2-dihydropyridin-4-yl)-4-(trifluoromethyl)benzamide (157)

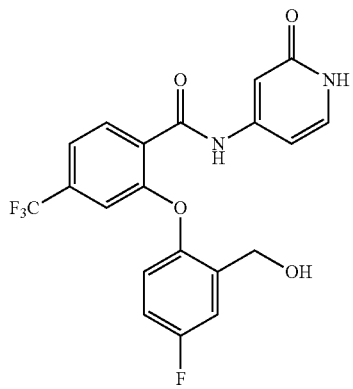 [SMILES: O=C(Nc1cc[nH]c(=O)c1)c1ccc(C(F)(F)F)cc1Oc1ccc(F)cc1CO]

2-Fluoro-N-(2-oxo-1H-pyridin-4-yl)-4-(trifluoromethyl)benzamide (625.3 mg, 2.08 mmol), potassium carbonate (287.9 mg, 2.08 mmol) and 4-fluoro-2-(hydroxymethyl)phenol (296 mg, 2.08 mmol) were added to 1-methylpyrrolidin-2-one (3.0 mL) and the reaction was stirred at 80° C. for 10 minutes. The reaction was filtered and the compound was purified by reverse phase preparative chromatography utilizing a gradient of 10-99% acetonitrile in water containing HCl as a modifier to yield 2-[4-fluoro-2-(hydroxymethyl)phenoxy]-N-(2-oxo-1H-pyridin-4-yl)-4-(trifluoromethyl)benzamide (157) (10.3 mg, 1%) as a white solid. $^1$H NMR (400 MHz, DMSO-d6) δ 11.44 (s, 1H), 10.66 (s, 1H), 7.86 (d, J=7.9 Hz, 1H), 7.61 (d, J=8.0 Hz, 1H), 7.41-7.27 (m, 2H), 7.24-7.12 (m, 1H), 7.12-7.07 (m, 1H), 7.04 (s, 1H), 6.80 (d, J=2.1 Hz, 1H), 6.43 (dd, J=7.3, 2.2 Hz, 1H), 4.47 (s, 2H) ppm. ESI-MS m/z calc. 422.09. found 423.2 (M+1)+; Retention time: 1.32 minutes (3 minutes run).

Example 16

Preparation of 2-(3-fluoro-4-methoxyphenoxy)-N-(2-oxo-1,2-dihydropyridin-4-yl)-4-(trifluoromethyl)benzamide (81)

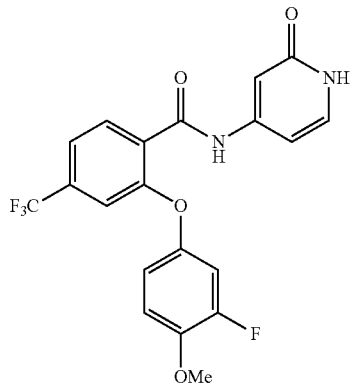 [SMILES: COc1ccc(Oc2cc(C(F)(F)F)ccc2C(=O)Nc2cc[nH]c(=O)c2)cc1F]

$Cs_2CO_3$ (651.6 mg, 2.0 mmol) was added to a solution of 2-fluoro-N-(2-oxo-1,2-dihydropyridin-4-yl)-4-(trifluoromethyl)benzamide (60.0 mg, 0.2 mmol) and 3-fluoro-4-methoxyphenol (284.3 mg, 2.0 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 2-(3-fluoro-4-methoxyphenoxy)-N-(2-oxo-1,2-dihydropyridin-4-yl)-4-(trifluoromethyl)benzamide (81) (45.6 mg, 54%). ESI-MS m/z calc. 422.09. found 423.3 (M+1)$^+$; Retention time: 1.65 minutes (3 minutes run).

Following a similar procedure as described above for compound 81, the following compounds were prepared from 2-fluoro-N-(2-oxo-1,2-dihydropyridin-4-yl)-4-(trifluoromethyl)benzamide in each case and using the alcohols described below.

| Cmpd No. | Product | Alcohol |
|---|---|---|
| 144 | N-(2-oxo-1,2-dihydropyridin-4-yl)-4-(trifluoromethyl)-2-((6-(trifluoromethyl)pyridin-3-yl)oxy)benzamide | 6-(trifluoromethyl)pyridin-3-ol |
| 116 | 2-(isopentyloxy)-N-(2-oxo-1,2-dihydropyridin-4-yl)-4-(trifluoromethyl)benzamide | isopentanol |
| 5 | 2-(4-fluorophenoxy)-N-(2-oxo-1,2-dihydropyridin-4-yl)-4-(trifluoromethyl)benzamide | 4-fluorophenol |
| 7 | 2-(2,4-difluorophenoxy)-N-(2-oxo-1,2-dihydropyridin-4-yl)-4-(trifluoromethyl)benzamide | 2,4-difluorophenol |
| 117 | 2-isobutoxy-N-(2-oxo-1,2-dihydropyridin-4-yl)-4-(trifluoromethyl)benzamide | isobutanol |
| 146 | 2-((6-methylpyridin-3-yl)oxy)-N-(2-oxo-1,2-dihydropyridin-4-yl)-4-(trifluoromethyl)benzamide | 6-methyl-3-pyridinol |
| 118 | 2-[(1R,2R,4S)-norbornan-2-yl]oxy-N-(2-oxo-1H-pyridin-4-yl)-4-(trifluoromethyl)benzamide | (1R,2R,4S)-norbornan-2-ol |
| 147 | 2-((2-methylpyridin-3-yl)oxy)-N-(2-oxo-1,2-dihydropyridin-4-yl)-4-(trifluoromethyl)benzamide | 2-methyl-3-pyridinol |
| 119 | 2-((1-methylcyclopropyl)methoxy)-N-(2-oxo-1,2-dihydropyridin-4-yl)-4-(trifluoromethyl)benzamide | 1-methylcyclopropyl)methanol |

-continued

| Cmpd No. | Product | Alcohol |
|---|---|---|
| 120 | 2-(cyclopentylmethoxy)-N-(2-oxo-1,2-dihydropyridin-4-yl)-4-(trifluoromethyl)benzamide | cyclopentylmethanol |
| 121 | N-(2-oxo-1,2-dihydropyridin-4-yl)-2-((tetrahydrofuran-3-yl)methoxy)-4-(trifluoromethyl)benzamide | tetrahydrofuran-3-ylmethanol |
| 122 | 2-cyclobutoxy-N-(2-oxo-1,2-dihydropyridin-4-yl)-4-(trifluoromethyl)benzamide | cyclobutanol |
| 123 | N-(2-oxo-1,2-dihydropyridin-4-yl)-2-(4,4,4-trifluorobutoxy)-4-(trifluoromethyl)benzamide | 4,4,4-trifluorobutanol |
| 124 | 2-((2,2-dimethylcyclopropyl)methoxy)-N-(2-oxo-1,2-dihydropyridin-4-yl)-4-(trifluoromethyl)benzamide | 2,2-dimethylcyclopropyl)methanol |
| 125 | 2-(((1R,5S)-bicyclo[3.1.0]hexan-3-yloxy)-N-(2-oxo-1,2-dihydropyridin-4-yl)-4-(trifluoromethyl)benzamide | (1R,5S)-3-bicyclo[3.1.0]hexanol |
| 126 | 2-((2,2-difluorocyclopropyl)methoxy)-N-(2-oxo-1,2-dihydropyridin-4-yl)-4-(trifluoromethyl)benzamide | 2,2-difluorocyclopropyl)methanol |
| 8 | 2-(4-(2-methoxyethoxy)phenoxy)-N-(2-oxo-1,2-dihydropyridin-4-yl)-4-(trifluoromethyl)benzamide | 4-(2-methoxyethoxy)phenol |
| 127 | 2-(bicyclo[2.2.1]heptan-2-yloxy)-N-(2-oxo-1,2-dihydropyridin-4-yl)-4-(trifluoromethyl)benzamide | norbornan-2-ol |
| 9 | N-(2-oxo-1,2-dihydropyridin-4-yl)-2-phenoxy-4-(trifluoromethyl)benzamide | phenol |
| 11 | N-(2-oxo-1,2-dihydropyridin-4-yl)-2-(o-tolyloxy)-4-(trifluoromethyl)benzamide | 2-methylphenol |
| 128 | 2-(cyclohexyloxy)-N-(2-oxo-1,2-dihydropyridin-4-yl)-4-(trifluoromethyl)benzamide | cyclohexanol |
| 12 | N-(2-oxo-1,2-dihydropyridin-4-yl)-2-(p-tolyloxy)-4-(trifluoromethyl)benzamide | 4-methylphenol |
| 77 | 2-(2-chloro-4-fluorophenoxy)-N-(2-oxo-1,2-dihydropyridin-4-yl)-4-(trifluoromethyl)benzamide | 2-chloro-4-fluoro-phenol |
| 78 | 2-(4-chlorophenoxy)-N-(2-oxo-1,2-dihydropyridin-4-yl)-4-(trifluoromethyl)benzamide | 4-chlorophenol |
| 80 | N-(2-oxo-1,2-dihydropyridin-4-yl)-2-(2-(trifluoromethoxy)phenoxy)-4-(trifluoromethyl)benzamide | 2-(trifluoromethoxy)phenol |
| 82 | 2-(4-(difluoromethoxy)phenoxy)-N-(2-oxo-1,2-dihydropyridin-4-yl)-4-(trifluoromethyl)benzamide | 4-(difluoromethoxy)phenol |
| 83 | 2-(2-(difluoromethoxy)phenoxy)-N-(2-oxo-1,2-dihydropyridin-4-yl)-4-(trifluoromethyl)benzamide | 2-(difluoromethoxy)phenol |
| 84 | 2-(2-fluoro-4-methoxyphenoxy)-N-(2-oxo-1,2-dihydropyridin-4-yl)-4-(trifluoromethyl)benzamide | 2-fluoro-4-methoxy-phenol |
| 87 | 2-(3-fluoro-2-methoxyphenoxy)-N-(2-oxo-1,2-dihydropyridin-4-yl)-4-(trifluoromethyl)benzamide | 3-fluoro-2-methoxy-phenol |
| 110 | 2-(2-chloro-3-fluoro-4-methoxyphenoxy)-N-(2-oxo-1,2-dihydropyridin-4-yl)-4-(trifluoromethyl)benzamide | 2-chloro-3-fluoro-4-methoxy-phenol |
| 158 | 2-(4-fluoro-2-methoxyphenoxy)-N-(2-oxo-1,2-dihydropyridin-4-yl)-4-(trifluoromethyl)benzamide | 4-fluoro-2-methoxyphenol |

Example 17

Preparation of 2-(4-fluoro-2-methoxyphenoxy)-N-(2-oxo-1,2-dihydropyridin-4-yl)-5-(trifluoromethyl)benzamide (30)

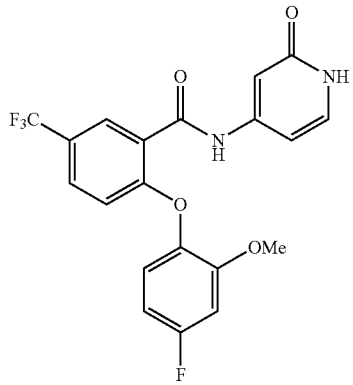 [SMILES: COc1cc(F)ccc1Oc1ccc(C(F)(F)F)cc1C(=O)Nc1cc[nH]c(=O)c1]

Cs$_2$CO$_3$ (651.6 mg, 2.0 mmol) was added to a solution of 2-fluoro-N-(2-oxo-1,2-dihydropyridin-4-yl)-5-(trifluoromethyl)benzamide (60.0 mg, 0.2 mmol) and 4-fluoro-3-methoxyphenol (228 µl, 2.0 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 2-(4-fluoro-2-methoxyphenoxy)-N-(2-oxo-1,2-dihydropyridin-4-yl)-5-(trifluoromethyl)benzamide (30) (67.9 mg, 80%). ESI-MS m/z calc. 422.09. found 423.2 (M+1)$^+$; Retention time: 1.56 minutes (3 minutes run).

Following a similar procedure as described above for compound 30, the following compounds were prepared from 2-fluoro-N-(2-oxo-1,2-dihydropyridin-4-yl)-5-(trifluoromethyl)benzamide and the following alcohols.

| Cmpd No. | Product | Alcohol |
|---|---|---|
| 72 | N-(2-oxo-1,2-dihydropyridin-4-yl)-2-(4-(trifluoromethoxy)phenoxy)-5-(trifluoromethyl)benzamide | 4-(trifluoromethoxy)phenol |
| 31 | 2-(4-fluoro-2-methylphenoxy)-N-(2-oxo-1,2-dihydropyridin-4-yl)-5-(trifluoromethyl)benzamide | 4-fluoro-2-methyl-phenol |
| 63 | 2-(4-methoxy-2-methylphenoxy)-N-(2-oxo-1,2-dihydropyridin-4-yl)-5-(trifluoromethyl)benzamide | 4-methoxy-2-methyl-phenol |
| 50 | 2-(4-chloro-2-methylphenoxy)-N-(2-oxo-1,2-dihydropyridin-4-yl)-5-(trifluoromethyl)benzamide | 4-chloro-2-methyl-phenol |
| 44 | 2-(4-ethoxyphenoxy)-N-(2-oxo-1,2-dihydropyridin-4-yl)-5-(trifluoromethyl)benzamide | 4-ethoxyphenol |
| 49 | 2-(2-chloro-4-methoxyphenoxy)-N-(2-oxo-1,2-dihydropyridin-4-yl)-5-(trifluoromethyl)benzamide | 2-chloro-4-methoxy-phenol |
| 90 | N-(2-oxo-1,2-dihydropyridin-4-yl)-5-(trifluoromethyl)-2-(2,3,4-trifluorophenoxy)benzamide | 2,3,4-trifluorophenol |
| 29 | 2-(2-chloro-4-fluorophenoxy)-N-(2-oxo-1,2-dihydropyridin-4-yl)-5-(trifluoromethyl)benzamide | 2-chloro-4-fluoro-phenol |
| 54 | 2-(3-fluoro-2-methoxyphenoxy)-N-(2-oxo-1,2-dihydropyridin-4-yl)-5-(trifluoromethyl)benzamide | 3-fluoro-2-methoxy-phenol |
| 59 | 2-(3-fluoro-4-methoxyphenoxy)-N-(2-oxo-1,2-dihydropyridin-4-yl)-5-(trifluoromethyl)benzamide | 3-fluoro-4-methoxy-phenol |
| 62 | N-(2-oxo-1,2-dihydropyridin-4-yl)-2-(2-propoxyphenoxy)-5-(trifluoromethyl)benzamide | 2-propoxyphenol |
| 73 | 2-(4-(difluoromethoxy)phenoxy)-N-(2-oxo-1,2-dihydropyridin-4-yl)-5-(trifluoromethyl)benzamide | 4-(difluoromethoxy)phenol |
| 28 | N-(2-oxo-1,2-dihydropyridin-4-yl)-2-(o-tolyloxy)-5-(trifluoromethyl)benzamide | 2-methylphenol |
| 53 | N-(2-oxo-1,2-dihydropyridin-4-yl)-2-(4-propoxyphenoxy)-5-(trifluoromethyl)benzamide | 4-propoxyphenol |
| 75 | N-(2-oxo-1,2-dihydropyridin-4-yl)-2-(2-(trifluoromethoxy)phenoxy)-5-(trifluoromethyl)benzamide | 2-(trifluoromethoxy)phenol |
| 2 | 2-(4-fluorophenoxy)-N-(2-oxo-1,2-dihydropyridin-4-yl)-5-(trifluoromethyl)benzamide | 4-fluorophenol |
| 76 | 2-(2-(difluoromethoxy)phenoxy)-N-(2-oxo-1,2-dihydropyridin-4-yl)-5-(trifluoromethyl)benzamide | 2-(difluoromethoxy)phenol |
| 58 | 2-(4-chlorophenoxy)-N-(2-oxo-1,2-dihydropyridin-4-yl)-5-(trifluoromethyl)benzamide | 4-chlorophenol |
| 24 | 2-(2,4-difluorophenoxy)-N-(2-oxo-1,2-dihydropyridin-4-yl)-5-(trifluoromethyl)benzamide | 2,4-difluorophenol |
| 46 | 2-(2-ethoxyphenoxy)-N-(2-oxo-1,2-dihydropyridin-4-yl)-5-(trifluoromethyl)benzamide | 2-ethoxyphenol |
| 45 | 2-(4-methoxyphenoxy)-N-(2-oxo-1,2-dihydropyridin-4-yl)-5-(trifluoromethyl)benzamide | 4-methoxyphenoxy |
| 56 | 2-(5-fluoro-2-methylphenoxy)-N-(2-oxo-1,2-dihydropyridin-4-yl)-5-(trifluoromethyl)benzamide | 5-fluoro-2-methyl-phenol |
| 55 | 2-(2-fluoro-4-methoxyphenoxy)-N-(2-oxo-1,2-dihydropyridin-4-yl)-5-(trifluoromethyl)benzamide | 2-fluoro-4-methoxy-phenol |

-continued

| Cmpd No. | Product | Alcohol |
|---|---|---|
| 51 | 2-(4-chloro-2-fluorophenoxy)-N-(2-oxo-1,2-dihydropyridin-4-yl)-5-(trifluoromethyl)benzamide | 4-chloro-2-fluoro-phenol |
| 52 | 2-(5-fluoro-2-methoxyphenoxy)-N-(2-oxo-1,2-dihydropyridin-4-yl)-5-(trifluoromethyl)benzamide | 5-fluoro-2-methoxy-phenol |
| 65 | 2-(2-chlorophenoxy)-N-(2-oxo-1,2-dihydropyridin-4-yl)-5-(trifluoromethyl)benzamide | 2-chlorophenol |
| 64 | 2-(2-isopropoxyphenoxy)-N-(2-oxo-1,2-dihydropyridin-4-yl)-5-(trifluoromethyl)benzamide | 2-isopropoxyphenol |
| 61 | 2-(4-fluoro-2-methylphenoxy)-N-(6-methyl-2-oxo-1,2-dihydropyridin-4-yl)-5-(trifluoromethyl)benzamide | 4-fluoro-2-methyl-phenol |
| 47 | 2-(2-methoxy-4-methylphenoxy)-N-(2-oxo-1,2-dihydropyridin-4-yl)-5-(trifluoromethyl)benzamide | 2-methoxy-4-methyl-phenol |
| 92 | 2-(2,3-difluoro-4-methylphenoxy)-N-(2-oxo-1,2-dihydropyridin-4-yl)-5-(trifluoromethyl)benzamide | 2,3-difluoro-4-methyl-phenol |
| 32 | N-(2-oxo-1,2-dihydropyridin-4-yl)-2-phenoxy-5-(trifluoromethyl)benzamide | phenol |
| 132 | N-(2-oxo-1,2-dihydropyridin-4-yl)-5-(trifluoromethyl)-2-(3,3,3-trifluoropropoxy)benzamide | 3,3,3-trifluoropropanol |
| 27 | N-(2-oxo-1,2-dihydropyridin-4-yl)-2-(p-tolyloxy)-5-(trifluoromethyl)benzamide | 4-methylphenol |
| 91 | -(2-oxo-1,2-dihydropyridin-4-yl)-5-(trifluoromethyl)-2-(2,3,5-trimethylphenoxy)benzamide | 2,3,5-trimethylphenol |
| 25 | 2-(4-cyanophenoxy)-N-(2-oxo-1,2-dihydropyridin-4-yl)-5-(trifluoromethyl)benzamide | 4-cyanophenol |
| 93 | N-(2-oxo-1,2-dihydropyridin-4-yl)-5-(trifluoromethyl)-2-(2,4,5-trimethylphenoxy)benzamide | 2,4,5-trimethylphenol |
| 131 | 2-isobutoxy-N-(2-oxo-1,2-dihydropyridin-4-yl)-5-(trifluoromethyl)benzamide | isobutanol |
| 135 | 2-[[(1R,5S)-3-bicyclo[3.1.0]hexanyl]oxy]-N-(2-oxo-1H-pyridin-4-yl)-5-(trifluoromethyl)benzamide | (1R,5S)-3-bicyclo[3.1.0]hexanol |
| 48 | 2-(2-fluoro-6-methoxyphenoxy)-N-(2-oxo-1,2-dihydropyridin-4-yl)-5-(trifluoromethyl)benzamide | 2-fluoro-6-methoxy-phenol |
| 86 | 2-(4-fluoro-2-methylphenoxy)-N-(5-methyl-2-oxo-1,2-dihydropyridin-4-yl)-4-(trifluoromethyl)benzamide | 4-fluoro-2-methyl-phenol |
| 130 | 2-(cyclopentylmethoxy)-N-(2-oxo-1,2-dihydropyridin-4-yl)-5-(trifluoromethyl)benzamide | cyclopentylmethanol |
| 74 | N-(2-oxo-1,2-dihydropyridin-4-yl)-5-(trifluoromethyl)-2-(4-(trifluoromethyl)phenoxy)benzamide | 4-(trifluoromethyl)phenol |
| 133 | N-(2-oxo-1,2-dihydropyridin-4-yl)-2-(4,4,4-trifluorobutoxy)-5-(trifluoromethyl)benzamide | 4,4,4-trifluorobutanol |
| 150 | 2-((2-methylpyridin-3-yl)oxy)-N-(2-oxo-1,2-dihydropyridin-4-yl)-5-(trifluoromethyl)benzamide | 2-methyl-3-pyridinol |
| 57 | 2-(3-fluoro-5-methoxyphenoxy)-N-(2-oxo-1,2-dihydropyridin-4-yl)-5-(trifluoromethyl)benzamide | 3-fluoro-5-methoxy-phenol |
| 26 | 2-(2,6-difluorophenoxy)-N-(2-oxo-1,2-dihydropyridin-4-yl)-5-(trifluoromethyl)benzamide | 2,6-difluorophenol |
| 134 | 2-((2,2-dimethylcyclopropyl)methoxy)-N-(2-oxo-1,2-dihydropyridin-4-yl)-5-(trifluoromethyl)benzamide | 2,2-dimethylcyclopropyl)methanol |

Example 18

Preparation of 5-chloro-2-(4-fluoro-2-methoxyphenoxy)-N-(2-oxo-1,2-dihydropyridin-4-yl)benzamide (70)

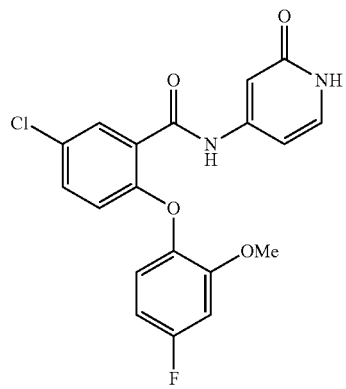 [SMILES: COc1cc(F)ccc1Oc1ccc(Cl)cc1C(=O)Nc1cc[nH]c(=O)c1]

Cs$_2$CO$_3$ (879.9 mg, 2.7 mmol) was added to a solution of 2-fluoro-N-(2-oxo-1,2-dihydropyridin-4-yl)-5-chlorobenzamide (72.0 mg, 0.27 mmol) and 4-fluoro-3-methoxyphenol (307.7 µl, 2.7 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 5-chloro-2-(4-fluoro-2-methoxyphenoxy)-N-(2-oxo-1,2-dihydropyridin-4-yl)benzamide (70) (31.8 mg, 30%). ESI-MS m/z calc. 388.06. found 389.10 (M+1)$^+$; Retention time: 1.52 minutes (3 minutes run).

Following a similar procedure as described above for compound 70, the following compounds were prepared from 5-chloro-2-(4-fluoro-2-methoxyphenoxy)-N-(2-oxo-1,2-dihydropyridin-4-yl)benzamide and the following alcohols.

| Cmpd No. | Product | Alcohol |
|---|---|---|
| 68 | 5-chloro-2-(4-fluoro-2-methylphenoxy)-N-(2-oxo-1,2-dihydropyridin-4-yl)benzamide | 4-fluoro-2-methyl-phenol |
| 66 | 5-chloro-2-(2-chloro-4-fluorophenoxy)-N-(2-oxo-1,2-dihydropyridin-4-yl)benzamide | 2-chloro-4-fluoro-phenol |
| 67 | 5-chloro-2-(4-fluorophenoxy)-N-(2-oxo-1,2-dihydropyridin-4-yl)benzamide | 4-fluorophenol |
| 71 | 5-chloro-2-(3-fluoro-4-methoxyphenoxy)-N-(2-oxo-1,2-dihydropyridin-4-yl)benzamide | 3-fluoro-4-methoxy-phenol |

Example 19

Preparation of 4-chloro-2-(4-fluoro-2-methoxyphenoxy)-N-(2-oxo-1,2-dihydropyridin-4-yl)benzamide (16)

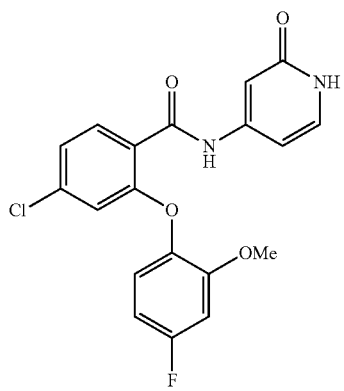 [SMILES: COc1cc(F)ccc1Oc1cc(Cl)ccc1C(=O)Nc1cc[nH]c(=O)c1]

Cs$_2$CO$_3$ (651.6 mg, 2.0 mmol) was added to a solution of 2-fluoro-N-(2-oxo-1,2-dihydropyridin-4-yl)-4-chlorobenzamide (53.3 mg, 0.20 mmol) and 4-fluoro-3-methoxyphenol (284.3 mg, 2.0 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 4-chloro-2-(4-fluoro-2-methoxyphenoxy)-N-(2-oxo-1,2-dihydropyridin-4-yl)benzamide (16) (22.1 mg, 28%). ESI-MS m/z calc. 388.06. found 389.15 (M+1)$^+$; Retention time: 1.53 minutes (3 minutes run).

Following a similar procedure as described above for compound 16, the following compounds were prepared from 4-chloro-2-(4-fluoro-2-methoxyphenoxy)-N-(2-oxo-1,2-dihydropyridin-4-yl)benzamide and the following alcohols.

| Cmpd No. | Product | Alcohol |
|---|---|---|
| 20 | 4-chloro-2-(4-fluoro-2-methylphenoxy)-N-(2-oxo-1,2-dihydropyridin-4-yl)benzamide | 4-fluoro-2-methyl-phenol |
| 14 | 4-chloro-2-(2-chloro-4-fluorophenoxy)-N-(2-oxo-1,2-dihydropyridin-4-yl)benzamide | 2-chloro-4-fluoro-phenol |
| 15 | 4-chloro-2-(4-fluorophenoxy)-N-(2-oxo-1,2-dihydropyridin-4-yl)benzamide | 4-fluorophenol |
| 13 | 4-chloro-2-(2,4-difluorophenoxy)-N-(2-oxo-1,2-dihydropyridin-4-yl)benzamide | 2,4-difluorophenol |
| 129 | 4-chloro-N-(2-oxo-1,2-dihydropyridin-4-yl)-2-(4,4,4-trifluorobutoxy)benzamide | 4,4,4-trifluorobutanol |
| 17 | 4-chloro-2-(2-fluoro-6-methylphenoxy)-N-(2-oxo-1,2-dihydropyridin-4-yl)benzamide | 2-fluoro-6-methyl-phenol |
| 143 | 4-chloro-N-(2-oxo-1,2-dihydropyridin-4-yl)-2-((6-(trifluoromethyl)pyridin-3-yl)oxy)benzamide | 6-(trifluoromethyl)-3-pyridinol |
| 19 | 4-chloro-2-(2,6-difluorophenoxy)-N-(2-oxo-1H-pyridin-4-yl)benzamide | 2,6-difluorophenol |
| 18 | 4-chloro-2-(2-chloro-6-fluorophenoxy)-N-(2-oxo-1,2-dihydropyridin-4-yl)benzamide | 2-chloro-6-fluoro-phenol |

Example 20

Preparation of 4,5-dichloro-2-(4-fluoro-2-methoxyphenoxy)-N-(2-oxo-1,2-dihydropyridin-4-yl)benzamide (114)

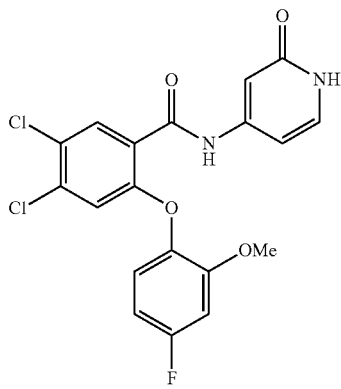 [SMILES: COc1cc(F)ccc1Oc1cc(Cl)c(Cl)cc1C(=O)Nc1cc[nH]c(=O)c1]

$Cs_2CO_3$ (97.7 mg, 0.3 mmol) was added to a solution of 4,5-dichloro-2-fluoro-N-(2-oxo-1,2-dihydropyridin-4-yl)benzamide (30.1 mg, 0.1 mmol) and 4-fluoro-3-methoxyphenol (42.6 mg, 0.3 mmol) in NMP (0.5 mL) and the reaction was stirred at 90° C. for 2 hours. The reaction was filtered and purified by reverse phase HPLC using a gradient of acetonitrile in water (1-99%) and HCl as a modifier to yield 4,5-dichloro-2-(4-fluoro-2-methoxyphenoxy)-N-(2-oxo-1,2-dihydropyridin-4-yl)benzamide (114) (13.2 mg, 30%). ESI-MS m/z calc. 422.02. found 423.3 $(M+1)^+$; Retention time: 1.57 minutes (3 minutes run).

Following a similar procedure as described above for compound 114, the following compounds were prepared from 4,5-dichloro-2-fluoro-N-(2-oxo-1,2-dihydropyridin-4-yl)benzamide and the following alcohols.

| Cmpd No. | Product | Alcohol |
|---|---|---|
| 113 | 4,5-dichloro-2-(4-fluorophenoxy)-N-(2-oxo-1,2-dihydropyridin-4-yl)benzamide | 4-fluorophenol |
| 115 | 4,5-dichloro-2-(3-fluoro-4-methoxyphenoxy)-N-(2-oxo-1,2-dihydropyridin-4-yl)benzamide | 3-fluoro-4-methoxyphenol |

Example 21

Preparation of 2-(4-fluoro-2-methylphenoxy)-N-(2-oxo-1,2-dihydropyridin-4-yl)-5-(trifluoromethoxy)benzamide (40)

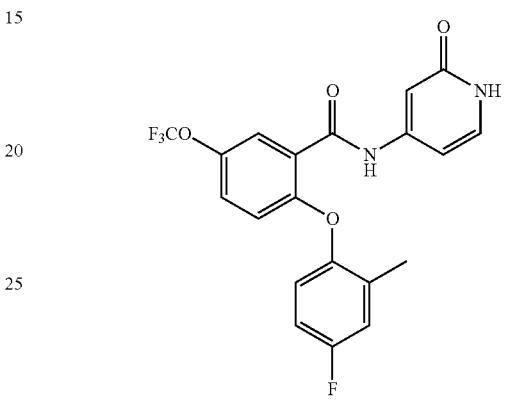

$Cs_2CO_3$ (651.6 mg, 2 mmol) was added to a solution of 2-fluoro-N-(2-oxo-1,2-dihydropyridin-4-yl)-5-(trifluoromethoxy)benzamide (63.2 mg, 0.2 mmol) and 4-fluoro-3-methylphenol (252.3 mg, 2 mmol) in DMF (1 mL) and the reaction was stirred at 100° C. for 1 hours. The reaction was filtered and purified by reverse phase HPLC using a gradient of acetonitrile in water (10-99%) and HCl as a modifier to yield 2-(4-fluoro-2-methylphenoxy)-N-(2-oxo-1,2-dihydropyridin-4-yl)-5-(trifluoromethoxy)benzamide (40) (36.3 mg, 43%). ESI-MS m/z calc. 422.09. found 423.9 $(M+1)^+$; Retention time: 1.64 minutes (3 minutes run).

Following a similar procedure as described above for compound 40, the following compounds were prepared from 2-fluoro-N-(2-oxo-1,2-dihydropyridin-4-yl)-5-(trifluoromethoxy)benzamide and the following alcohols.

| Cmpd No. | Product | Alcohol |
|---|---|---|
| 37 | 2-(2-chloro-4-fluorophenoxy)-N-(2-oxo-1,2-dihydropyridin-4-yl)-5-(trifluoromethoxy)benzamide | 2-chloro-4-fluoro-phenol |
| 42 | 2-(4-fluoro-2-methoxyphenoxy)-N-(2-oxo-1,2-dihydropyridin-4-yl)-5-(trifluoromethoxy)benzamide | 4-fluoro-2-methoxy-phenol |
| 38 | 2-(4-fluorophenoxy)-N-(2-oxo-1,2-dihydropyridin-4-yl)-5-(trifluoromethoxy)benzamide | 4-fluorophenol |
| 33 | 2-(2,4-difluorophenoxy)-N-(2-oxo-1,2-dihydropyridin-4-yl)-5-(trifluoromethoxy)benzamide | 2,4-difluorophenol |
| 36 | N-(2-oxo-1,2-dihydropyridin-4-yl)-2-(o-tolyloxy)-5-(trifluoromethoxy)benzamide | 2-methylphenol |
| 41 | N-(2-oxo-1,2-dihydropyridin-4-yl)-2-phenoxy-5-(trifluoromethoxy)benzamide | phenol |
| 35 | N-(2-oxo-1,2-dihydropyridin-4-yl)-2-(p-tolyloxy)-5-(trifluoromethoxy)benzamide | 4-methylphenol |
| 39 | 2-(2-fluoro-6-methylphenoxy)-N-(2-oxo-1,2-dihydropyridin-4-yl)-5-(trifluoromethoxy)benzamide | 2-fluoro-6-methyl-phenol |

-continued

| Cmpd No. | Product | Alcohol |
|---|---|---|
| 138 | N-(2-oxo-1,2-dihydropyridin-4-yl)-5-(trifluoromethoxy)-2-(3,3,3-trifluoropropoxy)benzamide | 3,3,3-trifluoropropanol |
| 136 | 2-(cyclopentylmethoxy)-N-(2-oxo-1,2-dihydropyridin-4-yl)-5-(trifluoromethoxy)benzamide | cyclopentylmethanol |
| 139 | N-(2-oxo-1,2-dihydropyridin-4-yl)-2-(4,4,4-trifluorobutoxy)-5-(trifluoromethoxy)benzamide | 4,4,4-trifluorobutanol |
| 151 | 2-((2-methylpyridin-3-yl)oxy)-N-(2-oxo-1,2-dihydropyridin-4-yl)-5-(trifluoromethoxy)benzamide | 2-methyl-3-pyridinol |
| 34 | 2-(2,6-difluorophenoxy)-N-(2-oxo-1,2-dihydropyridin-4-yl)-5-(trifluoromethoxy)benzamide | 2,6-difluorophenol |
| 137 | 2-(cyclohexyloxy)-N-(2-oxo-1,2-dihydropyridin-4-yl)-5-(trifluoromethoxy)benzamide | cyclohexanol |
| 140 | 2-((2,2-dimethylcyclopropyl)methoxy)-N-(2-oxo-1,2-dihydropyridin-4-yl)-5-(trifluoromethoxy)benzamide | 2,2-dimethylcyclopropyl)methanol |

Example 22

Preparation of 2-(4-fluoro-2-methoxyphenoxy)-N-(2-oxo-1,2-dihydropyridin-4-yl)-4-(perfluoroethyl)benzamide (111)

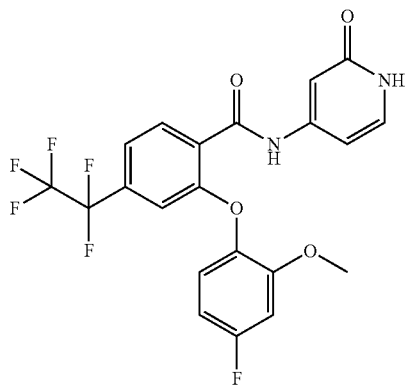 [SMILES: COc1cc(F)ccc1Oc1cc(C(F)(F)C(F)(F)F)ccc1C(=O)Nc1cc[nH]c(=O)c1]

Cs₂CO₃ (69.8 mg, 0.21 mmol) was added to a solution of 2-fluoro-N-(2-oxo-1,2-dihydropyridin-4-yl)-4-(perfluoroethyl)benzamide (25 mg, 0.07 mmol) and 4-fluoro-2-methoxyphenol (24.4 µL, 0.2 mmol) in NMP (0.3 mL) and the reaction was stirred at 100° C. for 45 minutes. The reaction mixture was poured into water:ethyl acetate (9:1). The mixture was shaken, and the solid was filtered off, washed with ether, then triturated with ethyl acetate and dried to give the desired product. The mother liquors were filtered and washed with ethyl acetate to give a second crop of material. Both solids were combined and dried under vacuum to give 2-(4-fluoro-2-methoxy-phenoxy)-N-(2-oxo-1H-pyridin-4-yl)-4-(1,1,2,2,2-pentafluoroethyl)benzamide (111) (15.4 mg, 45%) as a white solid. ESI-MS m/z calc. 472.08. found 473.3 (M+1)+; Retention time: 1.62 minutes. ¹H NMR (400 MHz, DMSO) δ 11.32 (s, 1H), 10.62 (s, 1H), 7.83 (d, J=7.9 Hz, 1H), 7.51 (d, J=7.9 Hz, 1H), 7.39-7.27 (m, 2H), 7.17 (dd, J=10.7, 2.8 Hz, 1H), 6.88 (dd, J=11.3, 5.7 Hz, 1H), 6.81 (s, 1H), 6.75 (s, 1H), 6.43 (d, J=7.1 Hz, 1H), 3.73 (s, 3H) ppm.

Following a similar procedure as described above for compound III, the following compounds were prepared from 2-fluoro-N-(2-oxo-1,2-dihydropyridin-4-yl)-4-(perfluoroethyl)benzamide and the following alcohols.

| Cmpd. No. | Product | Alcohol |
|---|---|---|
| 88 | 2-(4-fluorophenoxy)-N-(2-oxo-1,2-dihydropyridin-4-yl)-4-(perfluoroethyl)benzamide | 4-fluorophenol |
| 112 | 2-(4-fluoro-2-methylphenoxy)-N-(2-oxo-1,2-dihydropyridin-4-yl)-4-(perfluoroethyl)benzamide | 4-fluoro-2-methyl-phenol |
| 89 | 2-(3-fluoro-4-methoxyphenoxy)-N-(2-oxo-1,2-dihydropyridin-4-yl)-4-(perfluoroethyl)benzamide | 3-fluoro-4-methoxy-phenol |

Example 23

Preparation of 4-cyano-2-(4-fluoro-2-methoxyphenoxy)-N-(2-oxo-1,2-dihydropyridin-4-yl)benzamide (22)

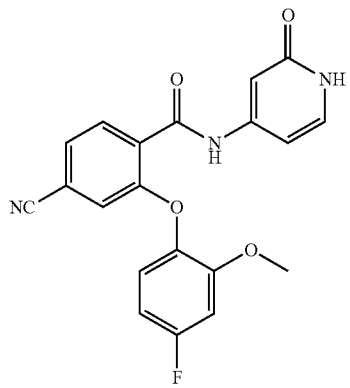 [SMILES: COc1cc(F)ccc1Oc1cc(C#N)ccc1C(=O)Nc1cc[nH]c(=O)c1]

Cs₂CO₃ (651.4 mg, 2.0 mmol) was added to a solution of 4-cyano-2-fluoro-N-(2-oxo-1,2-dihydropyridin-4-yl)benzamide (51.4 mg, 0.2 mmol) and 4-fluoro-2-methoxyphenol (244 µL, 2.0 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 4-cyano-2-(4-fluoro-2-methoxyphenoxy)-N-(2-oxo-1,2-dihydropyridin-4-yl)benzamide (22) (26.8 mg, 35%). ESI-MS m/z calc. 379.10. found 380.17 (M+1)+; Retention time: 1.30 minutes (3 minutes run).

Following a similar procedure as described above for compound 22, the following compounds were prepared from 2-fluoro-N-(2-oxo-1,2-dihydropyridin-4-yl)-5-(perfluoroethyl)benzamide and the following alcohols.

| Cmpd No. | Product | Alcohol |
|---|---|---|
| 21 | 4-cyano-2-(4-fluorophenoxy)-N-(2-oxo-1,2-dihydropyridin-4-yl)benzamide | 4-fluorophenol |
| 23 | 4-cyano-2-(4-fluoro-2-methylphenoxy)-N-(2-oxo-1,2-dihydropyridin-4-yl)benzamide | 4-fluoro-2-methyl-phenol |

Example 24

Preparation of 5-fluoro-N-(2-oxo-1,2-dihydropyridin-4-yl)-2-(4-(trifluoromethoxy)phenoxy)benzamide (101)

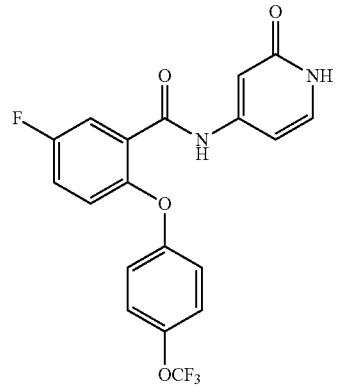 [SMILES: O=C(Nc1cc[nH]c(=O)c1)c1cc(F)ccc1Oc1ccc(OC(F)(F)F)cc1]

$Cs_2CO_3$ (146.6 mg, 0.45 mmol) was added to a solution of 2,5-difluoro-N-(2-oxo-1,2-dihydropyridin-4-yl)benzamide (37.5 mg, 0.15 mmol) and 4-trifluoro methoxyphenol (80.1 mg, 0.45 mmol) in DMF (0.9 mL) and the reaction was stirred at 100° C. for 8 hours. The reaction was filtered and purified by reverse phase HPLC using a gradient of acetonitrile in water (10-99%) and HCl as a modifier to yield 5-fluoro-N-(2-oxo-1,2-dihydropyridin-4-yl)-2-(4-(trifluoromethoxy)phenoxy)benzamide (101) (1.9 mg, 3%). ESI-MS m/z calc. 408.07. found 409.3 (M+1)+; Retention time: 1.68 minutes (3 minutes run).

Following a similar procedure as described above for compound 101, the following compounds were prepared from 2,5-difluoro-N-(2-oxo-1,2-dihydropyridin-4-yl)benzamide and the following alcohols.

| Cmpd No. | Product | Alcohol |
|---|---|---|
| 100 | 5-fluoro-N-(2-oxo-1,2-dihydropyridin-4-yl)-2-(4-propoxyphenoxy)benzamide | 4-propoxyphenol |
| 108 | 2-(4-(cyclopropylmethoxy)phenoxy)-5-fluoro-N-(2-oxo-1,2-dihydropyridin-4-yl)benzamide | 4-(cyclopropylmethoxy)phenol |
| 98 | 2-(4-ethoxyphenoxy)-5-fluoro-N-(2-oxo-1,2-dihydropyridin-4-yl)benzamide | 2-(4-ethoxyphenol |
| 103 | 2-(2-chloro-4-methoxyphenoxy)-5-fluoro-N-(2-oxo-1,2-dihydropyridin-4-yl)benzamide | 2-chloro-4-methoxy-phenol |
| 107 | 5-fluoro-N-(2-oxo-1,2-dihydropyridin-4-yl)-2-(4-(2,2,2-trifluoroethoxy)phenoxy)benzamide | 4-(2,2,2-trifluoroethoxy)phenol |
| 96 | 2-(4-cyclopropylphenoxy)-5-fluoro-N-(2-oxo-1,2-dihydropyridin-4-yl)benzamide | 2-(4-cyclopropylphenol |
| 97 | 2-(4-(tert-butoxy)phenoxy)-5-fluoro-N-(2-oxo-1,2-dihydropyridin-4-yl)benzamide | 2-(4-tert-butoxyphenol |
| 104 | 5-fluoro-2-(4-methoxyphenoxy)-N-(2-oxo-1,2-dihydropyridin-4-yl)benzamide | 4-methoxyphenol |
| 94 | 5-fluoro-N-(2-oxo-1,2-dihydropyridin-4-yl)-2-(2,3,5-trimethylphenoxy)benzamide | 2,3,5-trimethylphenol |
| 95 | 5-fluoro-N-(2-oxo-1,2-dihydropyridin-4-yl)-2-phenoxybenzamide | phenol |
| 105 | 5-fluoro-N-(2-oxo-1,2-dihydropyridin-4-yl)-2-(2,4,5-trimethylphenoxy)benzamide | 2,4,5-trimethylphenol |
| 99 | 5-fluoro-2-(4-isopropylphenoxy)-N-(2-oxo-1,2-dihydropyridin-4-yl)benzamide | 4-isopropylphenol |
| 102 | 5-fluoro-2-(4-(2-methoxyethyl)phenoxy)-N-(2-oxo-1,2-dihydropyridin-4-yl)benzamide | 4-(2-methoxyethyl)phenol |
| 160 | 5-fluoro-N-(2-oxo-1,2-dihydropyridin-4-yl)-2-(4-(4,4,4-trifluorobutoxy)phenoxy)benzamide | 4-(4,4,4-trifluorobutoxy)phenol |

Example 25

Preparation of 4-chloro-2-(2-chloro-4-fluorophenoxy)-5-fluoro-N-(2-oxo-1,2-dihydropyridin-4-yl)benzamide (109)

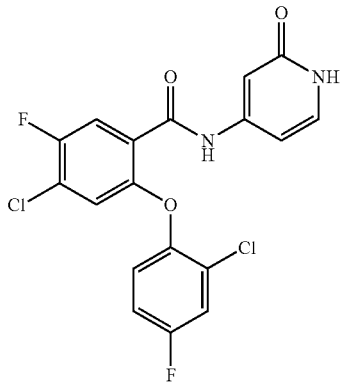 [SMILES: O=C(Nc1cc[nH]c(=O)c1)c1cc(F)c(Cl)cc1Oc1ccc(F)cc1Cl]

Cs$_2$CO$_3$ (244.4 mg, 0.75 mmol) was added to a solution of 4-chloro-2,5-difluoro-N-(2-oxo-1,2-dihydropyridin-4-yl)benzamide (71.2 mg, 0.25 mmol) and 2-chloro-4-fluorophenol (109.9 mg, 0.75 mmol) in DMF (2 mL) and the reaction was stirred at 100° C. for 1 hours. The reaction was filtered and purified by reverse phase HPLC using a gradient of acetonitrile in water (10-99%) and HCl as a modifier to yield 4-chloro-2-(2-chloro-4-fluorophenoxy)-5-fluoro-N-(2-oxo-1,2-dihydropyridin-4-yl)benzamide (109) (22.8 mg, 27%). ESI-MS m/z calc. 410.00. found 411.2 (M+1)+; Retention time: 1.76 minutes (3 minutes run).

Example 26

Preparation of 2-(4-fluoro-2-methylphenoxy)-N-(6-oxo-1,6-dihydropyridin-3-yl)-5-(trifluoromethyl)benzamide (106)

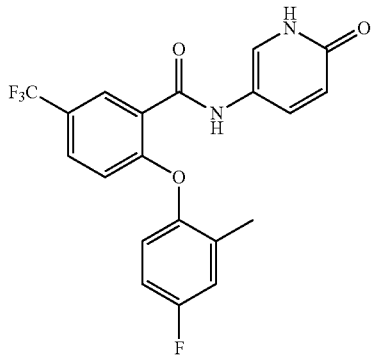 [SMILES: Cc1cc(F)ccc1Oc1ccc(C(F)(F)F)cc1C(=O)Nc1ccc(=O)[nH]c1]

To a solution of 6-methoxypyridin-3-amine (20.5 mg, 0.16 mmol) in dichloromethane (0.5 mL) was added 2-(4-fluoro-2-methyl-phenoxy)-5-(trifluoromethyl)benzoyl chloride (50 mg, 0.15 mmol) followed by di-isopropylethyl amine (26.2 µL, 0.15 mmol) and the reaction mixture was stirred at 25° C. for 16 hours and then the solvent was evaporated.

The crude material from the amide formation was dissolved in HBr (in AcOH) (250 µL of 33% w/v, 1.02 mmol) and heated at 80° C. for 8 hours. The reaction mixture was diluted with water and extracted with ethyl acetate (3×). The organics were combined and evaporated to dryness. Purification by HPLC (1-99% ACN in Water with HCl as a modifier) gave 2-(4-fluoro-2-methyl-phenoxy)-N-(6-oxo-1H-pyridin-3-yl)-5-(trifluoromethyl)benzamide (106) (29.97 mg, 45%) as a white solid. ESI-MS m/z calc. 406.09. found 407.10 (M+1)+; Retention time: 1.52 minutes (3 minutes run).

Example 27

Preparation of 4-(tert-butyl)-N-(2-oxo-1,2-dihydropyridin-4-yl)-2-((6-(trifluoromethyl)pyridin-3-yl)oxy)benzamide (141)

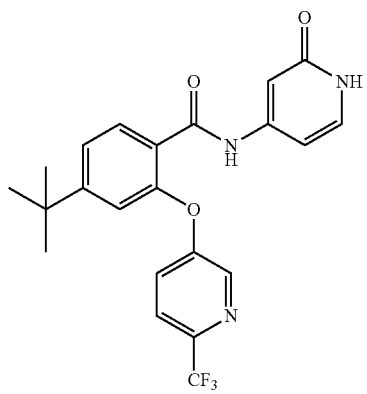 [SMILES: CC(C)(C)c1ccc(C(=O)Nc2cc[nH]c(=O)c2)c(Oc2ccc(C(F)(F)F)nc2)c1]

A solution of 4-(tert-butyl)-2-((6-(trifluoromethyl)pyridin-3-yl)oxy)benzoic acid (169.7 mg, 0.5 mmol), HATU (190 mg, 0.5 mmol), 2-methoxypyridin-4-amine (62.1 mg, 0.5 mmol) and tri-ethyl amine (278.8 µL, 2 mmol) in dichloromethane (5 mL) was stirred at room temperature over 72 hours. The reaction was purified by silica gel chromatography using gradient of ethyl acetate in hexanes (0-40%) to yield 4-(tert-butyl)-N-(2-methoxypyridin-4-yl)-2-((6-(trifluoromethyl)pyridin-3-yl)oxy)benzamide (137 mg, 60%). ESI-MS m/z calc. 445.16. found 446.3 (M+1)+; Retention time: 1.87 minutes (3 minutes run).

To the 4-(tert-butyl)-N-(2-methoxypyridin-4-yl)-2-((6-(trifluoromethyl)pyridin-3-yl)oxy)benzamide (137 mg, 0.3 mmol) in acetonitrile (4.9 mL) was added TMSI (93.3 µL, 0.66 mmol). The reaction was stirred at 50° C. for 12 hours. The reactions was cooled to 25° C., filtered and purified by reverse phase HPLC (10-99% ACN in Water with HCl as a modifier) to yield 4-(tert-butyl)-N-(2-oxo-1,2-dihydropyridin-4-yl)-2-((6-(trifluoromethyl)pyridin-3-yl)oxy)benzamide (141) (14.4 mg, 13%). ESI-MS m/z calc. 431.15. found 432.3 (M+1)+; Retention time: 1.78 minutes (3 minutes run).

The following products were prepared using a similar reaction sequence as described above for compound 141.

| Cmpd No. | Product |
|---|---|
| 6 | 2-(4-fluorophenoxy)-N-(6-oxo-1H-pyridin-3-yl)-4-(trifluoromethyl)benzamide |
| 4 | 2-(4-fluorophenoxy)-N-(6-oxo-1,6-dihydropyridin-3-yl)-5-(trifluoromethyl)benzamide |
| 43 | 2-(4-fluorophenoxy)-N-(2-oxo-1,2-dihydropyridin-4-yl)-6-(trifluoromethyl)benzamide |
| 142 | 4-(tert-butyl)-N-(6-oxo-1,6-dihydropyridin-3-yl)-2-((6-(trifluoromethyl)pyridin-3-yl)oxy)benzamide |
| 1 | 2-(4-fluorophenoxy)-N-(2-oxo-1,2-dihydropyridin-4-yl)benzamide |
| 145 | N-(6-oxo-1,6-dihydropyridin-3-yl)-4-(trifluoromethyl)-2-((6-(trifluoromethyl)pyridin-3-yl)oxy)benzamide |
| 3 | 2-(4-fluorophenoxy)-N-(6-oxo-1,6-dihydropyridin-3-yl)benzamide |

Example 28

Preparation of 4-(tert-butyl)-N-(1-methyl-2-oxo-1,2-dihydropyridin-4-yl)-2-((6-(trifluoromethyl)pyridin-3-yl)oxy)benzamide (148)

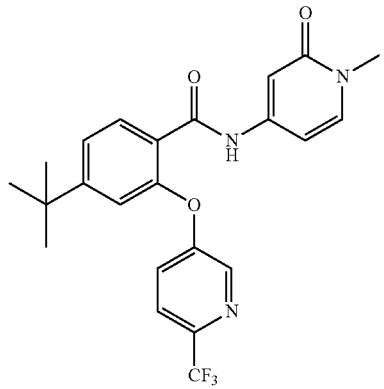 [SMILES: Cn1ccc(NC(=O)c2ccc(C(C)(C)C)cc2Oc2ccc(C(F)(F)F)nc2)cc1=O]

A solution of 4-(tert-butyl)-2-((6-(trifluoromethyl)pyridin-3-yl)oxy)benzoic acid (67.9 mg, 0.2 mmol), HATU (66 mg, 0.2 mmol), 5-amino-1-methylpyridyl-2-one (24.8 mg, 0.2 mmol) and triethylamine (111 μL, 0.8 mmol) in dichloromethane (0.9 mL) was stirred at room temperature over 72 hours. The reaction was filtered and purified by reverse phase HPLC using a gradient of acetonitrile in water (10-99%) and HCl as a modifier to yield 4-(tert-butyl)-N-(1-methyl-2-oxo-1,2-dihydropyridin-4-yl)-2-((6-(trifluoromethyl)pyridin-3-yl)oxy)benzamide (148) (1.2 mg, 1%). ESI-MS m/z calc. 445.16. found 446.3 (M+1)+; Retention time: 1.85 minutes (3 minutes run).

4-tert-Butyl-N-(1-methyl-6-oxo-3-pyridyl)-2-[[6-(trifluoromethyl)-3-pyridyl]oxy]benzamide (149) was prepared using a similar reaction sequence as described above for compound 148.

Example 29

Preparation of 2-(4-fluorophenoxy)-N-(1-(2-hydroxyethyl)-2-oxo-1,2-dihydropyridin-4-yl)-4-(trifluoromethyl)benzamide (85)

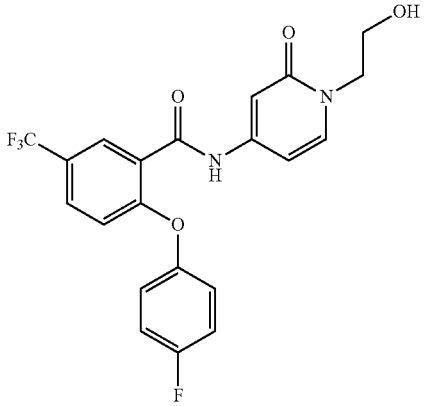 [SMILES: O=C(Nc1ccn(CCO)c(=O)c1)c1cc(C(F)(F)F)ccc1Oc1ccc(F)cc1]

To 2-(4-fluorophenoxy)-N-(2-oxo-1H-pyridin-4-yl)-5-(trifluoromethyl)benzamide (78.5 mg, 0.2 mmol), in DMF (1 ml) was added sodium hydride (4.8 mg, 0.20 mmol) and 2-bromoethanol (14.17 μL, 0.20 mmol) and the reaction was stirred at room temperature for 16 hours. The reaction was reloaded with sodium hydride (4.8 mg, 0.20 mmol) and 2-bromoethanol (14.17 μL, 0.20 mmol) and stirred for an additional 8 hours after which 2 additional equivalents of sodium hydride and 2-bromoethanol were added and the reaction was heated at 50° C. overnight. 29 mg NaH and 86 μL of 2-bromoethanol were added and the reaction was heated at 50° C. for 2.5 hours. Another 29 mg NaH and 86 μL of 2-bromoethanol were added and the reaction was heated at 100° C. for 5 hours. The reaction was quenched with methanol and the solvent was evaporated under reduced pressure. The crude product was dissolved in DMF, filtered and purified by reverse phase preparative chromatography utilizing a gradient of 10-99% acetonitrile in water containing HCl as a modifier to yield 2-(4-fluorophenoxy)-N-(1-(2-hydroxyethyl)-2-oxo-1,2-dihydropyridin-4-yl)-4-(trifluoromethyl)benzamide (85) (43.6 mg, 50%). $^1$H NMR (400 MHz, DMSO-d6) δ 10.63 (s, 1H), 7.99 (d, J=2.3 Hz, 1H), 7.83 (dd, J=8.8, 2.4 Hz, 1H), 7.54 (d, J=7.4 Hz, 1H), 7.38-7.22 (m, 4H), 6.98 (d, J=8.7 Hz, 1H), 6.85 (d, J=2.4 Hz, 1H), 6.42 (dd, J=7.4, 2.4 Hz, 1H), 3.87 (t, J=5.5 Hz, 2H), 3.57 (t, J=5.5 Hz, 2H) ppm. ESI-MS m/z calc. 436.1. found 437.3 (M+1)+; Retention time: 1.72 minutes (3 minutes run).

Example 30

Preparation of 2-(4-fluoro-2-methoxyphenoxy)-N-(2-oxo-1,2-dihydropyridin-4-yl)-4,6-bis(trifluoromethyl)benzamide (154)

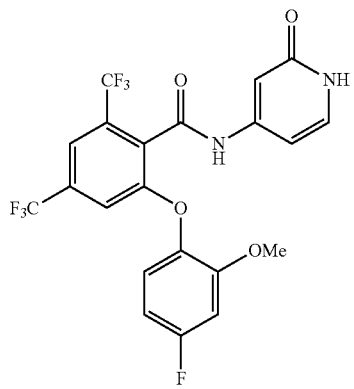 [SMILES: COc1cc(F)ccc1Oc1cc(C(F)(F)F)cc(C(F)(F)F)c1C(=O)Nc1cc[nH]c(=O)c1]

A solution of 2-fluoro-N-(2-oxo-1H-pyridin-4-yl)-4,6-bis(trifluoromethyl)benzamide (40 mg, 0.11 mmol), 4-fluoro-2-methoxyphenol (12.4 μl, 0.11 mmol), and potassium carbonate (45 mg, 0.33 mmol), were combined in DMF (0.5 mL) and heated at 90° C. for 16 h. The reaction was filtered, diluted with DMSO (0.5 mL) and purified by reverse phase HPLC using a gradient of 25-99% acetonitrile: water and 5 mM HCl as a modifier to provide 2-(4-fluoro-2-methoxyphenoxy)-N-(2-oxo-1,2-dihydropyridin-4-yl)-4,6-bis(trifluoromethyl)benzamide (154) (17.2 mg, 32%). $^1$H NMR (400 MHz, DMSO-d6) δ 11.38 (br s, 1H), 10.91 (s, 1H), 7.91 (s, 1H), 7.35 (d, J=7.2 Hz, 1H), 7.26 (dd, J=8.9, 5.8 Hz, 1H), 7.20 (dd, J=10.7, 2.9 Hz, 1H), 7.15 (s, 1H), 6.88 (td, J=8.5, 2.9 Hz, 1H), 6.73 (d, J=2.1 Hz, 1H), 6.37 (dd, J=7.2, 2.1 Hz, 1H), 3.79 (s, 3H) ppm. ESI-MS m/z calc. 490.08. found 491.3 (M+1)+; Retention time: 1.60 minutes (3 minutes run).

The following products were prepared using a similar reaction sequence as described above for compound 154.

| Cmpd No. | Product | Alcohol |
|---|---|---|
| 156 | N-(2-oxo-1,2-dihydropyridin-4-yl)-2-phenoxy-4,6-bis(trifluoromethyl)benzamide | Phenol |
| 155 | 2-(4-fluorophenoxy)-N-(2-oxo-1,2-dihydropyridin-4-yl)-4,6-bis(trifluoromethyl)benzamide | 4-fluorophenol |
| 153 | 2-(4-fluoro-2-methylphenoxy)-N-(2-oxo-1,2-dihydropyridin-4-yl)-4,6-bis(trifluoromethyl)benzamide | 4-fluoro-2-methyl-phenol |
| 152 | 2-(2,4-difluorophenoxy)-N-(2-oxo-1,2-dihydropyridin-4-yl)-4,6-bis(trifluoromethyl)benzamide | 2,4-difluorophenol |

Analytical data for the compounds of the present invention is provided below in Table 2. Mass Spec (e.g., M+1 data in Table 2), final purity and retention times were determined by reverse phase HPLC using a Kinetix C18 column (50×2.1 mm, 1.7 μm particle) from Phenomenex (pn: 00B-4475-AN)), and a dual gradient run from 1-99% mobile phase B over 3 minutes. Mobile phase A=$H_2O$ (0.05% $CF_3CO_2H$). Mobile phase B=$CH_3CN$ (0.05% $CF_3CO_2H$). Flow rate=2 mL/min, injection volume=3 μL, and column temperature=50° C.

TABLE 2

Analytical Data

| Cmpd. No. | LCMS Ret. Time in minutes | MS (M + 1) | $^1$H-NMR (400 MHz) |
|---|---|---|---|
| 1 | 1.48 | 325.3 | (DMSO-$d_6$) δ 11.23 (s, 1H), 10.44 (s, 1H), 7.62 (dd, J = 7.6, 1.7 Hz, 1H), 7.50 (m, 1H), 7.25 (ddd, J = 9.4, 8.6, 5.3 Hz, 4H), 7.12 (m, 2H), 6.91 (d, J = 8.0 Hz, 1H), 6.77 (d, J = 1.9 Hz, 1H), 6.40 (dd, J = 7.2, 2.0 Hz, 1H) ppm |
| 2 | 1.72 | 393.1 | (DMSO-$d_6$) δ 11.40 (s, 1H), 10.64 (s, 1H), 8.00 (d, J = 2.2 Hz, 1H), 7.83 (dd, J = 8.8, 2.3 Hz, 1H), 7.30 (tdd, J = 6.9, 5.9, 3.4 Hz, 5H), 6.99 (d, J = 8.8 Hz, 1H), 6.82 (d, J = 1.8 Hz, 1H), 6.43 (dd, J = 7.2, 2.0 Hz, 1H) ppm |
| 3 | 1.47 | 325.3 | (DMSO-$d_6$) δ 10.09 (s, 1H), 7.92 (d, J = 2.8 Hz, 1H), 7.63 (dd, J = 7.6, 1.7 Hz, 1H), 7.50 (m, 2H), 7.23 (m, 3H), 7.08 (m, 2H), 6.93 (d, J = 7.6 Hz, 1H), 6.38 (d, J = 9.7 Hz, 1H) ppm |
| 4 | 1.7 | 393.1 | (DMSO-$d_6$) δ 11.54 (m, 0H), 10.24 (s, 1H), 7.95 (dd, J = 19.3, 2.5 Hz, 2H), 7.81 (dd, J = 8.8, 2.1 Hz, 1H), 7.51 (dd, J = 9.7, 2.9 Hz, 1H), 7.27 (m, 4H), 7.01 (d, J = 8.6 Hz, 1H), 6.38 (d, J = 9.7 Hz, 1H) ppm |
| 5 | 1.72 | 393.1 | (DMSO-$d_6$) δ 11.31 (s, 1H), 10.63 (s, 1H), 7.85 (d, J = 7.9 Hz, 1H), 7.63 (d, J = 7.9 Hz, 1H), 7.29 (ddd, J = 8.2, 6.6, 4.6 Hz, 3H), 7.21 (m, 2H), 7.14 (s, 1H), 6.76 (d, J = 1.6 Hz, 1H), 6.39 (dd, J = 7.2, 2.0 Hz, 1H) ppm |
| 6 | 1.69 | 393.1 | (DMSO-$d_6$) δ 11.43 (s, 1H), 10.27 (s, 1H), 7.90 (d, J = 2.7 Hz, 1H), 7.84 (d, J = 7.9 Hz, 1H), 7.62 (d, J = 7.1 Hz, 1H), 7.48 (dd, J = 9.7, 2.9 Hz, 1H), 7.27 (dt, J = 12.2, 3.0 Hz, 2H), 7.18 (m, 3H), 6.37 (d, J = 9.7 Hz, 1H) ppm |
| 7 | 1.55 | 411.17 | |
| 8 | 1.52 | 449.26 | |
| 9 | 1.69 | 375.1 | (DMSO-$d_6$) δ 11.26 (s, 1H), 10.62 (s, 1H), 7.86 (d, J = 7.9 Hz, 1H), 7.63 (d, J = 8.0 Hz, 1H), 7.44 (m, 2H), 7.30 (d, J = 7.2 Hz, 1H), 7.23 (t, J = 7.4 Hz, 1H), 7.15 (dd, J = 7.1, 6.1 Hz, 3H), 6.75 (d, J = 1.7 Hz, 1H), 6.37 (dd, J = 7.2, 2.0 Hz, 1H) ppm |
| 10 | 1.79 | 407.1 | (DMSO-$d_6$) δ 11.27 (s, 1H), 10.63 (s, 1H), 7.84 (d, J = 7.8 Hz, 1H), 7.60 (d, J = 7.8 Hz, 1H), 7.31 (d, J = 7.2 Hz, 1H), 7.23 (m, 1H), 7.10 (m, 2H), 6.97 (s, 1H), 6.76 (d, J = 1.6 Hz, 1H), 6.38 (dd, J = 7.2, 2.0 Hz, 1H), 2.16 (s, 3H) ppm |
| 11 | 1.76 | 389.1 | (DMSO-$d_6$) δ 11.27 (s, 1H), 10.64 (s, 1H), 7.84 (d, J = 7.8 Hz, 1H), 7.60 (d, J = 7.9 Hz, 1H), 7.30 (m, 3H), 7.16 (td, J = 7.4, 1.1 Hz, 1H), 7.00 (m, 2H), 6.75 (d, J = 1.8 Hz, 1H), 6.38 (dd, J = 7.2, 2.1 Hz, 1H), 2.17 (s, 3H) ppm |
| 12 | 1.8 | 389.1 | (DMSO-$d_6$) δ 11.27 (s, 1H), 10.60 (s, 1H), 7.83 (d, J = 8.0 Hz, 1H), 7.59 (d, J = 8.0 Hz, 1H), 7.31 (d, J = 7.2 Hz, 1H), 7.25 (d, J = 8.2 Hz, 2H), 7.05 (d, J = 8.5 Hz, 3H), 6.76 (s, 1H), 6.38 (dd, J = 7.2, 2.0 Hz, 1H), 2.31 (s, 3H) ppm |
| 13 | 1.48 | 377.1 | |
| 14 | 1.55 | 393.1 | |
| 15 | 1.48 | 359.2 | (DMSO-$d_6$) δ 11.25 (s, 1H), 10.48 (s, 1H), 7.65 (t, J = 8.5 Hz, 1H), 7.29 (m, 4H), 7.19 (m, 2H), 6.91 (d, J = 1.9 Hz, 1H), 6.75 (d, J = 1.9 Hz, 1H), 6.38 (dd, J = 7.2, 2.1 Hz, 1H) ppm |
| 16 | 1.53 | 389.2 | |
| 17 | 1.53 | 373.2 | |
| 18 | 1.43 | 393.0 | |
| 19 | 1.43 | 377.1 | |

TABLE 2-continued

Analytical Data

| Cmpd. No. | LCMS Ret. Time in minutes | MS (M + 1) | ¹H-NMR (400 MHz) |
|---|---|---|---|
| 20 | 1.57 | 373.2 | (DMSO-d$_6$) δ 11.48 (s, 1H), 10.57 (s, 1H), 7.65 (d, J = 8.2 Hz, 1H), 7.36 (d, J = 7.2 Hz, 1H), 7.30 (dd, J = 8.2, 1.9 Hz, 1H), 7.21 (d, J = 9.3 Hz, 1H), 7.10 (m, 2H), 6.83 (d, J = 1.9 Hz, 1H), 6.74 (d, J = 1.9 Hz, 1H), 6.45 (dd, J = 7.2, 2.1 Hz, 1H), 2.16 (s, 3H) ppm |
| 21 | 1.26 | 350.1 | |
| 22 | 1.3 | 380.2 | |
| 23 | 1.4 | 364.1 | |
| 24 | 1.52 | 411.2 | |
| 25 | 1.28 | 400.3 | |
| 26 | 1.47 | 411.2 | (DMSO-d$_6$) δ 11.30 (s, 1H), 10.71 (d, J = 7.0 Hz, 1H), 8.03 (d, J = 2.1 Hz, 1H), 7.83 (d, J = 8.4 Hz, 1H), 7.39 (m, 4H), 7.03 (d, J = 8.7 Hz, 1H), 6.84 (d, J = 21.3 Hz, 1H), 6.46 (m, 1H) ppm |
| 27 | 1.62 | 389.3 | |
| 28 | 1.58 | 389.3 | (DMSO-d$_6$) δ 11.28 (s, 1H), 10.62 (s, 1H), 7.99 (d, J = 2.2 Hz, 1H), 7.80 (dd, J = 8.8, 2.2 Hz, 1H), 7.31 (ddd, J = 12.7, 9.2, 4.5 Hz, 3H), 7.20 (td, J = 7.4, 1.2 Hz, 1H), 7.12 (m, 1H), 6.81 (dd, J = 12.2, 5.3 Hz, 2H), 6.41 (dd, J = 7.2, 2.1 Hz, 1H), 2.15 (s, 3H) ppm |
| 29 | 1.57 | 427.2 | (DMSO-d$_6$) δ 11.29 (s, 1H), 10.62 (s, 1H), 8.02 (d, J = 2.2 Hz, 1H), 7.83 (dd, J = 8.8, 2.2 Hz, 1H), 7.69 (dd, J = 8.4, 3.0 Hz, 1H), 7.45 (dd, J = 9.1, 5.3 Hz, 1H), 7.40-7.30 (m, 2H), 6.92 (d, J = 8.7 Hz, 1H), 6.79 (d, J = 1.9 Hz, 1H), 6.42 (dd, J = 7.2, 2.1 Hz, 1H) ppm |
| 30 | 1.56 | 423.2 | |
| 31 | 1.6 | 407.2 | (DMSO-d$_6$) δ 11.77 (s, 1H), 10.79 (s, 1H), 8.00 (d, J = 2.2 Hz, 1H), 7.80 (dd, J = 8.8, 2.3 Hz, 1H), 7.45 (d, J = 7.2 Hz, 1H), 7.25 (dd, J = 9.3, 3.0 Hz, 1H), 7.16 (m, 2H), 6.95 (d, J = 1.9 Hz, 1H), 6.83 (d, J = 8.7 Hz, 1H), 6.56 (dd, J = 7.2, 2.0 Hz, 1H), 2.14 (s, 3H) ppm |
| 32 | 1.5 | 375.2 | (DMSO-d$_6$) δ 11.32 (s, 1H), 10.62 (s, 1H), 7.99 (s, 1H), 7.83 (m, 1H), 7.47 (t, J = 7.9 Hz, 2H), 7.29 (m, 2H), 7.19 (d, J = 7.6 Hz, 2H), 7.00 (d, J = 8.7 Hz, 1H), 6.79 (s, 1H), 6.41 (m, 1H) ppm |
| 33 | 1.59 | 427.1 | |
| 34 | 1.51 | 427.2 | |
| 35 | 1.64 | 405.2 | |
| 36 | 1.62 | 405.2 | |
| 37 | 1.61 | 443.1 | |
| 38 | 1.56 | 409.1 | |
| 39 | 1.6 | 423.1 | |
| 40 | 1.64 | 423.1 | |
| 41 | 1.54 | 391.1 | |
| 42 | 1.62 | 439.1 | |
| 43 | 1.51 | 393.3 | (DMSO-d$_6$) δ 11.29 (s, 1H), 10.80 (s, 1H), 7.69-7.56 (m, 2H), 7.34-7.25 (m, 3H), 7.22-7.14 (m, 3H), 6.71 (d, J = 2.0 Hz, 1H), 6.34 (dd, J = 7.2, 2.1 Hz, 1H) ppm |
| 44 | 1.83 | 419.3 | (DMSO-d$_6$) δ 11.43 (s, 1H), 10.62 (s, 1H), 7.95 (d, J = 2.4 Hz, 1H), 7.80 (dd, J = 8.9, 2.4 Hz, 1H), 7.35 (d, J = 7.1 Hz, 1H), 7.22-7.10 (m, 2H), 7.07-6.95 (m, 2H), 6.95-6.80 (m, 2H), 6.45 (dd, J = 7.3, 2.1 Hz, 1H), 4.03 (q, J = 6.9 Hz, 2H), 1.33 (t, J = 6.9 Hz, 3H) ppm |
| 45 | 1.73 | 405.4 | (DMSO-d$_6$) δ 11.51 (s, 1H), 10.66 (s, 1H), 7.96 (d, J = 2.2 Hz, 1H), 7.80 (dd, J = 8.9, 2.4 Hz, 1H), 7.38 (d, J = 7.2 Hz, 1H), 7.24-7.10 (m, 2H), 7.08-6.96 (m, 2H), 6.92-6.86 (m, 2H), 6.48 (dd, J = 7.2, 2.1 Hz, 1H), 3.77 (s, 3H) ppm |
| 46 | 1.81 | 419.3 | (DMSO-d$_6$) δ 11.31 (s, 1H), 10.50 (s, 1H), 7.95 (d, J = 2.3 Hz, 1H), 7.78 (dd, J = 8.8, 2.4 Hz, 1H), 7.33 (d, J = 7.2 Hz, 1H), 7.31-7.24 (m, 2H), 7.20 (dd, J = 8.3, 1.6 Hz, 1H), 7.04 (td, J = 7.6, 1.6 Hz, 1H), 6.89-6.74 (m, 2H), 6.43 (dd, J = 7.2, 2.1 Hz, 1H), 4.02 (q, J = 7.0 Hz, 2H), 1.12 (t, J = 6.9 Hz, 3H) ppm |
| 47 | 1.84 | 419.3 | (DMSO-d$_6$) δ 11.28 (s, 1H), 10.50 (s, 1H), 7.92 (d, J = 2.3 Hz, 1H), 7.75 (dd, J = 8.8, 2.3 Hz, 1H), 7.32 (d, J = 7.1 Hz, 1H), 7.16 (d, J = 8.1 Hz, 1H), 7.05 (d, J = 2.1 Hz, 1H), 6.85 (dd, J = 8.1, 2.1 Hz, 1H), 6.82 (d, J = 2.1 Hz, 1H), 6.74 (d, J = 8.7 Hz, 1H), 6.42 (dd, J = 7.3, 2.1 Hz, 1H), 3.72 (s, 3H), 2.35 (s, 3H) ppm |
| 48 | 1.73 | 423.3 | (DMSO-d$_6$) δ 11.52 (s, 1H), 10.64 (s, 1H), 7.97 (d, J = 2.3 Hz, 1H), 7.78 (dd, J = 8.9, 2.3 Hz, 1H), 7.41-7.36 (m, 1H), 7.36-7.30 (m, 1H), 7.14-7.00 (m, 2H), 6.90 (d, J = 2.0 Hz, 1H), 6.83 (d, J = 8.8 Hz, 1H), 6.51 (dd, J = 7.2, 2.1 Hz, 1H), 3.79 (s, 3H) ppm |
| 49 | 1.8 | 439.2 | |
| 50 | 1.89 | 423.3 | |

TABLE 2-continued

Analytical Data

| Cmpd. No. | LCMS Ret. Time in minutes | MS (M + 1) | $^1$H-NMR (400 MHz) |
|---|---|---|---|
| 51 | 1.79 | 427.1 | |
| 52 | 1.74 | 423.3 | |
| 53 | 1.94 | 433.4 | |
| 54 | 1.73 | 423.3 | |
| 55 | 1.74 | 423.3 | (DMSO-d$_6$) δ 11.50 (s, 1H), 10.70 (s, 1H), 7.98 (d, J = 2.3 Hz, 1H), 7.81 (dd, J = 8.8, 2.3 Hz, 1H), 7.43-7.28 (m, 2H), 7.10 (dd, J = 12.7, 2.9 Hz, 1H), 6.95-6.83 (m, 3H), 6.48 (dd, J = 7.3, 2.1 Hz, 1H), 3.79 (s, 3H) ppm |
| 56 | 1.8 | 407.4 | |
| 57 | 1.58 | 423.3 | (DMSO-d$_6$) δ 11.52 (s, 1H), 10.90 (s, 1H), 7.74 (d, J = 2.3 Hz, 1H), 7.47 (dd, J = 8.7, 2.4 Hz, 1H), 7.33 (d, J = 7.2 Hz, 1H), 6.87 (d, J = 8.6 Hz, 1H), 6.84-6.72 (m, 3H), 6.17 (d, J = 7.2 Hz, 1H), 6.06 (d, J = 2.1 Hz, 1H), 3.69 (s, 3H) ppm |
| 58 | 1.81 | 409.3 | |
| 59 | 1.72 | 423.3 | |
| 60 | 2.04 | 441.3 | (DMSO-d$_6$) δ 11.41 (s, 1H), 10.95 (s, 1H), 8.02 (d, J = 2.1 Hz, 1H), 7.81 (dd, J = 8.8, 2.3 Hz, 1H), 7.29-7.09 (m, 4H), 6.97 (s, 1H), 6.84 (d, J = 8.7 Hz, 1H), 2.13 (s, 3H) ppm |
| 61 | 1.85 | 421.3 | (DMSO-d$_6$) δ 11.45 (s, 1H), 10.57 (s, 1H), 7.97 (d, J = 2.2 Hz, 1H), 7.79 (dd, J = 8.8, 2.3 Hz, 1H), 7.26 (dd, J = 9.4, 2.9 Hz, 1H), 7.22-7.08 (m, 2H), 6.81 (d, J = 8.7 Hz, 1H), 6.67 (d, J = 1.3 Hz, 1H), 6.27 (s, 1H), 2.15 (s, 3H), 2.14 (s, 3H) ppm |
| 62 | 1.91 | 433.4 | (DMSO-d$_6$) δ 11.27 (s, 1H), 10.47 (s, 1H), 7.95 (d, J = 2.2 Hz, 1H), 7.77 (dd, J = 8.8, 2.3 Hz, 1H), 7.36-7.23 (m, 3H), 7.23-7.17 (m, 1H), 7.08-7.00 (m, 1H), 6.84-6.77 (m, 2H), 6.42 (dd, J = 7.2, 2.0 Hz, 1H), 3.90 (t, J = 6.3 Hz, 2H), 1.62-1.38 (m, 2H), 0.67 (t, J = 7.4 Hz, 3H) ppm |
| 63 | 1.81 | 419.3 | (DMSO-d$_6$) δ 11.38 (s, 1H), 10.62 (s, 1H), 7.96 (d, J = 2.2 Hz, 1H), 7.77 (dd, J = 8.8, 2.3 Hz, 1H), 7.35 (d, J = 7.2 Hz, 1H), 7.11 (d, J = 8.8 Hz, 1H), 6.94 (d, J = 2.9 Hz, 1H), 6.90-6.80 (m, 2H), 6.74 (d, J = 8.8 Hz, 1H), 6.45 (dd, J = 7.2, 2.0 Hz, 1H), 3.76 (s, 3H), 2.10 (s, 3H) ppm |
| 64 | 1.87 | 433.4 | (DMSO-d$_6$) δ 11.29 (s, 1H), 10.46 (s, 1H), 7.96 (d, J = 2.2 Hz, 1H), 7.78 (dd, J = 8.8, 2.0 Hz, 1H), 7.40-7.12 (m, 4H), 7.12-6.93 (m, 1H), 6.86-6.73 (m, 2H), 6.42 (dd, J = 7.2, 2.1 Hz, 1H), 4.69-4.41 (m, 1H), 1.07 (d, J = 6.0 Hz, 6H) ppm |
| 65 | 1.74 | 409.3 | (DMSO-d$_6$) δ 11.30 (s, 1H), 10.62 (s, 1H), 8.02 (d, J = 2.2 Hz, 1H), 7.84 (dd, J = 8.8, 2.3 Hz, 1H), 7.65 (dd, J = 7.9, 1.5 Hz, 1H), 7.54-7.39 (m, 1H), 7.39-7.24 (m, 3H), 6.91 (d, J = 8.7 Hz, 1H), 6.79 (d, J = 1.8 Hz, 1H), 6.41 (dd, J = 7.2, 2.1 Hz, 1H) ppm |
| 66 | 1.64 | 393.1 | |
| 67 | 1.46 | 359.2 | |
| 68 | 1.57 | 373.1 | |
| 69 | 1.46 | 377.1 | |
| 70 | 1.52 | 389.1 | |
| 71 | 1.46 | 389.2 | |
| 72 | 1.93 | 459.3 | (DMSO-d$_6$) δ 11.29 (s, 1H), 10.62 (s, 1H), 8.02 (d, J = 2.3 Hz, 1H), 7.86 (dd, J = 8.7, 2.4 Hz, 1H), 7.58-7.40 (m, 2H), 7.40-7.21 (m, 3H), 7.11 (d, J = 8.7 Hz, 1H), 6.76 (d, J = 2.1 Hz, 1H), 6.38 (dd, J = 7.2, 2.1 Hz, 1H) ppm |
| 73 | 1.83 | 441.5 | (DMSO-d$_6$) δ 11.77 (s, 1H), 10.79 (s, 1H), 8.01 (d, J = 2.3 Hz, 1H), 7.85 (dd, J = 8.9, 2.4 Hz, 1H), 7.49-6.99 (m, 7H), 6.94 (d, J = 2.0 Hz, 1H), 6.54 (dd, J = 7.2, 2.1 Hz, 1H) ppm |
| 74 | 1.75 | 443.5 | (DMSO-d$_6$) δ 11.55 (s, 1H), 10.93 (s, 1H), 7.83-7.67 (m, 3H), 7.61-7.45 (m, 3H), 7.33 (d, J = 7.0 Hz, 1H), 6.88 (d, J = 8.5 Hz, 1H), 6.11-5.98 (m, 2H) ppm |
| 75 | 1.83 | 459.3 | (DMSO-d$_6$) δ 11.28 (s, 1H), 10.63 (s, 1H), 8.04 (d, J = 2.3 Hz, 1H), 7.86 (dd, J = 8.7, 2.4 Hz, 1H), 7.60-7.54 (m, 1H), 7.54-7.43 (m, 1H), 7.43-7.34 (m, 1H), 7.34-7.28 (m, 2H), 7.05 (d, J = 8.7 Hz, 1H), 6.75 (d, J = 2.0 Hz, 1H), 6.38 (dd, J = 7.2, 2.1 Hz, 1H) ppm |
| 76 | 1.76 | 441.5 | (DMSO-d$_6$) δ 11.56 (s, 1H), 10.69 (s, 1H), 8.02 (d, J = 2.3 Hz, 1H), 7.84 (dd, J = 8.8, 2.4 Hz, 1H), 7.47-6.97 (m, 6H), 6.94 (d, J = 8.7 Hz, 1H), 6.87 (d, J = 2.0 Hz, 1H), 6.49 (dd, J = 7.2, 2.1 Hz, 1H) ppm |
| 77 | 1.78 | 427.3 | (DMSO-d$_6$) δ 11.29 (s, 1H), 10.64 (s, 1H), 7.87 (d, J = 8.0 Hz, 1H), 7.71-7.61 (m, 2H), 7.39-7.26 (m, 3H), 7.13-7.06 (m, 1H), 6.75 (d, J = 2.0 Hz, 1H), 6.39 (dd, J = 7.2, 2.1 Hz, 1H) ppm |
| 78 | 1.73 | 409.3 | (DMSO-d$_6$) δ 11.28 (s, 1H), 10.62 (s, 1H), 7.87 (d, J = 8.0 Hz, 1H), 7.67 (d, J = 7.1 Hz, 1H), 7.48 (m, 2H), 7.30 (m, 2H), 7.13 (m, 2H), 6.73 (s, 1H), 6.36 (dd, J = 7.2, 2.0 Hz, 1H) ppm |
| 79 | 1.8 | 459.5 | |

TABLE 2-continued

Analytical Data

| Cmpd. No. | LCMS Ret. Time in minutes | MS (M + 1) | $^1$H-NMR (400 MHz) |
|---|---|---|---|
| 80 | 1.74 | 459.3 | |
| 81 | 1.65 | 423.3 | |
| 82 | 1.71 | 441.3 | |
| 83 | 1.68 | 441.3 | |
| 84 | 1.67 | 423.3 | (DMSO-d$_6$) δ 11.34 (s, 1H), 10.67 (s, 1H), 7.83 (d, J = 7.8 Hz, 1H), 7.60 (d, J = 7.9 Hz, 1H), 7.32 (m, 2H), 7.09 (dd, J = 12.7, 3.0 Hz, 1H), 6.98 (s, 1H), 6.87 (m, 1H), 6.80 (d, J = 1.7 Hz, 1H), 6.42 (dd, J = 7.2, 2.0 Hz, 1H), 3.79 (s, 3H) ppm |
| 85 | 1.72 | 437.3 | (DMSO-d$_6$) δ 10.63 (s, 1H), 7.99 (d, J = 2.3 Hz, 1H), 7.83 (dd, J = 8.8, 2.4 Hz, 1H), 7.54 (d, J = 7.4 Hz, 1H), 7.38-7.22 (m, 4H), 6.98 (d, J = 8.7 Hz, 1H), 6.85 (d, J = 2.4 Hz, 1H), 6.42 (dd, J = 7.4, 2.4 Hz, 1H), 3.87 (t, J = 5.5 Hz, 2H), 3.57 (t, J = 5.5 Hz, 2H) ppm |
| 86 | 1.89 | 421.2 | (DMSO-d$_6$) δ 11.66 (s, 1H), 9.91 (s, 1H), 8.22 (d, J = 2.4 Hz, 1H), 7.85 (dd, J = 8.8, 2.4 Hz, 1H), 7.45-7.28 (m, 4H), 7.20 (td, J = 8.5, 3.1 Hz, 1H), 6.78 (d, J = 8.8 Hz, 1H), 2.17 (s, 3H), 1.96 (s, 3H) ppm |
| 87 | 1.67 | 423.1 | |
| 88 | 1.59 | 443.5 | (DMSO-d$_6$) δ 7.87 (d, J = 7.9 Hz, 1H), 7.59 (d, J = 7.6 Hz, 1H), 7.37-7.25 (m, 3H), 7.24-7.16 (m, 2H), 7.07 (s, 1H), 6.73 (s, 1H), 6.37 (d, J = 6.9 Hz, 1H) ppm |
| 89 | 1.58 | 473.3 | (DMSO-d$_6$) δ 11.28 (s, 1H), 10.62 (s, 1H), 7.87 (d, J = 8.0 Hz, 1H), 7.58 (d, J = 8.2 Hz, 1H), 7.31 (d, J = 6.9 Hz, 1H), 7.27-7.16 (m, 2H), 7.07 (s, 1H), 6.98 (d, J = 8.9 Hz, 1H), 6.76 (s, 1H), 6.38 (d, J = 7.1 Hz, 1H), 3.84 (s, 3H) ppm |
| 90 | 1.76 | 429.3 | |
| 91 | 1.98 | 417.4 | |
| 92 | 1.81 | 425.2 | |
| 93 | 1.99 | 417.4 | |
| 94 | 1.83 | 367.3 | |
| 95 | 1.5 | 325.5 | (DMSO-d$_6$) δ 11.24 (s, 1H), 10.49 (s, 1H), 7.54 (dd, J = 8.4, 3.2 Hz, 1H), 7.43-7.32 (m, 3H), 7.28 (d, J = 7.2 Hz, 1H), 7.12 (t, J = 7.4 Hz, 1H), 7.05 (dd, J = 9.0, 4.5 Hz, 1H), 7.03-6.97 (m, 2H), 6.71 (d, J = 1.9 Hz, 1H), 6.37 (dd, J = 7.2, 2.1 Hz, 1H) ppm |
| 96 | 1.69 | 365.3 | |
| 97 | 1.66 | 397.3 | (DMSO-d$_6$) δ 11.23 (s, 1H), 10.46 (s, 1H), 7.50 (dd, J = 8.4, 3.2 Hz, 1H), 7.40-7.32 (m, 1H), 7.28 (d, J = 7.1 Hz, 1H), 7.00 (dd, J = 9.1, 4.4 Hz, 1H), 6.98-6.92 (m, 4H), 6.72 (d, J = 1.8 Hz, 1H), 6.37 (dd, J = 7.2, 2.0 Hz, 1H), 1.24 (s, 9H) ppm |
| 98 | 1.61 | 369.3 | |
| 99 | 1.74 | 367.3 | |
| 100 | 1.73 | 383.3 | |
| 101 | 1.68 | 409.3 | |
| 102 | 1.53 | 383.3 | |
| 103 | 1.61 | 389.5 | (DMSO-d$_6$) δ 11.26 (s, 1H), 10.50 (s, 1H), 7.52 (dd, J = 8.4, 3.2 Hz, 1H), 7.36-7.27 (m, 2H), 7.17 (dd, J = 6.0, 3.0 Hz, 2H), 6.97 (dd, J = 9.0, 3.0 Hz, 1H), 6.81-6.73 (m, 2H), 6.43-6.36 (m, 1H), 3.77 (s, 3H) ppm |
| 104 | 1.54 | 355.5 | |
| 105 | 1.85 | 367.3 | |
| 106 | 1.52 | 407.1 | |
| 107 | 1.74 | 423.3 | (DMSO-d$_6$) δ 11.27 (s, 1H), 10.49 (s, 1H), 7.52 (dd, J = 8.4, 3.2 Hz, 1H), 7.41-7.23 (m, 2H), 7.13-7.00 (m, 4H), 6.94 (dd, J = 9.1, 4.3 Hz, 1H), 6.75 (d, J = 2.1 Hz, 1H), 6.39 (dd, J = 7.2, 2.1 Hz, 1H), 4.73 (q, J = 8.9 Hz, 2H) ppm |
| 108 | 1.78 | 395.3 | (DMSO-d$_6$) δ 11.28 (s, 1H), 10.48 (s, 1H), 7.49 (dd, J = 8.4, 3.3 Hz, 1H), 7.40-7.23 (m, 2H), 7.04-6.97 (m, 2H), 6.97-6.91 (m, 2H), 6.91-6.86 (m, 1H), 6.77 (d, J = 2.0 Hz, 1H), 6.40 (dd, J = 7.2, 2.1 Hz, 1H), 3.77 (d, J = 7.0 Hz, 2H), 1.28-1.07 (m, 1H), 0.62-0.42 (m, 2H), 0.39-0.20 (m, 2H) ppm |
| 109 | 1.76 | 411.2 | (DMSO-d$_6$) δ 11.39 (s, 1H), 10.60 (s, 1H), 7.88-7.79 (m, 1H), 7.61 (dd, J = 8.4, 2.9 Hz, 1H), 7.33 (d, J = 7.2 Hz, 1H), 7.31-7.16 (m, 3H), 6.74 (d, J = 2.1 Hz, 1H), 6.39 (d, J = 7.3, 2.1 Hz, 1H) ppm |
| 110 | 1.52 | 457.3 | (DMSO-d$_6$) δ 11.48 (s, 1H), 10.66 (s, 1H), 7.86 (d, J = 7.9 Hz, 1H), 7.63 (d, J = 7.9 Hz, 1H), 7.47 (d, J = 8.7 Hz, 1H), 7.41 (d, J = 11.6 Hz, 1H), 7.37 (d, J = 7.2 Hz, 1H), 7.03 (s, 1H), 6.83 (s, 1H), 6.45 (d, J = 7.1 Hz, 1H), 3.89 (s, 3H) ppm |
| 111 | 1.62 | 473.3 | (DMSO-d$_6$) δ 11.32 (s, 1H), 10.62 (s, 1H), 7.83 (d, J = 7.9 Hz, 1H), 7.51 (d, J = 7.9 Hz, 1H), 7.39-7.27 (m, 2H), 7.17 (dd, J = 10.7, 2.8 Hz, 1H), 6.88 (dd, J = 11.3, 5.7 Hz, 1H), 6.81 (s, 1H), 6.75 (s, 1H), 6.43 (d, J = 7.1 Hz, 1H), 3.73 (s, 3H) ppm |

TABLE 2-continued

Analytical Data

| Cmpd. No. | LCMS Ret. Time in minutes | MS (M + 1) | $^1$H-NMR (400 MHz) |
|---|---|---|---|
| 112 | 1.66 | 457.5 | (DMSO-d$_6$) δ 11.29 (s, 1H), 10.66 (s, 1H), 7.87 (d, J = 7.9 Hz, 1H), 7.57 (d, J = 7.9 Hz, 1H), 7.31 (d, J = 7.1 Hz, 1H), 7.24 (dd, J = 9.2, 2.7 Hz, 1H), 7.17-7.04 (m, 2H), 6.90 (s, 1H), 6.76 (d, J = 1.8 Hz, 1H), 6.38 (dd, J = 7.2, 2.0 Hz, 1H), 2.15 (s, 3H) ppm |
| 113 | 1.53 | 393.1 | (DMSO-d$_6$) δ 11.32 (s, 1H), 10.57 (s, 1H), 7.95 (s, 1H), 7.34-7.24 (m, 3H), 7.22-7.15 (m, 3H), 6.74 (s, 1H), 6.38 (d, J = 7.2 Hz, 1H) ppm |
| 114 | 1.57 | 423.3 | (DMSO-d$_6$) δ 11.27 (s, 1H), 10.49 (s, 1H), 7.90 (br s, 1H), 7.32 (d, J = 7.2 Hz, 1H), 7.28 (dd, J = 8.9, 5.8 Hz, 1H), 7.14 (dd, J = 10.7, 2.9 Hz, 1H), 6.89-6.82 (m, 2H), 6.77 (s, 1H), 6.39 (dd, J = 7.2, 2.1 Hz, 1H), 3.76 (s, 3H) ppm |
| 115 | 1.52 | 423.3 | (DMSO-d$_6$) δ 11.41 (s, 1H), 10.57 (s, 1H), 7.94 (s, 1H), 7.34 (d, J = 7.4 Hz, 1H), 7.30-7.12 (m, 3H), 6.96 (d, J = 8.5 Hz, 1H), 6.78 (s, 1H), 6.40 (d, J = 7.1 Hz, 1H), 3.83 (s, 3H) ppm |
| 116 | 1.85 | 369.1 | (DMSO-d$_6$) δ 11.41 (s, 1H), 10.35 (s, 1H), 7.71 (d, J = 7.8 Hz, 1H), 7.49 (s, 1H), 7.39 (dd, J = 15.4, 7.6 Hz, 2H), 6.83 (d, J = 1.7 Hz, 1H), 6.43 (dd, J = 7.2, 2.0 Hz, 1H), 4.18 (t, J = 6.4 Hz, 2H), 1.75 (td, J = 13.4, 6.6 Hz, 1H), 1.62 (q, J = 6.5 Hz, 2H), 0.90 (t, J = 8.0 Hz, 6H) ppm |
| 117 | 1.58 | 355.2 | |
| 118 | 1.77 | 393.3 | |
| 119 | 1.62 | 367.2 | |
| 120 | 1.72 | 381.2 | |
| 121 | 1.33 | 383.2 | |
| 122 | 1.55 | 353.2 | |
| 123 | 1.57 | 409.3 | |
| 124 | 1.72 | 381.2 | |
| 125 | 1.6 | 379.2 | |
| 126 | 1.5 | 389.2 | |
| 127 | 1.72 | 393.2 | |
| 128 | 1.85 | 381.1 | (DMSO-d$_6$) δ 11.36 (s, 1H), 10.32 (s, 1H), 7.70 (d, J = 7.8 Hz, 1H), 7.48 (s, 1H), 7.36 (dd, J = 14.6, 7.6 Hz, 2H), 6.81 (s, 1H), 6.42 (dd, J = 7.2, 2.0 Hz, 1H), 4.68 (m, 1H), 1.88 (m, 2H), 1.44 (m, 8H) ppm |
| 129 | 1.47 | 375.2 | |
| 130 | 1.64 | 381.3 | |
| 131 | 1.52 | 355.3 | |
| 132 | 1.56 | 395.2 | |
| 133 | 1.5 | 409.3 | |
| 134 | 1.64 | 381.3 | |
| 135 | 1.54 | 379.3 | |
| 136 | 1.71 | 397.2 | |
| 137 | 1.68 | 397.2 | |
| 138 | 1.58 | 411.1 | |
| 139 | 1.56 | 425.1 | |
| 140 | 1.7 | 397.2 | |
| 141 | 1.78 | 432.3 | |
| 142 | 1.78 | 432.5 | (DMSO-d$_6$) δ 10.12 (s, 1H), 8.45 (d, J = 2.8 Hz, 1H), 7.87 (d, J = 8.7 Hz, 1H), 7.77 (s, 1H), 7.66 (d, J = 8.1 Hz, 1H), 7.44 (m, 3H), 7.32 (d, J = 1.8 Hz, 1H), 6.33 (d, J = 9.6 Hz, 1H), 1.30 (s, 9H) ppm |
| 143 | 1.58 | 410.3 | (DMSO-d$_6$) δ 11.41 (s, 1H), 10.62 (s, 1H), 8.56 (d, J = 2.7 Hz, 1H), 7.92 (d, J = 8.7 Hz, 1H), 7.76 (d, J = 8.2 Hz, 1H), 7.62 (dd, J = 8.7, 2.7 Hz, 1H), 7.51 (m, 2H), 7.32 (d, J = 7.2 Hz, 1H), 6.72 (d, J = 1.9 Hz, 1H), 6.39 (dd, J = 7.2, 2.1 Hz, 1H) ppm |
| 144 | 1.67 | 444.3 | (DMSO-d$_6$) δ 11.29 (s, 1H), 10.69 (s, 1H), 8.57 (d, J = 2.8 Hz, 1H), 7.94 (t, J = 8.8 Hz, 2H), 7.82 (d, J = 8.2 Hz, 1H), 7.76 (s, 1H), 7.62 (dd, J = 8.7, 2.9 Hz, 1H), 7.29 (d, J = 7.0 Hz, 1H), 6.67 (s, 1H), 6.33 (d, J = 7.4 Hz, 1H) ppm |
| 145 | 1.64 | 444.3 | |
| 146 | 0.98 | 390.2 | |
| 147 | 0.97 | 390.2 | |
| 148 | 1.87 | 446.1 | (DMSO-d$_6$) δ 10.49 (s, 1H), 8.45 (d, J = 2.8 Hz, 1H), 7.88 (d, J = 8.7 Hz, 1H), 7.66 (d, J = 8.1 Hz, 1H), 7.57 (d, J = 7.4 Hz, 1H), 7.49 (dd, J = 8.1, 1.8 Hz, 1H), 7.42 (dd, J = 8.6, 2.8 Hz, 1H), 7.32 (d, J = 1.7 Hz, 1H), 6.70 (d, J = 2.3 Hz, 1H), 6.38 (dd, J = 7.4, 2.3 Hz, 1H), 3.33 (s, 3H), 1.29 (s, 9H) ppm |
| 149 | 1.85 | 446.3 | (DMSO-d$_6$) δ 10.15 (s, 1H), 8.45 (d, J = 2.7 Hz, 1H), 8.10 (d, J = 2.7 Hz, 1H), 7.88 (d, J = 8.7 Hz, 1H), 7.66 (d, J = 8.1 Hz, 1H), 7.48 (dd, J = 8.1, 1.7 Hz, 1H), 7.39 (m, 2H), 7.32 (d, J = 1.6 Hz, 1H), 6.37 (d, J = 9.7 Hz, 1H), 3.39 (s, 3H), 1.30 (s, 9H) ppm |
| 150 | 0.95 | 390.3 | |
| 151 | 0.98 | 406.2 | |

TABLE 2-continued

Analytical Data

| Cmpd. No. | LCMS Ret. Time in minutes | MS (M + 1) | $^1$H-NMR (400 MHz) |
|---|---|---|---|
| 152 | 1.57 | 479.3 | (DMSO-$d_6$) δ 11.37 (br s, 1H), 10.96 (s, 1H), 8.02 (s, 1H), 7.59-7.52 (m, 2H), 7.41 (td, J = 9.2, 5.5 Hz, 1H), 7.34 (d, J = 7.1 Hz, 1H), 7.24-7.15 (m, 1H), 6.70 (d, J = 2.0 Hz, 1H), 6.33 (dd, J = 7.2, 2.1 Hz, 1H) ppm |
| 153 | 1.64 | 475.3 | (DMSO-$d_6$) δ 11.36 (br s, 1H), 10.94 (s, 1H), 7.95 (s, 1H), 7.34 (d, J = 7.2 Hz, 1H), 7.29-7.24 (m, 2H), 7.21-7.11 (m, 2H), 6.70 (d, J = 2.0 Hz, 1H), 6.33 (dd, J = 7.2, 2.1 Hz, 1H), 2.16 (s, 3H) ppm |
| 154 | 1.6 | 491.3 | (DMSO-$d_6$) δ 11.38 (br s, 1H), 10.91 (s, 1H), 7.91 (s, 1H), 7.35 (d, J = 7.2 Hz, 1H), 7.26 (dd, J = 8.9, 5.8 Hz, 1H), 7.20 (dd, J = 10.7, 2.9 Hz, 1H), 7.15 (s, 1H), 6.88 (td, J = 8.5, 2.9 Hz, 1H), 6.73 (d, J = 2.1 Hz, 1H), 6.37 (dd, J = 7.2, 2.1 Hz, 1H), 3.79 (s, 3H) ppm |
| 155 | 1.58 | 461.3 | (DMSO-$d_6$) δ 11.34 (br s, 1H), 10.91 (s, 1H), 7.99 (s, 1H), 7.47 (s, 1H), 7.38-7.28 (m, 3H), 7.29-7.24 (m, 2H), 6.69 (d, J = 2.0 Hz, 1H), 6.31 (dd, J = 7.2, 2.1 Hz, 1H) ppm |
| 156 | 1.55 | 443.1 | (DMSO-$d_6$) δ 11.34 (br s, 1H), 10.92 (s, 1H), 7.99 (d, J = 1.5 Hz, 1H), 7.53-7.43 (m, 3H), 7.35-7.26 (m, 2H), 7.20 (d, J = 7.6 Hz, 2H), 6.69 (d, J = 2.0 Hz, 1H), 6.31 (dd, J = 7.2, 2.1 Hz, 1H) ppm |
| 157 | 1.32 | 423.2 | (DMSO-$d_6$) δ 11.44 (s, 1H), 10.66 (s, 1H), 7.86 (d, J = 7.9 Hz, 1H), 7.61 (d, J = 8.0 Hz, 1H), 7.41-7.27 (m, 2H), 7.24-7.12 (m, 1H), 7.12-7.07 (m, 1H), 7.04 (s, 1H), 6.80 (d, J = 2.1 Hz, 1H), 6.43 (dd, J = 7.3, 2.2 Hz, 1H), 4.47 (s, 2H) ppm |
| 158 | 1.7 | 423.3 | (DMSO-$d_6$) δ 11.33 (s, 1H), 10.58 (s, 1H), 7.81 (d, J = 7.8 Hz, 1H), 7.55 (d, J = 8.7 Hz, 1H), 7.37-7.26 (m, 2H), 7.17 (dd, J = 10.7, 2.9 Hz, 1H), 6.86 (m, 3H), 6.42 (dd, J = 7.2, 2.0 Hz, 1H), 3.76 (s, 3H) ppm |
| 159 | 1.83 | 423.3 | (DMSO-$d_6$) δ 11.52 (s, 1H), 10.49 (s, 1H), 10.04 (s, 1H), 7.84 (d, J = 8.2 Hz, 1H), 7.78 (d, J = 7.4 Hz, 1H), 7.33-7.23 (m, 2H), 7.05-6.91 (m, 2H), 6.91-6.79 (m, 2H), 6.61 (dd, J = 7.4, 2.4 Hz, 1H), 4.96 (s, 2H) ppm |
| 160 | 1.45 | 451.2 | |

Assays for Detecting and Measuring Na$_V$ Inhibition Properties of Compounds

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human Nav1.8 were seeded in 384-well poly-lysine coated plates at 15,000-20,000 cells per well. HEK cells were grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells were grown in vented cap flasks, in 90% humidity and 5% $CO_2$.

Reagents and Solutions 100 mg/mL Pluronic F-127 (Sigma #P2443), in dry DMSO

Compound Plates: 384-well round bottom plate, e.g. Corning 384-well Polypropylene Round Bottom #3656

Cell Plates: 384-well tissue culture treated plate, e.g. Greiner #781091-1B 10 mM DiSBAC$_6$(3) (Aurora #00-100-010) in dry DMSO 10 mM CC2-DMPE (Aurora #00-100-008) in dry DMSO 200 mM ABSCl in $H_2O$ Bath1 buffer: Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (made this prior to use, Sigma #C4767), 8 μM CC2-DMPE+ 2.5 μM DiSBAC$_6$(3). To make the solution added volume of 10% Pluronic F127 stock equal to volumes of CC2-DMPE+ DiSBAC$_6$(3). The order of preparation was first mixing Pluronic and CC2-DMPE, then adding DiSBAC$_6$(3) while vortexing, then adding Bath1+β-Cyclodextrin.

Assay Protocol

1) Pre-spotted compounds (in neat DMSO) into compound plates. Vehicle control (neat DMSO), the positive control (20 mM DMSO stock tetracaine, 125 μM final in assay) and test compounds were added to each well at 160× desired final concentration in neat DMSO. Final compound plate volume was 80 μL (80-fold intermediate dilution from 1 μL DMSO spot; 160-fold final dilution after transfer to cell plate). Final DMSO concentration for all wells in assay was 0.625%.

2) Prepared Hexyl Dye Solution.

3) Prepared cell plates. On the day of the assay, medium was aspirated and cells were washed three times with 100 μL of Bath1 Solution, maintaining 25 μL residual volume in each well.

4) Dispensed 25 μL per well of Hexyl Dye Solution into cell plates. Incubated for 20-35 minutes at room temp or ambient conditions.

5) Dispensed 80 μL per well of Bath1 into compound plates. Acid Yellow-17 (1 mM) was added and Potassium Chloride was altered from 4.5 to 20 mM depending on the NaV subtype and assay sensitivity.

6) Washed cell plates three times with 100 μL per well of Bath1, leaving 25 μL of residual volume. Then transferred 25 uL per well from Compound Plates to Cell Plates. Incubated for 20-35 minutes at room temp/ambient condition.

7) Read Plate on E-VIPR. Used the current-controlled amplifier to deliver stimulation wave pulses for 10 seconds and a scan rate of 200 Hz. A pre-stimulus recording was performed for 0.5 seconds to obtain the un-stimulated intensities baseline. The stimulatory waveform was followed by 0.5 seconds of post-stimulation recording to examine the relaxation to the resting state.

Data Analysis

Data was analyzed and reported as normalized ratios of emission intensities measured in the 460 nm and 580 nm channels. The response as a function of time was reported as the ratios obtained using the following formula:

$$R(t) = \frac{(intensity_{460\,nm} - background_{460\,nm})}{(intensity_{580\,nm} - background_{580\,nm})}$$

The data was further reduced by calculating the initial ($R_i$) and final ($R_f$) ratios. These were the average ratio values during part or all of the pre-stimulation period, and during sample points during the stimulation period. The response to the stimulus $R = R_f/R_i$ was then calculated and reported as a function of time.

Control responses were obtained by performing assays in the presence of a compound with the desired properties (positive control), such as tetracaine, and in the absence of pharmacological agents (negative control). Responses to the negative (N) and positive (P) controls were calculated as above. The compound antagonist activity A is defined as:

$$A = \frac{R - P}{N - P} * 100.$$

where R is the ratio response of the test compound

Electrophysiology Assays for $Na_v$ Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) were visually identified and probed with fine tip glass electrodes connected to an amplifier (Axon Instruments). The "voltage clamp" mode was used to assess the compound's $IC_{50}$ holding the cells at −60 mV. In addition, the "current clamp" mode was employed to test the efficacy of the compounds in blocking action potential generation in response to current injections. The results of these experiments contributed to the definition of the efficacy profile of the compounds.

The exemplified compounds in Table 1 herein are active against Nav1.8 sodium channels as measured using the assays described herein and as presented in Table 3 below.

TABLE 3

Nav1.8 $IC_{50}$ activity

| Cmpd. No | $Na_v1.8\ IC_{50}$ (μM) |
|---|---|
| 1 | 1.09 |
| 2 | 0.054 |
| 3 | 13.5 |
| 4 | 0.35 |
| 5 | 0.039 |
| 6 | 0.245 |
| 7 | 0.05 |
| 8 | 0.33 |
| 9 | 0.093 |
| 10 | 0.014 |
| 11 | 0.056 |
| 12 | 0.106 |
| 13 | 0.106 |
| 14 | 0.065 |
| 15 | 0.076 |
| 16 | 0.014 |
| 17 | 1.8 |
| 18 | 12 |
| 19 | 6 |
| 20 | 0.03 |
| 21 | 0.843 |
| 22 | 0.1 |
| 23 | 1.5 |
| 24 | 0.058 |
| 25 | 1.1 |
| 26 | 9.65 |
| 27 | 0.34 |
| 28 | 0.044 |
| 29 | 0.028 |
| 30 | 0.011 |
| 31 | 0.017 |
| 32 | 0.205 |
| 33 | 0.095 |
| 34 | 12 |
| 35 | 0.47 |
| 36 | 0.101 |
| 37 | 0.051 |
| 38 | 0.069 |
| 39 | 0.69 |
| 40 | 0.04 |
| 41 | 0.26 |
| 42 | 0.068 |
| 43 | 0.38 |
| 44 | 0.02 |
| 45 | 0.064 |
| 46 | 0.064 |
| 47 | 0.135 |
| 48 | 2.7 |
| 49 | 0.024 |
| 50 | 0.019 |
| 51 | 0.087 |
| 52 | 0.094 |
| 53 | 0.047 |
| 54 | 0.03 |
| 55 | 0.07 |
| 56 | 0.069 |
| 57 | 6.9 |
| 58 | 0.054 |
| 59 | 0.032 |
| 60 | 0.126 |
| 61 | 0.113 |
| 62 | 0.034 |
| 63 | 0.018 |
| 64 | 0.108 |
| 65 | 0.107 |
| 66 | 0.037 |
| 67 | 0.069 |

TABLE 3-continued

Nav1.8 IC$_{50}$ activity

| Cmpd. No | Na$_v$1.8 IC$_{50}$ (µM) |
|---|---|
| 68 | 0.03 |
| 69 | 0.112 |
| 70 | 0.013 |
| 71 | 0.092 |
| 72 | 0.013 |
| 73 | 0.035 |
| 74 | 5.175 |
| 75 | 0.051 |
| 76 | 0.054 |
| 77 | 0.029 |
| 78 | 0.031 |
| 79 | 0.011 |
| 80 | 0.105 |
| 81 | 0.026 |
| 82 | 0.036 |
| 83 | 0.046 |
| 84 | 0.046 |
| 85 | 2.8 |
| 86 | 3.55 |
| 87 | 0.027 |
| 88 | 0.012 |
| 89 | 0.016 |
| 90 | 0.026 |
| 91 | 0.42 |
| 92 | 0.135 |
| 93 | 1.45 |
| 94 | 1.4 |
| 95 | 3.45 |
| 96 | 0.4 |
| 97 | 0.745 |
| 98 | 0.3 |
| 99 | 5.15 |
| 100 | 0.155 |
| 101 | 0.12 |
| 102 | 17.1 |
| 103 | 0.33 |
| 104 | 1.15 |
| 105 | 3.55 |
| 106 | 0.099 |
| 107 | 0.39 |
| 108 | 0.285 |
| 109 | 0.019 |
| 110 | 0.89 |
| 111 | 0.003 |
| 112 | 0.016 |
| 113 | 0.006 |
| 114 | 0.001 |
| 115 | 0.007 |
| 116 | 0.488 |
| 117 | 1.145 |
| 118 | 0.765 |
| 119 | 14 |
| 120 | 0.15 |
| 121 | 19 |
| 122 | 4.2 |
| 123 | 0.355 |
| 124 | 0.485 |
| 125 | 17.5 |
| 126 | 1.4 |
| 127 | 1.3 |
| 128 | 0.56 |
| 129 | 0.94 |
| 130 | 5.1 |
| 131 | 1.5 |
| 132 | 0.33 |
| 133 | 5.8 |
| 134 | 21 |
| 135 | 1.65 |
| 136 | 2.6 |
| 137 | 12.65 |
| 138 | 1.45 |
| 139 | 3.05 |
| 140 | 15 |
| 141 | 0.078 |
| 142 | 0.653 |
| 143 | 3.35 |
| 144 | 0.615 |
| 145 | 5 |
| 146 | 4.6 |
| 147 | 3.8 |
| 148 | 0.45 |
| 149 | 1.65 |
| 150 | 6.6 |
| 151 | 8.4 |
| 152 | 0.044 |
| 153 | 0.01 |
| 154 | 0.005 |
| 155 | 0.011 |
| 156 | 0.052 |
| 157 | 0.058 |
| 158 | 0.002 |
| 159 | 2.6 |
| 160 | 1.39 |

IonWorks Assays.

This assay was performed to determine the activity for the compounds of the present invention against non Na$_v$1.8 channels. Sodium currents were recorded using the automated patch clamp system, IonWorks (Molecular Devices Corporation, Inc.). Cells expressing Na$_V$ subtypes were harvested from tissue culture and placed in suspension at 0.5-4 million cells per mL Bath1. The IonWorks instrument measured changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents were measured at the test potential.

Microsomal Stability Assay.

Compounds were incubated at 37° C. and shaken for 30 minutes in a phosphate buffered solution with either rat or human liver microsomes and the cofactor NADPH. A time zero control was similarly prepared, however with NADPH excluded. The final incubation concentrations were 1 uM substrate (0.2% DMSO), 0.5 mg/mL liver microsome, 2 mM NADPH, and 0.1 M phosphate. Reactions were quenched and proteins precipitated with the addition of 2 volume equivalents of ice cold acetonitrile containing an internal standard. Following a centrifugation step, aliquots from the quenched incubations were further diluted with 4 volume equivalents of a 50% aqueous methanol solution and then subjected to LC/MS/MS analysis for quantitation of parent compound. Microsome stability values were calculated as the percent of substrate remaining after 30 minutes referenced against the time zero control.

Microsomal stability in rat and human liver microsomes were determined for selected compounds of the present invention using the above assay. Table 4 provides the human liver microsomes ("HLM") and rat liver microsomes ("RLM") stability data as the percent of compound remaining after 30 minutes referenced against the time zero control.

TABLE 4

HLM and RLM Stability Data

| Cmpd. No | HLM (% remaining @ 30 minutes) | RLM (% remaining @ 30 minutes) |
| --- | --- | --- |
| 2 | 100 | 104 |
| 7 | 97 | 99 |
| 8 | 90 | 86 |
| 10 | 93 | 82 |
| 20 | 104 | 88 |
| 28 | 79 | 70 |
| 29 | 107 | 107 |
| 30 | 76 | 78 |
| 31 | 92 | 91 |
| 33 | 100 | 110 |
| 37 | 100 | 97 |
| 44 | 93 | 84 |
| 66 | 100 | 106 |
| 68 | 98 | 72 |
| 72 | 100 | 95.5 |
| 75 | 90 | 95 |
| 76 | 97 | 93 |
| 79 | 103 | 100 |
| 82 | 101 | 98 |
| 88 | 100 | 102 |
| 90 | 101 | 104 |
| 101 | 97 | 89 |
| 109 | 103 | 100 |
| 111 | 91 | 90 |
| 113 | 105 | 102 |
| 114 | 91 | 82 |
| 115 | 102 | 95 |
| 120 | 87 | 79 |
| 123 | 103 | 98 |
| 142 | 38 | 50 |
| 152 | 103 | 100 |
| 157 | 101.5 | 102 |

Many modifications and variations of the embodiments described herein may be made without departing from the scope, as is apparent to those skilled in the art. The specific embodiments described herein are offered by way of example only.

We claim:

1. A compound of formula I or I'

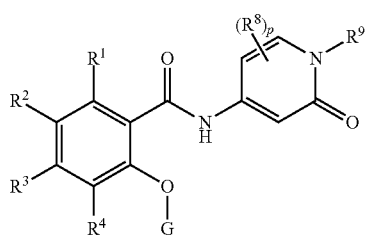

I

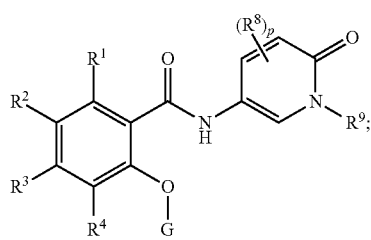

I' or a pharmaceutically acceptable salt thereof, wherein, independently for each occurrence:

G is

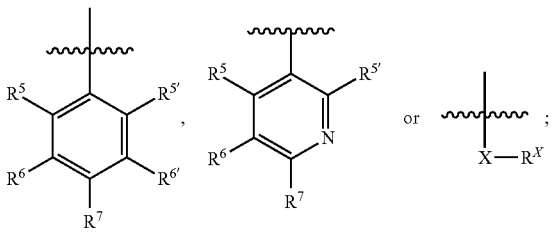

X is a bond or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^1$ is H, halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^2$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^3$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^4$ is H, halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

$R^5$ is H, halogen, CN, or —X—$R^X$;
$R^{5'}$ is H, halogen, CN, or —X—$R^X$;
$R^6$ is H, halogen, CN, or —X—$R^X$;
$R^{6'}$ is H, halogen, CN, or —X—$R^X$;
$R^7$ is H, halogen, CN, or —X—$R^X$;
$R^8$ is halogen, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

2. The compound according to claim 1, wherein $R^3$ is $C_1$-$C_6$ alkyl, wherein said $C_1$-$C_6$ alkyl is substituted with 0-6 halogen; and G is

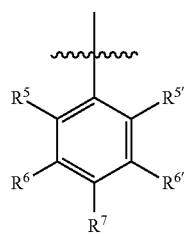

wherein:
$R^5$ is H, halogen, CN, or —X—$R^X$;
$R^{5'}$ is H, halogen, CN, or —X—$R^X$;

R⁶ is H, halogen, CN, or —X—R^X;

R⁶' is H, halogen, CN, or —X—R^X;

R⁷ is H, halogen, CN, or —X—R^X;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and R^X is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl.

3. The compound or pharmaceutically acceptable salt according to claim 2, wherein R³ is t-butyl, $CF_3$ or $CF_2CF_3$; and G is:

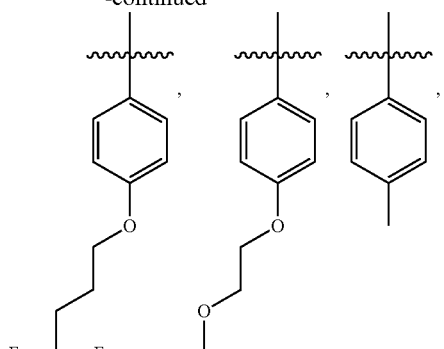

-continued

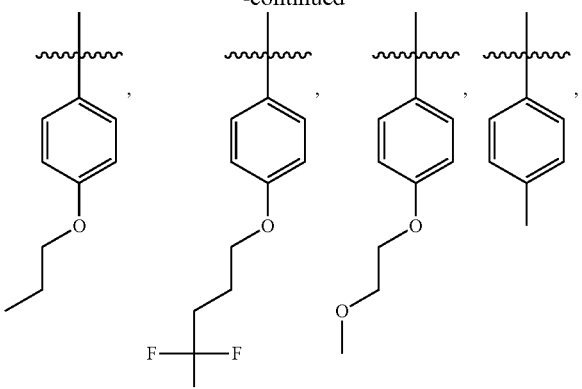

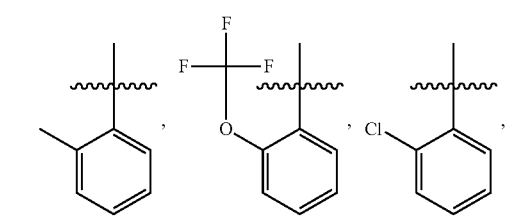

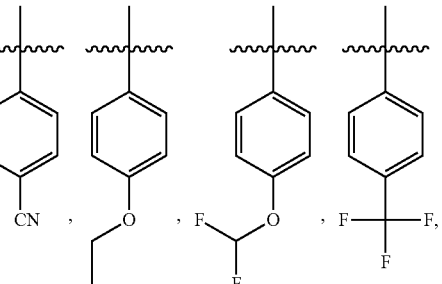

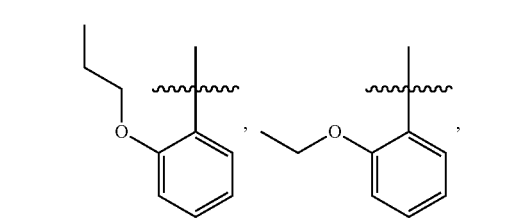

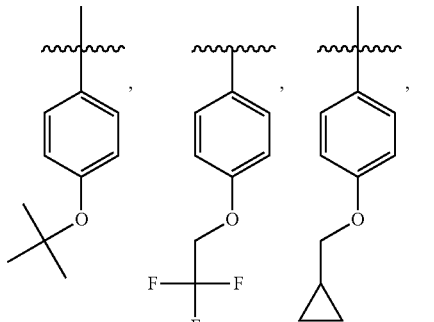

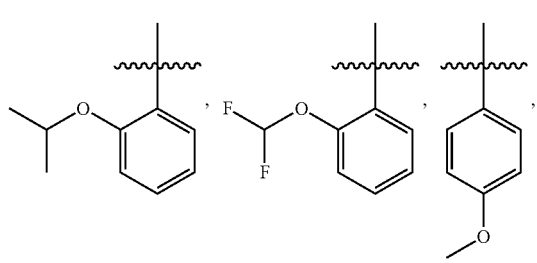

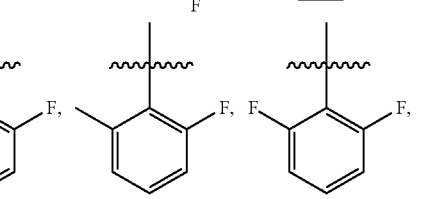

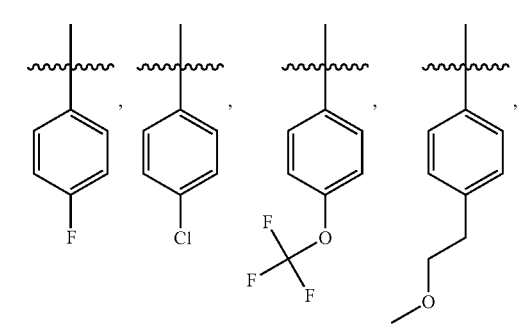

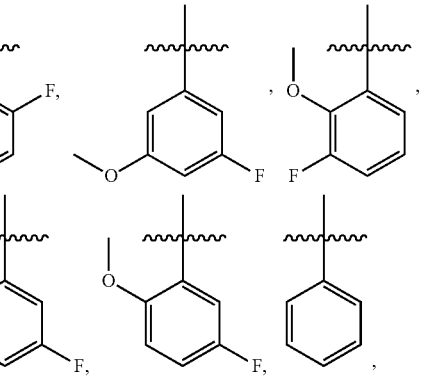

-continued

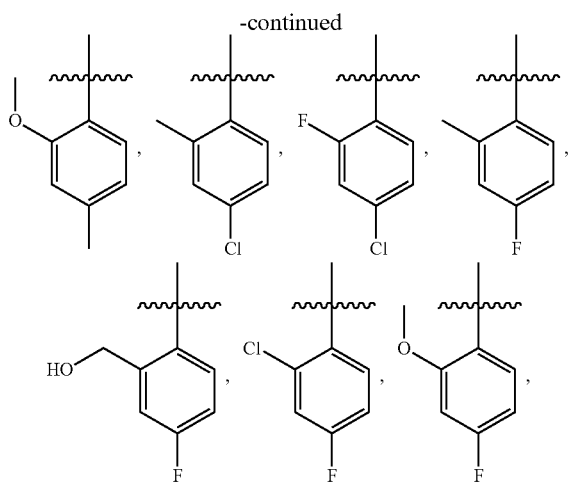

4. The compound or pharmaceutically acceptable salt according to claim 1, wherein G is:

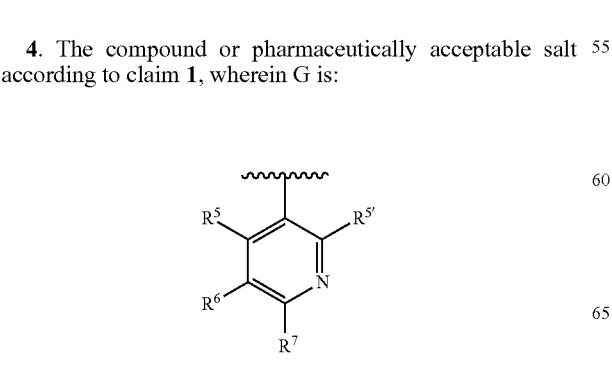

and G is

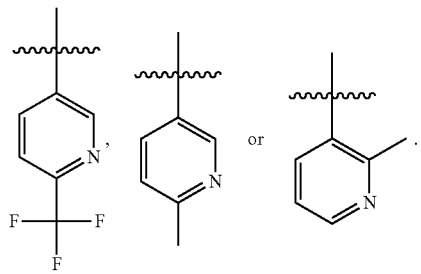

5. The compound or pharmaceutically acceptable salt according to claim 1, wherein G is —X—$R^X$ and —X—$R^X$ is:

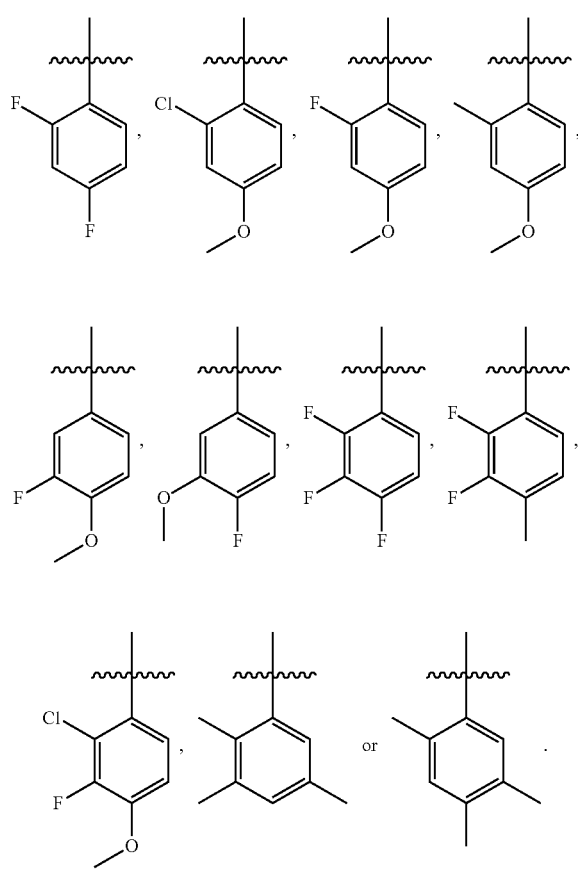

6. The compound or pharmaceutically acceptable salt according to claim 1, wherein p is 0; and $R^9$ is H.

7. The compound of claim 1, wherein the compound has formula I-F or I'-F:

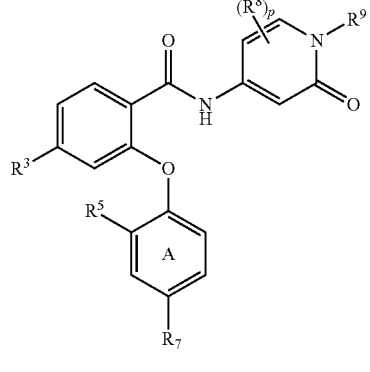

I'-F

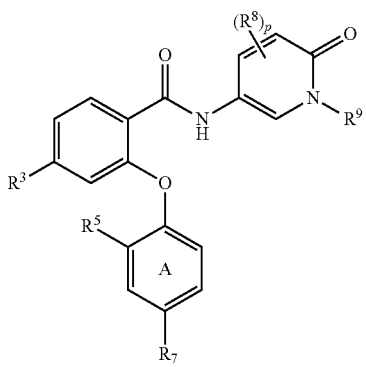

or a pharmaceutically acceptable salt thereof,
wherein, independently for each occurrence:
- $R^3$ is halogen, CN, or $C_1$-$C_6$ alkyl wherein said $C_1$-$C_6$ alkyl is substituted with 0-6 halogen, wherein up to two non-adjacent $CH_2$ units of said $C_1$-$C_6$ alkyl may be replaced with —O—;
- $R^5$ is halogen, CN, or —X—$R^X$;
- $R^7$ is halogen, CN, or —X—$R^X$;
- X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
- $R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;
- $R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
- p is an integer from 0 to 3 inclusive; and
- $R^9$ is H, or $C_1$-$C_6$ alkyl wherein up to two non-adjacent $CH_2$ units of said $C_1$-$C_6$ alkyl may be replaced with —O—.

8. The compound or pharmaceutically acceptable salt according to claim 7, wherein $R^3$ is $C_1$-$C_6$ alkyl wherein said $C_1$-$C_6$ alkyl is substituted with 0-6 halogen; and ring A is:

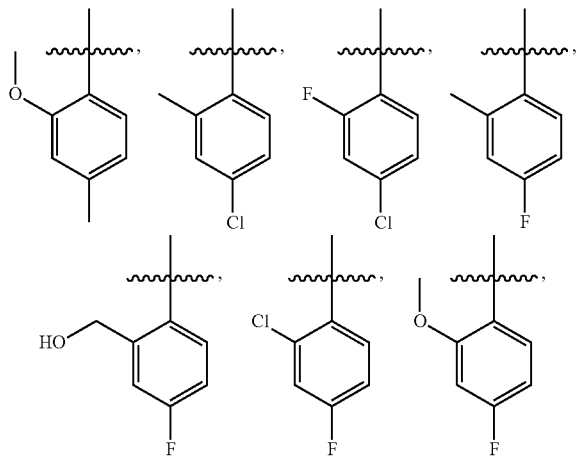

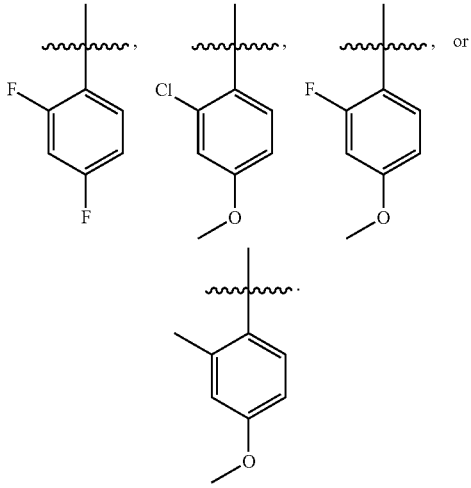

9. The compound or pharmaceutically acceptable salt according to claim 8, wherein $R^3$ is t-butyl, $CF_3$ or $CF_2CF_3$.

10. The compound according to claim 7, wherein p is 0; and $R^9$ is H.

11. The compound according to claim 1, wherein the compound has formula I-G or I'-G:

I-G

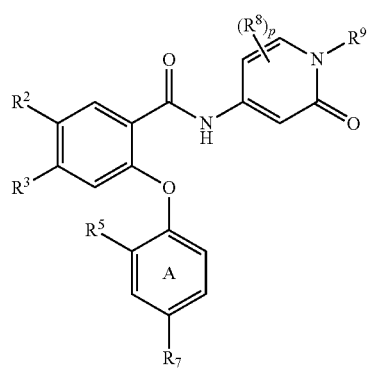

I'-G

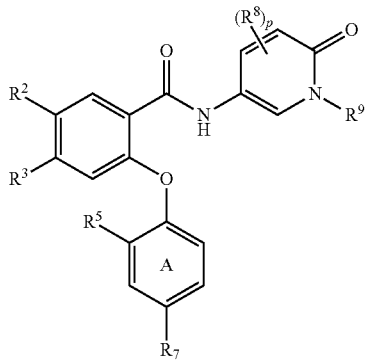

or a pharmaceutically acceptable salt thereof,
wherein, independently for each occurrence:
- $R^2$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^3$ is halogen, CN, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^5$ is halogen, CN, or —X—$R^X$;

$R^7$ is halogen, CN, or —X—$R^X$;

X is a bond or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

$R^X$ is absent, H, or $C_3$-$C_8$ cycloaliphatic, wherein up to two non-adjacent $CH_2$ units of said $C_3$-$C_8$ cycloaliphatic may be replaced with —O— and said $C_3$-$C_8$ cycloaliphatic is substituted with 0-3 substituents selected from halogen and $C_1$-$C_4$ alkyl;

$R^8$ is halogen or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;

p is an integer from 0 to 3 inclusive; and $R^9$ is H, or $C_1$-$C_6$ alkyl wherein up to two non-adjacent $CH_2$ units of said $C_1$-$C_6$ alkyl may be replaced with —O—.

12. The compound or pharmaceutically acceptable salt according to claim 11, wherein $R^2$ is F, Cl, CN, $CF_3$ or $OCF_3$; and $R^3$ is $C_1$-$C_6$ alkyl wherein said $C_1$-$C_6$ alkyl is substituted with 0-6 halogen.

13. The compound or pharmaceutically acceptable salt according to claim 12, wherein $R^3$ is t-butyl, $CF_3$ or $CF_2CF_3$.

14. The compound or pharmaceutically acceptable salt according to claim 12, wherein ring A is:

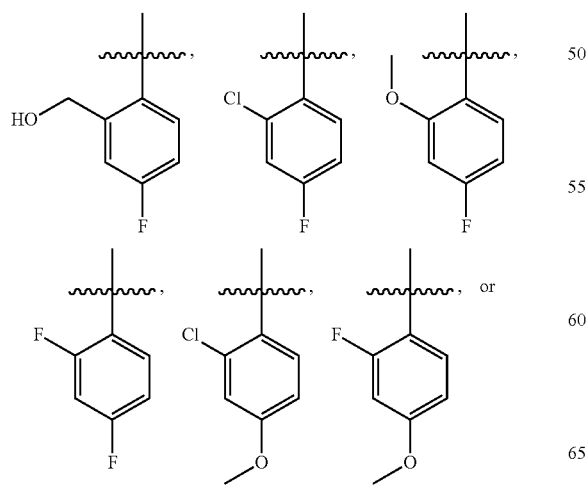

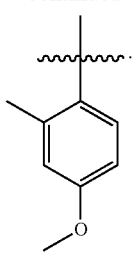

15. The compound or pharmaceutically acceptable salt according to claim 14, wherein p is 0.

16. The compound or pharmaceutically acceptable salt according to claim 14, wherein $R^9$ is H.

17. The compound or pharmaceutically acceptable salt of claim 1, wherein the compound or a pharmaceutically acceptable salt is selected from the group consisting of:

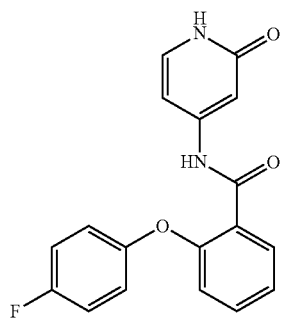

1

2-(4-fluorophenoxy)-N-(2-oxo-1,2-dihydropyridin-4-yl)benzamide

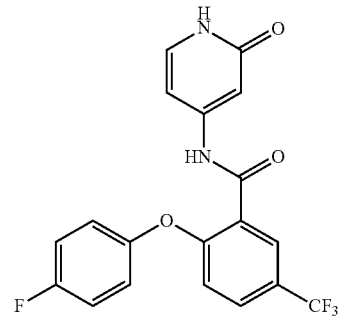

2

2-(4-fluorophenoxy)-N-(2-oxo-1,2-dihydropyridin-4-yl)-5-(trifluoromethyl)benzamide

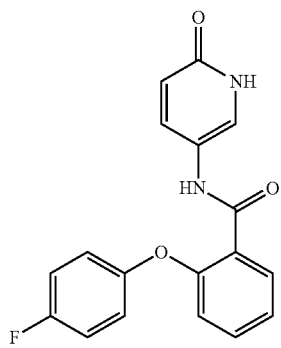

2-(4-fluorophenoxy)-N-(6-
oxo-1,6-dihydropyridin-3-
yl)benzamide

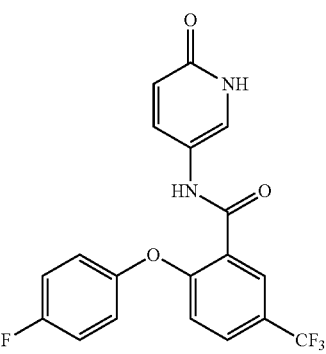

2-(4-fluorophenoxy)-N-(6-
oxo-1,6-dihydropyridin-3-yl)-
5-(trifluoromethyl)benzamide

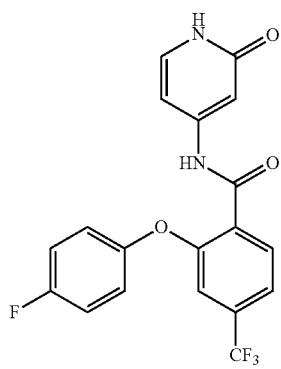

2-(4-fluorophenoxy)-N-(2-
oxo-1,2-dihydropyridin-4-yl)-
4-(trifluoromethyl)benzamide

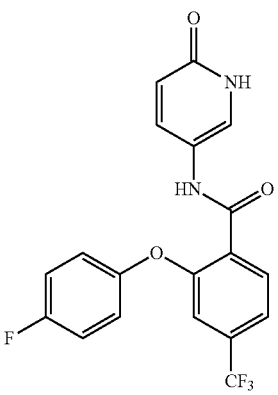

2-(4-fluorophenoxy)-N-(6-
oxo-1,6-dihydropyridin-3-yl)-
4-(trifluoromethyl)benzamide

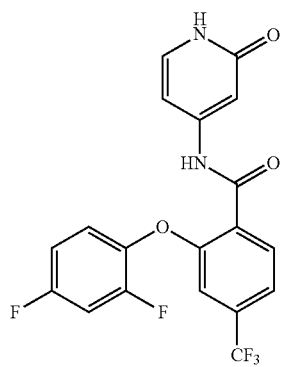

2-(2,4-difluorophenoxy)-N-(2-
oxo-1,2-dihydropyridin-4-yl)-
4-(trifluoromethyl)benzamide

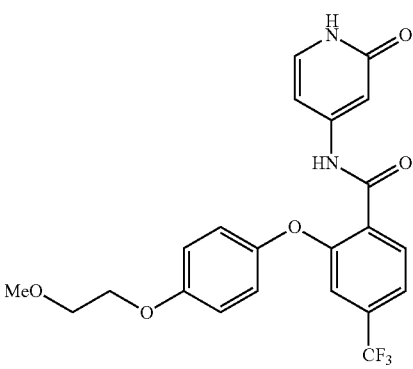

2-(4-(2-methoxyethoxy)phenoxy)-N-
(2-oxo-1,2-dihydropyridin-4-yl)-
4-(trifluoromethyl)benzamide -continued

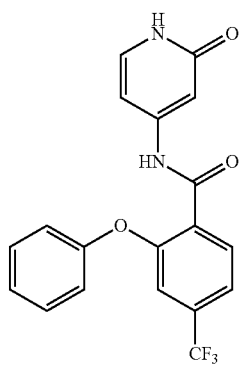

N-(2-oxo-1,2-dihydropyridin-4-yl)-2-phenoxy-4-(trifluoromethyl)benzamide

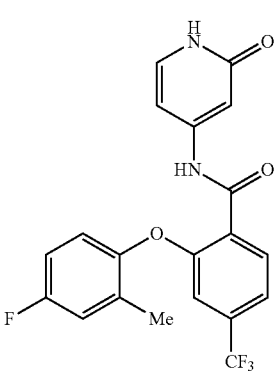

2-(4-fluoro-2-methylphenoxy)-N-(2-oxo-1,2-dihydropyridin-4-yl)-4-(trifluoromethyl)benzamide

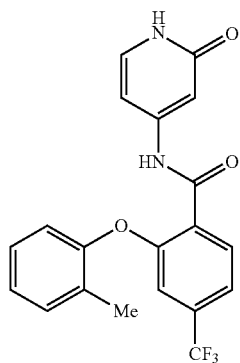

N-(2-oxo-1,2-dihydropyridin-4-yl)-2-(o-tolyloxy)-4-(trifluoromethyl)benzamide

-continued

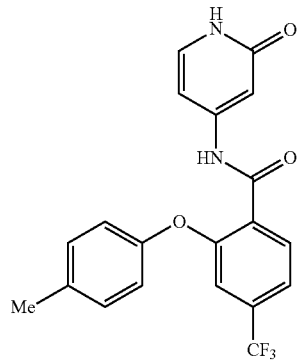

N-(2-oxo-1,2-dihydropyridin-4-yl)-2-(p-tolyloxy-4-(trifluoromethyl)benzamide

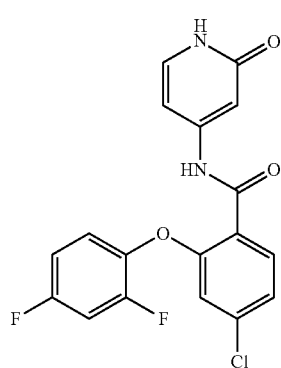

4-chloro-2-(2,4-difluorophenoxy)-N-(2-oxo-1,2-dihydropyridin-4-yl)benzamide

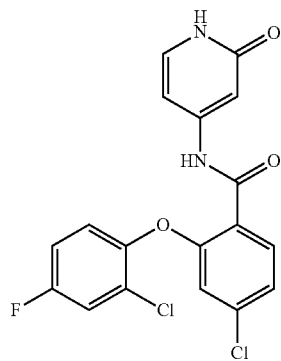

4-chloro-2-(2-chloro-4-fluorophenoxy)-N-(2-oxo-1,2-dihydropyridin-4-yl)benzamide -continued

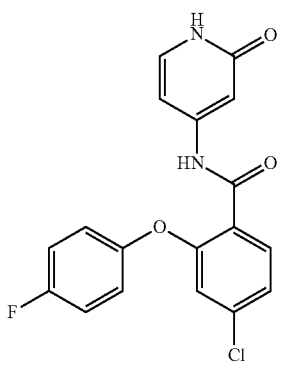

15

4-chloro-2-(4-fluorophenoxy)-N-(2-oxo-1,2-dihydropyridin-4-yl)benzamide

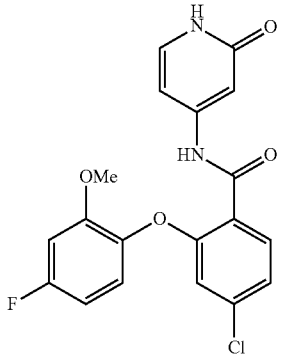

16

4-chloro-2-(4-fluoro-2-methoxyphenoxy)-N-(2-oxo-1,2-dihydropyridin-4-yl)benzamide

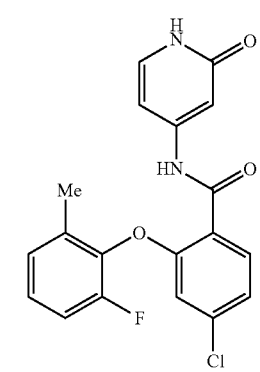

17

4-chloro-2-(2-fluoro-6-methylphenoxy)-N-(2-oxo-1,2-dihydropyridin-4-yl)benzamide -continued

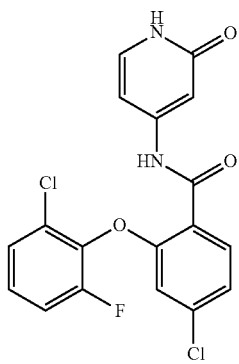

18

4-chloro-2-(2-chloro-6-fluorophenoxy)-N-(2-oxo-1,2-dihydropyridin-4-yl)benzamide

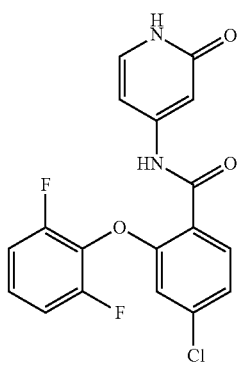

19

4-chloro-2-(2,6-difluorophenoxy)-N-(2-oxo-1,2-dihydropyridin-4-yl)benzamide

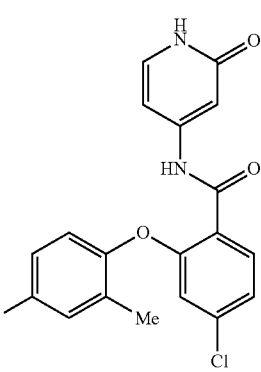

20

4-chloro-2-(4-fluoro-2-methylphenoxy)-N-(2-oxo-1,2-dihydropyridin-4-yl)benzamide -continued

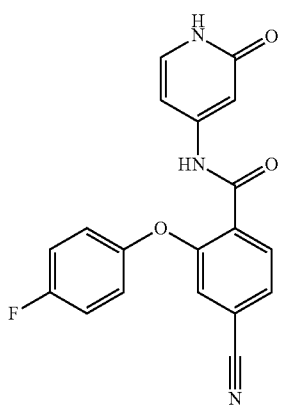

4-cyano-2-(4-fluorophenoxy)-
N-(2-oxo-1,2-dihydropyridin-
4-yl)benzamide

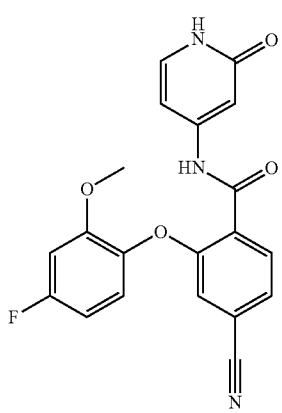

4-cyano-2-(4-fluoro-2-
methoxyphenoxy)-N-(2-oxo-
1,2-dihydropyridin-4-
yl)benzamide

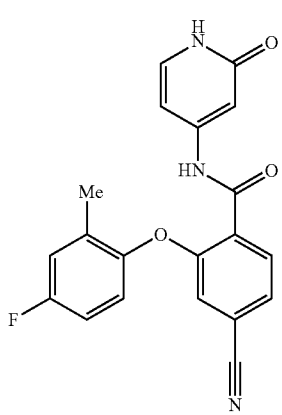

4-cyano-2-(4-fluoro-2-
methylphenoxy)-N-(2-oxo-
1,2-dihydropyridin-4-
yl)benzamide -continued

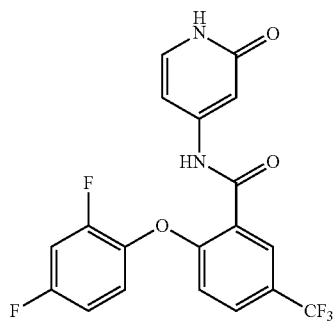

2-(2,4-difluorophenoxy)-N-(2-
oxo-1,2-dihydropyridin-4-yl)-
5-(trifluoromethyl)benzamide

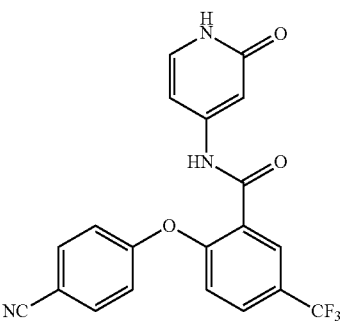

2-(4-cyanophenoxy)-N-(2-
oxo-1,2-dihydropyridin-4-yl)-
5-(trifluoromethyl)benzamide

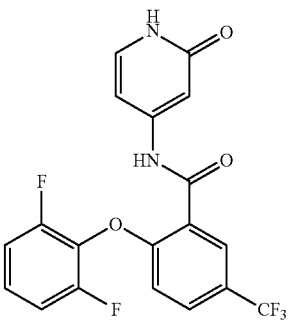

2-(2,6-difluorophenoxy)-N-(2-
oxo-1,2-dihydropyridin-4-yl)-
5-(trifluoromethyl)benzamide

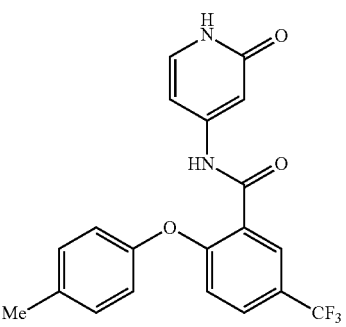

N-(2-oxo-1,2-dihydropyridin-
4-yl)-2-(p-tolyloxy)-5-
(trifluoromethyl)benzamide

-continued

28

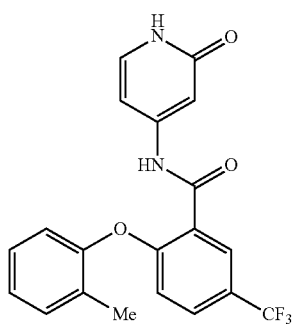

N-(2-oxo-1,2-dihydropyridin-
4-yl)-2-(o-tolyloxy)-5-
(trifluoromethyl)benzamide

29

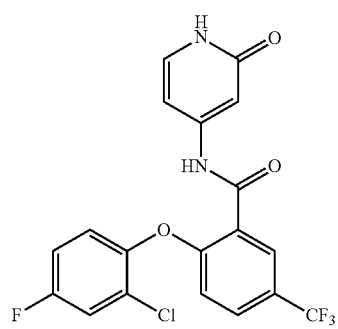

2-(2-chloro-4-
fluorophenoxy)-N-(2-oxo-1,2-
dihydropyridin-4-yl)-5-
(trifluoromethyl)benzamide

30

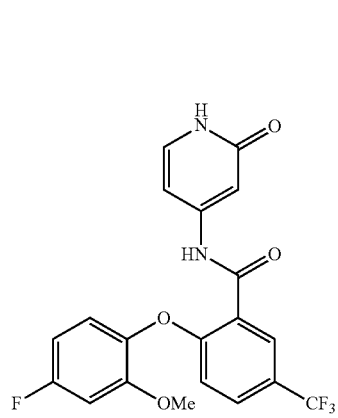

2-(4-fluoro-2-
methoxyphenoxy)-N-(2-oxo-
1,2-dihydropyridin-4-yl)-5-
(trifluoromethyl)benzamide -continued

31

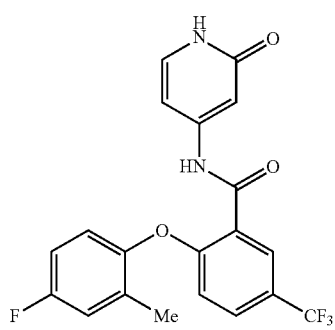

2-(4-fluoro-2-
methylphenoxy)-N-(2-oxo-
1,2-dihydropyridin-4-yl)-5-
(trifluoromethyl)benzamide

32

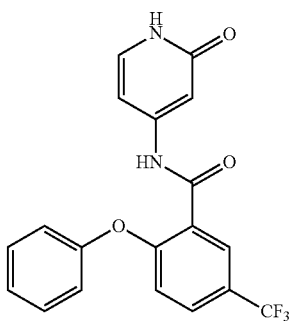

N-(2-oxo-1,2-dihydropyridin-
4-yl)-2-phenoxy-5-
(trifluoromethyl)benzamide

33

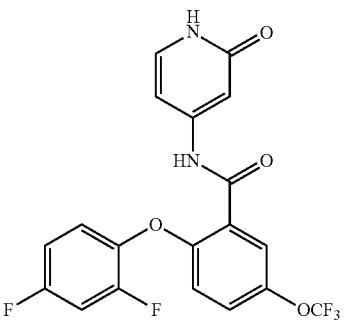

2-(2,4-difluorophenoxy)-N-(2-
oxo-1,2-dihydropyridin-4-yl)-
5-(trifluoromethoxy)benzamide

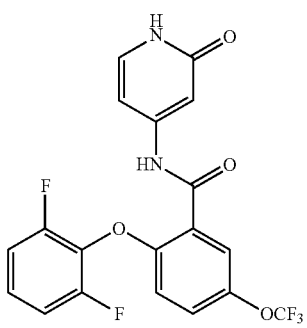

34

2-(2,6-difluorophenoxy)-N-(2-
oxo-1,2-dihydropyridin-4-yl)-
5-(trifluoromethoxy)benzamide

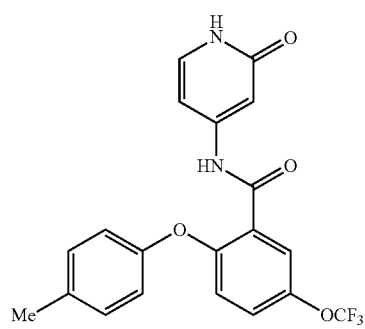

35

N-(2-oxo-1,2-dihydropyridin-
4-yl)-2-(p-tolyloxy-5-
(trifluoromethoxy)benzamide

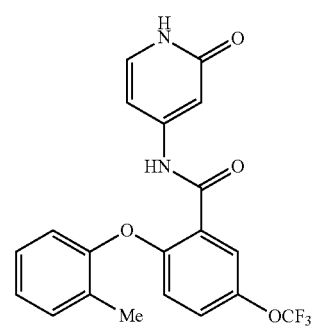

36

N-(2-oxo-1,2-dihydropyridin-
4-yl)-2-(o-tolyloxy)-5-
(trifluoromethoxy)benzamide

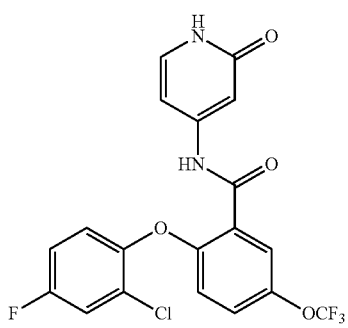

37

2-(2-chloro-4-
fluorophenoxy)-N-(2-oxo-1,2-
dihydropyridin-4-yl)-5-
(trifluoromethoxy)benzamide

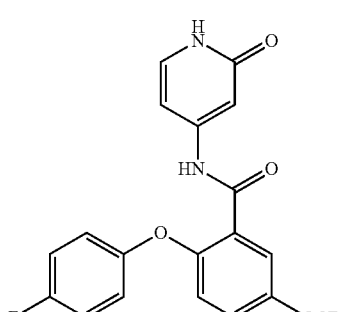

38

2-(4-fluorophenoxy)-N-(2-
oxo-1,2-dihydropyridin-4-yl)-
5-(trifluoromethoxy)benzamide

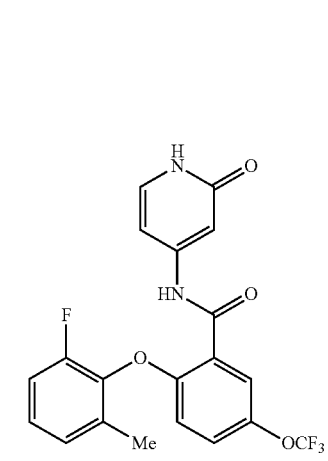

39

2-(2-fluoro-6-
methylphenoxy)-N-(2-oxo-
1,2-dihydropyridin-4-yl)-5-
(trifluoromethyl)benzamide

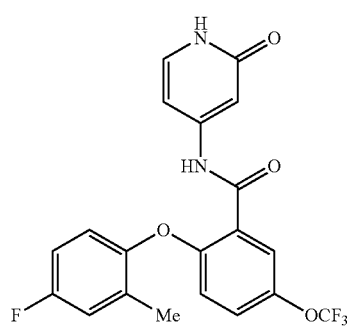

2-(4-fluoro-2-methylphenoxy)-N-(2-oxo-1,2-dihydropyridin-4-yl)-5-(trifluoromethoxy)benzamide

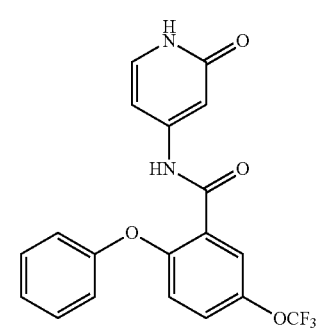

N-(2-oxo-1,2-dihydropyridin-4-yl)-2-phenoxy-5-(trifluoromethoxy)benzamide

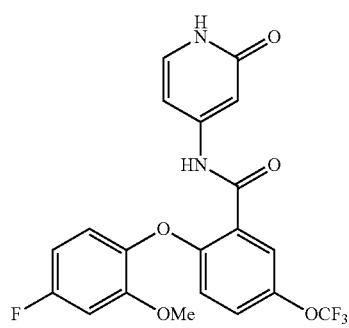

2-(4-fluoro-2-methoxyphenoxy)-N-(2-oxo-1,2-dihydropyridin-4-yl)-5-(trifluoromethoxy)benzamide

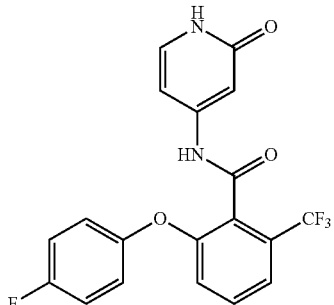

2-(4-fluorophenoxy)-N-(2-oxo-1,2-dihydropyridin-4-yl)-6-(trifluoromethyl)benzamide

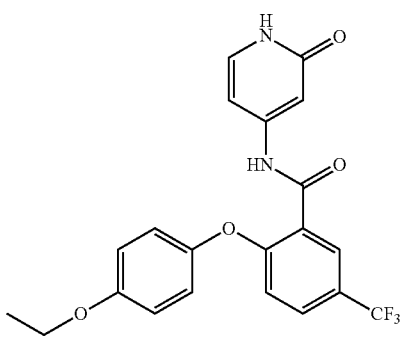

2-(4-ethoxyphenoxy)-N-(2-oxo-1,2-dihydropyridin-4-yl)-5-(trifluoromethyl)benzamide

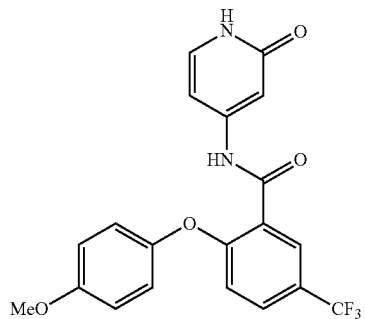

2-(4-methoxyphenoxy)-N-(2-oxo-1,2-dihydropyridin-4-yl)-5-(trifluoromethyl)benzamide

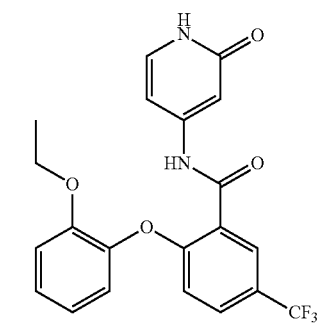

2-(2-ethoxyphenoxy)-N-(2-oxo-1,2-dihydropyridin-4-yl)-5-(trifluoromethyl)benzamide

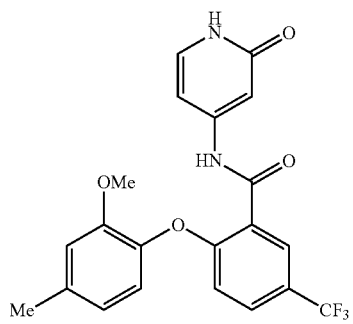

47

2-(2-methoxy-4-
methylphenoxy)-N-(2-oxo-
1,2-dihydropyridin-4-yl)-5-
(trifluoromethyl)benzamide

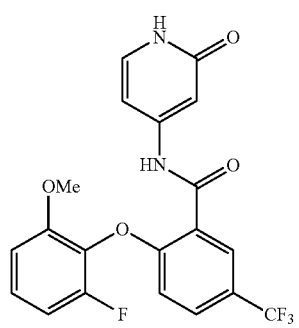

48

2-(2-fluoro-6-
methoxyphenoxy)-N-(2-oxo-
1,2-dihydropyridin-4-yl)-5-
(trifluoromethyl)benzamide

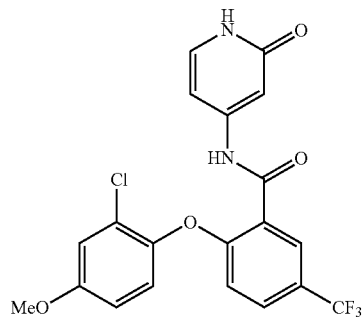

49

2-(2-chloro-4-
methoxyphenoxy)-N-(2-oxo-
1,2-dihydropyridin-4-yl)-5-
(trifluoromethyl)benzamide

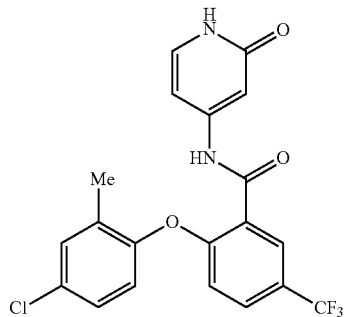

50

2-(4-chloro-2-
methylphenoxy)-N-(2-oxo-
1,2-dihydropyridin-4-yl)-5-
(trifluoromethyl)benzamide

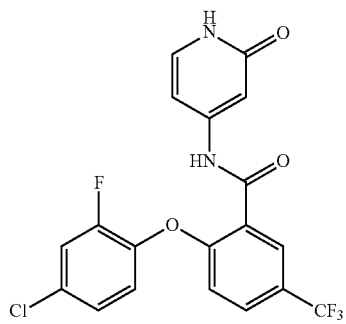

51

2-(4-chloro-2-
fluorophenoxy)-N-(2-oxo-1,2-
dihydropyridin-4-yl)-5-
(trifluoromethyl)benzamide

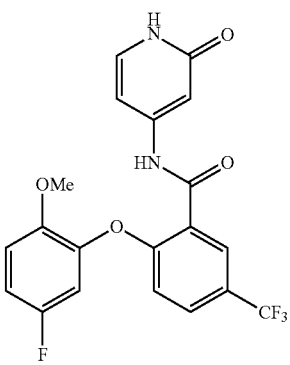

52

2-(5-fluoro-2-
methoxyphenoxy)-N-(2-oxo-
1,2-dihydropyridin-4-yl)-5-
(trifluoromethyl)benzamide

53

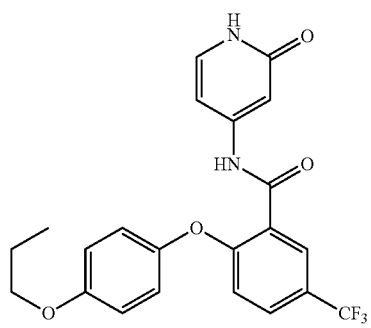

N-(2-oxo-1,2-dihydropyridin-
4-yl)-2-(4-propoxyphenoxy)-
5-(trifluoromethyl)benzamide

54

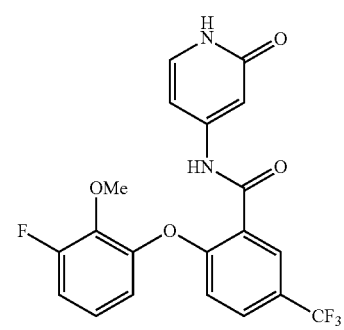

2-(3-fluoro-2-
methoxyphenoxy)-N-(2-oxo-
1,2-dihydropyridin-4-yl)-5-
(trifluoromethyl)benzamide

55

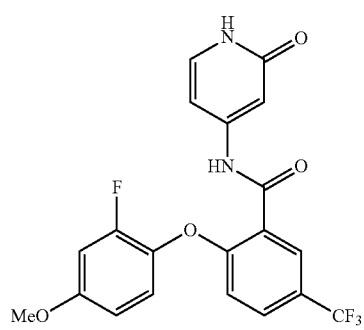

2-(2-fluoro-4-
methoxyphenoxy)-N-(2-oxo-
1,2-dihydropyridin-4-yl)-5-
(trifluoromethyl)benzamide

56

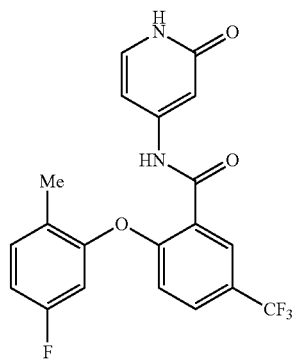

2-(5-fluoro-2-
methylphenoxy)-N-(2-oxo-
1,2-dihydropyridin-4-yl)-5-
(trifluoromethyl)benzamide

57

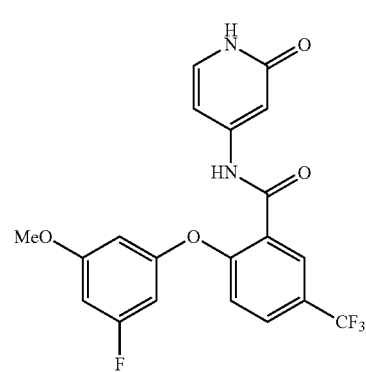

2-(3-fluoro-5-
methoxyphenoxy)-N-(2-oxo-
1,2-dihydropyridin-4-yl)-5-
(trifluoromethyl)benzamide

58

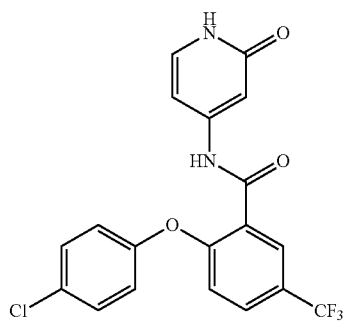

2-(4-chlorophenoxy)-N-(2-
oxo-1,2-dihydropyridin-4-yl)-
5-(trifluoromethyl)benzamide

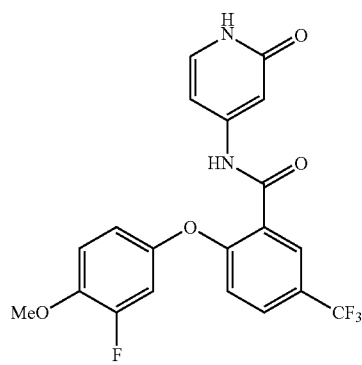

59

2-(3-fluoro-4-
methoxyphenoxy)-N-(2-oxo-
1,2-dihydropyridin-4-yl)-5-
(trifluoromethyl)benzamide

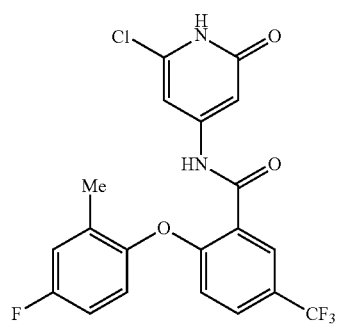

60

N-(6-chloro-2-oxo-1,2-
dihydropyridin-4-yl)-2-(4-
fluoro-2-methylphenoxy)-5-
(trifluoromethyl)benzamide

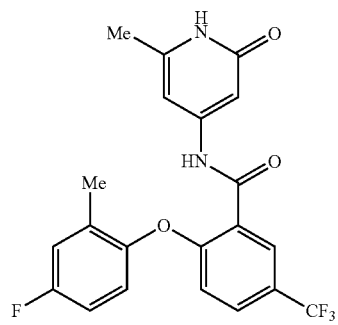

61

2-(4-fluoro-2-
methylphenoxy)-N-(6-methyl-
2-oxo-1,2-dihydropyridin-4-yl)-
5-(trifluoromethyl)benzamide

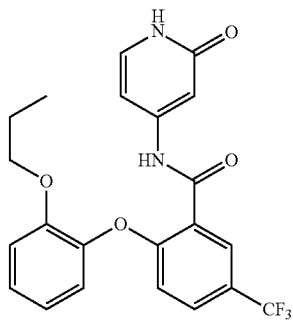

62

N-(2-oxo-1,2-dihydropyridin-
4-yl)-2-(2-propoxyphenoxy)-
5-(trifluoromethyl)benzamide

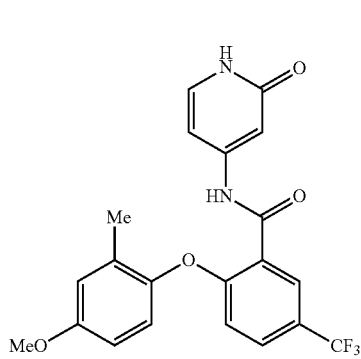

63

2-(4-methoxy-2-
methylphenoxy)-N-(2-oxo-
1,2-dihydropyridin-4-yl)-5-
(trifluoromethyl)benzamide

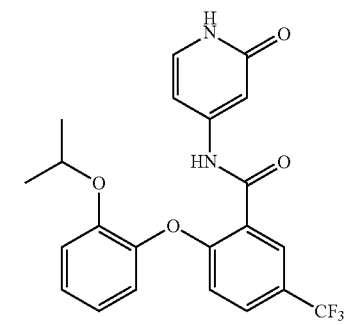

64

2-(2-isopropoxyphenoxy)-N-
(2-oxo-1,2-dihydropyridin-4-yl)-
5-(trifluoromethyl)benzamide -continued

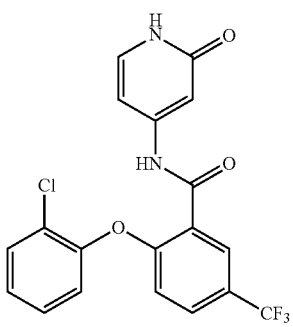

65

2-(2-chlorophenoxy)-N-(2-
oxo-1,2-dihydropyridin-4-yl)-
5-(trifluoromethyl)benzamide

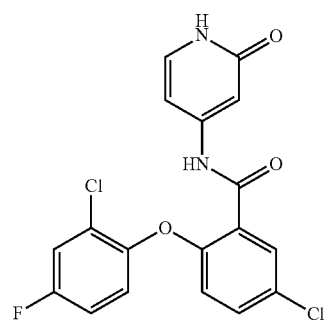

66

5-chloro-2-(2-chloro-4-
fluorophenoxy)-N-(2-oxo-1,2-
dihydropyridin-4-
yl)benzamide

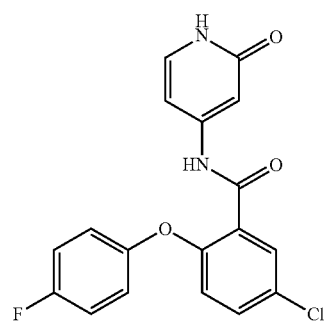

67

5-chloro-2-(4-
fluorophenoxy)-N-(2-oxo-1,2-
dihydropyridin-4-
yl)benzamide

-continued

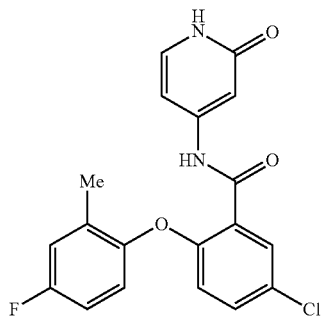

68

5-chloro-2-(4-fluoro-2-
methylphenoxy)-N-(2-oxo-
1,2-dihydropyridin-4-
yl)benzamide

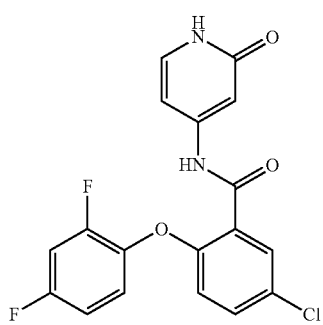

69

5-chloro-2-(2,4-
difluorophenoxy)-N-(2-oxo-
1,2-dihydropyridin-4-
yl)benzamide

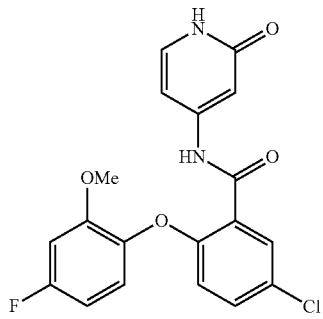

70

5-chloro-2-(4-fluoro-2-
methoxyphenoxy)-N-(2-oxo-
1,2-dihydropyridin-4-
yl)benzamide -continued

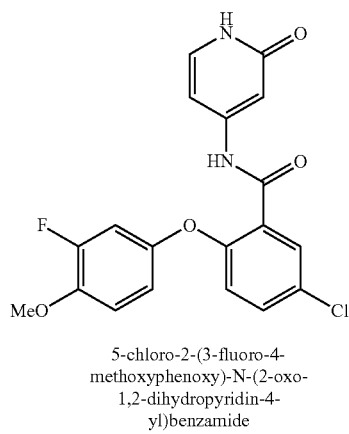

71

5-chloro-2-(3-fluoro-4-
methoxyphenoxy)-N-(2-oxo-
1,2-dihydropyridin-4-
yl)benzamide

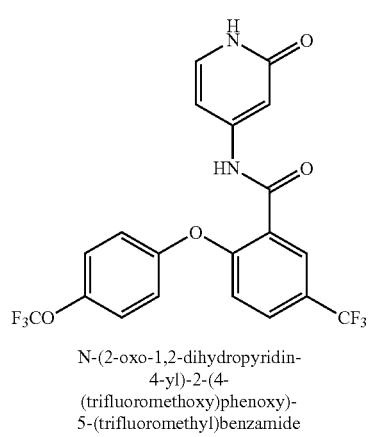

72

N-(2-oxo-1,2-dihydropyridin-
4-yl)-2-(4-
(trifluoromethoxy)phenoxy)-
5-(trifluoromethyl)benzamide

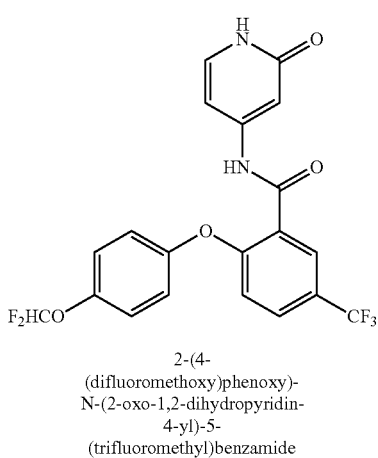

73

2-(4-
(difluoromethoxy)phenoxy)-
N-(2-oxo-1,2-dihydropyridin-
4-yl)-5-
(trifluoromethyl)benzamide -continued

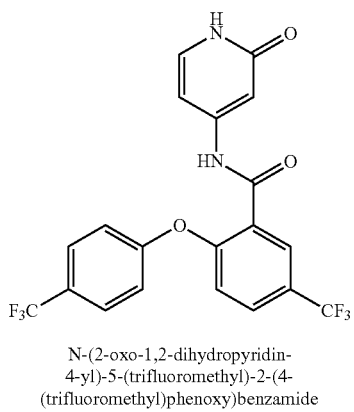

74

N-(2-oxo-1,2-dihydropyridin-
4-yl)-5-(trifluoromethyl)-2-(4-
(trifluoromethyl)phenoxy)benzamide

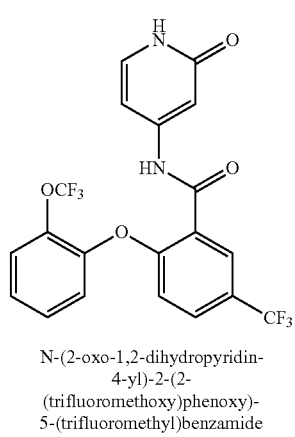

75

N-(2-oxo-1,2-dihydropyridin-
4-yl)-2-(2-
(trifluoromethoxy)phenoxy)-
5-(trifluoromethyl)benzamide

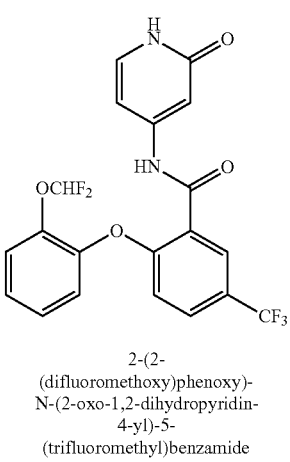

76

2-(2-
(difluoromethoxy)phenoxy)-
N-(2-oxo-1,2-dihydropyridin-
4-yl)-5-
(trifluoromethyl)benzamide

77

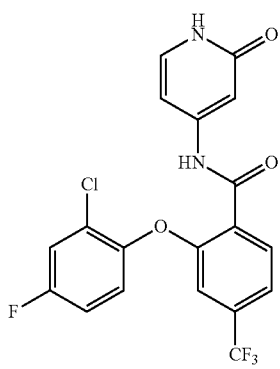

2-(2-chloro-4-fluorophenoxy)-N-(2-oxo-1,2-dihydropyridin-4-yl)-4-(trifluoromethyl)benzamide

78

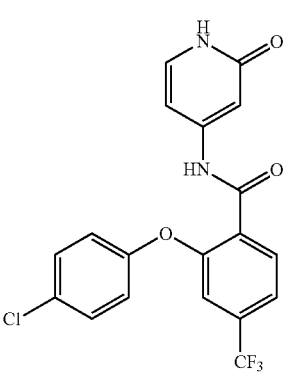

2-(4-chlorophenoxy)-N-(2-oxo-1,2-dihydropyridin-4-yl)-4-(trifluoromethyl)benzamide

79

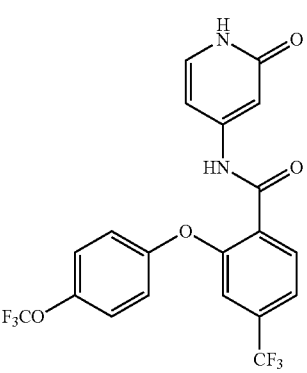

N-(2-oxo-1,2-dihydropyridin-4-yl)-2-(4-(trifluoromethoxy)phenoxy)-4-(trifluoromethyl)benzamide

80

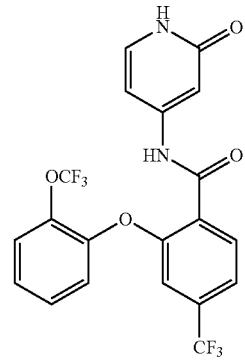

N-(2-oxo-1,2-dihydropyridin-4-yl)-2-(2-(trifluoromethoxy)phenoxy-4-(trifluoromethyl)benzamide

81

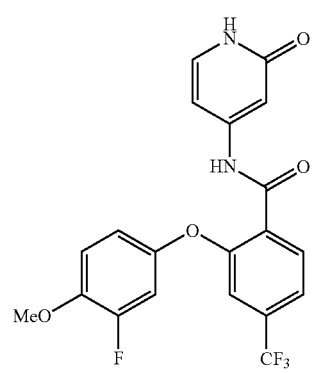

2-(3-fluoro-4-methoxyphenoxy)-N-(2-oxo-1,2-dihydropyridin-4-yl)-4-(trifluoromethyl)benzamide

82

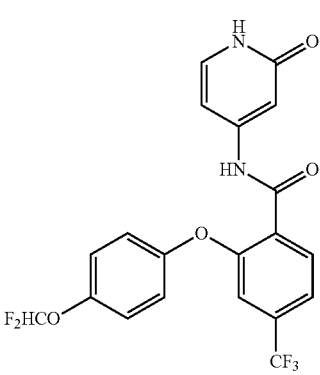

2-(4-(difluoromethoxy)phenoxy)-N-(2-oxo-1,2-dihydropyridin-4-yl)-2-(4-(trifluoromethyl)benzamide

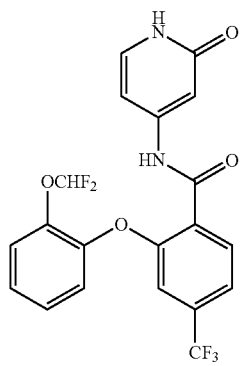

83

2-(2-(difluoromethoxy)phenoxy)-N-(2-oxo-1,2-dihydropyridin-4-yl)-4-(trifluoromethyl)benzamide

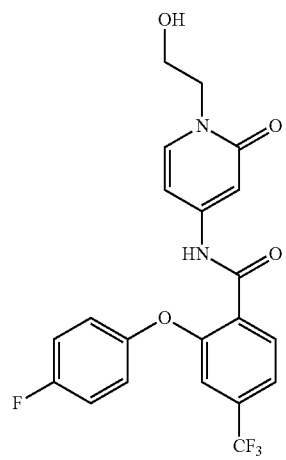

84

2-(2-fluoro-4-methoxyphenoxy)-N-(2-oxo-1,2-dihydropyridin-4-yl)-4-(trifluoromethyl)benzamide

85

2-(4-fluorophenoxy)-N-(1-(2-hydroxyethyl)-2-oxo-1,2-dihydropyridin-4-yl)-4-(trifluoromethyl)benzamide

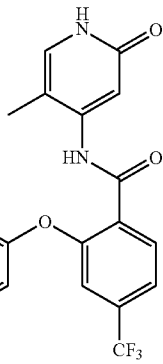

86

2-(4-fluoro-2-methylphenoxy)-N-(5-methyl-2-oxo-1,2-dihydropyridin-4-yl)-4-(trifluoromethyl)benzamide

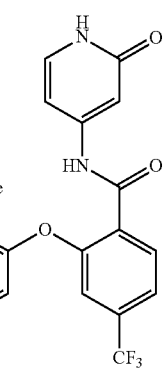

87

2-(3-fluoro-2-methoxyphenoxy)-N-(2-oxo-1,2-dihydropyridin-4-yl)-4-(trifluoromethyl)benzamide

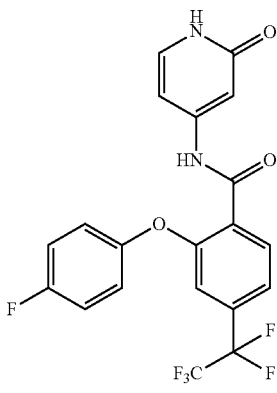

88

2-(4-fluorophenoxy)-N-(2-oxo-1,2-dihydropyridin-4-yl)-4-(perfluoroethyl)benzamide

89

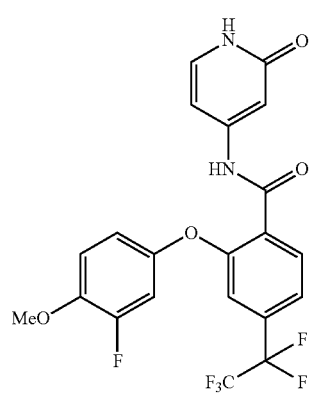

2-(3-fluoro-4-
methoxyphenoxy)-N-(2-oxo-
1,2-dihydropyridin-4-yl)-4-
(perfluoroethyl)benzamide

90

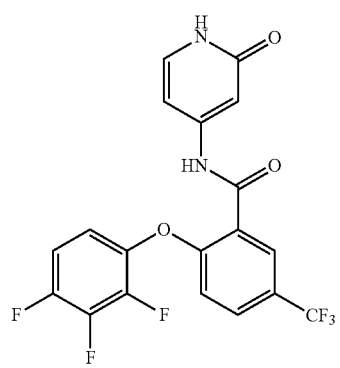

N-(2-oxo-1,2-dihydropyridin-
4-yl)-5-(trifluoromethyl)-2-
(2,3,4-
trifluorophenoxy)benzamide

91

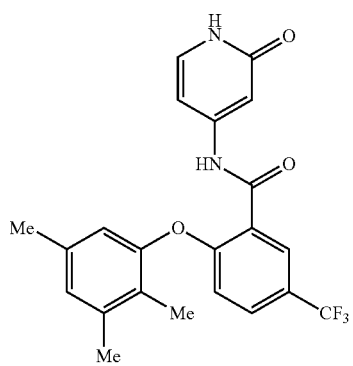

N-(2-oxo-1,2-dihydropyridin-
4-yl)-5-(trifluoromethyl)-2-
(2,3,5-
trimethylphenoxy)benzamide

92

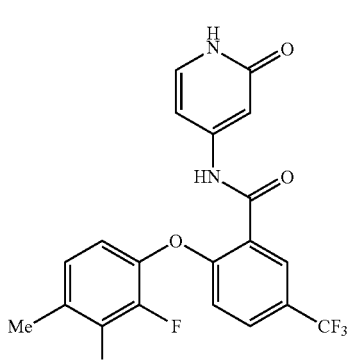

2-(2,3-difluoro-4-
methylphenoxy)-N-(2-oxo-
1,2-dihydropyridin-4-yl)-5-
(trifluoromethyl)benzamide

93

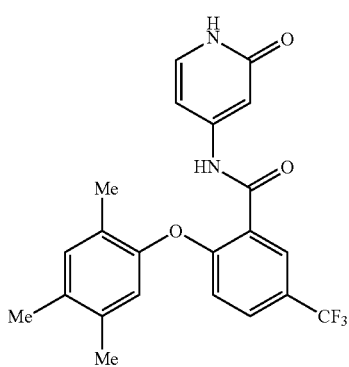

N-(2-oxo-1,2-dihydropyridin-
4-yl)-5-(trifluoromethyl)-2-
(2,4,5-
trimethylphenoxy)benzamide

94

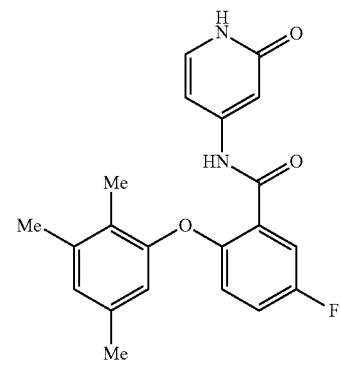

5- fluoro-N-(2-oxo-1,2-
dihydropyridin-4-yl)-2-(2,3,5-
trimethylphenoxy)benzamide

| | |
|---|---|
| 95 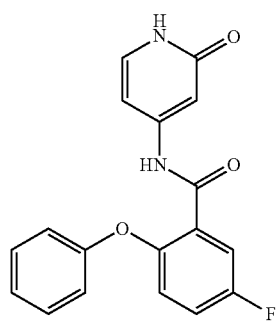 5-fluoro-N-(2-oxo-1,2-dihydropyridin-4-yl)-2-phenoxybenzamide | 98 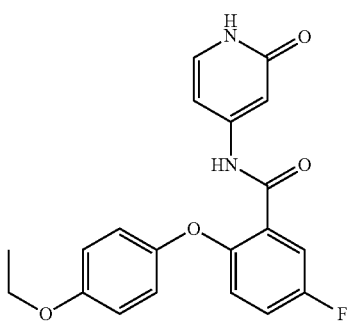 2-(4-ethoxyphenoxy)-5-fluoro-N-(2-oxo-1,2-dihydropyridin-4-yl)benzamide |
| 96 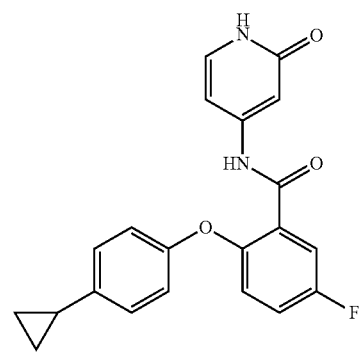 2-(4-cyclopropylphenoxy)-5-fluoro-N-(2-oxo-1,2-dihydropyridin-4-yl)benzamide | 99 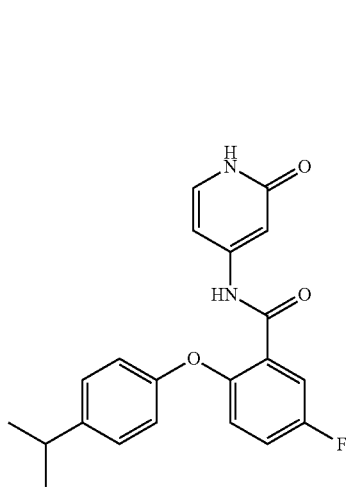 5-fluoro-2-(4-isopropylphenoxy)-N-(2-oxo-1,2-dihydropyridin-4-yl)benzamide |
| 97 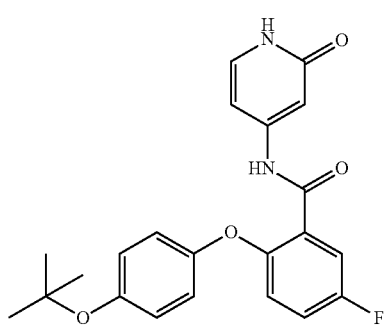 2-(4-(tert-butoxy)phenoxy)-5-fluoro-N-(2-oxo-1,2-dihydropyridin-4-yl)benzamide | 100 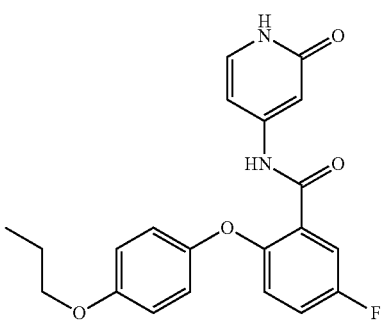 5-fluoro-N-(2-oxo-1,2-dihydropyridin-4-yl)-2-(4-propoxyphenoxy)benzamide |

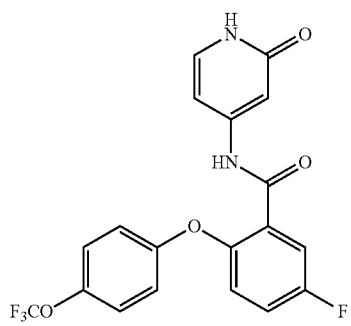

5-fluoro-N-(2-oxo-1,2-dihydropyridin-4-yl)-2-(4-(trifluoromethoxy)phenoxy)benzamide

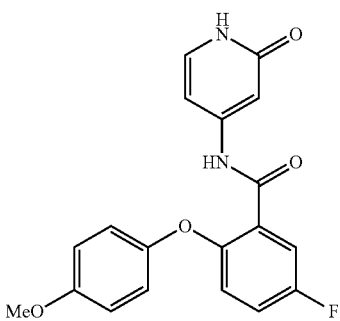

5-fluoro-2-(4-methoxyphenoxy)-N-(2-oxo-1,2-dihydropyridin-4-yl)benzamide

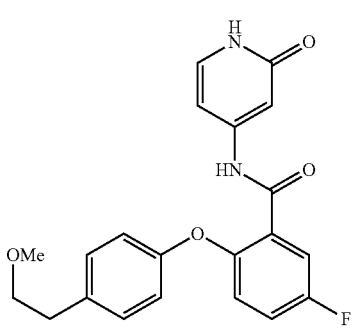

5-fluoro-2-(4-(2-methoxyethyl)phenoxy)-N-(2-oxo-1,2-dihydropyridin-4-yl)benzamide

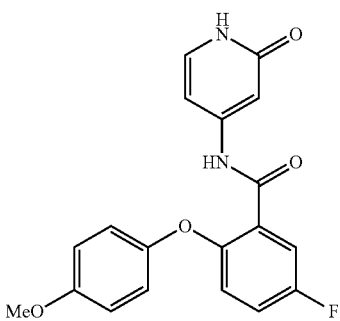

5-fluoro-N-(2-oxo-1,2-dihydropyridin-4-yl)-2-(2,4,5-trimethylphenoxy)benzamide

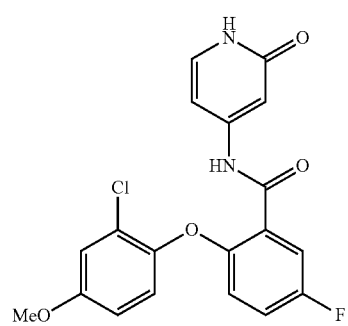

2-(2-chloro-4-methoxyphenoxy)-5-fluoro-N-(2-oxo-1,2-dihydropyridin-4-yl)benzamide

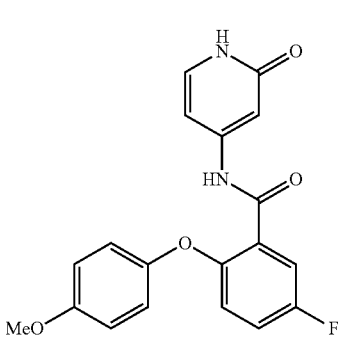

2-(4-fluoro-2-methylphenoxy)-N-(2-oxo-1,2-dihydropyridin-4-yl)-5-(trifluoromethyl)benzamide

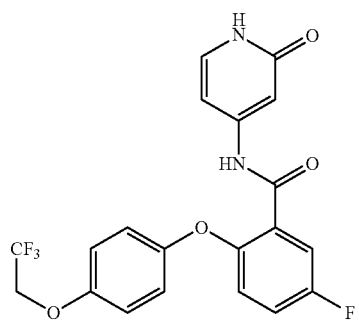

107

5-fluoro-N-(2-oxo-1,2-
dihydropyridin-4-yl)-2-(4-
(2,2,2-
trifluoroethoxy)phenoxy)benzamide

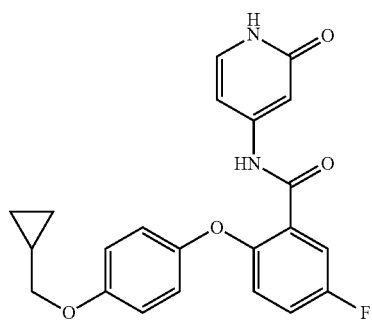

108

2-(4-
(cyclopropylmethoxy)phenoxy)-
5-fluoro-N-(2-oxo-1,2-
dihydropyridin-4-
yl)benzamide

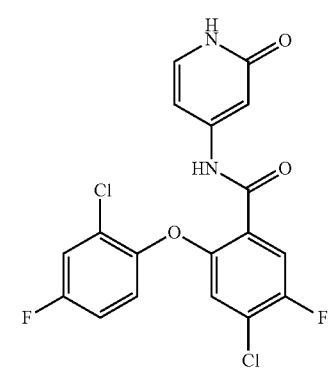

109

4-chloro-2-(2-chloro-4-
fluorophenoxy)-5-fluoro-N-(2-
oxo-1,2-dihydropyridin-4-
yl)benzamide

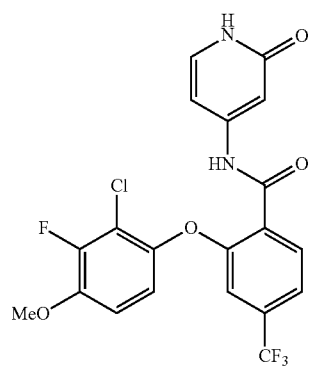

110

2-(2-chloro-3-fluoro-4-
methoxyphenoxy)-N-(2-oxo-
1,2-dihydropyridin-4-yl)-4-
(trifluoromethyl)benzamide

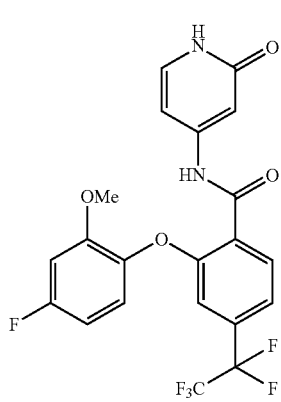

111

2-(4-fluoro-2-
methoxyphenoxy)-N-(2-oxo-
1,2-dihydropyridin-4-yl)-4-
(perfluoroethyl)benzamide

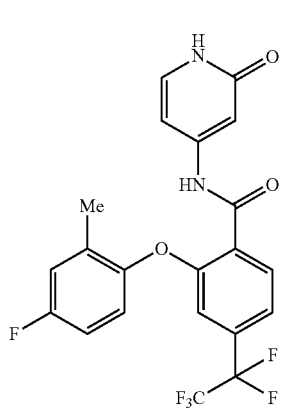

112

2-(4-fluoro-2-
methylphenoxy)-N-(2-oxo-
1,2-dihydropyridin-4-yl)-4-
(perfluoroethyl)benzamide

113

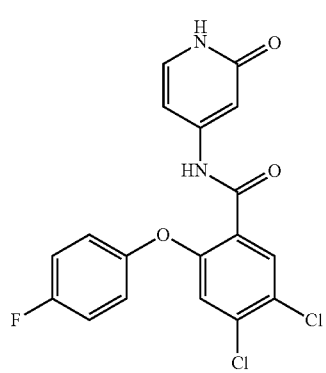

4,5-dichloro-2-(4-
fluorophenoxy)-N-(2-oxo-1,2-
dihydropyridin-4-
yl)benzamide

114

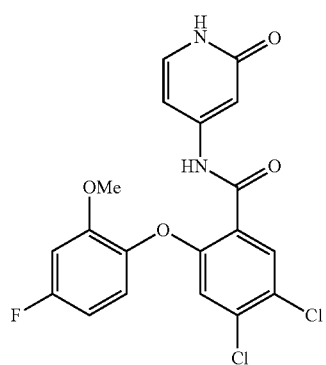

4,5-dichloro-2-(4-fluoro-2-
methoxyphenoxy)-N-(2-oxo-
1,2-dihydropyridin-4-
yl)benzamide

115

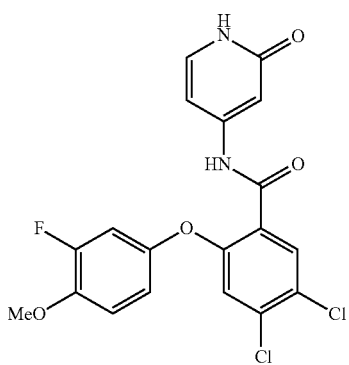

4,5-dichloro-2-(3-fluoro-4-
methoxyphenoxy)-N-(2-oxo-
1,2-dihydropyridin-4-
yl)benzamide

116

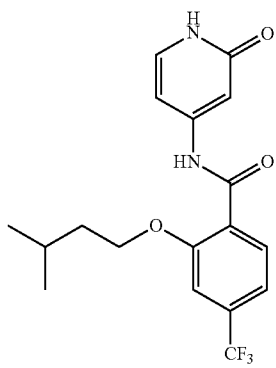

2-(isopentyloxy)-N-(2-oxo-
1,2-dihydropyridin-4-yl)-4-
(trifluoromethyl)benzamide

117

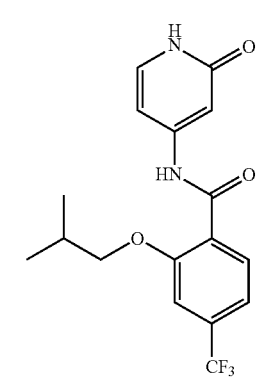

2-(isobutoxy)-N-(2-oxo-1,2-
dihydropyridin-4-yl)-4-
(trifluoromethyl)benzamide

118

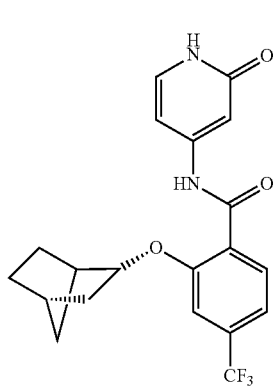

2-(($2R$)-bicyclo[2.2.1]heptan-
2-yloxy)-N-(2-oxo-1,2-
dihydropyridin-4-yl)-4-
(trifluoromethyl)benzamide

119

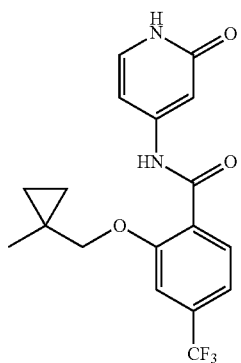

2-((1-methylcyclopropyl)methoxy)-N-(2-oxo-1,2-dihydropyridin-4-yl)-4-(trifluoromethyl)benzamide

120

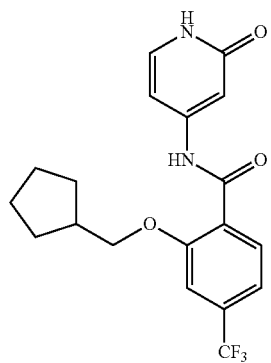

2-(cyclopentylmethoxy)-N-(2-oxo-1,2-dihydropyridin-4-yl)-4-(trifluoromethyl)benzamide

121

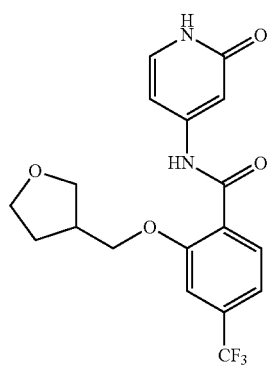

N-(2-oxo-1,2-dihydropyridin-4-yl)-2-((tetrahydrofuran-3-yl)methoxy)-4-(trifluoromethyl)benzamide

122

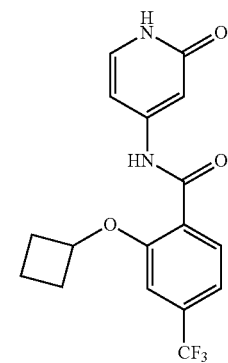

2-cyclobutoxy-N-(2-oxo-1,2-dihydropyridin-4-yl)-4-(trifluoromethyl)benzamide

123

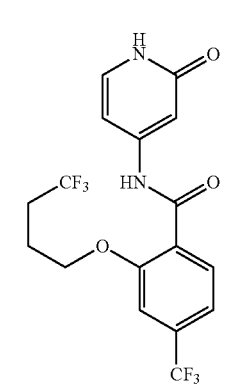

N-(2-oxo-1,2-dihydropyridin-4-yl)-2-(4,4,4-trifluorobutoxy)-4-(trifluoromethyl)benzamide

124

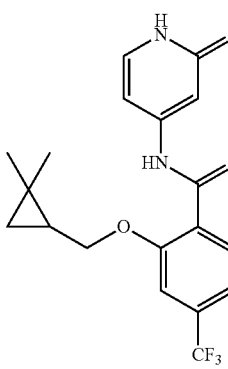

2-((2,2-dimethylcyclopropyl)methoxy)-N-(2-oxo-1,2-dihydropyridin-4-yl)-4-(trifluoromethyl)benzamide

125

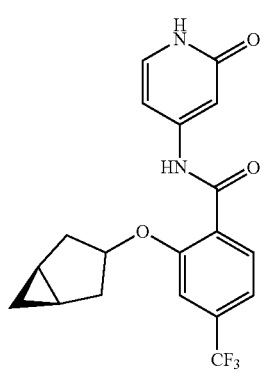

2-((1R,5S)-
bicyclo[3.1.0]hexan-3-yloxy)-
N-(2-oxo-1,2-dihydropyridin-
4-yl)-4-
(trifluoromethyl)benzamide

126

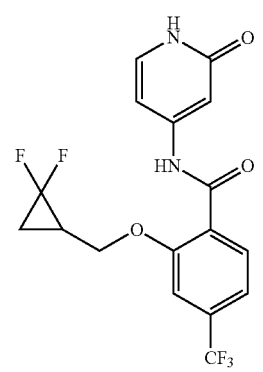

2-((2,2-
difluorocyclopropyl)methoxy)-
N-(2-oxo-1,2-dihydropyridin-
4-yl)-4-
(trifluoromethyl)benzamide

127

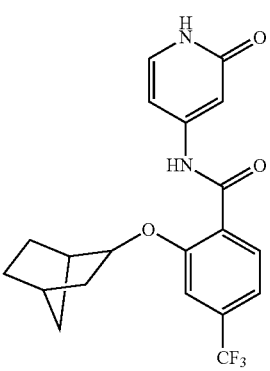

2-(bicyclo[2.2.1]heptan-2-
yloxy)-N-(2-oxo-1,2-
dihydropyridin-4-yl)-4-
(trifluoromethyl)benzamide

128

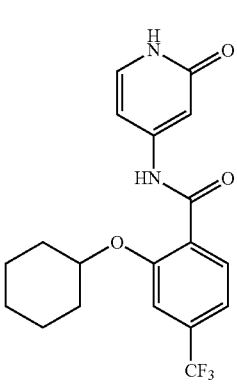

2-(cyclohexyloxy)-N-(2-oxo-
1,2-dihydropyridin-4-yl)-4-
(trifluoromethyl)benzamide

129

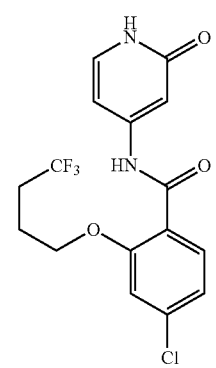

4-chloro-N-(2-oxo-1,2-
dihydropyridin-4-yl)-2-(4,4,4-
trifluorobutoxy)benzamide

130

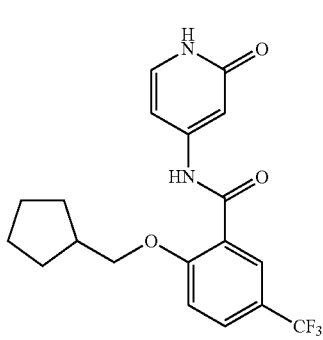

2-(cyclopentylmethoxy)-N-(2-
oxo-1,2-dihydropyridin-4-yl)-
5-(trifluoromethyl)benzamide

131

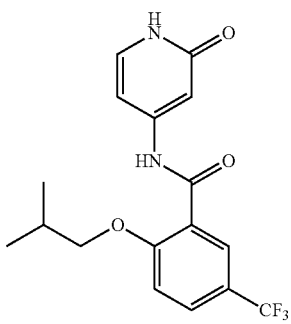

2-isobutoxy-N-(2-oxo-1,2-
dihydropyridin-4-yl)-5-
(trifluoromethyl)benzamide

132

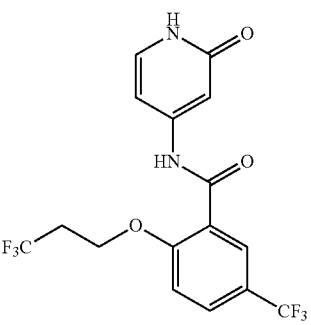

N-(2-oxo-1,2-dihydropyridin-
4-yl)-5-(trifluoromethyl)-2-
(3,3,3-
trifluoropropoxy)benzamide

133

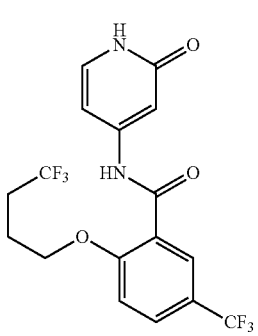

N-(2-oxo-1,2-dihydropyridin-
4-yl)-2-(4,4,4-
trifluorobutoxy)-5-
(trifluoromethyl)benzamide

134

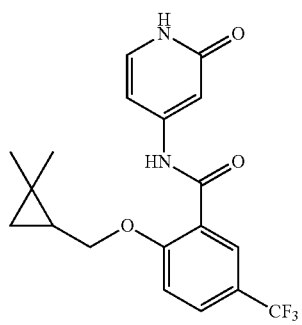

2-((2,2-
dimethylcyclopropyl)methoxy)-
N-(2-oxo-1,2-
dihydropyridin-4-yl)-5-
(trifluoromethyl)benzamide

135

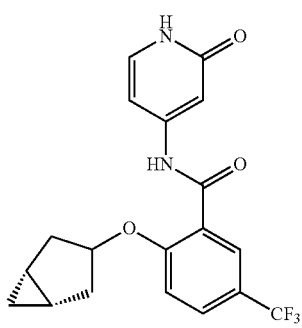

2-((1R,5S)-bicyclo[3.1.0]hexan-3-
N-(2-oxo-1,2-dihydropyridin-4-yl)-5-
(trifluoromethyl)benzamide

136

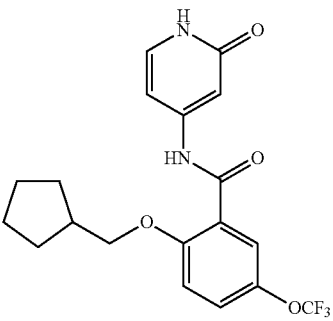

2-(cyclopentylmethoxy)-N-(2-
oxo-1,2-dihydropyridin-4-yl)-
5-(trifluoromethoxy)benzamide -continued

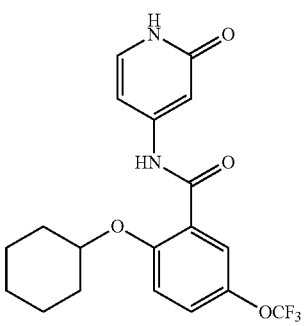

137

2-(cyclohexyloxy)-N-(2-oxo-
1,2-dihydropyridin-4-yl)-5-
(trifluoromethoxy)benzamide

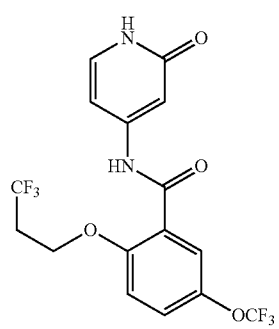

138

N-(2-oxo-1,2-dihydropyridin-
4-yl)-5-(trifluoromethoxy)-2-
(3,3,3-
(trifluoropropoxy)benzamide

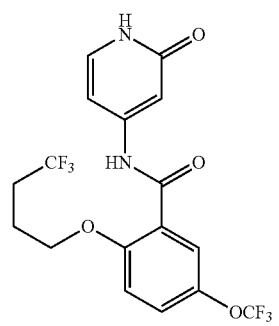

139

N-(2-oxo-1,2-dihydropyridin-
4-yl)-2-(4,4,4-
trifluorobutoxy-5-
(trifluoromethoxy)benzamide -continued

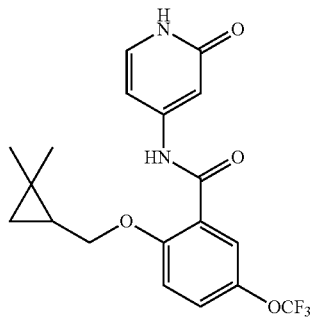

140

2-((2,2-
dimethylcyclopropyl)methoxy)-
N-(2-oxo-1,2-
dihydropyridin-4-yl)-5-
(trifluoromethoxy)benzamide

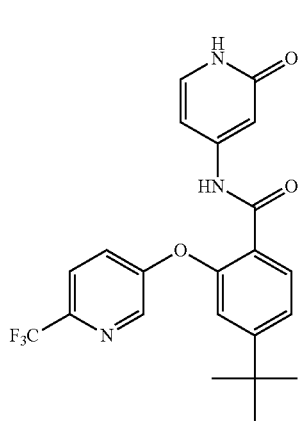

141

4-(tert-butyl)-N-(2-oxo-1,2-
dihydropyridin-4-yl)-2-((6-
(trifluoromethyl)pyridin-3-
yl)oxy)benzamide

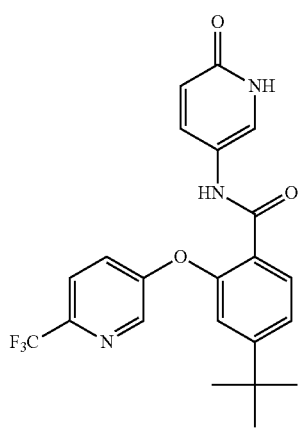

142

4-(tert-butyl)-N-(6-oxo-1,6-
dihydropyridin-3-yl)-2-((6-
(trifluoromethyl)pyridin-3-
yl)oxy)benzamide

143

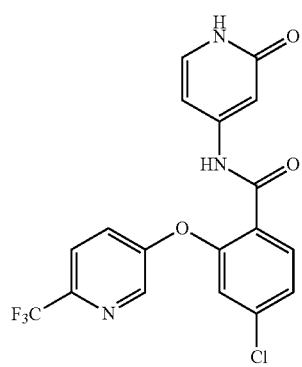

4-chloro-N-(2-oxo-1,2-
dihydropyridin-4-yl)-2-((6-
(trifluoromethyl)pyridin-3-
yl)oxy)benzamide

144

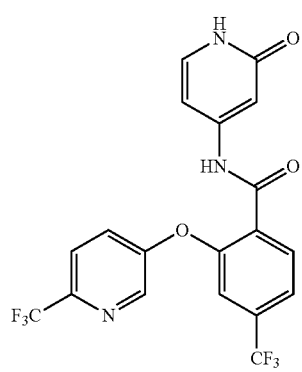

N-(2-oxo-1,2-dihydropyridin-
4-yl)-4-(trifluoromethyl)-2-((6-
(trifluoromethyl)pyridin-3-
yl)oxy)benzamide

145

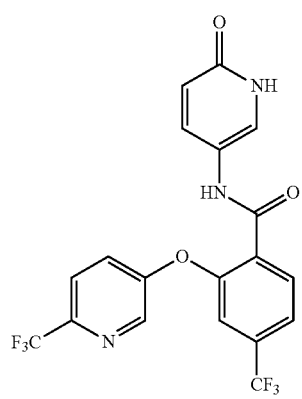

N-(6-oxo-1,6-dihydropyridin-
3-yl)-4-(trifluoromethyl)-2-((6-
(trifluoromethyl)pyridin-3-
yl)oxy)benzamide

146

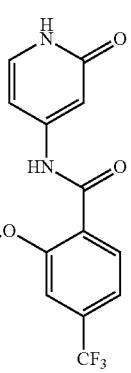

2-((6-methylpyridin-3-yl)oxy)-
N-(2-oxo-1,2-dihydropyridin-
4-yl)-4-
(trifluoromethyl)benzamide

147

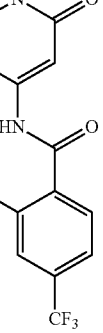

2-((2-methylpyridin-3-yl)oxy)-
N-(2-oxo-1,2-dihydropyridin-
4-yl)-4-
(trifluoromethyl)benzamide

148

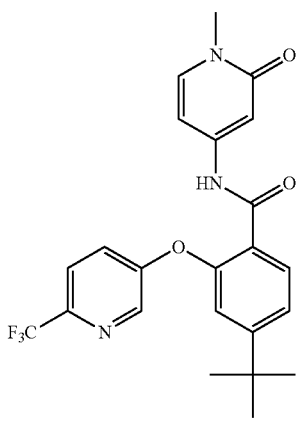

4-(tert-butyl)-N-(1-methyl-2-
oxo-1,2-dihydropyridin-4-yl)-
2-((6-(trifluoromethyl)pyridin-
3-yl)oxy)benzamide

149

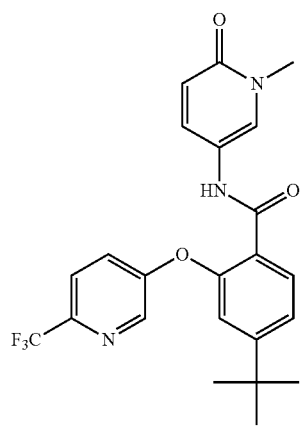

4-(tert-butyl)-N-(1-methyl-6-
oxo-1,6-dihydropyridin-3-yl)-
2-((6-(trifluoromethyl)pyridin-
3-yl)oxy)benzamide

150

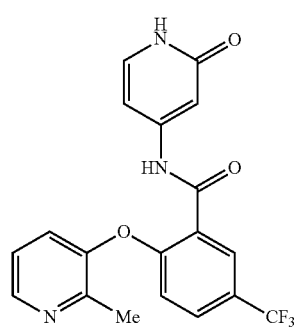

2-((2-methylpyridin-3-yl)oxy)-
N-(2-oxo-1,2-dihydropyridin-
4-yl)-5-
(trifluoromethyl)benzamide

151

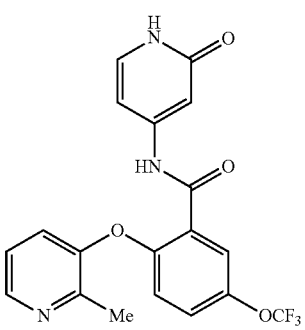

2-((2-methylpyridin-3-yl)oxy)-
N-(2-oxo-1,2-dihydropyridin-
4-yl)-5-
(trifluoromethoxy)benzamide

152

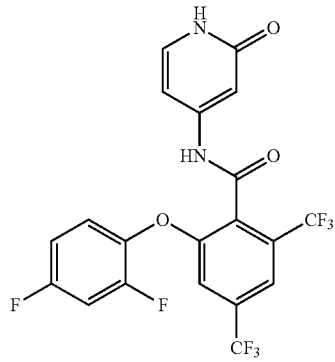

2-(2,4-difluorophenoxy)-N-(2-
oxo-1,2-dihydropyridin-4-yl)-
4,6-
bis(trifluoromethyl)benzamide

153

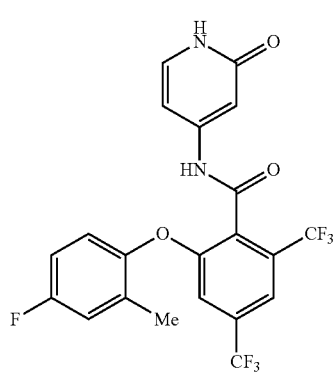

2-(4-fluoro-2-
methylphenoxy)-N-(2-oxo-
1,2-dihydropyridin-4-yl)-4,6-
bis(trifluoromethyl)benzamide

154

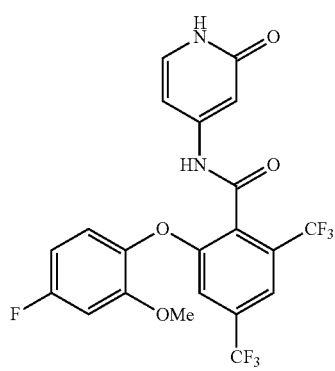

2-(4-fluoro-2-
methoxyphenoxy)-N-(2-oxo-
1,2-dihydropyridin-4-yl)-4,6-
bis(trifluoromethyl)benzamide

155

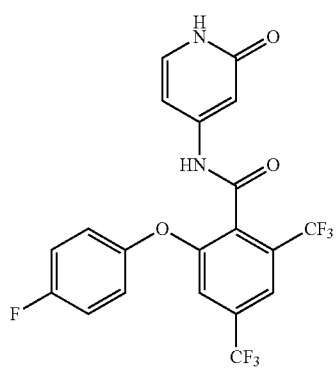

2-(4-fluorophenoxy)-N-(2-
oxo-1,2-dihydropyridin-4-yl)-
4,6-
bis(trifluoromethyl)benzamide

156

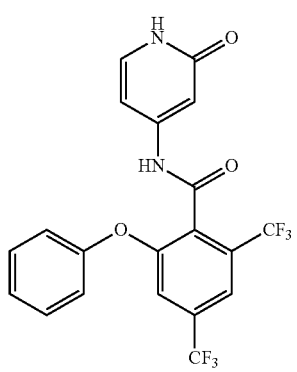

N-(2-oxo-1,2-dihydropyridin-
4-yl)-2-phenoxy-4,6-
bis(trifluoromethyl)benzamide

157

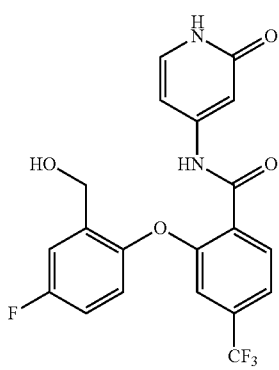

2-(4-fluoro-2-
(hydroxymethyl)phenoxy)-N-
(2-oxo-1,2-dihydropyridin-4-
yl)-4-
(trifluoromethyl)benzamide

158

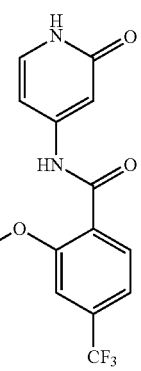

2-(4-fluoro-2-
methoxyphenoxy)-N-(2-oxo-
1,2-dihydropyridin-4-yl)-4-
(trifluoromethyl)benzamide

159

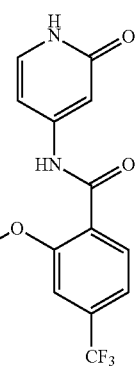

2-((5-fluoro-2-
hydroxybenzyl)oxy)-N-(2-
oxo-1,2-dihydropyridin-4-yl)-
4-(trifluoromethyl)benzamide

160

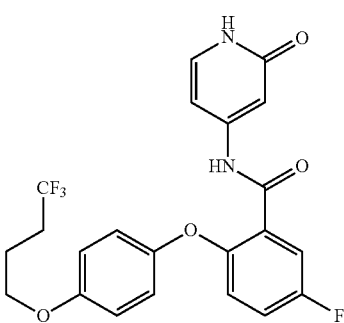

5-fluoro-N-(2-oxo-1,2-
dihydropyridin-4-yl)-2-(4-
(4,4,4-
trifluorobutoxy)phenoxy)benzamide or a pharmaceutically acceptable salt thereof.

18. A pharmaceutical composition comprising a therapeutically effective amount of the compound or a pharmaceutically acceptable salt thereof of claim 1 and one or more pharmaceutically acceptable carriers or vehicles.

19. A method of inhibiting a voltage-gated sodium channel in a subject comprising administering to the subject a compound or a pharmaceutically acceptable salt thereof of claim 1.

20. A method of treating or lessening the severity in a subject of chronic pain, gut pain, neuropathic pain, musculoskeletal pain, acute pain, inflammatory pain, cancer pain, or idiopathic pain comprising administering an effective amount of a compound or a pharmaceutically acceptable salt thereof of claim 1.

21. The compound or pharmaceutically acceptable salt of claim 1, wherein the compound or pharmaceutically acceptable salt is

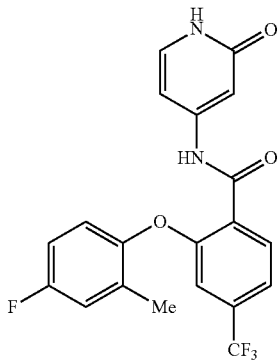 [SMILES: Cc1cc(F)ccc1Oc1cc(C(F)(F)F)ccc1C(=O)Nc1cc[nH]c(=O)c1]

2-(4-fluoro-2-methylphenoxy)-N-(2-oxo-1,2-dihydropyridin-4-yl)-4-(trifluoromethyl)benzamide;
or a pharmaceutically acceptable salt thereof.

22. The compound or pharmaceutically acceptable salt of claim 1, wherein the compound or pharmaceutically acceptable salt is

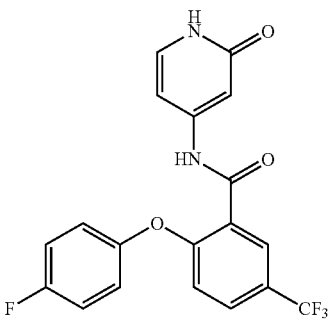 [SMILES: O=C(Nc1cc[nH]c(=O)c1)c1cc(C(F)(F)F)ccc1Oc1ccc(F)cc1]

2-(4-fluorophenoxy)-N-(2-oxo-1,2-dihydropyridin-4-yl)-5-(trifluoromethyl)benzamide;
or a pharmaceutically acceptable salt thereof.

23. The compound or pharmaceutically acceptable salt of claim 1, wherein the compound or pharmaceutically acceptable salt is

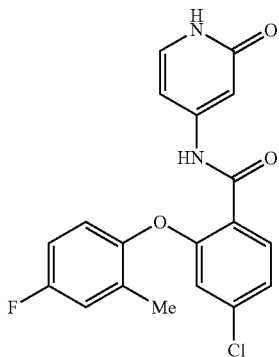 [SMILES: Cc1cc(F)ccc1Oc1cc(Cl)ccc1C(=O)Nc1cc[nH]c(=O)c1]

4-chloro-2-(4-fluoro-2-methylphenoxy)-N-(2-oxo-1,2-dihydropyridin-4-yl)benzamide;
or a pharmaceutically acceptable salt thereof.

24. The compound or pharmaceutically acceptable salt of claim 1, wherein the compound or pharmaceutically acceptable salt is

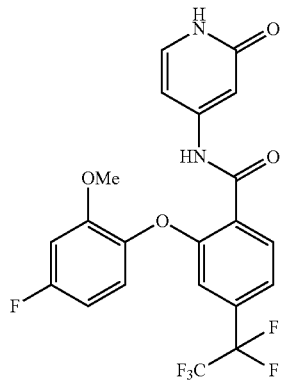 [SMILES: COc1cc(F)ccc1Oc1cc(C(F)(F)C(F)(F)F)ccc1C(=O)Nc1cc[nH]c(=O)c1]

2-(4-fluoro-2-methoxyphenoxy)-N-(2-oxo-1,2-dihydropyridin-4-yl)-4-(perfluoroethyl)benzamide;
or a pharmaceutically acceptable salt thereof.

25. The compound or pharmaceutically acceptable salt of claim 1, wherein the compound or pharmaceutically acceptable salt is

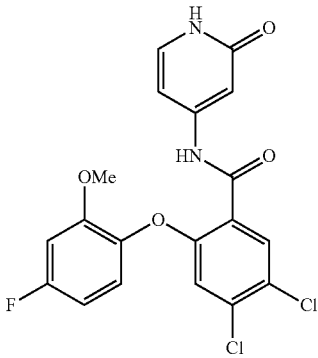 [SMILES: COc1cc(F)ccc1Oc1cc(Cl)c(Cl)cc1C(=O)Nc1cc[nH]c(=O)c1]

4,5-dichloro-2-(4-fluoro-2-methoxyphenoxy)-N-(2-oxo-1,2-dihydropyridin-4-yl)benzamide;
or a pharmaceutically acceptable salt thereof.

26. The method of claim 20, wherein the method comprises treating or lessening the severity in a subject of neuropathic pain.

27. The method of claim 20, wherein the method comprises treating or lessening the severity in a subject of musculoskeletal pain.

28. The method of claim 27, wherein the musculoskeletal pain comprises osteoarthritis pain.

29. The method of claim 20, wherein the method comprises treating or lessening the severity in a subject of inflammatory pain.

* * * * *

UNITED STATES PATENT AND TRADEMARK OFFICE
CERTIFICATE OF CORRECTION

PATENT NO.        : 9,051,270 B2
APPLICATION NO.   : 14/167759
DATED             : June 9, 2015
INVENTOR(S)       : Sara Sabina Hadida-Ruah et al.

Page 1 of 1

It is certified that error appears in the above-identified patent and that said Letters Patent is hereby corrected as shown below:

On the Title Page

Left column, item (72), after "Vijayalaksmi Arumugam," replace "San Marco," with --San Marcos,--.

Signed and Sealed this
Fifth Day of January, 2016

Michelle K. Lee
*Director of the United States Patent and Trademark Office*